(12) United States Patent
Eichner et al.

(10) Patent No.: US 8,287,850 B2
(45) Date of Patent: *Oct. 16, 2012

(54) CONJUGATES OF HYDROXYALKYL STARCH AND A PROTEIN, PREPARED BY REDUCTIVE AMINATION

(75) Inventors: Wolfram Eichner, Butzbach (DE); Michele Orlando, Munich (DE); Norbert Zander, Meine (DE); Harald S. Conradt, Braunschweig (DE); Frank Hacket, Altenstadt (DE); Klaus Langer, Erlangen (DE); Ronald Frank, Meine-Grassel (DE)

(73) Assignee: Fresenius Kabi Deutschland GmbH, Bad Homburg v.d.H.

( * ) Notice: Subject to any disclaimer, the term of this patent is extended or adjusted under 35 U.S.C. 154(b) by 714 days.

This patent is subject to a terminal disclaimer.

(21) Appl. No.: 11/518,352

(22) Filed: Sep. 8, 2006

(65) Prior Publication Data

US 2007/0134197 A1    Jun. 14, 2007

Related U.S. Application Data

(63) Continuation-in-part of application No. PCT/EP2005/002653, filed on Mar. 11, 2005.

(60) Provisional application No. 60/552,217, filed on Mar. 11, 2004.

(30) Foreign Application Priority Data

Mar. 11, 2004  (EP) .................................. 04005855

(51) Int. Cl.
*A61K 38/19* (2006.01)
*A61K 38/36* (2006.01)
*A61K 38/21* (2006.01)

(52) U.S. Cl. .............. 424/85.1; 514/8; 514/12; 530/351; 530/395; 530/383; 530/400

(58) Field of Classification Search .................. 424/85.1; 514/12, 8; 530/351, 395, 383, 400
See application file for complete search history.

(56) References Cited

U.S. PATENT DOCUMENTS

| 3,191,291 | A | 6/1965 | Maier |
|---|---|---|---|
| 3,226,395 | A | 12/1965 | Schimmelschmidt et al. |
| 4,001,200 | A | 1/1977 | Bonsen et al. |
| 4,001,401 | A | 1/1977 | Bonsen et al. |
| 4,053,590 | A | 10/1977 | Bonsen et al. |
| 4,061,736 | A | 12/1977 | Morris et al. |
| 4,064,118 | A | 12/1977 | Wong |
| 4,125,492 | A | 11/1978 | Cuatrecasas et al. |
| 4,179,337 | A | 12/1979 | Davis et al. |
| 4,261,973 | A | 4/1981 | Lee et al. |
| 4,412,989 | A | 11/1983 | Iwashita et al. |
| 4,454,161 | A | 6/1984 | Okada et al. |
| 4,496,689 | A | 1/1985 | Mitra |
| 4,667,016 | A | 5/1987 | Lai et al. |
| 4,703,008 | A | 10/1987 | Lin |
| 4,766,106 | A | 8/1988 | Katre et al. |
| 4,847,325 | A | 7/1989 | Shadle et al. |
| 4,863,964 | A | 9/1989 | Hedlund et al. |
| 4,900,780 | A | 2/1990 | Cerny |
| 4,904,584 | A | 2/1990 | Shaw |
| 4,925,677 | A | 5/1990 | Feijen |
| 4,939,239 | A | 7/1990 | Matsuhashi et al. |
| 4,952,496 | A | 8/1990 | Studier et al. |
| 5,068,321 | A | 11/1991 | Buysch et al. |
| 5,073,628 | A | 12/1991 | Matsuhashi et al. |
| 5,079,337 | A | 1/1992 | Leonard et al. |
| 5,110,909 | A | 5/1992 | Dellacherie et al. |
| 5,214,132 | A | 5/1993 | Kuga et al. |
| 5,217,998 | A | 6/1993 | Hedlund et al. |
| 5,218,092 | A | 6/1993 | Sasaki et al. |
| 5,218,108 | A | 6/1993 | Sommermeyer et al. |
| 5,281,698 | A | 1/1994 | Nitecki |
| 5,362,853 | A | 11/1994 | Kuga et al. |
| 5,420,105 | A | 5/1995 | Gustavson et al. |
| 5,470,843 | A | 11/1995 | Stahl et al. |
| 5,484,903 | A | 1/1996 | Szablikowski et al. |
| 5,543,332 | A | 8/1996 | Lihme et al. |
| 5,581,476 | A | 12/1996 | Osslund |
| 5,622,718 | A | 4/1997 | Al-Shamkhani et al. |
| 5,723,589 | A | 3/1998 | Miljkovic et al. |
| 5,736,533 | A | 4/1998 | Simon et al. |
| 5,770,645 | A | 6/1998 | Stamler et al. |
| 5,824,778 | A | 10/1998 | Ishikawa et al. |
| 5,840,900 | A | 11/1998 | Greenwald et al. |

(Continued)

FOREIGN PATENT DOCUMENTS

| AU | 5238393 | 9/1993 |
|---|---|---|
| CA | 2110543 | 6/1994 |
| CA | 2 233 725 | 9/1999 |
| CA | 2 441 442 | 9/2003 |
| CA | 2 478 478 | 1/2004 |
| CA | 2 478 480 | 1/2004 |
| DE | 22 33 977 | 2/1973 |
| DE | 26 16 086 | 11/1977 |
| DE | 30 29 307 | 3/1982 |
| DE | 3501616 | 7/1986 |

(Continued)

OTHER PUBLICATIONS

Abuchowski and Davis, "Soluble Polymer-Enzyme Adducts," *Enzymes as Drugs*, 1981, Holcenberg and Rubberts (eds.), Chapter 13, pp. 367-383, John Wiley & Sons N.Y.

(Continued)

*Primary Examiner* — Chih-Min Kam
(74) *Attorney, Agent, or Firm* — Fish & Richardson P.C.

(57) ABSTRACT

Conjugates of hydroxyalkyl starch and a protein are provided. The conjugates are formed by a reductive amination reaction between at least one aldehyde group or keto group or hemiacetal group of the hydroxyalkyl starch or of a derivative of the hydroxyalkyl starch, and at least one amino group of the protein, so that the hydroxyalkyl starch or the derivative thereof is covalently linked to the protein via an azomethine linkage or a amino linkage. Methods of producing these conjugates and specific uses of the conjugates also are provided.

59 Claims, 34 Drawing Sheets

U.S. PATENT DOCUMENTS

| | | | |
|---|---|---|---|
| 5,851,984 | A | 12/1998 | Matthews et al. |
| 5,876,980 | A | 3/1999 | DeFrees et al. |
| 5,880,270 | A | 3/1999 | Berninger et al. |
| 5,952,347 | A | 9/1999 | Arison et al. |
| 5,977,163 | A | 11/1999 | Li et al. |
| 5,981,507 | A | 11/1999 | Josephson et al. |
| 5,990,237 | A | 11/1999 | Bentley et al. |
| 6,011,008 | A | 1/2000 | Domb et al. |
| 6,083,909 | A | 7/2000 | Sommermeyer et al. |
| 6,172,208 | B1 | 1/2001 | Cook |
| 6,261,800 | B1 | 7/2001 | Nikolics et al. |
| 6,299,881 | B1 | 10/2001 | Lees et al. |
| 6,340,746 | B1 | 1/2002 | Roberts et al. |
| 6,375,846 | B1 | 4/2002 | Jarrett et al. |
| 6,395,266 | B1 | 5/2002 | Martinez et al. |
| 6,417,347 | B1 | 7/2002 | Herrmann et al. |
| 6,451,337 | B1 | 9/2002 | Smith et al. |
| 6,500,930 | B2 | 12/2002 | Adamson |
| 6,544,503 | B1 | 4/2003 | Vanderhoff et al. |
| 6,555,660 | B2 | 4/2003 | Nissen et al. |
| 6,586,398 | B1 | 7/2003 | Kinstler et al. |
| 6,596,135 | B1 | 7/2003 | Mitsui |
| 6,596,861 | B1 | 7/2003 | Moreau |
| 6,624,142 | B2 | 9/2003 | Greenwald et al. |
| 6,660,843 | B1 | 12/2003 | Feige et al. |
| 6,875,594 | B2 | 4/2005 | Muir et al. |
| 6,916,962 | B2 | 7/2005 | Rosen et al. |
| 7,115,576 | B2 | 10/2006 | Sommermeyer |
| 7,125,843 | B2 | 10/2006 | DeFrees et al. |
| 7,157,546 | B2 | 1/2007 | Kozlowski |
| 7,179,617 | B2 | 2/2007 | DeFrees et al. |
| 7,279,176 | B1 | 10/2007 | West et al. |
| 7,285,661 | B2 | 10/2007 | Sommermeyer et al. |
| 7,538,092 | B2 | 5/2009 | Orlando et al. |
| 7,541,328 | B2 | 6/2009 | Hemberger et al. |
| 7,629,456 | B2 | 12/2009 | Lange et al. |
| 7,815,893 | B2 | 10/2010 | Zander et al. |
| 7,816,516 | B2 | 10/2010 | Sommermeyer et al. |
| 8,017,739 | B2 | 9/2011 | Eichner et al. |
| 2002/0065410 | A1 | 5/2002 | Antrim |
| 2003/0087877 | A1 | 5/2003 | Calias et al. |
| 2003/0191291 | A1 | 10/2003 | Kochendoerfer et al. |
| 2004/0023306 | A1 | 2/2004 | Aebersold et al. |
| 2004/0043446 | A1 | 3/2004 | DeFrees et al. |
| 2004/0180858 | A1 | 9/2004 | Sommermeyer |
| 2005/0063943 | A1 | 3/2005 | Sommermeyer et al. |
| 2005/0181985 | A1 | 8/2005 | Hemberger et al. |
| 2005/0238723 | A1 | 10/2005 | Zander et al. |
| 2006/0019877 | A1 | 1/2006 | Conradt et al. |
| 2006/0121062 | A1 | 6/2006 | Eichner et al. |
| 2006/0188472 | A1 | 8/2006 | Sommermeyer et al. |
| 2006/0194940 | A1 | 8/2006 | Kozlowski |
| 2006/0217293 | A1 | 9/2006 | Orlando et al. |
| 2007/0087961 | A1 | 4/2007 | Eichner et al. |
| 2007/0134197 | A1 | 6/2007 | Eichner et al. |
| 2008/0206182 | A1 | 8/2008 | Sommermeyer et al. |
| 2008/0207562 | A1 | 8/2008 | Zander et al. |
| 2008/0274948 | A1 | 11/2008 | Eichner et al. |
| 2009/0091549 | A1 | 4/2009 | Matsumoto et al. |
| 2009/0233847 | A1 | 9/2009 | Hemberger et al. |
| 2010/0062973 | A1 | 3/2010 | Frank et al. |
| 2010/0297078 | A1 | 11/2010 | Hacket et al. |
| 2010/0305033 | A1 | 12/2010 | Hacket et al. |
| 2010/0311670 | A1 | 12/2010 | Zander et al. |
| 2010/0317609 | A1 | 12/2010 | Zander et al. |
| 2011/0054152 | A1 | 3/2011 | Zander et al. |
| 2011/0200555 | A1 | 8/2011 | Eichner et al. |

FOREIGN PATENT DOCUMENTS

| | | |
|---|---|---|
| DE | 26 46 854 | 5/1989 |
| DE | 38 36 600 | 5/1990 |
| DE | 279 486 | 6/1990 |
| DE | 41 30 807 | 3/1993 |
| DE | 26 07 706 | 5/1993 |
| DE | 196 28 705 | 1/1998 |
| DE | 198 08 079 | 8/1999 |
| DE | 101 12 825 | 2/2002 |
| DE | 100 41 541 | 3/2002 |
| DE | 101 26 158 | 12/2002 |
| DE | 101 35 694 | 2/2003 |
| DE | 101 29 369 | 3/2003 |
| DE | 101 55 098 | 5/2003 |
| DE | 102 09 821 | 9/2003 |
| DE | 102 17 994 | 11/2003 |
| DE | 102 54 745 | 6/2004 |
| DE | 102 56 558 | 9/2004 |
| EP | 0 019 403 | 11/1980 |
| EP | 0 138 572 | 4/1985 |
| EP | 0 243 929 | 11/1987 |
| EP | 0 304 183 | 2/1989 |
| EP | 0 307 827 | 3/1989 |
| EP | 0 315 349 | 5/1989 |
| EP | 0 218 825 | 9/1989 |
| EP | 0 338 916 | 10/1989 |
| EP | 0 402 724 | 6/1990 |
| EP | 0 148 605 | 7/1990 |
| EP | 0 205 564 | 5/1991 |
| EP | 0 428 267 | 5/1991 |
| EP | 0 411 678 | 1/1992 |
| EP | 0 127 839 | 7/1992 |
| EP | 0 331 471 | 12/1992 |
| EP | 0 549 721 | 4/1994 |
| EP | 0 605 963 | 7/1994 |
| EP | 0 609 968 | 8/1994 |
| EP | 0 342 557 | 11/1994 |
| EP | 0661294 | 12/1994 |
| EP | 0 640 619 | 3/1995 |
| EP | 0 646 130 | 4/1995 |
| EP | 0 418 523 | 6/1995 |
| EP | 0 668 351 | 8/1995 |
| EP | 0 809 996 | 5/1996 |
| EP | 0806140 | 8/2000 |
| EP | 1 230 935 | 8/2002 |
| EP | 1 400 533 | 9/2002 |
| EP | 1 398 322 | 9/2003 |
| EP | 1 398 327 | 9/2003 |
| EP | 1 398 328 | 9/2003 |
| EP | 1 424 086 | 6/2004 |
| EP | 1496076 | 1/2005 |
| EP | 1591467 | 11/2005 |
| EP | 1660134 | 5/2006 |
| EP | 1 064 951 | 8/2007 |
| EP | 2070950 | 6/2009 |
| EP | 2 143 736 | 1/2010 |
| EP | 2 154 160 | 2/2010 |
| FR | 2 378 094 | 8/1978 |
| GB | 1 419 080 | 12/1975 |
| GB | 1 549 246 | 10/1976 |
| GB | 1 540 428 | 2/1979 |
| GB | 1 549 246 | 7/1979 |
| IL | 166506 | 2/2010 |
| JP | 10-287554 | 10/1998 |
| JP | 2001-294601 | 10/2001 |
| JP | 2002-003398 | 9/2002 |
| WO | WO 80/02374 | 11/1980 |
| WO | WO 90/07939 | 7/1990 |
| WO | WO 90/12874 | 11/1990 |
| WO | WO 90/15628 | 12/1990 |
| WO | WO 92/11037 | 7/1992 |
| WO | WO 93/23062 | 11/1993 |
| WO | 93/24476 | 12/1993 |
| WO | WO 94/01483 | 1/1994 |
| WO | WO 94/05332 | 3/1994 |
| WO | WO 94/07536 | 4/1994 |
| WO | WO 94/13697 | 6/1994 |
| WO | WO 94/28024 | 12/1994 |
| WO | WO 94/29370 | 12/1994 |
| WO | WO 95/06058 | 3/1995 |
| WO | WO 95/13090 | 5/1995 |
| WO | WO 96/11953 | 4/1996 |
| WO | WO 96/19242 | 6/1996 |
| WO | WO 96/40662 | 12/1996 |
| WO | WO 96/41813 | 12/1996 |
| WO | WO 97/21452 | 6/1997 |
| WO | WO 97/30148 | 8/1997 |
| WO | WO 97/33552 | 9/1997 |

| | | |
|---|---|---|
| WO | WO 97/38727 | 10/1997 |
| WO | WO 97/42225 | 11/1997 |
| WO | WO 98/01158 | 1/1998 |
| WO | 98/05689 | 2/1998 |
| WO | 98/07713 | 2/1998 |
| WO | WO 98/08856 | 3/1998 |
| WO | 98/14212 | 4/1998 |
| WO | 98/14215 | 4/1998 |
| WO | WO 98/20905 | 5/1998 |
| WO | WO 98/32466 | 7/1998 |
| WO | WO 98/56424 | 12/1998 |
| WO | WO 99/07719 | 2/1999 |
| WO | 99/17783 | 4/1999 |
| WO | WO 99/49897 | 10/1999 |
| WO | WO 00/07738 | 2/2000 |
| WO | 00/18893 | 4/2000 |
| WO | 00/66633 | 11/2000 |
| WO | WO 00/78355 | 12/2000 |
| WO | WO 01/70272 | 9/2001 |
| WO | 01/78682 | 10/2001 |
| WO | WO 01/83522 | 11/2001 |
| WO | WO 01/93862 | 12/2001 |
| WO | WO 02/09766 | 2/2002 |
| WO | WO 02/20033 | 3/2002 |
| WO | WO 02/28841 | 4/2002 |
| WO | WO 02/40057 | 5/2002 |
| WO | WO 02/80979 | 10/2002 |
| WO | WO 03/000738 | 1/2003 |
| WO | WO 03/031464 | 4/2003 |
| WO | WO 03/031581 | 4/2003 |
| WO | 03/049699 | 6/2003 |
| WO | WO 03/059246 | 7/2003 |
| WO | WO03/070772 | 8/2003 |
| WO | WO 03/070772 | 8/2003 |
| WO | WO 03/074087 | 9/2003 |
| WO | WO 03/074088 | 9/2003 |
| WO | WO 2004/009082 | 1/2004 |
| WO | 2004/022630 | 3/2004 |
| WO | WO 2004/024761 | 3/2004 |
| WO | WO 2004/024776 | 3/2004 |
| WO | WO 2004/024777 | 3/2004 |
| WO | WO 2004/030701 | 4/2004 |
| WO | WO 2004/033651 | 4/2004 |
| WO | WO 2004/050710 | 6/2004 |
| WO | WO 2004/065425 | 8/2004 |
| WO | WO 2005/014024 | 2/2005 |
| WO | WO 2005/014035 | 2/2005 |
| WO | WO 2005/014050 | 2/2005 |
| WO | WO 2005/014655 | 2/2005 |
| WO | 2005/072778 | 8/2005 |
| WO | WO 2005/074993 | 8/2005 |
| WO | 2005/083103 | 9/2005 |
| WO | 2005/092369 | 10/2005 |
| WO | WO 2005/092390 | 10/2005 |
| WO | 2005/112954 | 12/2005 |
| WO | WO 2006/108052 | 10/2006 |
| WO | 2007/053292 | 5/2007 |
| WO | 2010/042638 | 4/2010 |

OTHER PUBLICATIONS

Alayash and Cashon, "Hemoglobin and free radicals: implications for the development of a safe blood substitute," *Molec. Med. Today*, 1995, 1(3):122-127.

Ashwell, "Carbohydrate Antigens: Coupling of Carbohydrates to Proteins by a Mixed Anhydride Reaction," *Meth. Enzymol.*, 1972, 28:219-222.

Avigad, "A Simple Spectrophotometric Determination of Formaldehyde and Other Aldehydes: Application to Periodate-Oxidized Glycol Systems," *Anal. Biochem.*, 1983, 134:499-504.

Baldwin et al., "Synthesis of Polymer-Bound Hemoglobin Samples," *Tetrahedron*, 1981, 37:1723-1726.

Balland et al., "Intracellular distribution of ampicillin in murine macrophages infected with *Salmonella typhimurium* and treated with ($^3$H)ampicillin-loaded nanoparticles," *J. Antimicrob. Chemother.*, 1996, 37:105-115.

Barbone et al., "Reticulocyte measurements as a bioassay for erythropoietin," *J. Pharm. Biomed. Anal.*, 1994, 12(4):515-522.

Bårström et al., "New derivatives of reducing oligosaccharides and their use in enzymatic reactions: efficient synthesis of sialyl Lewis a and sialyl dimeric Lewis x glycoconjugates," *Carbohydr. Res.*, 2000, 328:525-531.

Bauer et al., "Synthesis of ω-(Aminooxy)alkanethiols," *J. Org. Chem.*, 1965, 30:949-951.

Bauer and Suresh, "S-[ω-(Aminoöxy)alkyl]isothiuronium Salts, ω,ω'-Bis(aminoöxy)alkanes and Related Compounds," *J. Org. Chem.*, 1963, 28:1604-1608.

Bendele et al., "Short Communication: Renal Tubular Vacuolation in Animals Treated with Polyethylene-Glycol-Conjugated Proteins," *Toxicol. Sci.*, 1998, 42:152-157.

Benesch, "Bis(pyridoxal) Polyphosphates as Specific Intramolecular Cross-Linking Agents for Hemoglobin," *Meth. Enzymol.*, 1994, 231:267-274.

Bepperling et al., "HES 130/0.4, a new HES specification: tissue storage after multiple infusions in rats," *Crit. Care*, 1999, 3(suppl 1):P153.

Berger et al., "Galactosyltransferase-dependent sialylation of complex and endo-N-acetylglucosaminidase H-treated core N-glycans in vitro," *FEBS Lett.*, 1986, 203(1):64-68.

Black et al., "N-Bromoacetyl-glycopyranosylamines as affinity labels for a β-glucosidase and a cellulase," *Carbohydr. Res.*, 1993, 250:195-202.

Bobbitt, "Periodate Oxidation of Carbohydrates," *Carbohydr. Chem.*, 1956, 11:1-41.

Boissel et al., "Erythropoietin Structure-Function Relationships. Mutant proteins that test a model of tertiary structure," *J. Biol. Chem.*, 1993, 268(21):15983-15993.

Boturyn et al., "Synthesis of Fluorescent Probes for the Detection of Abasic Sites in DNA," *Tetrahedron*, 1997, 53(15):5485-5492.

Bowen et al., "Estimation of Effective and Total Erythropoiesis in Myelodysplasia Using Serum Transferrin Receptor and Erythropoietin Concentrations, with Automated Reticulocyte Parameters," *Leukemia*, 1994, 8(1):151-155.

Bronzino, *The Biomedical Engineering Handbook*, CRC Press, USA, Salem, 1995, (TOC only).

Bunn & Jandl, "The Renal Handling of Hemoglobin. II. Catabolism," *J. Exp. Med.*, 1967, 129:925-934.

Burgess et al., "Stimulation by Human Placental Conditioned Medium of Hemopoietic Colony Formation by Human Marrow Cells," *Blood*, 1977, 49(4):573-583.

Bystrický et al., "Determination of the cross-linking effect of adipic acid dihydrazide on glycoconjugate preparation," *Glycoconj. J.*, 1999, 16:691-695.

Cabacungan et al., "Amine Boranes as Alternative Reducing Agents for Reductive Alkylation of Proteins," *Anal. Biochem.*, 1982, 124:272-278.

Carlsson et al., "Protein Thiolation and Reversible Protein-Protein Conjugation," *Biochem J.*, 1978, 173:723-737.

Cerami, "Beyond Erythropoiesis: Novel Applications for Recombinant Human Erythropoietin," *Semin. Hematol.*, 2001, 38:(3 Suppl 7):33-39.

Cerny et al., "A Hydroxyethyl Starch-Hemoglobin Polymer as a Blood Substitute," *Clinical Hemorheology*, 1982, 2(4):355-365.

Chamow et al., "Conjugation of Soluble CD4 without Loss of Biological Activity via a Novel Carbohydrate-directed Cross-linking Reagent," *J. Biol. Chem.*, 1992, 267(22):15916-15922.

Chang, "Blood Substitutes Based on Modified Hemoglobin Prepared by Encapsulation or Crosslinking: An Overview," *Biomat., Art. Cells & Immob. Biotech.*, 1992, 20:159-179.

Chagnon et al., "Murine renal cell carcinoma: evaluation of a dendritic-cell tumour vaccine," *BJU Int.*, 2001, 88:418-424.

Chaplin, "Monosaccharides," *Carbohydrate analysis: a practical approach*, 1996, Chaplin and Kennedy (eds.), Chapter 1, "Oligosaccharides," pp. 37-54.

Chaplin, "A Rapid and Sensitive Method for the Analysis of Carbohydrate Components in Glycoproteins Using Gas-Liquid Chromatography," *Anal. Biochem.*, 1982, 123:336-341.

Chapman et al., "Therapeutic antibody fragments with prolonged in vivo half-lives," *Nature Biotech.*, 1999, 17:780-783.

Chow et al., "In vitro Induction of apoptosis of neoplastic cells in low-grade non-Hodgkin's lymphomas using combinations of established cytotoxic drugs with bendamustine," *Haematologica*, 2001, 86:485-493.

Chu et al., "Further Studies on the Immunogenicity of *Haemophilus influenzae* Type b and Pneumococcal Type 6A Polysaccharide-Protein Conjugates," *Infect. Immun.*, 1983, 40:245-256.

Cumber et al., "Preparation of Antibody-Toxin Conjugates," *Meth. Enzymol.*, 1985, 112:207-225.

Delgado et al., "The Uses and Properties of PEG-Linked Proteins," *Crit. Rev. Ther. Drug Carrier Syst.*, 1992, 9(3,4):249-304.

Delorme et al., "Role of Glycosylation on the Secretion and Biological Activity of Erythropoietin," *Biochemistry*, 1992, 31(41):9871-9876.

Dittmar et al., "Human Glycoproteins and Derived Variants from Recombinant Mammalian Cell Lines," *Advances in Protein Design*, 1989, 12:145-156.

Dorner et al., "Increased Synthesis of Secreted Proteins Induces Expression of Glucose-regulated Proteins in Butyrate-treated Chinese Hamster Ovary Cells," *J. Biol. Chem.*, 1989, 264(34):20602-20607.

Dowling and Russell, "Pharmacokinetics of a long-acting oxytetracycline-polyethylene glycol formulation in horses," *J. Vet. Pharmacol. Therap.*, 2000, 23:107-110.

Dreborg and Åkerblom, "Immunotherapy with Monomethoxypolyethylene Glycol Modified Allergens," *Crit. Rev. Ther. Drug Carrier Syst.*, 1990, 6(4):315-365.

Edmunds et al., "Transgenically Produced Human Antithrombin: Structural and Functional Comparison to Human Plasma-Derived Antithrombin," *Blood*, 1998, 91(12):4561-4571.

Blum et al., "Improved silver staining of plant proteins, RNA and DNA in polyacrylamide gels," *Electrophoresis*, 1987, 8:93-99.

Elliott et al., "Mapping of the Active Site of Recombinant Human Erythropoietin," *Blood*, 1997, 89(2): 493-502.

European Pharmacopoeia, "Erythropoietin Concentrated Solution," 3rd Edition, 2000, Monography, pp. 655-660.

European Pharmacopoeia, "Erythropoietin Concentrated Solution," 4th Edition, 2002, Monography, pp. 1123-1128.

Fernández-Santana et al., "Conjugation of 5-azido-3-oxapentyl glycosides with thiolated proteins through the use of thiophilic derivatives," *Glycoconj. J.*, 1998, 15:549-553.

Fibi et al., "Evidence for the Location of the Receptor-Binding Site of Human Erythropoietin at the Carboxyl-Terminal Domain," *Blood*, 1991, 77(6):1203-1210.

Fibi et al., "N- and O-Glycosylation Muteins of Recombinant Human Erythropoietin Secreted From BHK-21 Cells," *Blood*, 1995, 85(5):1229-1236.

Fissekis et al., "*N*-Pantyol-(substituted)amines, Pantothenic Acid Analogues," *J. Med. Pharm. Chem.*, 1960, 2:47-56.

Forno et al., "N- and O-linked carbohydrates and glycosylation site occupancy in recombinant human granulocyte-macrophage colony-stimulating factor secreted by a Chinese hamster ovary cell line," *Eur. J. Biochem.*, 2004, 271:907-919.

Gaertner and Offord, "Site-Specific Attachment of Functionalized Poly(ethylene glycol) to the Amino Terminus of Proteins," *Bioconjugate Chemistry*, 1996, 7(1):38-44.

Gervais et al., "NMR investigations of the role of the sugar moiety in glycosylated recombinant human granulocyte-colony-stimulating factor," *Eur. J. Biochem.*, 1997, 247:386-395.

Gillis et al., "T Cell Growth Factor: Parameters of Production and a Quantitative Microassay for Activity," *J. Immunol.*, 1978, 120(6):2027-2032.

Gonzalez Lio and Thiem, "Chemoenzymatic synthesis of spacer-linked oligosaccharides for the preparation of neoglycoproteins," *Carbohydr. Res.*, 1999, 317:180-190.

Gould et al., "The Development of Hemoglobin Solutions as Red Cell Substitutes: Hemoglobin Solutions," *Transfus. Sci.*, 1995, 16:5-17.

Grabenhorst et al., "Construction of stable BHK-21 cells coexpressing human secretory glycoproteins and human Gal($\beta$1-4)GlcNAc-R $\alpha$2,6-sialyltransferase: $\alpha$2,6-Linked NeuAc is preferentially attached to the Gal($\beta$1-4)GlcNAc($\beta$1-2)Man($\alpha$1-3)-branch of diantennary oligosaccharides from secreted recombinant $\beta$-trace protein," *Eur. J. Biochem.*, 1995, 232:718-725.

Grabenhorst and Conradt, "The Cytoplasmic, Transmembrane, and Stem Regions of Glycosyltransferases Specify Their in vivo Functional Sublocalization and Stability in the Golgi," *J. Biol. Chem.*, 1999, 274(51):36107-36116.

Grabenhorst et al., "Biosynthesis and secretion of human interleukin 2 glycoprotein variants from baculovirus-infected Sf21 cells. Characterization of polypeptides and posttranslational modifications," *Eur. J. Biochem.*, 1993, 215:189-197.

Grabenhorst et al., "In Vivo Specificity of Human $\alpha$1,3/4-Fucosyltransferases III-VII in the Biosynthesis of Lewis$^x$ and Sialyl Lewis$^x$ Motifs on Complex-type *N*-Glycans. Coexpression studies from BHK-21 cells together with human $\beta$-trace protein," *J. Biol. Chem.*, 1998, 273(47):30985-30994.

Grabenhorst et al., "Genetic engineering of recombinant glycoproteins and the glycosylation pathway in mammalian host cells," *Glycoconj J.*, 1999, 16(2):81-97.

Gray, "The Direct Coupling of Oligosaccharides to Proteins and Derivatized Gels," *Arch. Biochem. Biophys.*, 1974, 163:426-428 (Fig. 2.1a).

Greenfield et al., "Evaluation in Vitro of Adriamycin Immunoconjugates Synthesized Using an Acid-sensitive Hydrazone Linker," *Cancer Research*, 1990, 50:6600-6607.

Grimmecke and Brade, "Studies on the reductive amination of 3-deoxy-D-*manno*-octulosonic acid (Kdo)," *Glycoconj. J.*, 1998, 15:555-562.

Habeeb, "Determination of Free Amino Groups in Proteins by Trinitrobenzenesulfonic Acid," *Anal. Biochem.*, 1966, 14:328-336.

Hai et al., "Diaspirin Crosslinked Hemoglobin (DCLHb™) Polymerization," *Art. Cells, Blood Subs., and Immob. Biotech.*, 1994, 22(3):923-931.

Hallaway et al., "Modulation of Deferoxamine Toxicity and Clearance by Covalent Attachment to Biocompatible Polymers," *Proc. Natl. Acad. Sci. USA*, 1989, 86:10108-10112.

Hamma and Miller et al., "4-(2-Aminooxyethoxy)-2-(ethylureido)quinoline-Oligonucleotide Conjugates: Synthesis, Binding Interactions, and Derivatization with Peptides," *Bioconj. Chem.*, 2003, 14:320-330.

Hartman and Wold, "Cross-Linking of Bovine Pancreative Ribonuclease A with Dimethyl Adipimidate," *Biochemistry*, 1967, 6(8):2439-2448.

Hashimoto et al., "Chemical Modification of the Reducing Chain End in Dextrans and Trimethylsilylation of Its Hydroxyl Groups," *J. Polymer Science: Part A: Polymer Chemistry*, 1991, 29:1271-1279.

Hattori et al., "Reduced Immunogenicity of $\beta$-Lactoglobulin by Conjugation with Carboxymethyl Dextran," *Bioconjug. Chem.*, 2000, 11:84-93.

Herman et al., "Characterization, Formulation, and Stability of Neupogen® (Filgrastim), a Recombinant Human Granulocyte-Colony Stimulating Factor," *Formulation, Characterization, and Stability of Protein Drugs*, Pearlman and Wang (eds.), Plenum Press, Chapter 7, 1996, pp. 303-328.

Hermanson, *Bioconjugate Techniques*, 1996 (TOC only).

Hermentin et al., "A Strategy for the Mapping of *N*-Glycans by High-pH Anion-Exchange Chromatography with Pulsed Amperometric Detection," *Anal. Biochem.*, 1992, 203(2):281-289.

Higuchi et al., "Role of Sugar Chains in the Expression of the Biological Activity of Human Erythropoietin," *J. Biol. Chem.*, 1992, 267(11):7703-7709.

Sharaf et al., "Studies on Aroyl- and Aryl-Hydrazide Derivatives from D-*glycero*-D-*gulo*-Heptono-1,4-Lactone," *Carbohydrate Res.*, 1981, 91:39-48.

Inoue et al., "An Improved Method for the Purification of Human Erythropoietin with High in Vivo Activity from the Urine of Anemic Patients," *Biol. Pharm. Bull.*, 1994, 17(2):180-184.

Iwamoto et al., "Polysaccharide-Coated Oil Droplets in Oil-in-Water Emulsions as Targetable Carriers for Lipophilic Drugs," *J. Pharm. Sci.*, 1991, 80(3):219-224.

Jia et al., "S-nitrosohaemoglobin: a dynamic activity of blood involved in vascular control," *Nature*, 1996, 380:221-226.

Jones et al., "A convenient synthesis of N-(tert-butyloxycarbonyl)aminooxy ethers," *Tetrahedron Letters*, 2000, 41(10):1531-1533.

Jones et al., "Multivalent Poly(ethylene glycol)-Containing Conjugates for In Vivo Antibody Suppression," *Bioconj. Chem.*, 2003, 14(6):1067-1076.

Kallin, "Coupling of Oligosaccharides to Proteins Using p-Trifluoroacetamidoaniline," *Meth. Enzymol.*, 1994, 242:119-123.

Keaney, Jr. et al., "NO Forms an Adduct with Serum Albumin that Has Endothelium-derived Relaxing Factor-like Properties," *J. Clin. Invest.*, 1993, 91:1582-1589.

Keipert et al., "Functional properties of a new crosslinked hemoglobin designed for use as a red cell substitute," *Transfusion*, 1989, 29:768-773.

Kitamura et al., "Establishment and Characterization of a Unique Human Cell Line That Proliferates Dependently on GM-CSF, IL-3, or Erythropoietin," *J. Cell. Phys.*, 1989, 140:323-334.

Kitamura et al., "Chemical Engineering of the Monoclonal Antibody A7 by Polyethylene Glycol for Targeting Cancer Chemotherapy," *Cancer Res.*, 1991, 51:4310-4315.

Kleine-Tebbe et al., "Allergen Immunotherapy—A Position Paper of the German Society for Allergology and Clinical Immunology," *Pneumologie*, 2001, 55:438-444 (w/English summary).

Klemm et al., "Esterification of Cellulose," *Comprehensive Cellulose Chemistry*, 1998, vol. 2, Wiley-VCH, Weinheim, New York, especially chapter 4.4, pp. 99-207.

Kobayashi et al., "Reduced Immunogenicity of β-Lactoglobulin by Conjugation with Carboxymethyl Dextra Differing in Molecular Weight," *J. Agric. Food Chem.*, 2001, 49(2):823-831.

Kojima et al., "Mitomycin C-dextran conjugate: a novel high molecular weight pro-drug of mitomycin C," *J. Pharm. Pharmacol.*, 1980, 32:30-34.

Komatsu et al., "Cloning of granulocyte colony-stimulating factor cDNA from human macrophages and its expression in *Escherichia coli*," *Jpn. J. Cancer Res.*, 1987, 78(11):1179-1181.

Krantz, "Erythropoietin," *Blood*, 1991, 77(3):419-434.

Krystal, "Physical and Biological Characterization of Erythroblast Enhancing Factor (EEF), a Late Acting Erythropoietic Stimulator in Serum Distinct from Erythropoietin," *Exp. Hematol.*, 1983, 11(1):18-31.

Krystal, "A Simple Microassay for Erythropoietin Based on $^3$H-Thymidine Incorporation into Spleen Cells from Phenylhydrazine Treated Mice," *Exp. Hematol.*, 1983, 11(7):649-660.

Krystal et al., "Purification of Human Erythropoietin to Homogeneity by a Rapid Five-Step Procedure," *Blood*, 1986, 67(1):71-79.

Kuberan et al., "Preparation and isolation of neoglycoconjugates using biotin-streptavidin complexes," *Glycoconj. J.*, 1999, 16:271-281.

Kurtz and Eckardt, "Assays for Erythropoietin," *Nephron.*, 1989, 51(suppl 1):11-14 (w/English summary).

Larionova et al., "Conjugation of the Bowman-Birk Soybean Proteinase Inhibitor with Hydroxyethylstarch," *Appl. Biochem. Biotech.*, 1997, 62:175-182.

Lee (ed.), "Synthesis of Peptides and Proteins," *Peptide and Protein Drug Delivery*, 1991, p. 65.

Lee and Lee, "Neoglycoproteins," *Glycoproteins II*, 1997, Chapter 17, Elsevier Science B.V., pp. 301-620.

Leenders et al., "β-Glucuronyl Carbamate Based Pro-moieties Designed for Prodrugs in ADEPT," *Tetrahedron Letters*, 1995, 36(10):1701-1704.

Lees et al., "Activation of soluble polysaccharides with 1-cyano-4-dimethylaminopyridinium tetrafluoroborate for use in protein-polysaccharide conjugate vaccines and immunological reagents," *Vaccine*, 1996, 14(3):190-198.

Lesnefsky et al., "High-Dose Iron-Chelator Therapy During Reperfusion with Deferoxamine-Hydroxyethyl Starch Conjugate Fails to Reduce Canine Infarct Size," *J. Cardiovasc. Pharmacol.*, 1990, 16(4):523-528.

Levy et al., "Recombinant Antithrombin: Production and Role in Cardiovascular Disorder," *Sem. Thromb. Hem.*, 2001, 27(4):405-416.

Lin et al., "Cloning and expression of the human erythropoietin gene," *Proc. Natl. Acad. Sci. USA*, 1985, 82:7580-7584.

Lindsey at al., "Porphyrin Building Blocks for Modular Construction of Bioorganic Model Systems," *Tetrahedron*, 1994, 50(30):8941-8968, especially p. 8956.

Lomant and Fairbanks, "Chemical Probes of Extended Biological Structures: Synthesis and Properties of the Cleavable Protein Cross-linking Reagent [$^{35}$S]Dithiobis(succinimidyl propionate)," *J. Mol. Biol.*, 1976, 104:243-261.

Lönngren and Goldstein, "Coupling of Aldobionic Acids to Proteins Using Water-Soluble Carbodiimide," *Meth. Enzymol.*, 1994, 242:116-118.

Manger et al., "1-N-Glycyl β-Oligosaccharide Derivatives as Stable Intermediates for the Formation of Glycoconjugate Probes," *Biochemistry*, 1992, 31:10724-10732.

Manger et al., "Synthesis of 1-N-Glycyl β-Oligosaccharide Derivatives. Reactivity of *Lens culinaris* Lectin with a Fluorescent Labeled Streptavidin Pseudoglycoprotein and Immobilized Neoglycolipid," *Biochemistry*, 1992, 31:10733-10740.

Maout et al., "Hydroxyethylstarch Conjugated to Human Hemoglobin for use in Blood Transfusion: Comparison with Dextran Conjugates," *Carbohydrates and Carbohydrate Polymers—Analysis, Biotechnology, Modification, Antiviral and Other Applications*, 1993, Chapter 12, pp. 132-140.

McMahon et al., "Pharmacokinetics and Effects of Recombinant Human Erythropoietin After Intravenous and Subcutaneous Injections in Healthy Volunteers," *Blood*, 1990, 76(9):1718-1722.

Meinjohanns et al., "Novel sequential solid-phase synthesis of N-linked glycopeptides from natural sources," *J. Chem. Soc., Perkin Trans. 1*, 1998, 1:549-560.

Mikola and Hänninen, "Introduction of Aliphatic Amino and Hydroxy Groups to Keto Steroids Using O-Substituted Hydroxylamines," *Bioconj. Chem.*, 1992, 3(2):182-186.

Minnema et al., "Recombinant human antithrombin III improves survival and attenuates inflammatory responses in baboons lethally challenged with *Escherichia coli*," *Blood*, 2000, 95(4): 1117-1123.

Miyake et al., "Purification of Human Erythropoietin," *J. Biol. Chem.*, 1977, 252(15):5558-5564.

Montreuil et al., "Hexuronic acids," *Carbohydrate analysis: a practical approach*, 1996, Chaplin and Kennedy (eds.), Chapter 5, pp. 175-204.

Mosbech et al., "Hyposensitization in asthmatics with mPEG-modified and unmodified house dust mite extract," *Allergy*, 1990, 45(2):130-141.

Mosmann, "Rapid Colorimetric Assay for Cellular Growth and Survival: Application to Proliferation and Cytotoxicity Assays," *J. Immunol. Meth.*, 1983, 65:55-63.

Mueller et al., "Recombinant Glycoprotein Product Quality in Proliferation-Controlled BHK-21 Cells," *Biotechnol. Bioeng.*, 1999, 65(5):529-536.

Davis and Flitsch, "A Novel Method for the Specific Glycosylation of Proteins," *Tetrahedron Lett.*, 1991, 32(46):6793-6796.

Nagata et al., "The chromosomal gene structure and two mRNAs for human granulocyte colony-stimulating factor," *EMBO J.*, 1986, 5(3):575-581.

Nagata et al., "Molecular cloning and expression of cDNA for human granulocyte colony-stimulating factor," *Nature*, 1986, 319:415-418.

Nakane et al., "The Accumulation Mechanism of Cationic Mitomycin C-dextran Conjugates in the Liver: In-vivo Cellular Localization and In-vitro Interaction with Hepatocytes," *J. Pharm. Pharmacol.*, 1988, 40:1-6.

Nedospasov and Khomutov, "Synthesis and some properties of aminooxyalkylcelluloses," *Bulletin of the Academy of Sciences of the USSR*, 1976, Division of Chemical Science, Consultants Bureau, New York, 25:1105-1110.

Nimtz et al., "Structural characterization of the oligosaccharide chains of native and crystallized boar seminal plasma spermadhesin PSP-I and PSP-II glycoforms," *Eur. J. Biochem.*, 1999, 265:703-718.

Nimtz et al., "Structures of sialylated oligosaccharides of human erythropoietin expressed in recombinant BHK-21 cells," *Eur. J. Biochem.*, 1993, 213:39-56.

Nimtz et al., "Carbohydrate structures of a human tissue plasminogen activator variant expressed in recombinant Chinese hamster ovary cells," *FEBS Lett.*, 1990, 271:14-18.

Nohynek et al., "Comparison of the potency of glycosylated and nonglycosylated recombinant human granulocyte colony-stimulating factors in neutropenic and nonneutropenic CD rats," *Cancer Chemother Pharmacol.*, 1997, 39:259-266.

Nomura et al., "Pharmacokinetic characteristics and therapeutic effects of mitomycin C-dextran conjugates after intratumoural injection," *J. Controlled Release*, 1998, 52:239-252.

O'Shannessy and Wilchek, "Immobilization of Glycoconjugates by Their Oligosaccharides: Use of Hydrazido-Derivatized Matrices," *Analytical Biochemistry*, 1990, 191:1.

Pawlowski et al., "A new method of non-cross-linking conjugates of polysaccharides to protein via thioether bonds for the preparation of saccharide-protein conjugate vaccines," *Vaccine*, 1999, 17:1474-1483.

Pazur, "Neutral polysaccharides," *Carbohydrate analysis: a practical approach*, 1996, Chaplin and Kennedy (eds.), Chapter 3, pp. 55-96.

Pedley et al., "The potential for enhanced tumour localization by poly)ethylene glycol) modification of anti-CEA antibody," *Br. J. Cancer*, 1994, 70:1126-1130.

Peeters et al., "Comparison of four bifunctional reagents for coupling peptides to proteins and the effect of the three moieties on the immunogenicity of the conjugates," *J. Immunol. Meth.*, 1989, 120:133-143.

Peron et al., "Hydroxyethyl starch-induced renal insufficiency after plasma exchange in a patient with polymyositis and liver cirrhosis," *Clin. Nephrol.*, 2001, 55(5):408-411.

*Pharma Business*, Jul./Aug. 2000, pp. 45-60.

Quelle et al., "High-Level Expression and Purification of a Recombinant Human Erythropoietin Produced Using a Baculovirus Vector," *Blood*, 1989, 74(2):652-657.

Rabiner et al., "Evaluation of a stroma-free hemoglobin solution for use as a plasma expander," *J. Exp. Med.*, 1967, 126:1127-1142.

Ragupathi et al., "A novel and efficient method for synthetic carbohydrate conjugate vaccine preparation: synthesis of sialyl Tn-KLH conjugate using a 4-(4-N-maleimidomethyl) cyclohexane-1-carboxyl hydrazide (MMCCH) linker arm," *Glycoconj. J.*, 1998, 15:217-221.

Ramos et al., "Enzymatic Synthesis of Neoglycopeptide Building Blocks," *Angew. Chem. Int. Ed.*, 2000, 39(2):396-398.

Reidhaar-Olson et al., "Identification of Residues Critical to the Activity of Human Granulocyte Colony-Stimulating Factor," *Biochemistry*, 1996, 35:9034-9041.

Relihan et al., "Clearance Rate and Effect on Renal Function of Stroma-Free Hemoglobin Following Renal Ischemia," *Ann. Surg.*, 1972, 176(6):700-704.

Richter and de Belder, "Antibodies against Hydroxyethylstarch Produced in Rabbits by Immunization with a Protein-Hydroxyethylstarch Conjugate," *Int. Arch. Allergy Appl. Immun.*, 1976, 52:307-314.

Rogers et al., "Effects of polymerization on the oxygen carrying and redox properties of diaspirin cross-linked hemoglobin," *Biochim. Biophys. Acta*, 1995, 1248:135-142.

Rohrling et al., "Synthesis and testing of a novel fluorescene label for carbonyls in carbohydrates and cellulosics," *Synlett*, 2001, 5:682-684.

Rose, "Facile Synthesis of Homogeneous Artificial Proteins," *J. Am. Chem. Soc.*, 1994, 116:30-33.

Rudolph et al., "Circulation persistence and biodistribution of lyophilized liposome-encapsulated hemoglobin: An oxygen-carrying resuscitative fluid," *Crit. Care Med.*, 1994, 22:142-150.

Rudolph, "The Freeze-Dried Preservation of Liposome Encapsulated Hemoglobin: A Potential Blood Substitute," *Cryobiology*, 1988, 25:277-284.

Rush et al., "Microheterogeneity of Erythropoietin Carbohydrate Structure," *Anal. Chem.*, 1995, 67(8):1442-1452.

Ruttmann et al., "In vivo investigation into the effects of haemodilution with hydroxyethylstarch (200/0.5) and normal saline on coagulation," *Br. J. Anaesthesia*, 1998, 80(5):612-616.

Sadamoto et al., "Control of Bacteria Adhesion by Cell-Wall Engineering," *J. Am. Chem. Soc.*, 2004, 126:3755-3761.

Sadrzadeh et al., "The Long-Acting Parenteral Iron Chelator, Hydroxyethyl Starch-Deferoxamine, Fails to Protect Against Alcohol-Induced Liver Injury in Rats," *J. Pharmacol. Exp. Ther.*, 1997, 280(2):1038-1042.

Sakai et al., "Synthesis and Physicochemical Characterization of a Series of Hemoglobin-Based Oxygen Carriers: Objective Comparison between Cellular and Acellular Types," *Bioconj. Chem.*, 2000, 11:56-64.

Sato et al., "Disposition of a Polymeric Prodrug of Mitomycin C, Mitomycin C-Dextran Conjugate, in the Perfused Rat Liver," *J. Pharm. Sci.*, 1989, 78:11-16.

Sawaikar et al., "Products active on mosquitoes. Part VII, Synthesis and biological activity of longifolene derivatives," *Indian Journal of Chemistry*, 1995, 34B:832-835.

Scaglione et al., "A New Model Examining Intracellular and Extracellular Activity of Amoxicillin, Azithromycin, and Clarithromycin in Infected Cells," *Chemotherapie*, 1993, 39:416-423.

Schäfer et al., "Two-year double-blind trial of a monomethoxy polyethylene glycol (mPEG) modified grass pollen extract at different dose levels," *Ann. Allergy*, 1992, 68(4):334-339.

Schlenke et al., "Construction and characterization of stably transfected BHK-21 cells with human-type sialylation characteristic," *Cytotechnology*, 1999, 30:17-25.

Schottelius et al., "Improvement of Pharmacokinetics of Radioiodinated Tyr$^3$-Octreotide by Conjugation with Carbohydrates," *Bioconjugate Chem.*, 2002, 13:1021-1030.

Schröter et al., "Male-specific Modification of Human CD52," *J. Biol. Chem.*, 1999, 274(42):29862-29873.

Shafer et al., "Activation of soluble polysaccharides with 1-cyano-4-dimethylaminopyridinium tetrafluoroborate (CDAP) for use in protein-polysaccharide conjugate vaccines and immunological reagents. II. Selective crosslinking of proteins to CDAP-activated polysaccharides," *Vaccine*, 2000, 18:1273-1281.

Shah et al., "Characterization of Colony-stimulating Activity Produced by Human Monocytes and Phytohemagglutinin-stimulated Lymphocytes," 1977, *Blood*, 50(5):811-821.

Shirafuji et al., "A new bioassay for human granulocyte colony-stimulating factor (hG-CSF) using murine myeloblastic NFS-60 cells as targets and estimation of its levels in sera from normal healthy persons and patients with infectious and hematological disorders," *Exp. Hematol.*, 1989, 17:116-119.

Simmons et al., "Potent inhibition of HIV-1 infectivity in macrophages and lymphocytes by a novel CCR5 antagonist," *Science*, 1997, 276:276-279.

Snyder et al., "HbXL99α A hemoglobin derivative that is cross-linked between the α subunits is useful as a blood substitute," *Proc. Natl. Acad. Sci. USA*, 1987, 84:7280-7284.

Shu, "Somogyi Micro Copper Method," *Method in Carbohydride Chemistry*, 1962, 1:383-388.

Song et al., "Toxicity and Antitumor Activity of the Conjugate of Mitomycin C with Carboxymethyl-chitin," *Arch. Pract. Pharm.*, 1993, 53(3):141-147.

Souza et al., "Recombinant human granulocyte colony-stimulating factor: effects on normal and leukemic myeloid cells," *Science*, 1986, 232:61-65.

Soyez et al., "Biological evaluation of mitomycin C bound to a biodegradable polymeric carrier," *J. Controlled Release*, 1997, 47:71-80.

Spivak and Hogans, "The In Vivo Metabolism of Recombinant Human Erythropoietin in the Rat," *Blood*, 1989, 73:90-99.

Staros, "N-Hydroxysulfosuccinimide Active Esters: Bis(N-hydroxysulfosuccinimide) Esters of Two Dicarboxylic Acids Are Hydrophilic, Membrane-Impermeant, Protein Cross-Linkers," *Biochemistry*, 1982, 21:3950-3955.

Sunamoto and Iwamoto, "Protein-Coated and Polysaccharide-Coated Liposomes as Drug Carriers," *CRC Critical Review in Therapeutic Drug Carrier Systems*, 1986, 2:117-136.

Sytkowski et al., "Human erythropoietin dimers with markedly enhanced in vivo activity," *Proc. Natl. Acad. Sci. USA*, 1998, 95(3):1184-1188.

Sytkowski et al., "An Erythropoietin Fusion Protein Comprised of Identical Repeating Domains Exhibits Enhanced Biological Properties," *J. Biol. Chem.*, 1999, 274(35):24773-24778.

Takeuchi et al., "Relationship between sugar chain structure and biological activity of recombinant human erythropoietin produced in Chinese hamster ovary cells," *Proc. Natl. Acad. Sci. USA*, 1989, 86:7819-7822.

Takeuchi and Kobata, "Structures and functional roles of the sugar chains of human erythropoietins," *Glycobiology*, 1991, 1(4):337-346.

Tam et al., "Soluble Dextran-Hemoglobin Complex as a Potential Blood Substitute," *Proc. Natl. Acad. Sci. USA*, 1976, 73(6):2128-2131.

Tanaka et al., "Pharmacokinetics of recombinant human granulocyte colony-stimulating factor conjugated to polyethylene glycol in rats," *Cancer Research*, 1991, 51:3710-3714.

Thomas et al., "Measuring blood volume with fluorescent-labeled hydroxyethyl starch," *Crit. Care Med.*, 2000, 28(3):627-631.

Thomas, "Carbohydrate Binding Sites," *Meth. Enzymol.*, 1977, 46:362-368.

Thorpe et al., "Blockade of the galactose-binding sites of ricin by its linkage to antibody," *Eur. J. Biochem.*, 1984, 140:63-71.

Toyama et al., "Surface design of SPR-based immunosensor for the effective binding of antigen or antibody in the evanescent field using mixed polymer matrix," *Sensors and Actuators B*, 1998, 52:65-71.

De Velasco et al., "Synthetic Peptides Representing T-Cell Epitopes Act as Carriers in Pneumococcal Polysaccharide Conjugate Vaccines," *Infect. Immun.*, 1995, 63(3):961-968.

Van Patten et al., "Oxidation of Methionine Residues in Antithrombin," *J. Biol. Chem.*, 1999, 274(15):10268-10276.

Veronese et al., "Surface Modification of Proteins. Activation of Monomethoxy-Polyethylene Glycols by Phenylchloroformates and Modification of Ribonuclease and Superoxide Dismutase," *Appl. Biochem. Biotech.*, 1985, 11:141-152.

Vilaseca et al., "Protein conjugates of defined structure: Synthesis and use of a new carrier molecule," *Bioconjugate Chemistry*, 1993, 4(6):515-520.

Webb II and Kaneko, "Synthesis of 1-(Aminooxy)-4-[(3-nitro-2-pyridyl)dithio]butane and 1-(Aminooxy)-4-[(3-nitro-2-pyridyl)dithio]but-2-ene, Novel Heterobifunctional Cross-Linking Reagents," *Bioconjugate Chem.*, 1990, 1:96-99.

Weidler et al., "Pharmakokinetische Merkmale als Kriterien fur den klinischen Einsatz von Hydroxyethylstärke," Arzneim.-Forsch./Drug Res., 1991, 41:494-498 (w/English summary).

White and Kennedy, "Oligosaccharides," *Carbohydrate analysis: a practical approach*, 1996, Chaplin and Kennedy (eds.), Chapter 2, pp. 1-36.

Whitesides et al., "Rates of Thiol-Disulfide Interchange Reactions between Mono- and Dithiols and Ellman's Reagent," *J. Org. Chem.*, 1977, 42(2):332-338.

Wong et al., "Analysis of carbohydrate-protein interactions with synthetic N-linked neoglycoconjugate probes," *Biochem. J.*, 1993, 296:817-825.

Wong et al., "Synthetic glycosylation of proteins using N-(β-saccharide) iodoacetamides: applications in site-specific glycosylation and solid-phase enzymic oligosaccharide synthesis," *Biochem. J.*, 1994, 300:843-850.

Wong, *Chemistry of protein conjugation and cross-linking*, 1993, CRCS, Inc. (TOC only).

Xue and Wong; "Preparation of Conjugated Hemoglobins," *Meth. Enzymol.*, 1994, 231:308-322.

Yalpani et al., "Selective Chemical Modifications of Dextran," *J. Polymer Science: Polymer Chemistry Edition*, 1985, 23:1395-1405.

Yamaguchi et al., "Effects of site-directed removal of N-glycosylation sites in human erythropoietin on its production and biological properties," *J. Biol. Chem.*, 1991, 266(30):20434-20439.

Yoshida, "Glycamine Formation via Reductive Amination of Oligosaccharides with Benzylamine," *Meth. Enzymol.*, 1994, 247:55-64.

Zalipsky, "Functionalized Poly(ethylene glycol) for Preparation of Biologically Relevant Conjugates," *Bioconjugate Chem.*, 1995, 6:150-165.

Zara et al., "A Carbohydrate-Directed Heterobifunctional Cross-Linking Reagent for the Synthesis of Immunoconjugates," *Anal. Biochem.*, 1991, 194:156-162.

Zettlmeissl et al., "Characterization of Recombinant Human Antithrombin III Synthesized in Chinese Hamster Ovary Cells," *J. Biol. Chem.*, 1989, 264 (35):21153-21159.

Zhou et al., "Application of capillary electrophoresis, liquid chromatography, electrospray-mass spectrometry and matrix-assisted laserdesorption/ionization—time of flight—mass spectrometry to the characterization of recombinant human erythropoietin," *Electrophoresis*, 1998, 19(13):2348-2355.

Zou et al., "Allylmalonamide as a bivalent linker: Synthesis of biantennary $Gm_3$-saccharide-Keyhole limpet hemocyanin glycoconjugate and the immune response in mice," *Glycoconj. J.*, 1999, 16:507-515.

Zucali and Sulkowski, "Purification of human urinary erythropoietin on controlled-pore glass and silicic acid," *Exp. Hematol.*, 1985, 13(3):833-837.

Cera C., et al: "Water-Soluble Polysaccharide-Anthracycline Conjugates: Biological Activity, Anti-Cancer Drug Design," vol. 7, No. 2, Apr. 1992, pp. 143-151, XP000791063, ISSN: 0266:9536.

Dieterich et al., "Hydroxyethyl Starch Antibodies in Humans: Incidence and Clinical Relevance," *Anesth. Analg.* 1998, 86:1123-1126.

Merck Index 2006, Definition of Dimethyl Sulfoxide, Merck & Co., 14th Edition, accessed online: http//themerckindex.cambridgesoft.com/themerckindex/index.asp on Sep. 4, 2007.

Gaucher et al., "Stereospecific synthesis and characterization of aminoglycoside ligands from diethylenetriamine," *J. Organic Chem.*, 1999, 64:4012-4015.

Guillaumie et al., "Immobilization of pectin fragments on solid supports: Novel coupling by thiazolidine formation," *Bioconjugate Chem.*, 2002, 13:285-294.

Liu et al., "Characterization of the structural and functional changes of hemoglobin in dimethyl sulfoxide by spectroscopic techniques," *Biochim. Biophys. Acta*, 1998, 138:53-60.

Okamoto et al., "A facile incorporation of the aldehyde function into DNA: 3-formylindole nucleoside as an aldehyde-containing universal nucleoside," *Tetrahedron Lett.*, 2002, 43:4581-4583.

Radomsky and Temeriusz, "Thiazolidine-4(R)-carboxylic acids derived from sugars: part I, C-2-epimerisation in aqueous solutions," *Carb. Res.*, 1989, 187:223-237.

Shao and Tam, "Unprotected peptides as building blocks for the synthesis of peptide dendrimers with oxime, hydrazone and thiazolidine linkages," *J. Am. Chem. Soc.*, 1995, 117(14):3893-3899.

Yang et al., "Functional changes of carboxymethyl potato starch by conjugation with amino acids," *Biosci. Biotechnol. Biochem.*, 1995, 59(12):2203-2206.

Adamczyk and Fishpaugh, "A Solid Supported Synthesis of Thiol Esters,"*Tetrahedron Lett.*, 1996, 37(25):4305-4308.

Aly et al., "Hemophilia A due to mutations that create new N-glycosylation sites," *Proc. Natl. Acad.Sci. USA*, 1992, 89(11):4933-4937.

Anderson and Meister, "Inhibition of γ-glutamyl transpeptidase and induction of glutathionuria by γ-glutamyl amino acids," *Proc. Natl. Acad. Sci. USA*, 1986, 83:5029-5032.

Andersson et al., "Isolation and characterization of human factor VIII: molecular forms in commercial factor VIII concentrate, cryoprecipitate, and plasma," *Proc. Natl. Acad. Sci. USA*, 1986, 83(9):2979-2983.

Armitage, "Emerging applications of recombinant human granulocyte-macrophage colony-stimulating factor," *Blood*, 1998, 92(12):4491-4508.

Balland et al., "Characterisation of two differently processed forms of human recombinant factor IX synthesised in CHO cells transformed with a polycistronic vector," *Eur. J. Biochem.*, 1988, 172(3):565-572.

Bauer and Rosenberg, "Role of antithrombin III as a regulator of in vivo coagulation," *Semin. Hematol.*, 1991, 28(1):10-18.

Berg et al., "Engineering the proteolytic specificity of activated protein C improves its pharmacological properties," *Proc. Natl. Acad. Sci. USA*, 2003, 100(8):4423-4428.

Bhattacharyya et al., "Recombinant Factor VIII for Haemophilia," *CRIPS*, 2003, 4(3):2-8.

Bjork and Danielsson, "Antithrombin and related inhibitors of coagulation proteinases," *Proteinase Inhibitors*, Barrett and Salvesen (eds.), 1986, Chapter 17, Amsterdam, The Netherlands, Elsevier Science Publishers (Biomedical Devision), pp. 489-513.

Boorsma et al., "Bioprocess applications of a Sindbis virus-based temperature-inducible expression system," *Biotechnol. Bioeng.*, 2002, 79(6):602-609.

Carrell et al., "Human alpha 1-antitrypsin: carbohydrate attachment and sequence homology," *FEBS Letters*, 1981, 135(2):301-303.

Carrell et al., "Structural mobility of antithrombin and its modulation by heparin," *Thromb. Haemost.*, 1997, 78(1):516-519.

Carver et al., "Expression of human alpha 1 antitrypsin in transgenic sheep," *Cytotechnology*, 1992, 9(1-3):77-84.

Castillo et al., "Sensitive substrates for human leukocyte and porcine pancreatic elastase: a study of the merits of various chromophoric and fluorogenic leaving groups in assays for serine proteases," *Anal. Biochem.*, 1979, 99(1):53-64.

Cebon et al., "Granulocyte-macrophage colony stimulating factor from human lymphocytes. The effect of glycosylation on receptor binding and biological activity," *J. Biol. Chem.*, 1990, 265(8):4483-4491.

Cera et al., "Water-soluble polysaccharide-anthracycline conjugates: biological activity," *Anti-Cancer Drug Design*, 1992, 7(2):143-151.

Chan et al., "Preparation of O-esters from the corresponding thiol esters: tert-butyl cyclohexanecarboxylate," *Organic Syntheses*, 1990, 7:87-93.

Chaplin and Kennedy (eds.), *Carbohydrate Analysis: a practical approach*, 1994, 2nd Edition, Chapter 1 "Monosaccharides" pp. 1-41, Chapter 2 "Oligosaccharides" pp. 42-72, Chapter 3 "Neutral Polysaccharides" pp. 73-124, Chapter 5 "Glycoproteins" pp. 175-177 and 181-293, IRL Press.

Chen et al., "Purification of alpha 1 proteinase inhibitor from human plasma fraction IV-1 by ion exchange chromatography," *VoxSanguinis*, 1998, 74(4):232-241.

Choay et al., "Structural studies on a biologically active hexasaccharide obtained from heparin," *Ann. NY Acad. Sci.*, 1981, 370:644-649.

Choay et al., "Structure-activity relationship in heparin: a synthetic pentasaccharide with high affinity for antithrombin III and eliciting high anti-factor Xa activity," *Biochem. Biophys. Res. Commun.*, 1983, 116(2):492-499.

Colman, "Production of therapeutic proteins in the milk of transgenic livestock," *Biochem. Soc. Symp.*, 1998, 63:141-147.

Conradt et al., "Expression of human interleukin-2 in recombinant baby hamster kidney, Ltk-, and Chinese hamster ovary cells. Structure of O-linked carbohydrate chains and their location within the polypeptide," *J. Biol. Chem.*, 1989, 264:17368-17373.

Corey and Clark, "A New Method for the Synthesis of 2-Pyridinethiol Carboxylic Esters," *Tetrahedron Lett.*, 1979, 2875-2878.

De Koning et al., "An approach to the synthesis of peptide-PNA-peptide conjugates via native ligation," *Tetrahedron Lett.*, 2002, 43(45):8173-8176.

Denzlinger et al., "Differential activation of the endogenous leukotriene biosynthesis by two different preparations of Granulocyte-Macrophage Colony-Stimulating Factor in healthy volunteers," *Blood*, 1993, 81(8):2007-2013.

Dieterich et al., "Hydroxyethyl Starch Antibodies in Humans: Incidence and Clinical Relevance," *Anesth. Analg.*, 1998, 86:1123-1126.

Donahue et al., "Effects of N-linked carbohydrates on the in vivo properties of human GM-CSF," *Cold Spring Harbor Symp. Quant. Biol.*, 1986, 51:685-692.

Franzen et al., "Structural studies on the carbohydrate portion of human antithrombin III," *J. Biol. Chem.*, 1980, 255(11):5090-5093.

Fujiki et al., "Studies on the disulfide bonds in human pituitary follicle-stimulating hormone," *Biochim. Biophys. Acta*, 1980, 624:428-435.

Goldstein and Gelb, "An alternate preparation of thioester resin linkers for solid-phase synthesis of peptide C-terminal thioacids," *Tetrahedron Lett.*, 2000, 41(16):2797-2800.

Goronzy et al., "T-Cell Derived Lymphokines as Regulators of Chronic Inflammation: Potential Targets for Immunomodulation," *Am. J. Therap.*, 1996, 3(2):109-114.

Gribben et al., "Development of antibodies to unprotected glycosylation sites on recombinant GM-CSF," *Lancet*, 1990, 335:434-437.

Harris et al., "Pegylation. A novel process for modifying pharmacokinetics," *Clin. Pharmacokinet*, 2001, 40(7):539-551.

He et al., "A simplified system for generating recombinant adenoviruses," *Proc. Natl. Acad. Sci. USA*, 1998, 95(5):2509-2514.

Hodges and Chan, "Locations of oligosaccharide chains in human alpha 1-protease inhibitor and oligosaccharide structures at each site," *Biochemistry*, 1982, 21(11):2805-2810.

Hodges et al., "Structure of the oligosaccharide chains in human alpha 1-protease inhibitor," *J. Biol. Chem.*, 1979, 254(17):8208-8212.

Hovgaard et al., "Clinical pharmacokinetic studies of a human haemopoietic growth factor, GM-CSF," *Eur. J. Clin. Inv.*, 1992, 22:45-49.

Hovinen et al., "Ethyl[2-deoxy-5-0-(4,4'-dimethoxytrityl)-α-and β-D-erythro-pentofuranosyl] acetates as versatile intermediates in nucleic acid chemistry," *Nucleosides Nucleotides*, 1999, 18:1263-1264.

Iakovenko et al., "Semi-synthetic Rab proteins as tools for studying intermolecular interactions," *FEBS Letters*, 2000, 468:155-158.

Ingenito et al., "Solid Phase Synthesis of Peptide C-Terminal Thioesters by Fmoc/t-Bu Chemistry," *J. Am. Chem. Soc.*, 1999, 121:11369-11374.

Jaques et al., "N.M.R. spectroscopy and calcium binding of sialic acids: N-glycolylneuraminic acid and periodate-oxidized N-acetylneuraminic acid," *Carb. Res.*, 1980, 83:21-32.

Karpusas et al., "Commercial preparations of interferon beta are Betaseron (IFN beta 1b), Avonex and Rebif (IFN beta 1a)," *Proc. Natl. Acad. Sci. USA*, 1997, 94:11813-11818.

Kaufman et al., "Synthesis, processing, and secretion of recombinant human factor VIII expressed in mammalian cells," *J. Biol. Chem.*, 1988, 263(13):6352-6362.

Kaushansky et al., "Role of carbohydrate in the function of human Granulocyte-Macrophage Colony-Stimulating Factor," *Biochemistry*, 1987, 26:4861-4867.

Keene et al., "Expression of biologically active human follitropin in Chinese hamster ovary cells," *J. Biol. Chem.*, 1989, 264:4769-4775.

Kochendoerfer et al., "Design and chemical synthesis of a homogeneous polymer-modified erythropoiesis protein," *Science*, 2003, 299(5608):884-887.

Kraehenbuhl et al., "Preparation and Characterization of an Immuno Electron Microscope Tracer consisting of a Heme Octa Peptide coupled to FAB," *J. Exp. Med.*, 1974, 139(1):208-223.

Lahiri et al., "Antithrombin-heparin cofactor: an inhibitor of plasma kallikrein," *Arch. Biochem. Biophys.*, 1976, 175:737-747.

Lapthorn et al., "Crystal structure of human chorionic gonadotropin," *Nature*, 1994, 369:455-461.

Li et al., "Direct preparation of peptide thioesters using an Fmoc solid-phase method," *Tetrahedron Lett.*, 1998, 39(47):8669-8672.

Lin et al., "L-Cysteine as a water-soluble cation scavenger in the removal of the 2,4,6-trimethoxybenzyl group from thiols," *Tetrahedron Lett.*, 2002, 43:4531-4533.

Lio and Thiem, "Chemoenzymatic synthesis of spacer-linked oligosaccharides for the preparation of neoglycoproteins," *Carb. Res.*, 1999, 317:180-190.

Luo et al., "Controlled DNA delivery systems," *Pharm. Res.*, 1999, 16(8):1300-1308.

March, J., *Advanced Organic Chemistry*, 1992, 4th edition, John Wiley and Sons, New York, p. 409.

Masamune et al., "A General, Selective Synthesis of Thiol Esters," *Can. J. Chem.*, 1975, 53:3693-3695.

Masamune et al., "Tylonolide hemiacetal, the aglycone of tylosin, and its partial synthesis," *J. Am. Chem. Soc.*, 1976, 98(24):7874-7875.

Masuda et al., "Synthesis and anti-influenza evaluation of orally active bicyclic ether derivatives related to zanamivir," *Bioorganic & Medicinal Chemistry Letters*, 2003, 13(4):669-673.

Mega et al., "Studies on the oligosaccharide chains of human alpha 1-protease inhibitor. I. Isolation of glycopeptides," *J. Biol. Chem.*, 1980, 255(9):4053-4056.

Mega et al., "Studies on the Oligosaccharide Chains of Human α1-Protease Inhibitor. II. Structure of oligosaccharides," *J. Biol. Chem.*, 1980, 255(9):4057-4061.

Menache, "Antithrombin III: introduction," *Semin. Hematol.*, 1991, 28(1):1-2.

Menache et al., "Antithrombin III: physiology, deficiency, and replacement therapy," *Transfusion*, 1992, 32(6):580-588.

Ming et al., "Interleukin 6 is the principal cytolytic T lymphocyte differentiation factor for thymocytes in human leukocyte conditioned medium," *J. Mol. Cell. Immunol.*, 1989, 4:203-211.

Moonen et al., "Increased biological activity of deglycosylated recombinant human granulocyte-macrophage colony-stimulating factor produced by yeast or animal cells," *Proc. Natl. Acad. Sci. USA*, 1987, 84(13):4428-4431.

Mon et.al., "The activation of type 1 and type 2 plasminogen by type I and type II tissue plasminogen activator," *J. Biol. Chem.*, 1995, 270(7):3261-3267.

Muir et al., "Expressed protein ligation: a general method for protein engineering," *Proc. Natl. Acad. Sci. USA*, 1998, 95(12):6705-6710.

Mukaiyama et al., "Peptide Synthesis via Oxidation-Reduction Condensation by the Use of Non-metallic Compound as a Mercaptan Scavenger," *Bull. Chem. Soc. Jpn.*, 1970, 43:1271.

Mumberg et al., "Regulatable promoters of *Saccharomyces cerevisiae*: comparison of transcriptional activity and their use for heterologous expression," *Nucl. Acids Res.*, 1994, 22(25):5767-5768.

Murano et al., "Some properties of antithrombin-III and its concentration in human plasma," *Thromb. Res.*, 1980, 18(1-2):259-262.

Ohta et al., "Usefulness of Glycopeptide Mapping by Liquid Chromatography/Mass Spectrometry in Comparability Assessment of Glycoprotein Products," *Biologicals*, 2002, 30(3):235-244.

Okamoto et al., "Purification and characterization of three forms of differently glycosylated recombinant human Granulocyte-Macrophage Colony-Stimulating Factor," *Arch. Biochem. Biophys.*, 1991, 286(2):562-568.

Olson and Bjork, "Predominant contribution of surface approximation to the mechanism of heparin acceleration of the antithrombin-thrombin reaction. Elucidation from salt concentration effects," *J. Biol. Chem.*, 1991, 266(10):6353-6364.

Olson et al., "Role of the antithrombin-binding pentasaccharide in heparin acceleration of antithrombin-proteinase reactions. Resolution of the antithrombin conformational change contribution to heparin rate enhancement," *J. Biol. Chem.*, 1992, 267(18):12528-12538.

Opal et al., "Antithrombin, heparin, and heparan sulfate," *Crit. Care Med.*, 2002, 30(5):S325-S331.

Pelter et al., "Synthesis of Thioesters by Reactions of Carboxylic Acids with Tris-(ethylthio)borane," *J. Am. Chem. Soc., Perkin Trans I*, 1977, 1672-1674.

Peterson, *The Physiological Inhibitions of Blood Coagulation and Fibrinolysis*, Elsevier/ North-Holland Biomedical Press 1979, p. 43.

Pike et al., "Heparin-dependent Modification of the Reactive Center Arginine of Antithrombin and Consequent Increase in Heparin Binding Affinity," *J. Biol. Chem.*, 1997, 272(32):19652-19655.

Ragnhammar et al., "Induction of anti-recombinant human Granulocyte-Macrophage Colony-Stimulating Factor (*Escherichia coli*-derived) antibodies and clinical effects in nonimmunocompromised patients," *Blood*, 1994, 84:4078-4087.

Rapoport et al., "Protein transport across the eukaryotic endoplasmic reticulum and bacterial inner membranes," *Annu. Rev. Biochem.*, 1996, 65:271-303.

Reddy et al., "Use of peginterferon alfa-2a (40 KD) (Pegasys) for the treatment of hepatitis C," *Advanced Drug Delivery Reviews*, 2002, 54:571-586.

Revoltella et al., "Natural and therapy-induced anti-GM-CSF and anti-G-CSF antibodies in human serum," *Leukemia and Lymphoma*, 1997, 26:29-34.

Roemisch et al., "Antithrombin: a new look at the actions of a serine protease inhibitor," *Blood Coagul Fibrinolysism*, 2002, 13(8):657-670.

Römpp Chemielexikon, Thieme Verlag Stuttgart, Germany, 9th edition, 1990, vol. 9, pp. 2281-2285.

Rosenberg, "Role of heparin and heparinlike molecules in thrombosis and atherosclerosis," *Fed. Proc.*, 1985, 44:404-409.

Rosenberg et al., "Antithrombin-III," *Rev. Hematol.*, 1986, 2:351-416.

Schlesinger, "Alphaviruses—vectors for the expression of heterologous genes," *Trends Biotechnol.*, 1993, 11(1):18-22.

Shin et al., "Fmoc-Based Synthesis of Peptide-αThioesters: Application to the Total Chemical Synthesis of Glycoprotein by Native Chemical Ligation," *J. Am. Chem. Soc.*, 1999, 121:11684-11689.

Somogyi, "Determination of reducing sugars," *Meth. Carb. Chem.*, 1962, 1:384-386.

Spellman et al., "Carbohydrate structures of human tissue plasminogen activator expressed in Chinese hamster ovary cells," *J. Biol. Chem.*, 1989, 264:14100-14111.

Stetsenko et al, "Efficient conjugation of peptides to oligonucleotides by native ligation," *J. Org. Chem.*, 2000, 65(16):4900-4908

Stewart et al., "Identification of the mechanism responsible for the increased fibrin specificity of TNK-tissue plasminogen activator relative to tissue plasminogen activator," *J. Biol. Chem.*, 2000, 275(14):10112-10120.

Tebbutt, "Technology evaluation: transgenic alpha-1-antitrypsin (AAT), PPL therapeutics," *Curr. Opin. Mol. Ther.*, 2000, 2(2):199-204.

Thim et al., "Amino acid sequence and posttranslational modifications of human factor VIIa from plasma and transfected baby hamster kidney cells," *Biochemistry*, 1988, 27:7785-7793.

Toole et al., "Molecular cloning of a cDNA encoding human antihaemophilic factor," *Nature*, 1984, 312(5992):342-347.

Travis and Salvesen, "Human plasma proteinase inhibitors," *Ann. Rev. Biochem.*, 1983, 52:655-709.

Ubeda and Habener, "The large subunit of the DNA replication complex C (DSEB/RF-C140) cleaved and inactivated by caspase-3 (CPP32/YAMA) during Fas-induced apoptosis," *J. Biol. Chem.*, 1997, 272(31):19562-19568.

Veronese, "Peptide and protein PEGylation: a review of problems and solutions," *Biomaterials*, 2001, 22(5):405-417.

Wadhwa et al., "Immunogenicity of Granulocyte-Macrophage Colony-Stimulating Factor (GM-CSF) products in patients undergoing combination therapy with GM-CSF," *Clin. Cancer Res.*, 1999, 5:1351-1361.

Wasley et al., "The Importance of N- and O-Linked Oligosaccharides for the Biosynthesis and In Vitro and In Vivo Biologic Activities of Erythropoietin," *Blood*, 1991, 77(12):2624-2632.

Watanabe et al., "A facile synthesis of carboxylic thiol esters from carboxylic acids and thiols," *Chem. Lett.*, 1976, 741-742.

Weisshaar et al., "NMR investigations of the N-linked oligosaccharides at individual glycosylation sites of human lutropin," *Eur. J. Biochem.*, 1991, 195:257-268.

Wright et al., "High level expression of active human alpha-1-antitrypsin in the milk of transgenic sheep," *Biotechnology NY*, 1991, 9:830-834.

Yoshitake et al., "Nucleotide sequence of the gene for human factor IX (antihemophilic factor B)," *Biochemistry*, 1985, 24:3736-3750.

Cervigni et al., "Synthesis of Glycopeptides and Lipopeptides by Chemoselective Ligation," *Angewandte Chemie International Edition in English*, 1996, 35(11):1230-1232.

Lee and Park, "Conjugation of trypsin by temperature-sensitive polymers containing a carbohydrate moiety: thermal modulation of enzyme activity," *Biotechnol. Prog.*, 1998, 14(3):508-516.

*Dictionary of Chemistry and Chemical Technology*, 2003, p. 769 (English translation provided).

Axèn et al., "Chemical Coupling of Peptides and Proteins to Polysaccharides by Means of Cyanogen Halides," *Nature*, 1967, 214:1302-1304.

Bayer et al., "The Avidin-Biotin Complex in Affinity Cytochemistry," *Meth. Enzymol.*, 1979,62:308-315.

Boyer et al., "Reaction in Biphasic Water/Organic Solvent System in the Presence of Surfactant: Inverse Phase Transfer Catalysis versus Interfacial Catalysis," *Tetrahedron*, 2000, 56:303-307.

Heitzmann and Richards, "Use of the Avidin-Biotin Complex for Specific Staining of Biological Membranes in Electron Microscopy," *Proc. Natl. Acad. Sci. USA*, 1974, 71(9):3537-3561.

Lewis et al., "The phase transfer catalysed synthesis of isoflavone-O-glucosides," *J. Chem. Soc. Perkins Trans. 1*, 1998, pp. 2481-2484.

Lewis and Wähälä, "Regiospecific 4'-O-β-glucosidation of isoflavones," *Tetrahedron Letters*, 1998, 39(51):9559-9562.

Organikum, Organisch-chemisches Grundpraktikum, 1984, VEB Deutscher Verlag der Wissenschaften, p. 472 (with English translation and verification).

Tam et al., "Peptide Synthesis Using Unprotected Peptides Through Orthogonal Coupling Methods," *Proc. Natl. Acad. Sci. USA*, 1995, 92:12485-12489.

Pierce Chemical Technical Library, "cross-linking," 1994, 45 pages.

Carey and Sundberg, "Organische Chemie," VCH Verlagsgesellschaft mbH, Weinheim (DE), 1995, pp. 432-433 and 455 (English translation provided).

Peri et al., "Chemo- and Stereoselective Glycosylation of Hydroxylamino Derivatives: A Versatile Approach to Glycoconjugates," *Tetrahedron*, 1998, 54:12269-12278.

Heindel et al., "Hydrazide Pharmaceuticals as Conjugates to Polyaldehyde Dextran: Syntheses, Characterization, and Stability," *Bioconj. Chem.*, 1990, 1:77-82.

Wilchek and Bayer, "Labeling Glycoconjugates with Hydrazide Reagents," *Meth. Enzymol.*, 1987, 138:429-442.

Anno et al., "Sugar Chemistry," 1995, p. 31 (English translation provided).

Lund et al., "Assessment of methods for covalent binding of nucleic acids to magnetic beads, Dynabeads™, and the characteristics of the bound nucleic acids in hybridization reactions," *Nucl. Acids Res.*, 1988, 16(22):10861-10880.

Wang et al., "Delivery of Antisense Oligonucleotides Using HPMA Polymer: Synthesis of A Thiol Polymer and Its Conjugation to Water-Soluble Molecules," *Bioconj. Chem.*, 1998, 9:749-757.

Alagon et al., "Activation of Polysaccharides with 2-Iminothiolane and its Uses", Biochem. 19:4341-4345 (1980).

Balazy et al., "S-Nitroglutathione, a Product of the Reaction between Peroxynitrite and Glutathione That Generates Nitric Oxide", J. Biol. Chem. 273(48):32009-32015 (1998).

Etrych et al., "New HPMA Copolymers containing doxorubicin bound via pH-sensitive linkage: synthesis and preliminary in vitro and in vivo biological properties", Journal of Controlled Release 73:89-102 (2001).

European Pharmacopoeia, Supplemental 2001, "Haemodialysis Solutions" pp. 911-918.

Ganson et al., "Control of Hyperuricemia in Subjects with refractory gout, and induction of antibody against poly (ethylene glycol) (PEG), in a phase I trial of subcutaneous PEGylated urate oxidase", Arthritis Research & Therapy, 8: R12 (2005).

Glederblom et al., "Cremophor EL: the drawbacks and advantages of vehicle selection for drug formulation", European Journal of Cancer, 37:1590-1598 (2001).

Gerwech et al., "Tumor pH controls the in vivo efficacy of weak acid and base chemotherapeutics", Mol. Cancer Ther. 5(5):1275-1279 (2006).

Greenwald et al., "Drug Delivery Systems: Water Soluble Taxol 2'-Poly(ethylene glycol) Ester Prodrugs—Design and in Vivo Effectiveness" J. Med. Chem., 39:424-431 (1996).

Hamilton et al., "Characterization of a Human Ovarian Carcinoma Cell Line (NIH:OVCAR-3) with Androgen and Estrogen Receptors", Cancer Research, 43:5379-5389 (1983).

Jungheinrich et al., "Pharmacokinetics of Hydroxyethyl Starch", Clin Pharmacokinet, 44(7):681-699 (2005).

Katsumi et al., "Development of Polyethylene Glycol-Conjugated Poly-S-Nitrosated Serum Albumin, a Novel S-Nitrosothiol for Prolonged Delivery of Nitric Oxide in the Blood Circulation in Vivo", Journal of Pharmacology and Experimental Therapeutics, 314(3):1117-1124 (2005).

Kinstler et al., "Characterization and Stability of N-terminally PEGylated rhG-CSF", Pharmaceutical Research, 13 (7):996-1002 (1996).

Kulicke et al., "Measurements of the Refractive Index Increment on Hydroxyethyl Starch as a Basis for Absolute Molecutlar Weight Determinations", Starch, 43(10):392-396 (1991).

Laine et al., "Polyethylene Glycol Nephrotoxicity secondary to prolonged High-Dose Intravenous Lorazepam", Annals of Pharmacotherapy, 29:1110-1114 (1995).

Bernardes et al., "The Direct Formation of Glycosyl Thiols from Reducing Sugars Allows One-Pot Protein Glycoconjugation", Angew. Chem. 118:4111-4115 (2006).

Besheer et al., "Enzymatically Catalyzed HES Conjugation Using Microbial Transglutaminase:Proof of Feasibility", Journal of Pharmaceutical Sciences, 98(11):4420-4428 (2009).

Lee et al., "Functional Polymers for Layer-by-Layer Construction of Multilayer via Chemoselective Immobilization", Macromolecules, 37:1849-1856, (2004).

Lieber et al., "A Continuous Tumor-Cell Line From a Human Lung Carcinoma with Properties of Type II Alveolar Epithelial Cells", Int. J. Cancer, 17:62-70, (1976).

Lipke et al., "Localized Delivery of Nitric Oxide from Hydrogels Inhibits Neointima Formation in Rat Cartoid Ballon Injury Model", Acta Biomaterialia, 1:597-606, (2005).

Megson et al., "Inhibition of Human Platelet Aggregation by a Novel S-Nitrosothiol is Abolished by Haemoglobin and Red Blood Cell in vitro: Implications for Anti-Thrombotic Therapy", British Journal of Pharmacology, 131:1391-1398, (2000).

Nathan et al., "Strategies for Covalent Attachment of Doxorubicin to Poly(PEG-Lys), a New Water Soluble Poly(ether urethane)", Journal of Bioactive and Compatible Polymers, 9:239-251 (1994).

Naundorf et al., "Characterization of two human mammary carcinomas, MT-1 and MT-3, suitable for in vivo testing of either lipids and their dirivatives", Breast Cancer Research and Treatment, 23:87-95, (1992).

Ph. Eur. Nachtrag, "Erythropoietini solutio concentrata", pp. 780, (2000).

Ph. Eur. Nachtrag, "Erythropoietini solutio concentrata", pp. 911, (2001).

Pharmeuropa, "erythropoietin Concentrated Solution", 8(3):371. (1996).

Thermo Scientific Pierce "Crosslinking Technical Handbook", 48pgs. (2009).

Reynolds et al., "S-nitrosohemoglobin deficiency: A mechanism for loss of physiological activity in banked blood", PNAS, 104(43):17058-17062, (2007).

Rodrigues et al., "Correlation of the acid-sensitivity of polyethylene glycol daunorubicin conjugates with their in vitro antiproliferative activity", Bioorganic & Medicinal Chemistry, 14:4110-4117, (2006).

Salo et al., "Aminooxy Functionalized Oligonucleotides: Preparation, On-Support Derivatization, and Postsynthetic Attachment to Polymer Support", Bioconjugate Chem., 10:815-823, (1999).

Schneerson et al., "Preparation, characterization and immunogenicity of haemophilus influenzae type b polysaccharide-protein conjugates", Journal of Experimental Medicine, 152:361-376 (1980).

Skopp et al., "Fingerprinting of proteins cleaved in solution by cyanogen bromide", Appl. and Theoret. Electrophoresis, 1:61-64, (1989).

Skwarczynski et al., "Paclitaxel Prodrugs Toward Smarter Delivery of Anticancer Agents", Journal of Medicinal Chemistry, 49(25):7253-7269, (2006).

Stien et al., "Development and characterisation of novel human multidrug resistant mammary carcinoma lines in vitro and in vivo", Int. J. Cancer, 72:885-891, (1997).

Tomasik et al., "Chemical Modification of Starch", Advaces in Carbohydrate Chemistry and Biochemistry, 59:179-403, (2004).

Velasco et al., "Synthetic Peptides Representing T-Cell Epitopes Act as Carriers in Pneumococcal Polysaccharide Conjugate Vaccines", Infection and Immunity, 63(3):961-968, (1995).

Vasey et al., :Phase I Clinical and Pharmacokinetic Study of PKI [N-(2-Hydroxypropyl)methacrylamide Copolymer Doxorubicin]: First Member of a New Class of Chemotherapeutic Agents-Drug-Polymer Conjugates, Clinial Cancer Research, 5:83-94, (1999).

Waltzinger et al., "Pharmacokinetics and Tolerability of a New Hydroxyethyl Starch (HES) Specification [HES (130/0.4)] after Single-Dose Infusion of 6% or 10% Solutions in Healthy Volunteers", Pharmacokinetics, 16(2):151-160, (1998).

Wong, Chemical Dictionary Entry Concerning Carbohydrates, *Chemistry of Protein Conjugation and Cross-Linking*, 1993, CRCS, Inc., 6 pages including English-language Abstract.

Frie, "Evaluating a Novel Method for Coupling of Low Molecular Hydroxyethylstarch with Model Compounds and Application of this Method to further Selected Proteins," Diploma Thesis dated Feb. 2, 1998, Diplomarbeit, Fachhochschule, Hamburg, Germany, 82 pages including English-language Abstract.

Schmoll et al. (eds.), "Summary of Basics of Oncology and Current Therapeutic Approaches," *Compendium for Internistic Oncology*, 1996, Table of Contents with English Summary.

Sommermeyer et al., "Hydroxyethylstarch for Clinical Application: Physical and Chemical Characterisation," *Krankenhauspharmazie*, 1987, 8:271-278.

Klimek et al., "Specific Immunotherapy (Hyposensibilisation)," *Allergologie und Umweltmedizin*, Chapter 15, pp. 157-195, (2009).

Staab, "New Methods in Preparatory Organic Chemistry IV. Synthesis using heterocyclic amides (azolides)," *Angew. Chem.*, 1962, 74(12):407-422.

Stille et al., "Atherosclerosis as Consequence of Chronic Infection by Chlamydia Pneumoniae," *Herz*, 1998, 23:185-192 (w/English summary).

Lee et al., "Conjugation of Trypsin by Temperature-Sensitive Polymers Containing a Carbohydrate Moiety: Thermal Modulation of Enzyme Activity," Biotechnol. Prog., 1998, 14:508-516.

Lee. V.H.L., Ed. Peptide and Protein Drug Delivery, Marcel Dekker, 1991, p. 65.

Svenson, Lindberg, A.A; Journal of Immunological Methods, 25 (1979), 323-335.

Svenson, Journal of Immunology, vol. 120, No. 5 (1978), 1750-1757.

Caliceti et al., "Immunological properties of unease conjugated to neutral soluble polymers," *Bioconjugate Chem.*, 2001, 12:515-522.

De Koning et al., "An approach to the synthesis of peptide-PNA-peptide conjugates via native ligation," *Tetrahedron Letters*, 2002, 43(45):8173-8176.

De Velasco et al., "Synthetic peptides representing T-cell epitopes act as carriers in pneumococcal polysaccharide conjugate vaccines," *Infect. Immun.*, 1995, 36(3):961-968.

Dorwald, *Side Reactions in Organic Synthesis, A Guide to Successful Synthesis Design*, 2005, Published by Wiley-VCH Verlag GmbH & Co. Preface p. IX-X.

European Pharmacopoeia, "Erythropoietin concentrated solution," *Pharmaeuropa.*, 1996, 8:371-377.

Heterobifunctional Crosslinkers by Molecular Biosciences [http://web.archive.org/web/20011104182428/http://www.molbio.com/Heterobi.htm], retrieved Jun. 6, 2011.

Johnson, "Oxime," from McGraw-Hill's Access Science [http://accessscience.com/content.aspx?searchStr=oxime&id=480600], retrieved May 9, 2011.

March, "Delocalized Chemical Bonding," *Advanced Organic Chemistry*, 4th edition, Ch. 2, John Wiley and Sons, New York (1992) pp. 26-74.

Pierce Company, Crosslinking Agents [http://www.piercenet.com/browse.cfm?fldID=0203], retrieved Aug. 25, 2011.

Reischl (ed)., *Molecular Diagnosis of Infectious Diseases*, 1997, vol. 13, Humana Press Inc., Totowa, NJ (TOC Only).

Riess, "Oxygen carriers ('blood substitutes')—raison d'etre, chemistry, and some physiology," *Chem. Rev.*, 2001, 101:2797-2919.

Svenson et al., "Oligosaccharide-protein conjugate: A novel approach for making *Salmonella* O- antigen immunogens," *FEMS Microbiology Letters*, 1977, 1:145-148.

Cavallaro et al., "Folate-mediated targeting of polymeric conjugates of gemcitabine", International Journal of Pharmaceutics, 307:258-269, (2006).

Chamow and Ashkenazi(eds.), "Antibody Fusion Proteins", 312 pages, John Wiley & Sons, Inc., (1999) (TOC).

Grieco et al., "Aryl Selenocyanates and Aryl Thiocyanates: Reagents for the Preparation of Activated Esters", J. Org. Chem., 43(6), 1283-1285, (1978).

Harada et al., "Carrier and dose effects on the pharmacokinetics of T-0128, a camptothecin analogue-carboxymethyl dextran conjugate, in non-tumor- and tumor bearing rats ", Journal of controlled release, 71(1):71-86, (2001).

Harada et al., "Determinants for the drug release from T-0128, camptothecin analogue-carboxymethyl dextran conjugate", Journal of controlled release, 69(3):399-412, (2000).

Pasut et al., "Antitumoral activity of PEG-gemcitabine prodrugs targeted by folic acid", Journal of controlled release, 127(3):239-248, (2008).

Peluso et al., "Aspargine surrogates for the assembly of N-linked glycopeptides mimetics by chemoselective ligation" Tetrahedron Letters, 42:2085-2087, (2001).

Rotondaro et al., "Purification and Characterization of Two Recombinant Human Granulocyte Colony-Stimulating Factor Glycoforms", Molecular Biotechnology, 11:117-128, (1999).

Zhang, L. et al. "Thiazolidine formation as a general and site-specific conjugation method . . . " Anal. Biochem.. 233:87-93, (1996).

Ernst B., G.W. Hart and P.Sinay eds., Carbohydrates in Chemistry and Biology part I, vols. 1+2, Published 2000, Whiley-VCH Weinheim-New York-Chichester-Brisbane-Toronto, ISBN 3-527-29511-9.

Seymour et al., "A phase I study of Bay 38-3441 given as a short infusion daily for five days every 3 weeks. A National Cancer Institute of Canada Clinical Trials Group Study", European Journal of Cancer, 37(1):73, (2001).

Grieco et al., "Favored reduction of α-chlorosilanes vs. α-chloroalkanes with tri-n-butyltin hydride," *J. Org. Chem.*, 1978, 43(6):1285.

Lane A B C D E

Lane A B C D

X  A  B  C  D  E  F  G

Lane:  A  B  C  D

CONJUGATES OF HYDROXYALKYL STARCH AND A PROTEIN, PREPARED BY REDUCTIVE AMINATION

CROSS-REFERENCE TO RELATED APPLICATIONS

This application is a continuation-in-part and claims benefit under 35 U.S.C. §120 of International Application No. PCT/EP2005/002653 having an International Filing Date of Mar. 11, 2005, which published in English as International Publication Number WO 2005/092928, and which claims the benefit of priority of U.S. Provisional Application Ser. No. 60/552,217, filed on Mar. 11, 2004, and European Application Serial No. 04005855.4, filed on Mar. 11, 2004.

TECHNICAL FIELD

The present invention relates to conjugates of hydroxyalkyl starch, and a protein, wherein the conjugates are formed by a reductive amination reaction between at least one aldehyde group of the hydroxyalkyl starch or of a derivative of the hydroxyalkyl starch, and at least one amino group of the protein, so that the hydroxyalkyl starch or the derivative thereof is covalently linked to the protein via an azomethine linkage or a aminomethylene linkage. The present invention also relates to the method of producing these conjugates and specific uses of the conjugates.

BACKGROUND

It is generally accepted that the stability of proteins can be improved and the immune response against these proteins is reduced when these proteins are coupled to polymeric molecules. WO 94/28024 discloses that physiologically active proteins modified with polyethylene glycol (PEG) exhibit reduced immunogenicity and antigenicity and circulate in the bloodstream considerably longer than non-conjugated proteins, i.e., have a longer plasma half-life.

WO 03/074087 relates to a method of coupling proteins to a starch-derived modified polysaccharide. The binding action between the protein and the polysaccharide, hydroxyalkyl starch, is a covalent linkage which is formed between the terminal aldehyde group or a functional group resulting from chemical modification of said terminal aldehyde group of the hydroxy alkyl starch molecule, and a functional group of the protein. As reactive group of the protein, amino groups, thio groups and carboxyl groups are disclosed. Moreover, while a vast variety of possibilities of different linkages is given in the form of many lists, including different functional groups, theoretically suitable different linker molecules, and different chemical procedures, the working examples describe only two alternatives: first, an oxidized hydroxyethyl starch is used and coupled directly to proteins using ethyldimethylaminopropyl carbodiimide (EDC) activation, or a non-oxidized hydroxyethyl starch is used and coupled directly, i.e. without linking compound to a protein forming a Schiff's base which is subsequently reduced to the respective amine. Thus, the working examples of WO 03/074087 do not disclose a single conjugate comprising hydroxyethyl starch, the protein, and one or more linker molecules. Additionally, as far as the conjugates formed by reductive amination are concerned, WO 03/074087 does not contain any information as to a preferred amino group of the protein the reductive amination is carried out with.

SUMMARY

Therefore, it is an object of the present invention to provide novel conjugates of hydroxyalkyl starch, preferably hydroxyethyl starch, and a protein which conjugates have beneficial therapeutic effects when administered to a subject in need thereof.

It was a further object of the present invention to provide novel conjugates of hydroxyalkyl starch, preferably hydroxyethyl starch, and a protein which are formed by reductive amination by reacting an amino group of the oligopeptide or the polypeptide with an aldehyde or a keto group or a hemiacetal group of hydroxyalkyl starch, preferably hydroxyethyl starch, or with an aldehyde functionalized derivative thereof.

It was yet another object of the present invention to provide a method for producing said novel conjugates wherein said method is applied using specific and selected reaction conditions.

Therefore, the present invention relates to a method for preparing a conjugate comprising a protein and a polymer or a polymer derivative, wherein the polymer is a hydroxyalkyl starch, said method comprising covalently linking at least one aldehyde group or keto group or hemiacetal group of the polymer or the polymer derivative to at least one amino group of the protein by reductive amination, said method further comprising either introducing at least two aldehyde groups in the polymer by a ring-opening oxidation reaction and reacting at least one of said aldehyde groups of the polymer with an amino group of the protein, or reacting the polymer with an at least bifunctional compound, said compound comprising two functional groups M and Q, one functional group M being reacted with the polymer and one functional group Q being chemically modified to give an aldehyde or keto or hemiacetal functionalized polymer derivative which is reacted with an amino group of the protein by reductive amination.

Accordingly, the present invention also relates to a conjugate comprising a protein and a polymer or a polymer derivative, wherein the polymer is a hydroxyalkyl starch, obtainable by a method for preparing a conjugate, said method comprising covalently linking at least one aldehyde group or keto group or hemiacetal group of the polymer or the polymer derivative to at least one amino group of the protein by reductive amination, said method further comprising either introducing at least two aldehyde groups in the polymer by a ring-opening oxidation reaction and reacting at least one of said aldehyde groups of the polymer with an amino group of the protein, or reacting the polymer with an at least bifunctional compound, said compound comprising two functional groups M and Q, one functional group M being reacted with the polymer and one functional group Q being chemically modified to give an aldehyde or keto or hemiacetal functionalized polymer derivative which is reacted with an amino group of the protein by reductive amination.

In one aspect, this document features a method for preparing a conjugate comprising a protein and a polymer, wherein the polymer is a hydroxyalkyl starch. The method can include (a)(1) introducing at least one aldehyde group in the polymer by a ring-opening oxidation reaction, or (a)(2) reacting the polymer with an at least bifunctional compound, the compound comprising two functional groups M and Q, one functional group M being reacted with the polymer and one functional group Q being (i) an aldehyde group or keto group or hemiacetal group; or (ii) a functional group being chemically modified to give the aldehyde or keto or hemiacetal functionalized polymer derivative; and (b) covalently linking the at least one aldehyde group or keto group or hemiacetal group of the polymer or a derivative thereof, to at least one amino group of the protein by reductive amination.

The hydroxyalkyl starch can be hydroxyethyl starch. The hydroxyethyl starch can have a molecular weight of from 2 to 200 kD, preferably of from 4 to 130 kD, more preferably of from 4 to 70 kD. The reductive amination can be carried out in an aqueous medium. The reductive amination can be carried out in the presence of $NaCNBH_3$. The reductive amination can be carried out at a pH of 7.5, preferably 7 or less. The pH can be 6 or less. The reductive amination can be carried out at a temperature of from 0 to 25° C.

In step (a)(1), the polymer can be subjected to a ring-opening oxidation reaction using a periodate to give a polymer derivative having at least one aldehyde group. The ring-opening oxidation reaction can be carried out in an aqueous medium. The ring-opening oxidation reaction can be carried out at a temperature of from 0 to 5° C. The polymer can be employed with its reducing end in the non-oxidized form.

In step (a)(2)(i), the functional group M can be a carboxy group or a reactive carboxy group and the functional group Q is an aldehyde group or keto group or hemiacetal group. The bifunctional compound comprising M and Q can be selected from the group consisting of formylbenzoic acid, 4-formylbenzoic acid pentafluorophenyl ester, 4-formylbenzoic acid N-hydroxysuccinimide ester, and 4-(4-formyl-3,5-dimethoxyphenoxy)butyric acid. In step (a)(2)(ii), the functional group M can be an amino group and the functional group Q is an amino group. The compound comprising two amino groups M and Q can be an optionally substituted diaminoalkane having from 2 to 20 carbon atoms. The diaminoalkane can be selected from the group consisting of 1,2-diaminoethane, 1,3-diaminopropane, and 1,4-diaminobutane.

The method can additionally include reacting the polymer derivative resulting from the reaction of the polymer with the at least bifunctional compound comprising two amino groups M and Q, at the amino group Q with a further bifunctional compound comprising a carboxy group or a reactive carboxy group and an aldehyde group or a keto group or a hemiacetal group to give a polymer derivative having an aldehyde group or a keto group or a hemiacetal group. The further bifunctional compound can be selected from the group consisting of formylbenzoic acid, 4-formylbenzoic acid pentafluorophenyl ester, 4-formylbenzoic acid N-hydroxysuccinimide ester, and 4-(4-formyl-3,5-dimethoxyphenoxy)butyric acid. The amino group Q of the compound comprising two amino groups M and Q can be a beta hydroxy amino group. The beta hydroxyamino group can be oxidized to give an aldehyde group. The compound comprising two amino groups M and Q, Q being a beta hydroxy amino group, can be 1,3-diamino-2-hydroxypropane. The oxidation reaction can be carried out using a periodate.

The protein can be selected from the group consisting of EPO, G-CSF, IFN alpha, IFN beta, AT III, IL-2, IL-3, myoglobin, SOD, and BSA, preferably from the group consisting of rhEPO, rhG-CSF, rhIFN alpha, rhIFN beta, rhAT III, rhIL-2, rhIL-3, myoglobin, SOD, and BSA, or from the group consisting of A1AT, factor VII, factor VIII, factor IX, tPA, and APC.

In another aspect, this document features a conjugate comprising a protein and a polymer, as obtainable by a method described herein. The polymer or derivative thereof can be predominantly coupled to the N-terminal amino group of the protein via an azomethine and/or amino linkage, the protein used for the reaction comprising the N-terminal amino group and at least one further amino group, preferably a further lysine group. The employed polymer comprising at least one aldehyde group introduced in the polymer by a ring-opening oxidation reaction can have at least one structure according to formula

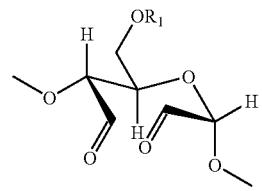

wherein $R_1$ is hydrogen or a hydroxyalkyl group, a hydroxyaryl group, a hydroxyaralkyl group or a hydroxyalkaryl group having of from 2 to 10 carbon atoms.

The protein can be covalently linked to the polymer derivative via an azomethine and/or amino linkage, the derivative resulting from the reaction of the polymer with the compound comprising two amino groups M and Q via functional group M, the resulting compound having been further reacted via Q with a further bifunctional compound comprising a carboxy group or a reactive carboxy group and an aldehyde group or a keto group or a hemiacetal group, the carboxy group or reactive carboxy group forming an amide linkage with the amino group Q, and the aldehyde group or keto group or hemiacetal group having been reacted with an amino group of the protein by reductive amination. The further bifunctional compound comprising a carboxy group or a reactive carboxy group and an aldehyde group or keto group or hemiacetal group can be selected from the group consisting of formylbenzoic acid, 4-formylbenzoic acid pentafluorophenyl ester, 4-formylbenzoic acid N-hydroxysuccinimide ester, and 4-(4-formyl-3,5-dimethoxyphenoxy)butyric acid. The conjugate can have the structure

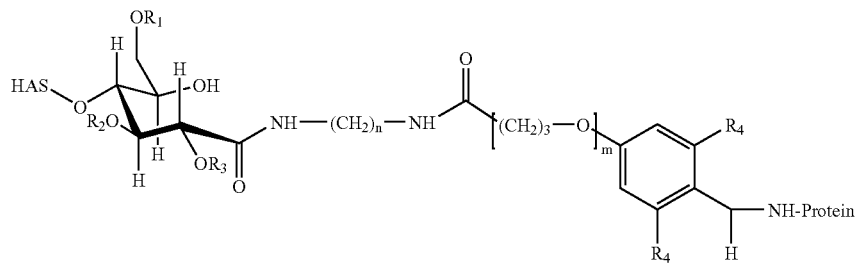

wherein the polymer was reacted via its oxidized reducing end, $R_1$, $R_2$ and $R_3$ being independently hydrogen or a hydroxyalkyl group, and n=2, 3, or 4, $R_4$ being independently hydrogen or a methoxy group, and m=0 when $R_4$ is hydrogen and m=1 when $R_4$ is methoxy.

The protein can be covalently linked to the polymer derivative via an azomethine and/or amino linkage, the derivative resulting from the reaction of the polymer with the compound comprising two amino groups M and Q, Q being a beta hydroxy amino group, and oxidation of the beta hydroxyamino group Q to give an aldehyde group. The compound comprising two amino groups M and Q, Q being a beta hydroxy amino group, can be 1,3-diamino-2-hydroxypropane. The conjugate can have the structure

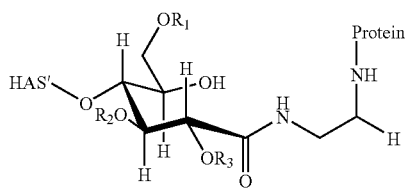

wherein the polymer was reacted with its oxidized reducing end, $R_1$, $R_2$ and $R_3$ being independently hydrogen or a hydroxyalkyl group.

The protein can be selected from the group consisting of EPO, G-CSF, IFN alpha, IFN beta, AT III, IL-2, IL-3, myoglobin, SOD, and BSA. The protein can be selected from the group consisting of rhEPO, rhG-CSF, rhIFN alpha, rhIFN beta, rhAT III, rhIL-2, rhIL-3, myoglobin, SOD, and BSA. The protein can be selected from the group consisting of A1AT, factor VII, factor VIII, factor IX, tPA, and APC.

In another aspect, this document features a method for the treatment of a human or animal body, comprising administering a conjugate as described herein a human or animal in need of treatment.

This document also features a pharmaceutical composition comprising in a therapeutically effective amount a conjugate as described herein, or a conjugate obtainable by a method as described herein. The pharmaceutical composition can further include at least one pharmaceutically acceptable diluent, adjuvant, or carrier.

In another aspect, this document features a composition for the treatment of anemic disorders or hematopoietic dysfunction disorders or diseases related thereto, comprising a conjugate as described herein, wherein the protein is EPO and the polymer is HAS.

In still another aspect, this document features a composition for the treatment of a disorder characterized by a reduced hematopoietic or immune function, the disorder preferably being a result of chemotherapy, radiation therapy, infectious disease, severe chronic neutropenia, or leukemia, comprising a conjugate as described herein, wherein the protein is G-CSF and the polymer is HAS.

In yet another aspect, this document features a composition for the treatment of hereditary deficiency, veno-occlusive disease, burns and heparin resistance in coronary arterial bypass graft (CABG) surgery, prevention of micro-clot formation associated with ventilation therapy, treatment of bowel perforation resulting from trauma or gastrointestinal surgery; disseminated intravascular coagulation (DIC) and/or sepsis, comprising a conjugate as described herein, wherein the protein is AT III and the polymer is HAS.

This document also features a composition for the treatment of haemophilia A, comprising a conjugate as described herein, wherein the protein is Factor VIII and the polymer is HAS.

In another aspect, this document features a composition for the treatment of emphysema, cystic fibrosis, atopic dermatitis, chronic obstructive pulmonary disease (COPD) and/or bronchitis, comprising a conjugate as described herein, wherein the protein is A1AT and the polymer is HAS.

In another aspect, this document features a composition for the treatment of myocardial infarctions (heart attacks), thrombosis, thromboembolism or occlusive diseases, especially occlusive arterial diseases, comprising a conjugate as described herein, wherein the protein is tPA and the polymer is HAS.

In another aspect, this document features a composition for the treatment of severe sepsis, thrombosis, thromboembolism or occlusive diseases, especially occlusive arterial diseases, comprising a conjugate as described herein, wherein the protein is APC and the polymer is HAS.

In another aspect, this document features a composition for the treatment of leukaemia e.g. hairy cell leukaemia, chronic myelogeneous leukaemia, multiple myeloma, follicular lymphoma, cancer, e.g. carcinoid tumour, malignant melanoma and hepatitis, eg. chronic hepatitis B and chronic hepatitis C comprising a conjugate as described herein, wherein the protein is IFN alpha and the polymer is HAS.

In another aspect, this document features a composition for the treatment of multiple sclerosis, preferably relapsing forms of multiple sclerosis comprising a conjugate as described herein, wherein the protein is IFN beta and the polymer is HAS.

In another aspect, this document features a conjugate comprising hydroxyalkyl starch and a protein, wherein hydroxyalkyl starch is coupled with its oxidized reducing end via an amide linkage to a first crosslinking compound, the crosslinking compound being additionally linked via an amide linkage to a second crosslinking compound, the second crosslinking compound being linked via an azomethine and/or amino linkage to a protein, wherein the first crosslinking compound was preferably employed as an diamino functionalized compound and the second crosslinking compound was preferably employed as a carboxy and aldehyde or keto or hemiacetal, more preferably as a carboxy and aldehyde functionalized compound.

In yet another aspect, this document features a conjugate, comprising a protein and a polymer or a derivative thereof, wherein the polymer is a hydroxyalkyl starch (HAS), having a structure according to the formula

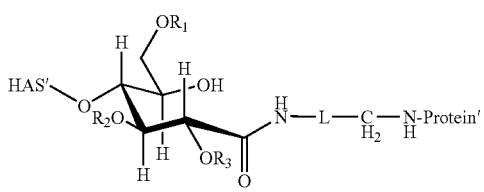

wherein $R_1$, $R_2$ and $R_3$ are independently hydrogen or a hydroxyalkyl group, a hydroxyaryl group, a hydroxyaralkyl group or a hydroxyalkaryl group having of from 1, preferably from 2 to 10 carbon atoms, preferably hydrogen or a hydroxyalkyl group, more preferably hydrogen or a hydroxyethyl group, and wherein L is an optionally substituted, linear, branched and/or cyclic hydrocarbon residue, optionally comprising at least one heteroatom, having from 1 to 60 preferably from 1 to 40, more preferably from 1 to 20, more preferably from 1 to 10, more preferably from 1 to 6 more preferably from 1 to 2 carbon atoms and especially preferably 1 carbon atom, L being in particular $CH_2$.

This document also features a conjugate, comprising a protein and a polymer or a derivative thereof, wherein the polymer is a hydroxyalkyl starch (HAS), having a structure according to the formula

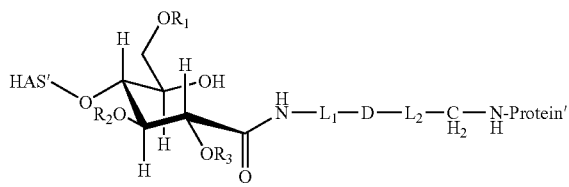

wherein $R_1$, $R_2$ and $R_3$ are independently hydrogen or a hydroxyalkyl group, a hydroxyaryl group, a hydroxyaralkyl group or a hydroxyalkaryl group having of from 1, preferably from 2 to 10 carbon atoms, preferably hydrogen or a hydroxyalkyl group, more preferably hydrogen or a hydroxyethyl group, and wherein $L_1$ and $L_2$ are independently an optionally substituted, linear, branched and/or cyclic hydrocarbon residue, optionally comprising at least one heteroatom, comprising an alkyl, aryl, aralkyl, heteroalkyl, and/or heteroaralkyl moiety, the residue having from 1 to 60 preferably from 1 to 40, more preferably from 1 to 20, more preferably from 1 to 10 carbon atoms, and wherein D is a linkage, preferably a covalent linkage which was formed by a suitable functional group $F_2$ linked to $L_1$ and a suitable functional group $F_3$ linked to $L_2$, wherein $F_3$ is capable of forming a chemical linkage with $F_2$. $L_1$ can be —$(CH_2)_n$— with n=2, 3, 4, 5, 6, 7, 8, 9, 10, preferably 2, 3, 4, 5, 6, more preferably 2, 3, 4, and especially preferably 4. $L_2$ can comprise an optionally suitably substituted aryl moiety, preferably an aryl moiety containing 6 carbon atoms, $L_2$ being especially preferably $C_6H_4$.

$F_2$ and $F_3$ can be independently selected from the group consisting of a C—C-double bond or a C—C-triple bond or an aromatic C—C-bond;

a thio group or the a hydroxy group;

an alkyl sulfonic acid hydrazide, or an aryl sulfonic acid hydrazide;

a 1,2-diol;

a 1,2 amino-thioalcohol;

an azide;

a 1,2-aminoalcohol;

an amino group —$NH_2$ or a derivative of an amino group comprising the structure unit —NH— such as aminoalkyl groups, aminoaryl group, aminoaralkyl groups, or alkarylamino groups;

a hydroxylamino group —O—$NH_2$, or a derivative of a hydroxylamino group comprising the structure unit —O—NH—, such as hydroxylalkylamino groups, hydroxylarylamino groups, hydroxylaralkylamino groups, or hydroxalalkarylamino groups;

an alkoxyamino group, an aryloxyamino group, an aralkyloxyamino group, or an alkaryloxyamino group, each comprising the structure unit —NH—O—;

a residue having a carbonyl group, -Q-C(=G)-M, wherein G is O or S, and M is, for example, —OH or —SH;

an alkoxy group, an aryloxy group, an aralkyloxy group, or an alkaryloxy group;

an alkylthio group, an arylthio group, an aralkylthio group, or an alkarylthio group;

an alkylcarbonyloxy group, an arylcarbonyloxy group, an aralkylcarbonyloxy group, or an alkarylcarbonyloxy group;

an activated ester having imide imid structure such as N-hydroxysuccinimide or having a structure unit O—N where N is part of a heteroaryl compound or, with G=O and Q absent, such as an aryloxy compound compounds with a substituted aryl residue such as pentafluorophenyl, paranitrophenyl or trichlorophenyl;

wherein Q is absent or NH or a heteroatom such as S or O;

—NH—$NH_2$, or —NH—NH—;

—$NO_2$;

a the nitril group;

a carbonyl group such as an aldehyde group or keto group;

a carboxy group;

a —N═C═O group or a —N═C═S group;

a vinyl halide group such as vinyl iodide, vinyl bromide group or triflate;

—C≡C—H;

—(C═NH2Cl)—OAlkyl;

a group —(C═O)—$CH_2$-Hal wherein Hal is Cl, Br, or I;

—CH═CH—$SO_2$—;

a disulfide group comprising the structure —S—S—;

the group

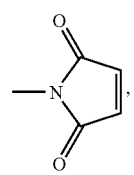

and
the group

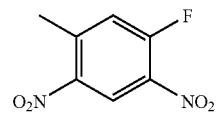

and wherein $F_3$ is a functional group capable of forming a chemical linkage with $F_2$ and is preferably selected from the above-mentioned group, $F_2$ preferably comprising the moiety —NH—, more preferably comprising an amino group, $F_3$ preferably comprising the moiety —(C═G)-, more preferably —(C═O)—, more preferably the moiety —(C═G)-G-, still more preferably —(C═O)-G-, and especially preferably —(C═O)—O, D being particularly preferably an amide linkage.

The conjugate can have a structure according to the formula

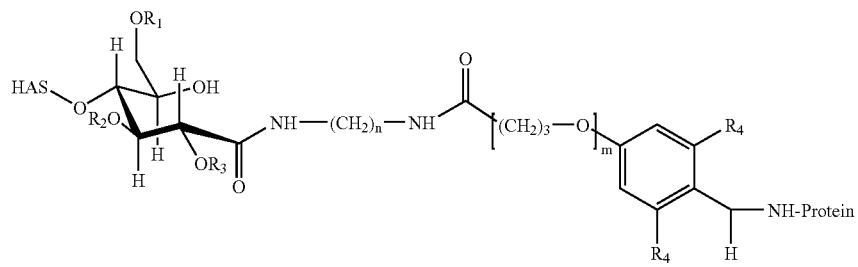

n=2, 3, or 4, $R_4$ being independently hydrogen or a methoxy group, and m=0 when $R_4$ is hydrogen and m=1 when $R_4$ is methoxy.

In another aspect, this document features a conjugate, comprising a protein and a polymer or a derivative thereof, wherein the polymer is a hydroxyalkyl starch (HAS), having a structure according to the formula

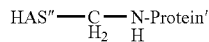

wherein the carbon atom of the moiety —$CH_2$—NH— is derived from an aldehyde group which was introduced in the polymer by a ring-opening oxidation reaction, and wherein the nitrogen atom is derived from an amino group of the protein.

In any of the conjugates described herein, the protein can be selected from the group consisting of EPO, G-CSF, IFN alpha, IFN beta, AT III, IL-2, IL-3, myoglobin, SOD, and BSA, preferably from the group consisting of rhEPO, rhG-CSF, rhIFN alpha, rhIFN beta, rhAT III, rhIL-2, rhIL-3, myoglobin, SOD, and BSA, and/or from the group consisting of A1AT, factor VII, factor VIII, factor IX, tPA, and APC.

This document also features a composition for the treatment of episodes in hemophilia A or B patients with inhibitors to Factor VIII or Factor IX, comprising a conjugate as described herein, wherein the protein is Factor VII and the polymer is HAS.

In another aspect, this document features a composition for the control and prevention of hemorrhagic episodes in patients with hemophillia B, preferably congenital factor IX deficiency or Christmas disease, including control and prevention of bleeding in surgical settings, comprising a conjugate as described herein, wherein the protein is Factor IX and the polymer is HAS.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

Lane A: Protein marker SeeBlue®Plus2 (Invitrogen GmbH, Karlsruhe, D) Molecular weight marker from top to bottom: 188 kD, 98 kD, 62 kD, 49 kD, 38 kD, 28 kD, 17 kD, 14 kD, 6 kD, 3 kD.

Lane B: Crude product after conjugation of G-CSF (Neupogen®) with HES as described in Example 2.1(a).

Lane C: G-CSF starting material.

Figure 1A:
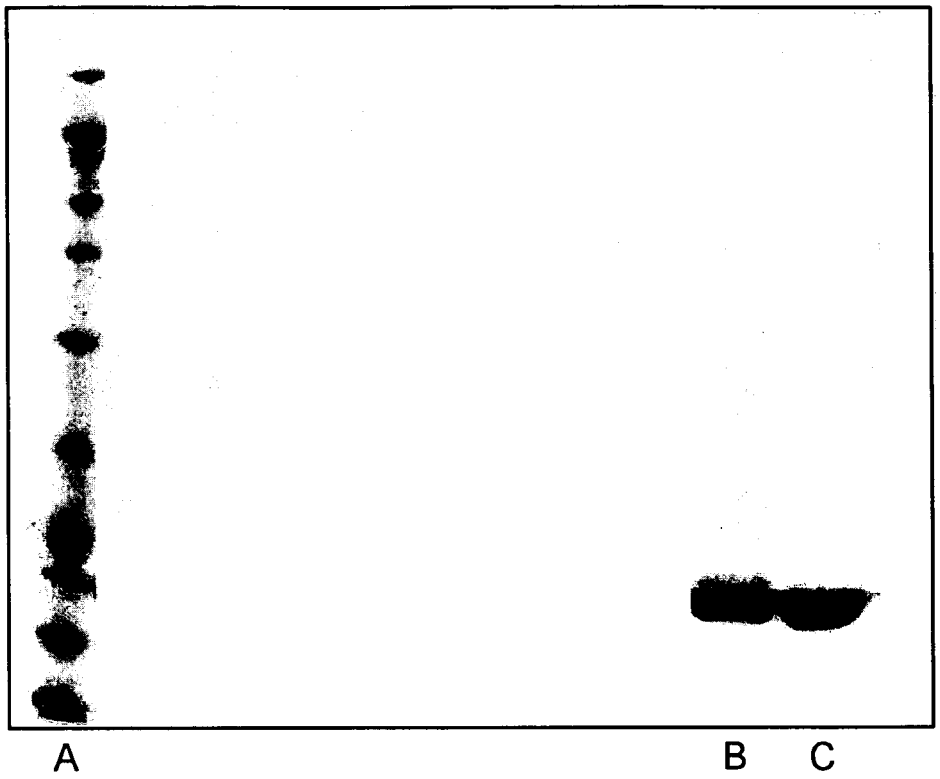
FIG. 1a shows an SDS page analysis of the HES-G-CSF conjugate, produced according to Example 2.1(a), Neupogen®. For gel electrophoresis, a XCell Sure Lock Mini Cell (Invitrogen GmbH, Karlsruhe, D) and a Consort E143 power supply (CONSORTnv, Turnhout, B) were employed. A 12% Bis-Tris gel together with a MOPS SDS running buffer at reducing conditions (both Invitrogen GmbH, Karlsruhe, D) were used according to the manufactures instruction.
Figure 1B:
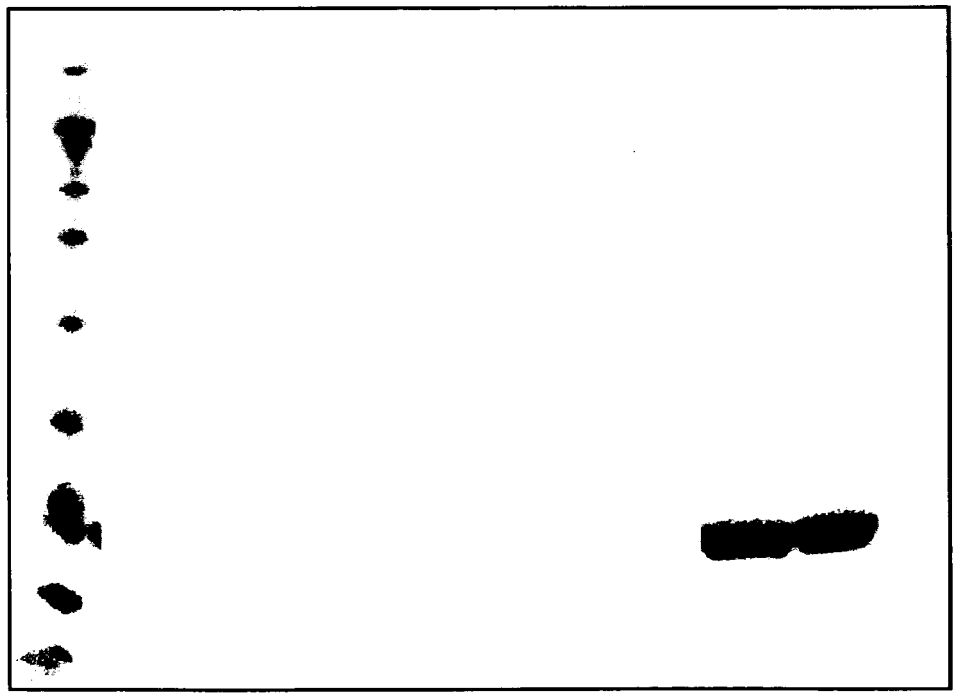

FIG. 1b shows an SDS page analysis of the HES-G-CSF conjugate, produced according to Example 2.1(a), Granocyte®. For gel electrophoresis, a XCell Sure Lock Mini Cell (Invitrogen GmbH, Karlsruhe, D) and a Consort E143 power supply (CONSORTnv, Turnhout, B) were employed. A 12% Bis-Tris gel together with a MOPS SDS running buffer at reducing conditions (both Invitrogen GmbH, Karlsruhe, D) were used according to the manufactures instruction.

Lane A: Protein marker SeeBlue®Plus2 (Invitrogen GmbH, Karlsruhe, D). Molecular weight marker from top to bottom: 188 kD, 98 kD, 62 kD, 49 kD, 38 kD, 28 kD, 17 kD, 14 kD, 6 kD, 3 kD.

Lane B: Crude product after conjugation of G-CSF (Granocyte®) with HES as described in Example 2.1(a).

Lane C: G-CSF starting material.

Figure 2:
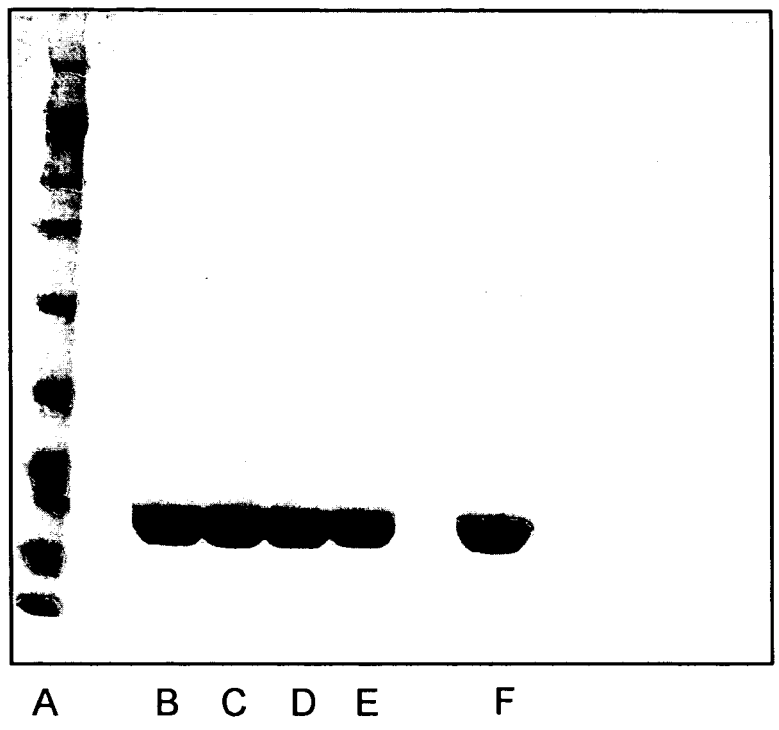

FIG. 2 shows an SDS page analysis of the HES-G-CSF conjugate, produced according to Example 2.1(b), G-CSF being purified hG-CSF having essentially the same characteristics as the commercial product Neupogen®. For gel electrophoresis a XCell Sure Lock Mini Cell (Invitrogen GmbH, Karlsruhe, D) and a Consort E143 power supply (CONSORTnv, Turnhout, B) were employed. A 12% Bis-Tris gel together with a MOPS SDS running buffer at reducing conditions (both Invitrogen GmbH, Karlsruhe, D) were used according to the manufactures instruction.

Lane A: Protein marker SeeBlue®Plus2 (Invitrogen GmbH, Karlsruhe, D). Molecular weight marker from top to bottom: 188 kD, 98 kD, 62 kD, 49 kD, 38 kD, 28 kD, 17 kD, 14 kD, 6 kD, 3 kD Lane B: Crude product after conjugation of G-CSF with HES10/0.4 in 0.1 M NaOAc buffer pH 5.0.

Lane C: Crude product after conjugation of G-CSF with HES10/0.7 in 0.1 M NaOAc buffer pH 5.0.

Lane D: Crude product after conjugation of G-CSF with HES50/0.4 in 0.1M NaOAc buffer pH 5.0.

Lane E: Crude product after conjugation of G-CSF with HES50/0.7 in 0.1 M NaOAc buffer pH 5.0.
Lane F: G-CSF starting material.

Figure 3:
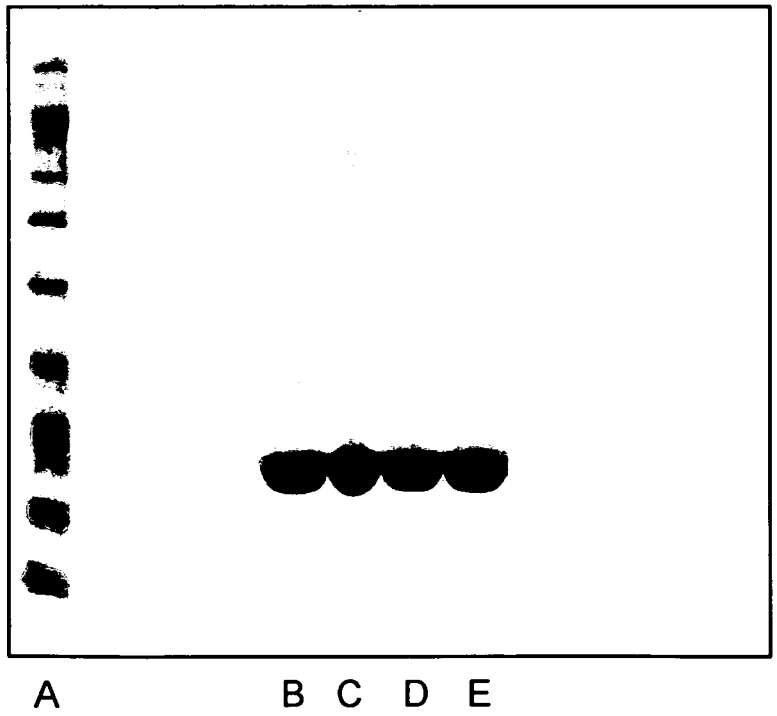

FIG. 3 shows an SDS page analysis of the HES-G-CSF conjugates, produced according to Example 2.2, G-CSF being purified hG-CSF having essentially the same characteristics as the commercial product Neupogen®. For gel electrophoresis a XCell Sure Lock Mini Cell (Invitrogen GmbH, Karlsruhe, D) and a Consort E143 power supply (CONSORTnv, Turnhout, B) were employed. A 12% Bis-Tris gel together with a MOPS SDS running buffer at reducing conditions (both Invitrogen GmbH, Karlsruhe, D) were used according to the manufactures instruction.
Lane A: Protein marker SeeBlue®Plus2 (Invitrogen GmbH, Karlsruhe, D). Molecular weight marker from top to bottom: 188 kD, 98 kD, 62 kD, 49 kD, 38 kD, 28 kD, 17 kD, 14 kD, 6 kD, 3 kD.
Lane B: Crude product after conjugation of G-CSF with oxidized HES10/0.7 in 0.1 M NaOAc buffer pH 5.0.
Lane C: Crude product after conjugation of G-CSF with oxidized HES50/0.4 in 0.1 M NaOAc buffer pH 5.0.
Lane D: Crude product after conjugation of G-CSF with oxidized HES50/0.7 in 0.1M NaOAc buffer pH 5.0.
Lane E: G-CSF starting material.

Figure 4:
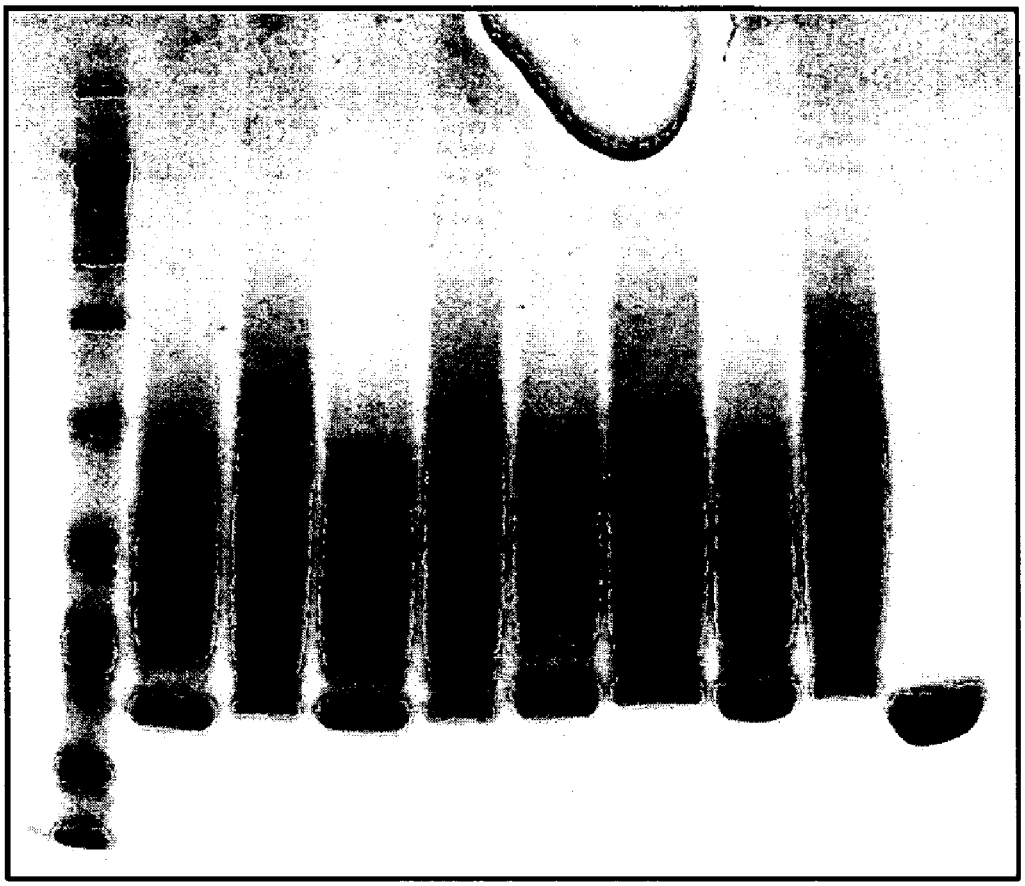

FIG. 4 shows an SDS page analysis of the HES-G-CSF conjugates, produced according to Example 2.3, G-CSF is Neupogen® or Granocyte®. For gel electrophoresis a XCell Sure Lock Mini Cell (Invitrogen GmbH, Karlsruhe, D) and a Consort E143 power supply (CONSORTnv, Turnhout, B) were employed. A 12% Bis-Tris gel together with a MOPS SDS running buffer at reducing conditions (both Invitrogen GmbH, Karlsruhe, D) were used according to the manufactures instruction.
Lane A: Protein marker SeeBlue®Plus2 (Invitrogen GmbH, Karlsruhe, D). Molecular weight marker from top to bottom: 188 kD, 98 kD, 62 kD, 49 kD, 38 kD, 28 kD, 17 kD, 14 kD, 6 kD, 3 kD.
Lane B: Crude product (i-N) according to Example 2.3.
Lane C: Crude product (ii-N) according to Example 2.3.
Lane D: Crude product (iii-N) according to Example 2.3.
Lane E: Crude product (iv-N) according to Example 2.3.
Lane F: Crude product (i-G) according to Example 2.3.
Lane G: Crude product (ii-G) according to Example 2.3.
Lane H: Crude product (iii-G) according to Example 2.3.
Lane I: Crude product (iv-G) according to Example 2.3.
Lane J: Neupogen®.

Figure 5:
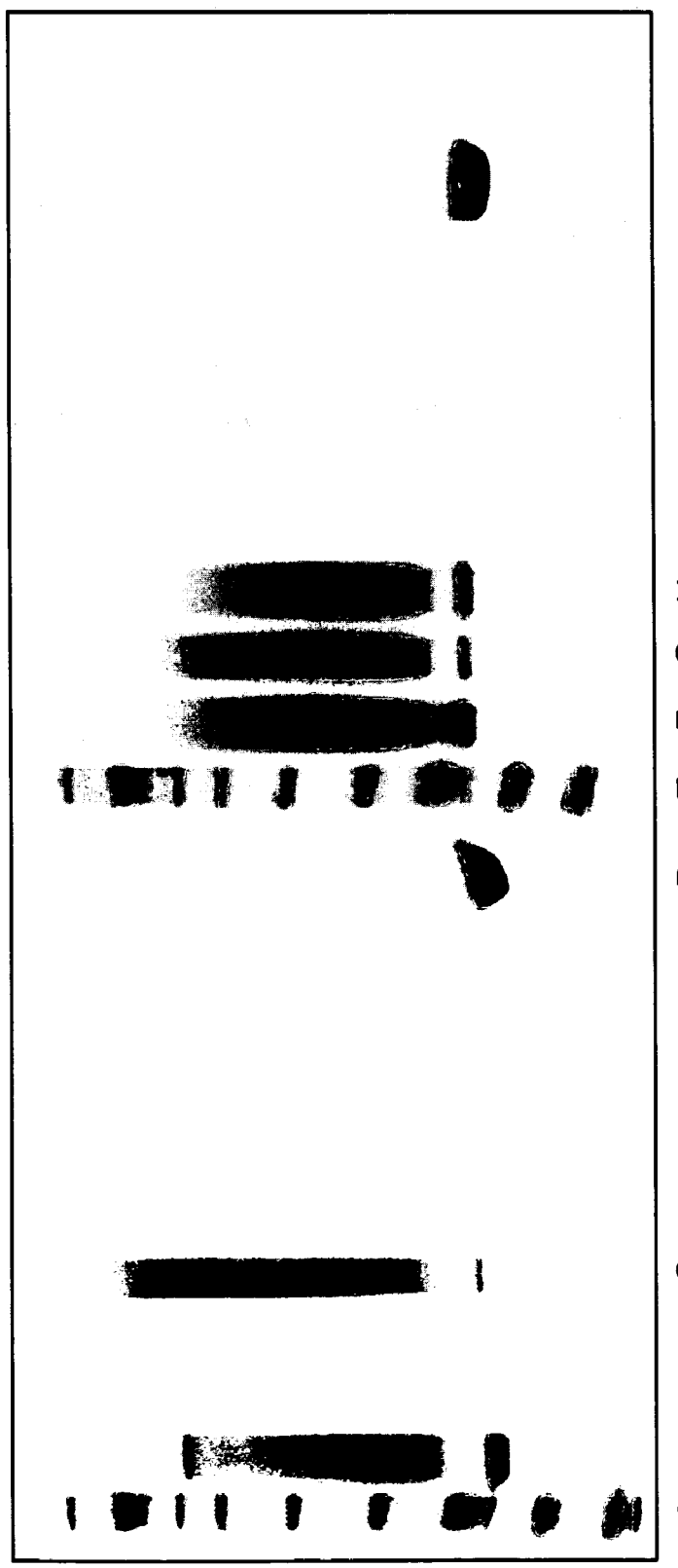

FIG. 5 shows an SDS page analysis of the HES-G-CSF conjugates, produced according to Example 2.4, G-CSF being purified hG-CSF having essentially the same characteristics as the commercial product Neupogen®. For gel electrophoresis a XCell Sure Lock Mini Cell (Invitrogen GmbH, Karlsruhe, D) and a Consort E143 power supply (CONSORTnv, Turnhout, B) were employed. A 12% Bis-Tris gel together with a MOPS SDS running buffer at reducing conditions (both Invitrogen GmbH, Karlsruhe, D) were used according to the manufactures instruction.
Lane A: Protein marker SeeBlue®Plus2 (Invitrogen GmbH, Karlsruhe, D). Molecular weight marker from top to bottom: 188 kD, 98 kD, 62 kD, 49 kD, 38 kD, 28 kD, 17 kD, 14 kD, 6 kD, 3 kD.
Lane B: Crude product (vi) according to Example 2.4.
Lane C: Crude product (v) according to Example 2.4.
Lane D: G-CSF starting material.
Lane E: Protein marker SeeBlue®Plus2 (Invitrogen GmbH, Karlsruhe, D). Molecular weight marker from top to bottom: 188 kD, 98 kD, 62 kD, 49 kD, 38 kD, 28 kD, 17 kD, 14 kD, 6 kD, 3 kD.
Lane F: Crude product (ix) according to Example 2.4.
Lane G: Crude product (viii) according to Example 2.4.
Lane H: Crude product (vii) according to Example 2.4.
Lane I: G-CSF starting material.

Figure 6:
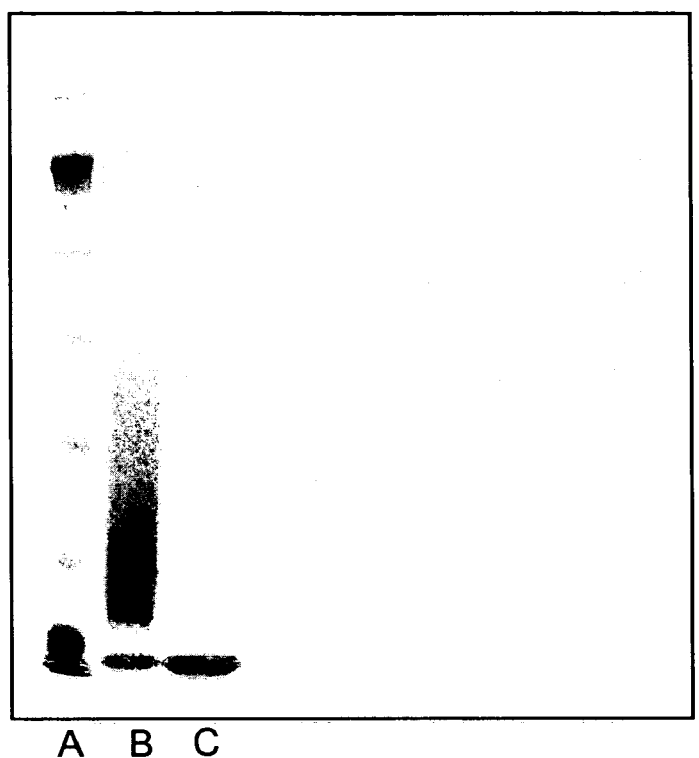

FIG. 6 shows an SDS page analysis of the HES-G-CSF conjugate, produced according to Example 2.5, G-CSF being purified hG-CSF having essentially the same characteristics as the commercial product Neupogen®. For gel electrophoresis a XCell Sure Lock Mini Cell (Invitrogen GmbH, Karlsruhe, D) and a Consort E143 power supply (CONSORTnv, Turnhout, B) were employed. A 10% Bis-Tris gel together with a MOPS SDS running buffer at reducing conditions (both Invitrogen GmbH, Karlsruhe, D) were used according to the manufactures instruction.
Lane A: Protein marker SeeBlue®Plus2 (Invitrogen GmbH, Karlsruhe, D). Molecular weight marker from top to bottom: 188 kD, 98 kD, 62 kD, 49 kD, 38 kD, 28 kD, 17 kD, 14 kD, 6 kD, 3 kD.
Lane B: Crude product according to Example 2.5.
Lane C: G-CSF starting material.

Figure 7:
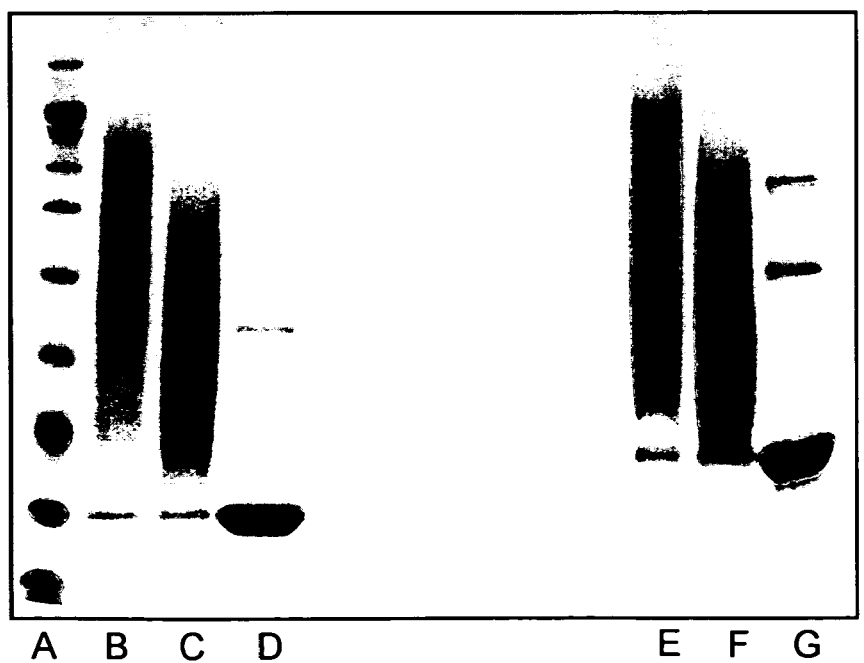

FIG. 7 shows an SDS page analysis of the HES-Protein conjugates, produced according to Example 2.6. For gel electrophoresis a XCell Sure Lock Mini Cell (Invitrogen GmbH, Karlsruhe, D) and a Consort E143 power supply (CONSORTnv, Turnhout, B) were employed. A 12% Bis-Tris gel together with a MOPS SDS running buffer at reducing conditions (both Invitrogen GmbH, Karlsruhe, D) were used according to the manufactures instruction. Samples with a volume grater then 15 µl were concentrated in vacuo to this volume.
Lane A: Protein marker SeeBlue®Plus2 (Invitrogen GmbH, Karlsruhe, D). Molecular weight marker from top to bottom: 188 kD, 98 kD, 62 kD, 49 kD, 38 kD, 28 kD, 17 kD, 14 kD, 6 kD, 3 kD.
Lane B: Conjugation of IL-2 with aldehydo-HES synthesized as described in Example 1.9.
Lane C: Conjugation of IL-2 with aldehydo-HES synthesized as described in Example 1.10.
Lane D: Control: IL-2, treated with sodium borohydride without aldehydo-HES.
Lane E: Conjugation of IFN-alpha with aldehydo-HES synthesized as described in Example 1.9.
Lane F: Conjugation of IFN-alpha with aldehydo-HES synthesized as described in Example 1.10.
Lane G: Control: IFN-alpha, treated with sodium borohydride without aldehydo-HES.

Figure 8:
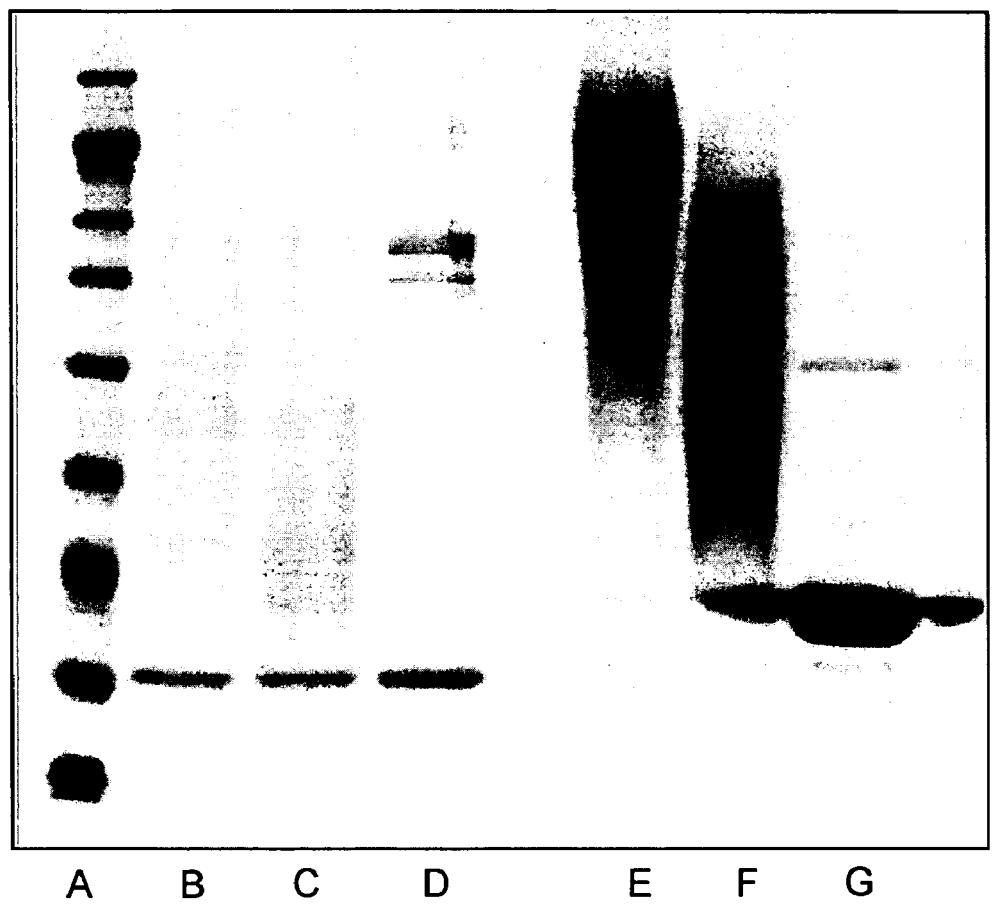

FIG. 8 shows an SDS page analysis of the HES-Protein conjugates, produced according to Example 2.6. For gel electrophoresis a XCell Sure Lock Mini Cell (Invitrogen GmbH, Karlsruhe, D) and a Consort E143 power supply (CONSORTnv, Turnhout, B) were employed. A 12% Bis-Tris gel together with a MOPS SDS running buffer at reducing conditions (both Invitrogen GmbH, Karlsruhe, D) were used according to the manufactures instruction. Samples with a volume grater then 15 µL were concentrated in vacuo to this volume.
Lane A: Protein marker SeeBlue®Plus2 (Invitrogen GmbH, Karlsruhe, D). Molecular weight marker from top to bottom: 188 kD, 98 kD, 62 kD, 49 kD, 38 kD, 28 kD, 17 kD, 14 kD, 6 kD, 3 kD.
Lane B: Conjugation of IL-3 with aldehydo-HES synthesized as described in Example 1.9.
Lane C: Conjugation of IL-3 with aldehydo-HES synthesized as described in Example 1.10.
Lane D: Control: IL-3, treated with sodium borohydride without aldehydo-HES.

Lane E: Conjugation of Myoglobin with aldehydo-HES synthesized as described in Example 1.9.
Lane F: Conjugation of Myoglobin with aldehydo-HES synthesized as described in Example 1.10.
Lane G: Control: Myoglobin, treated with sodium borohydride without aldehydo-HES.

Figure 9:

FIG. 9 shows an SDS page analysis of the HES-Protein conjugates, produced according to Example 2.6. For gel electrophoresis a XCell Sure Lock Mini Cell (Invitrogen GmbH, Karlsruhe, D) and a Consort E143 power supply (CONSORTnv, Turnhout, B) were employed. A 3-8% Tris-Acetate gel together with a Tris-Acetate SDS running buffer at reducing conditions (both Invitrogen GmbH, Karlsruhe, D) were used according to the manufactures instruction.
Lane A: Protein marker SeeBlue®Plus2 (Invitrogen GmbH, Karlsruhe, D). Molecular weight marker from top to bottom: 188 kD, 98 kD, 62 kD, 49 kD, 38 kD, 28 kD, 17 kD, 14 kD, 6 kD, 3 kD.
Lane B: Conjugation of BSA with aldehydo-HES synthesized as described in Example 1.9.
Lane C: Conjugation of BSA with aldehydo-HES synthesized as described in Example 1.10.
Lane D: Control: BSA, treated with sodium borohydride without aldehydo-HES.

Figure 10:
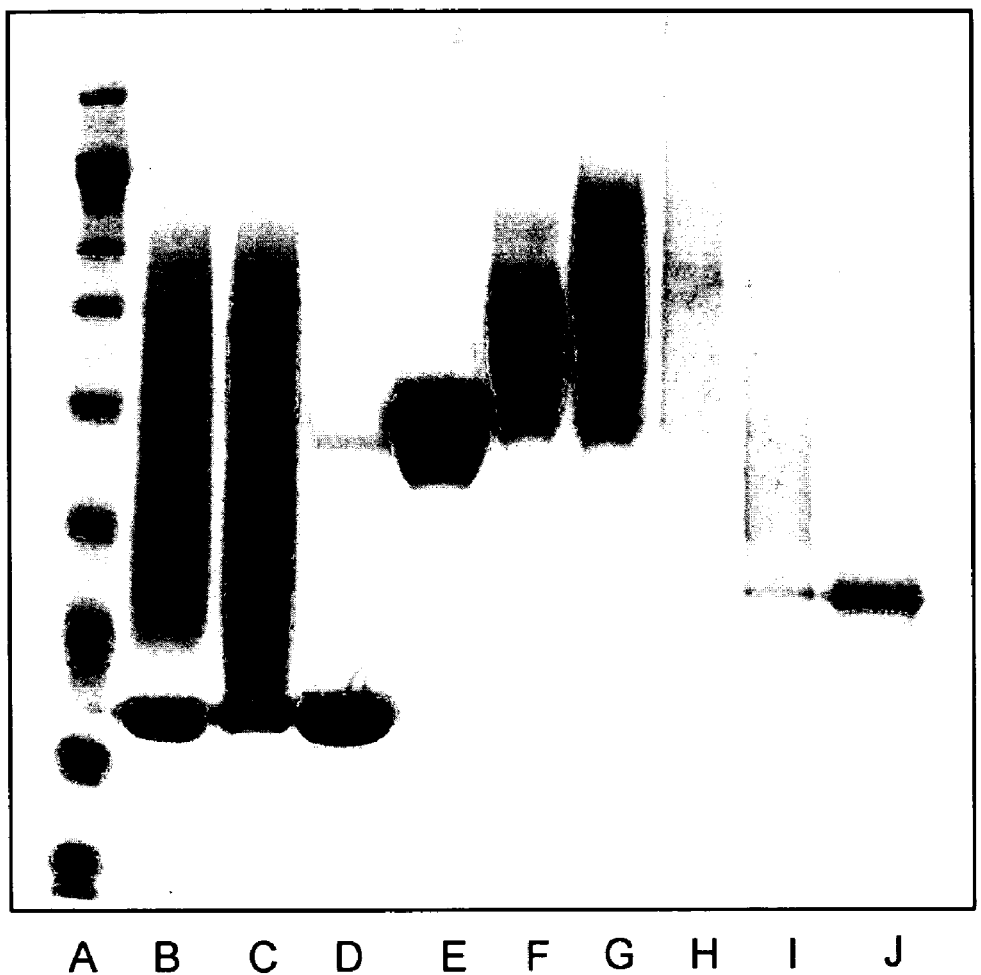

FIG. 10 shows an SDS page analysis of the HES-Protein conjugates, produced according to Example 2.6. For gel electrophoresis a XCell Sure Lock Mini Cell (Invitrogen GmbH, Karlsruhe, D) and a Consort E143 power supply (CONSORTnv, Turnhout, B) were employed. A 12% Bis-Tris gel together with a MOPS SDS running buffer at reducing conditions (both Invitrogen GmbH, Karlsruhe, D) were used according to the manufactures instruction. Samples with a volume grater then 15 µL were concentrated in vacuo to this volume.
Lane A: Protein marker SeeBlue®Plus2 (Invitrogen GmbH, Karlsruhe, D) Molecular weight marker from top to bottom: 188 kD, 98 kD, 62 kD, 49 kD, 38 kD, 28 kD, 17 kD, 14 kD, 6 kD, 3 kD.
Lane B: Conjugation of SOD with aldehydo-HES synthesized as described in Example 1.9.
Lane C: Conjugation of SOD with aldehydo-HES synthesized as described in Example 1.10.
Lane D: Control: SOD, treated with sodium borohydride without aldehydo-HES.
Lane E: Control: EPO, treated with sodium borohydride without aldehydo-HES.
Lane F: Conjugation of EPO with aldehydo-HES synthesized as described in Example 1.9.
Lane G: Conjugation of EPO with aldehydo-HES synthesized as described in Example 1.10.
Lane H: Conjugation of IFN-beta with aldehydo-HES synthesized as described in Example 1.9.
Lane I: Conjugation of IFN-beta with aldehydo-HES synthesized as described in Example 1.10.
Lane J: Control: IFN-beta, treated with sodium borohydride without aldehydo-HES.

Figure 11:
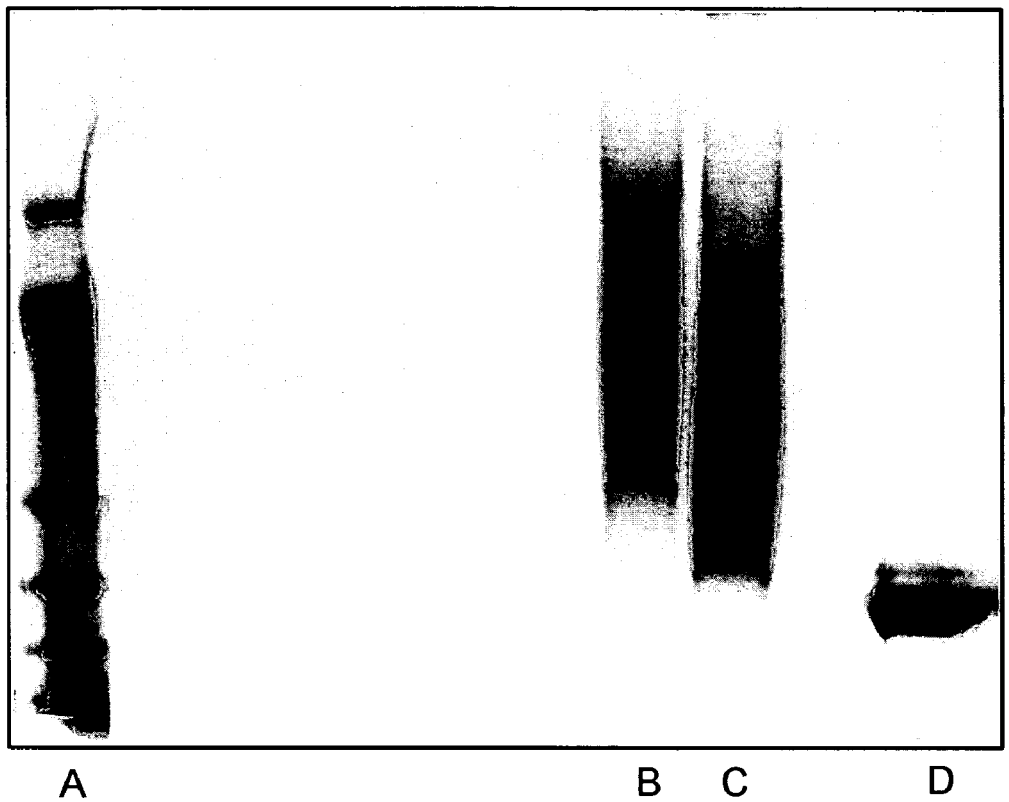

FIG. 11 shows an SDS page analysis of the HES-Protein conjugates, produced according to Example 2.6. For gel electrophoresis a XCell Sure Lock Mini Cell (Invitrogen GmbH, Karlsruhe, D) and a Consort E143 power supply (CONSORTnv, Turnhout, B) were employed. A 3-8% Tris-Acetate gel together with a Tris-Acetate SDS running buffer at reducing conditions (both Invitrogen GmbH, Karlsruhe, D) were used according to the manufactures instruction.
Lane A: Protein marker SeeBlue®Plus2 (Invitrogen GmbH, Karlsruhe, D) Molecular weight marker from top to bottom: 188 kD, 98 kD, 62 kD, 49 kD, 38 kD, 28 kD, 17 kD, 14 kD, 6 kD, 3 kD.
Lane B: Conjugation of AT III with aldehydo-HES synthesized as described in Example 1.9.
Lane C: Conjugation of AT III with aldehydo-HES synthesized as described in Example 1.10.
Lane D: Control: AT III, treated with sodium borohydride without aldehydo-HES.

Figure 12:
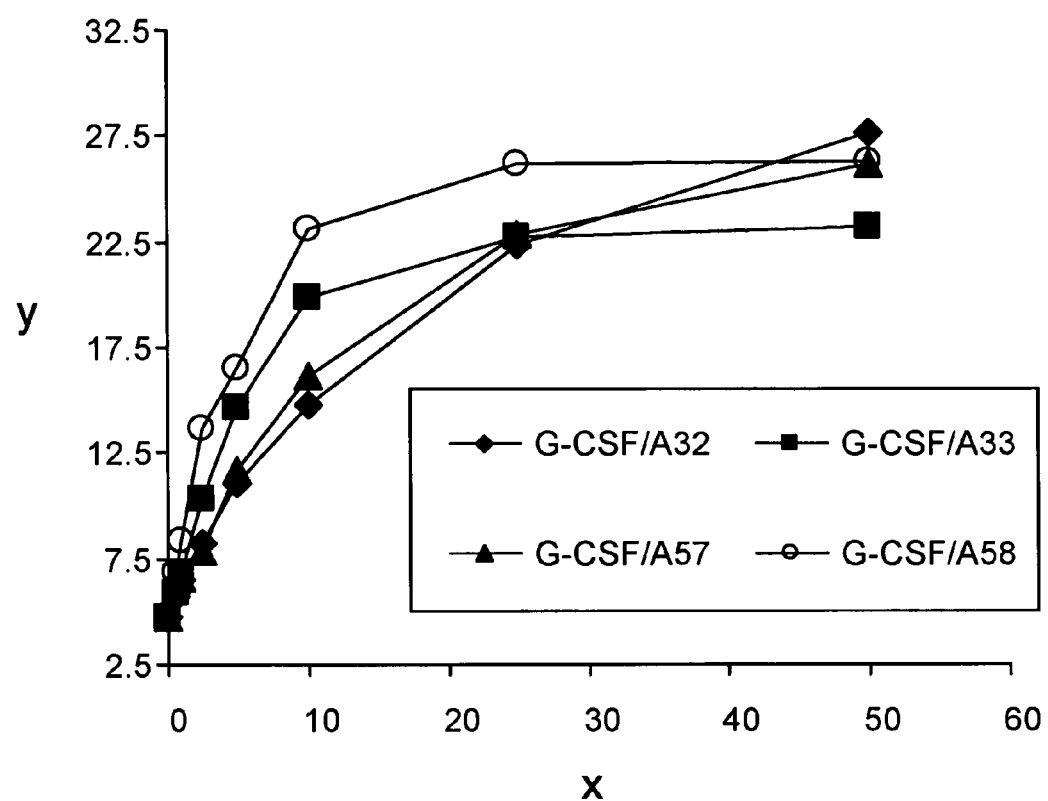

FIG. 12 shows the in vitro results of Example 4.
In the diagram, the x axis shows the concentration in pg/ml, the y axis refers to the number of cells/100,000.
In the diagram, the following abbreviations refer to
G-CSF/A32 G-CSF conjugate as prepared according to Example 2.5
G-CSF/A33 G-CSF starting material, used for the conjugate of Example 2.5
G-CSF/A57 non-modified Neulasta®
G-CSF/A58 non-modified Neupogen®

Figure 13:
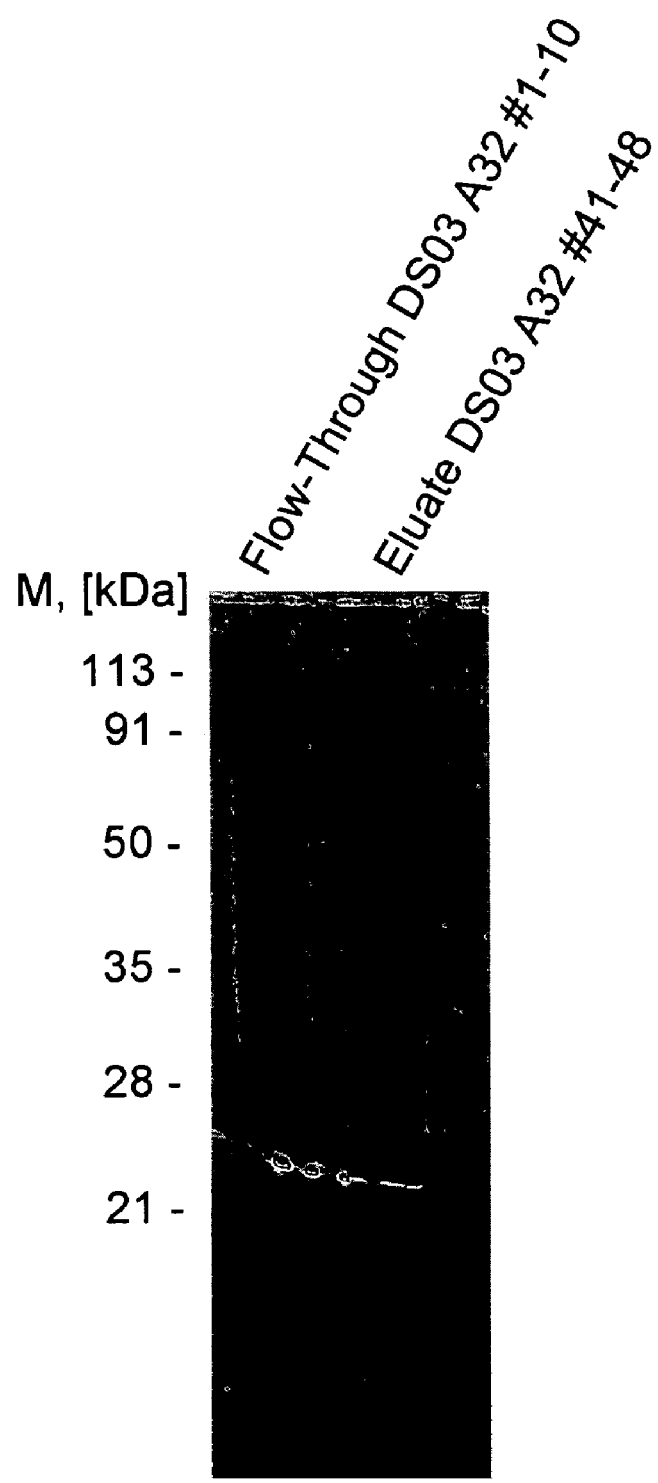

FIG. 13 shows an SDS-PAGE gel of the flow-through and eluate of HES-modified G-CSF according to Example 2.5 after chromatography (see Example 3) on DEAE-Sepharose CL-6B; 1.5% of the indicated fractions were desalted by ultrafiltration, dried in a SpeedVac and were applied onto a 12.5% polyacrylamide gel.

Figure 14:
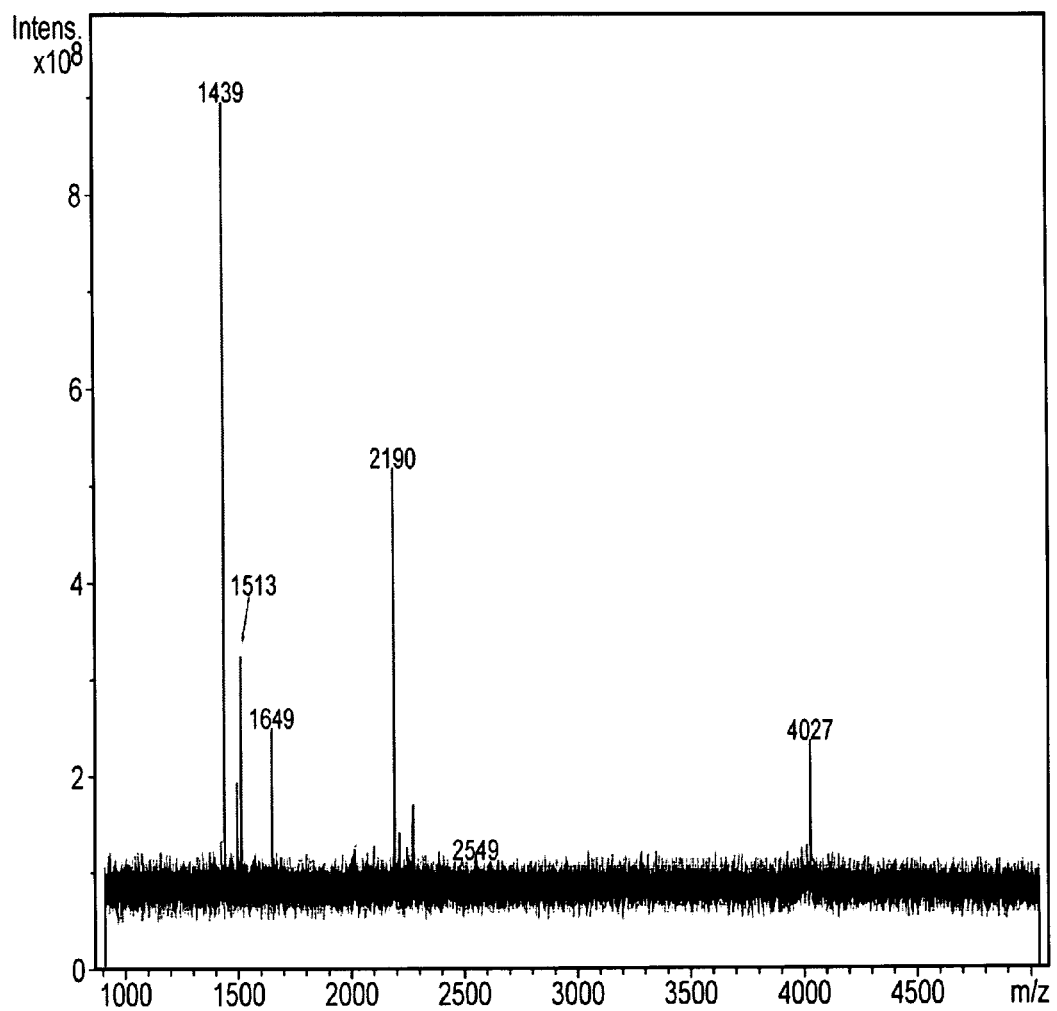

FIG. 14 is a MALDI/TOF spectrum of G-CSF (see Example 3)

Figure 15:
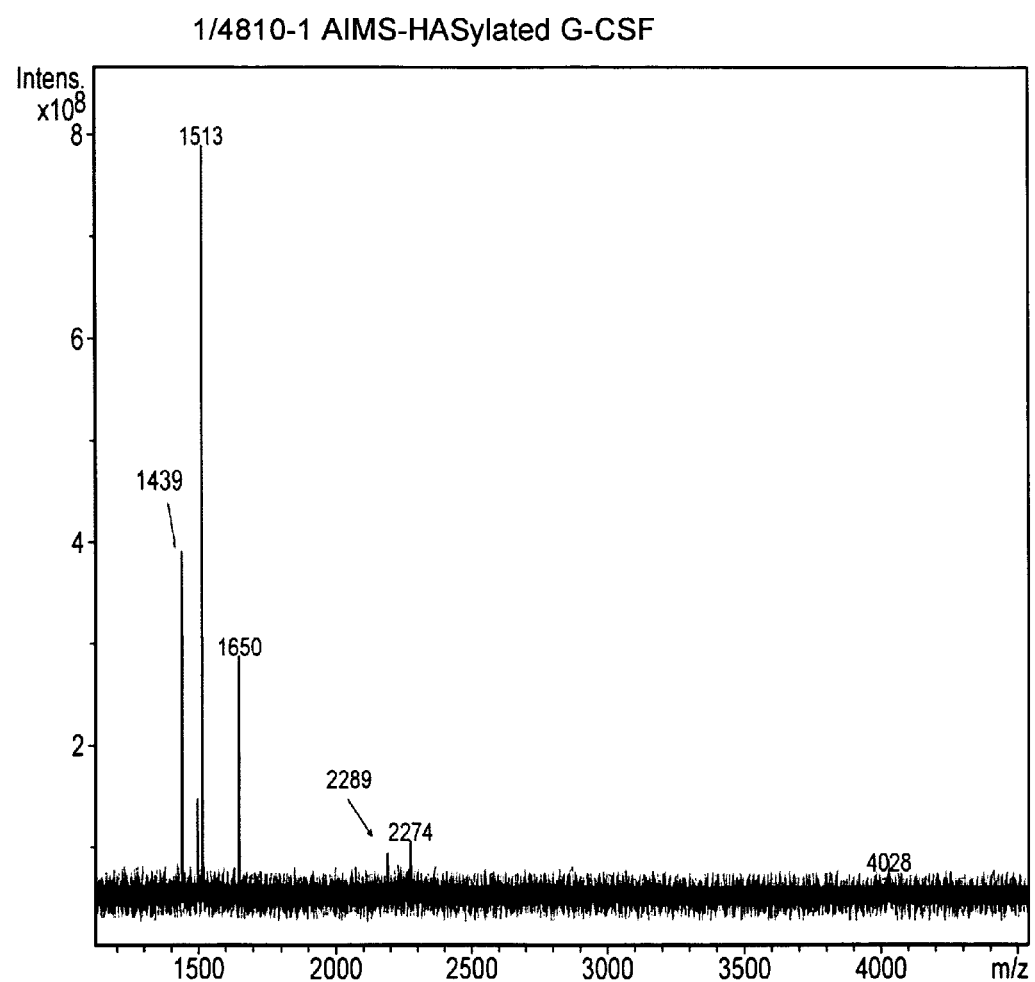

FIG. 15 is a MALDI/TOF spectrum of HES-modified G-CSF (see Example 3)

Figure 16:
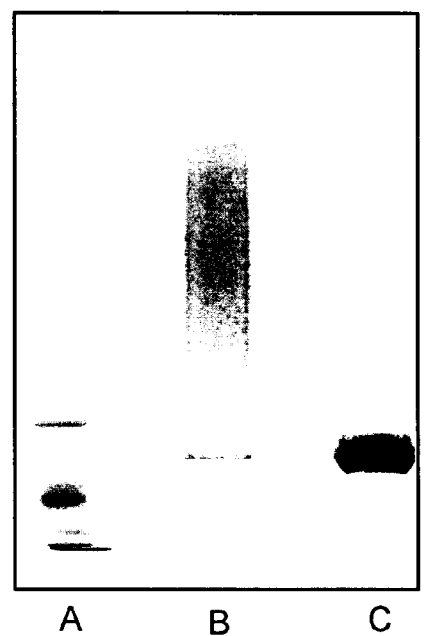

FIG. 16 shows results of example 5 (analysis of the crude α1AT-HES conjugates prepared as described in example 5.5 by gel electrophoresis).
For gel electrophoresis a XCell Sure Lock Mini Cell (Invitrogen GmbH, Karlsruhe, D) and a Power Pac 200 power supply (Bio-Rad, München, D) were employed. A 3-8% Tris-Acetate gel together with a Tris-Acetate SDS running buffer at reducing conditions (both Invitrogen GmbH, Karlsruhe, D) were used according to the manufactures instruction.
Lane A: Unstained SDS Page Protein Marker 6.5-200 KDa (SERVA Elektrophoresis GmbH, Heidelberg, D) Molecular weight marker from top to bottom: 200 KD, 116 KD, 67 KD, 45 KD, 29 KD, 21 KD, 14.3 KD, 6.5 KD;
Lane B: Conjugation to aldehydo-HES as described in example 5.5;
Lane C: Conjugation to HES as described in example 5.6.

Figure 17:
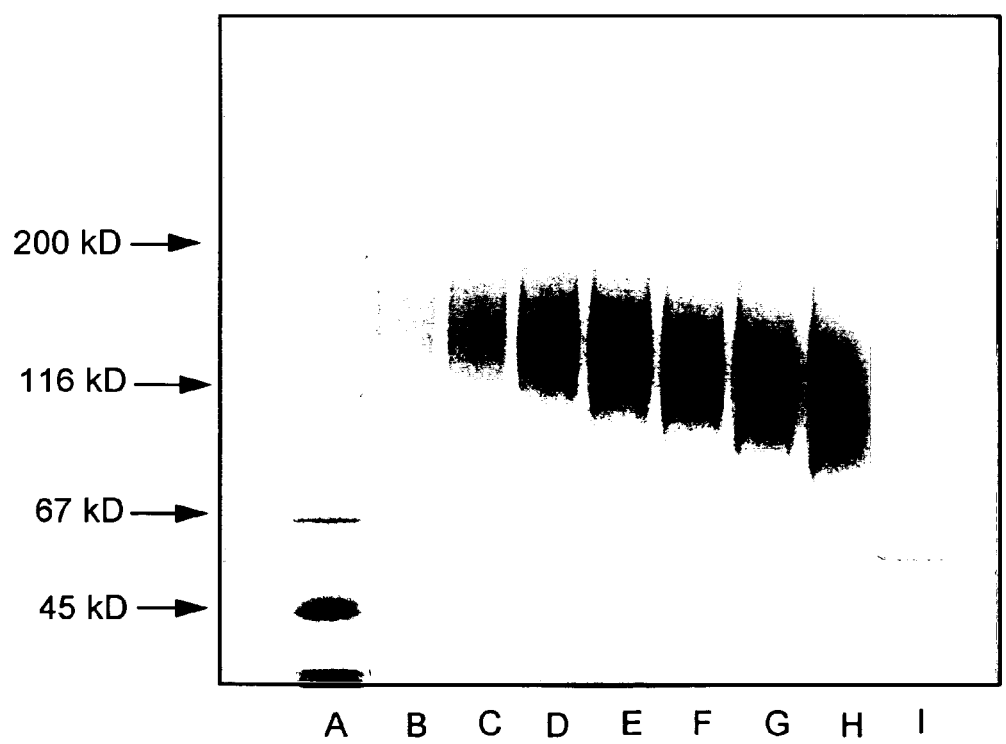

FIG. 17 shows results of example 5 (analysis of the fractions B1-C6 collected after Ion Exchange Chromatography (see example 5.7)
Lane A: Unstained SDS Page Protein Marker 6.5-200 KDa (SERVA Elektrophoresis GmbH, Heidelberg, D) Molecular weight marker from top to bottom: 200 KD, 116 KD, 67 KD, 45 KD, 29 KD, 21 KD, 14.3 KD, 6.5 KD;
Lane B: Fraction B1
Lane C: Fraction C1
Lane D: Fraction C2
Lane E: Fraction C3
Lane F: Fraction C4
Lane G: Fraction C5
Lane H: Fraction C6
Lane I: A1AT (GTC Biotherapeutics Inc., Framingham, Mass., lot No. 080604A)

Figure 18:
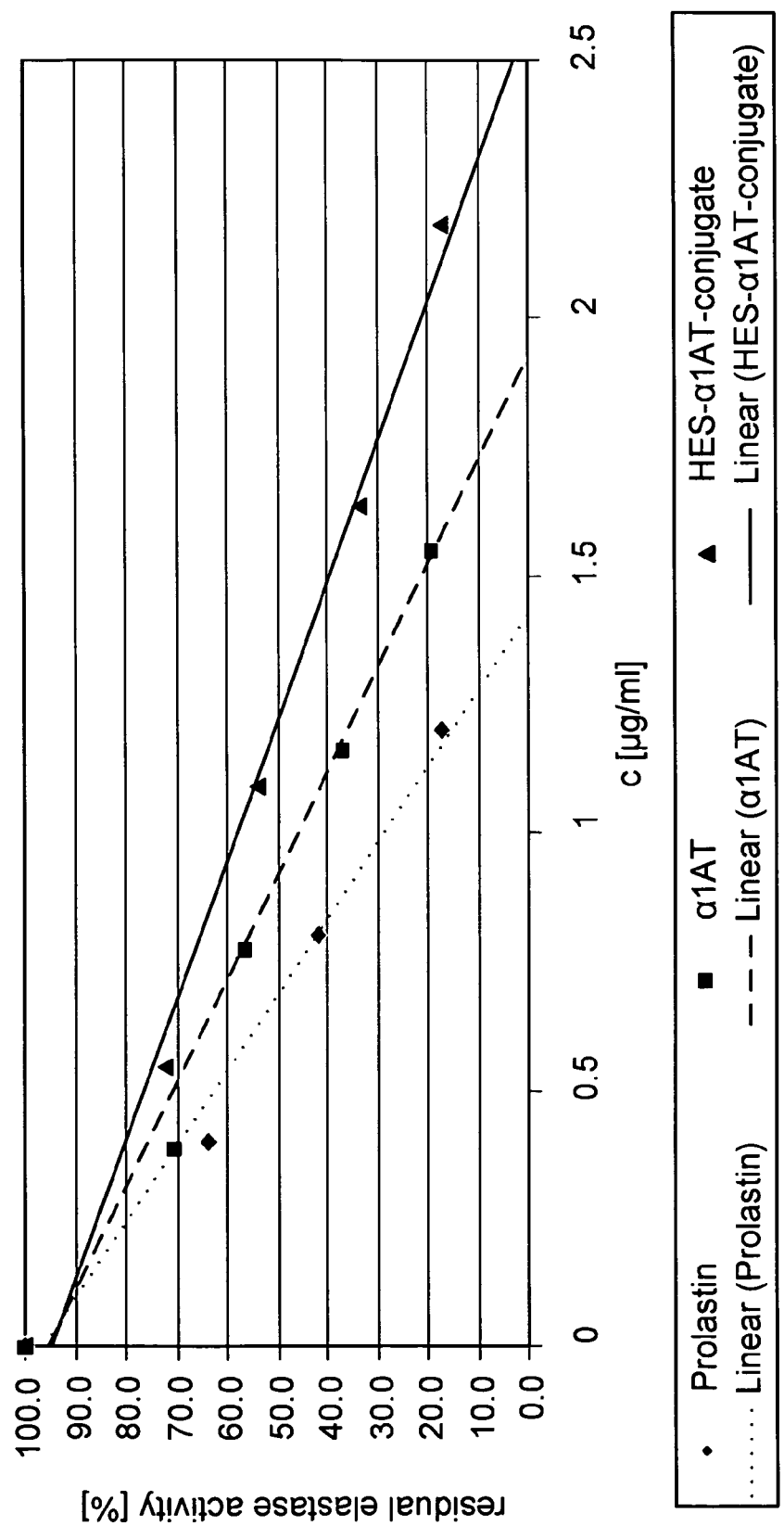

FIG. 18 shows the residual enzyme activity vs. concentration plot of Prolastin® HS (Bayer Vital GmbH, Leverkusen, Germany, Lot No. PR4HA43), A1AT (GTC Biotherapeutics Inc., Framingham, Mass., lot No. 080604A) and a HES-A1AT-conjugate synthesized as described in example 5.5

Figure 19:
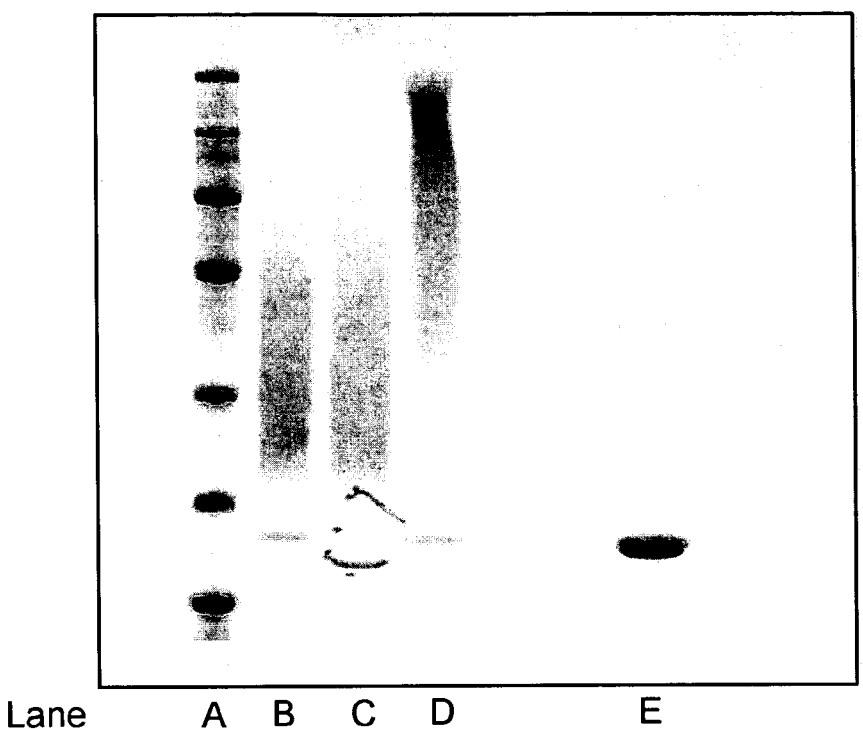

FIG. 19 shows the gel electrophoresis of the reaction mixtures of example 6.2(b).

For gel electrophoresis a XCell Sure Lock Mini Cell (Invitrogen GmbH, Karlsruhe, D) and a Consort E143 power supply (CONSORTnv, Turnhout, B) were employed. A 12% Bis-Tris gel together with a MOPS SDS running buffer at reducing conditions (both Invitrogen GmbH, Karlsruhe, D) were used according to the manufactures instruction. The gel was stained with Roti-Blue (Carl Roth GmbH+Co. KG, Karlsruhe, D) according to the manufacturer's instruction.

Lane A: Protein marker Roti-Mark STANDARD (Carl Roth GmbH+Co. KG, Karlsruhe, D) Molecular weight marker from top to bottom: 200 KD, 119 KD, 66 KD, 43 KD, 29 KD, 20 KD, 14.3 KD
Lane B: Crude product after conjugation of hG-CSF with the HES derivative prepared in example 6.1(d)
Lane C: Crude product after conjugation of hG-CSF with the HES derivative prepared in example 6.1(b)
Lane D: Crude product after conjugation of hG-CSF with the HES derivative prepared in example 6.1(j)
Lane E: Reaction control: HES 50/0.7 (Mw 47,000, DS=0.76)

Figure 20:
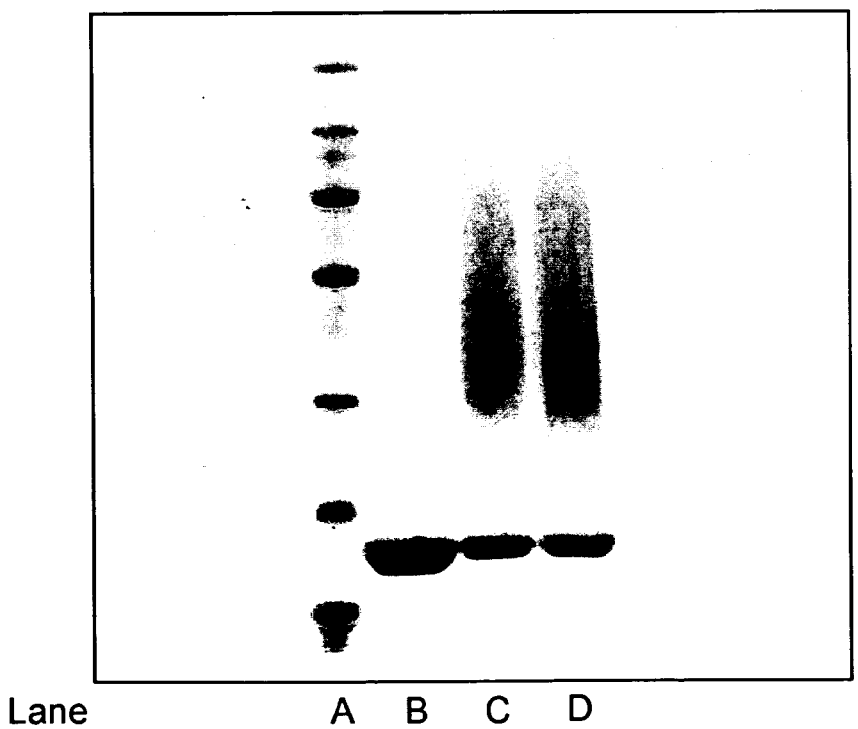

FIG. 20 shows the gel electrophoresis of the reaction mixtures of example 6.2(d).

For gel electrophoresis a XCell Sure Lock Mini Cell (Invitrogen GmbH, Karlsruhe, D) and a Consort E143 power supply (CONSORTnv, Turnhout, B) were employed. A 12% Bis-Tris gel together with a MOPS SDS running buffer at reducing conditions (both Invitrogen GmbH, Karlsruhe, D) were used according to the manufactures instruction. The gel was stained with Roti-Blue (Carl Roth GmbH+Co. KG, Karlsruhe, D) according to the manufacturer's instruction.

Lane A: Protein marker Roti-Mark STANDARD (Carl Roth GmbH+Co. KG, Karlsruhe, D) Molecular weight marker from top to bottom: 200 KD, 119 KD, 66 KD, 43 KD, 29 KD, 20 KD, 14.3 KD.
Lane B: hG-CSF after buffer exchange as described in Example 6.2(c).
Lane C: Crude product after conjugation of hG-CSF with the HES derivative prepared as described in Example 6.1(f).
Lane D: Crude product after conjugation of hG-CSF with the HES derivative prepared as described in Example 6.1(h).

Figure 21:
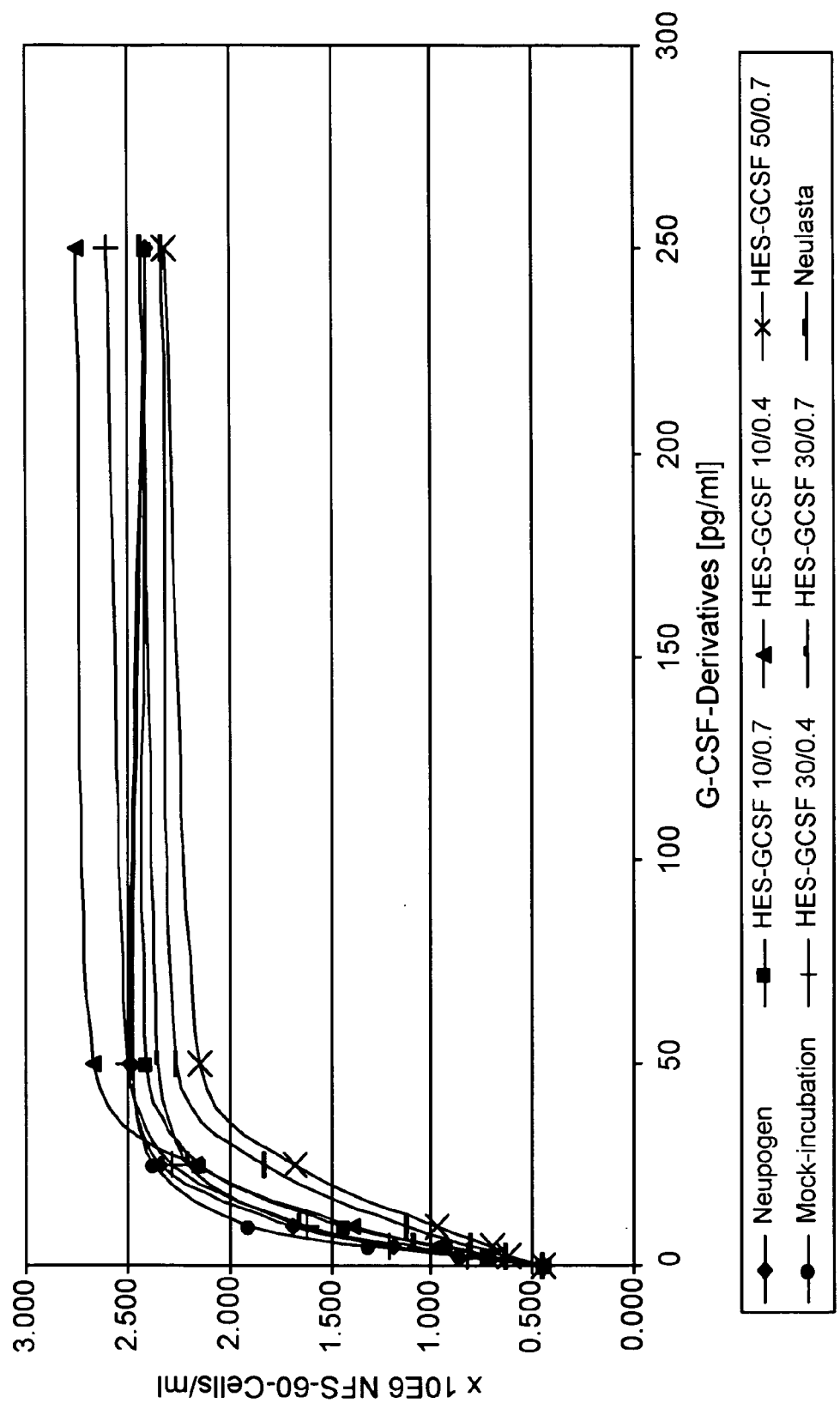

FIG. 21 shows the results of the mitogenicity assay of example 6.3. The Y axis indicates number of NFS-60-Cells/ml and the X-axis the concentration in pg/ml.

Figure 22:
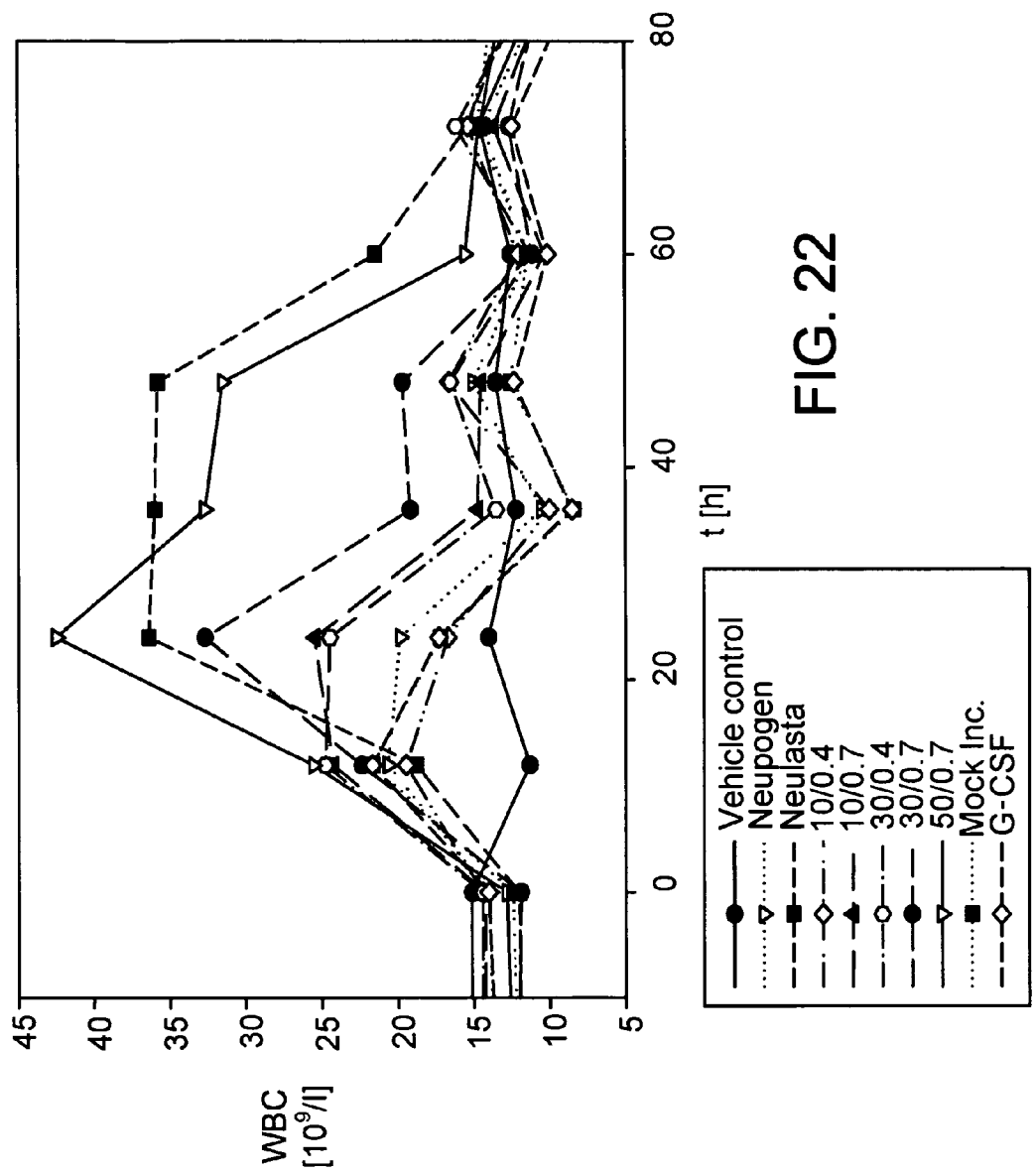

FIG. 22 shows the results of the in vivo assay of example 6.4.

Figure 23:
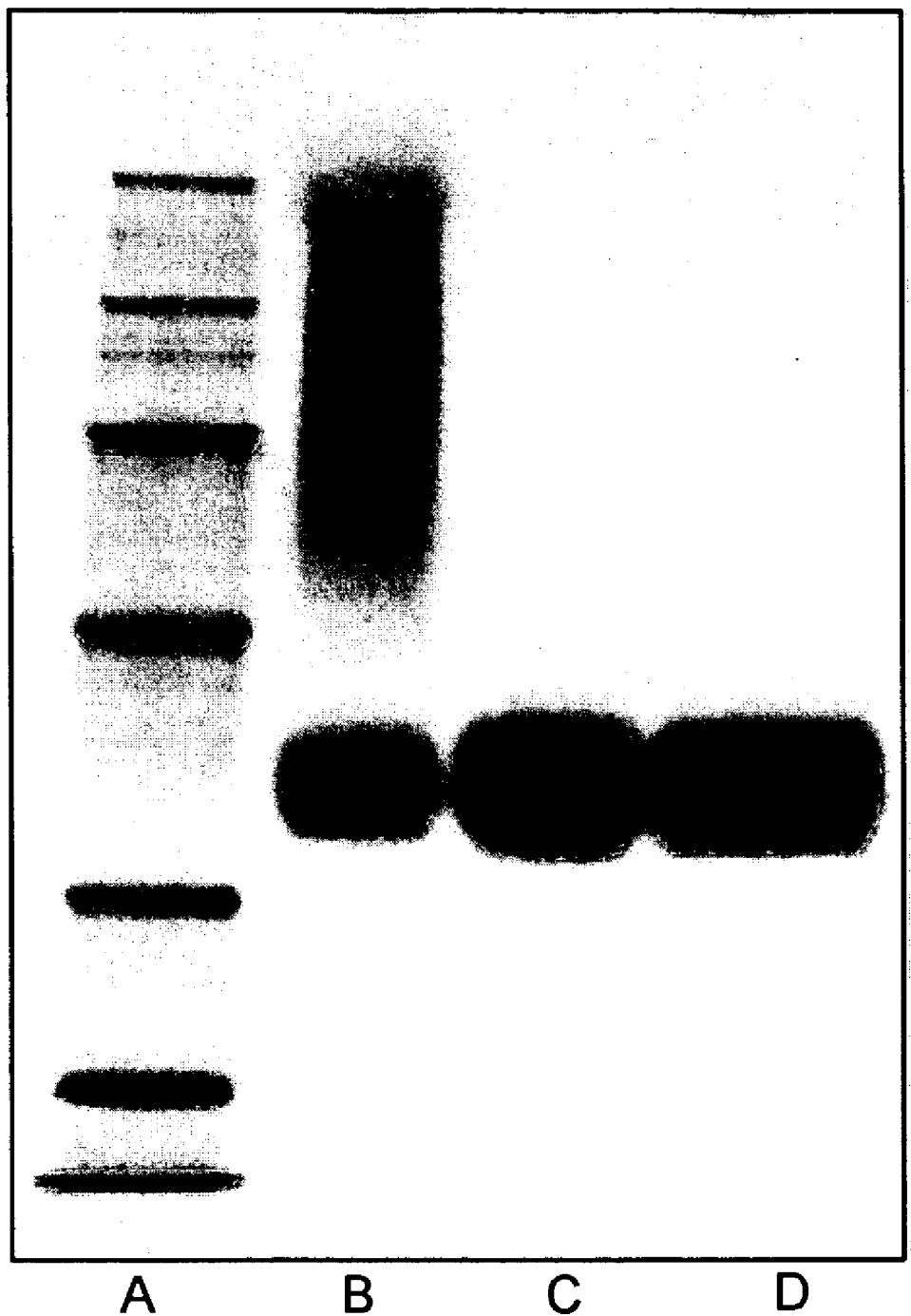

FIG. 23 shows the analysis of the crude EPO-HES conjugates of example 7 by gel electrophoresis.

For gel electrophoresis a XCell Sure Lock Mini Cell (Invitrogen GmbH, Karlsruhe, D) and a Consort E143 power supply (CONSORTnv, Turnhout, B) were employed. A 10% Bis-Tris gel together with a MOPS SDS running buffer at reducing conditions (both Invitrogen GmbH, Karlsruhe, D) were used according to the manufacturer's instruction.

Lane A: Roti®-Mark STANDARD (Carl Roth GmbH+Co. KG, Karlsruhe, D) Molecular weight marker from top to bottom: 200 KD, 119 KD, 66 KD, 43 KD, 29 KD, 20 KD, 14.3 KD;
Lane B: Conjugation of EPO to aldehydo-HES as described in example 7.3;
Lane C: Reaction of EPO and aldehydo-HES without sodium cyanoborohydride (Reaction Control A) as described in example 7.4;
Lane D: Reaction of EPO and sodium cyanoborohydride without aldehydo-HES (Reaction Control B) as described in example 7.5.

No reaction was observed for the reaction controls A and B either without aldehydo-HES or without sodium cyanoborohydride.

Figure 24:
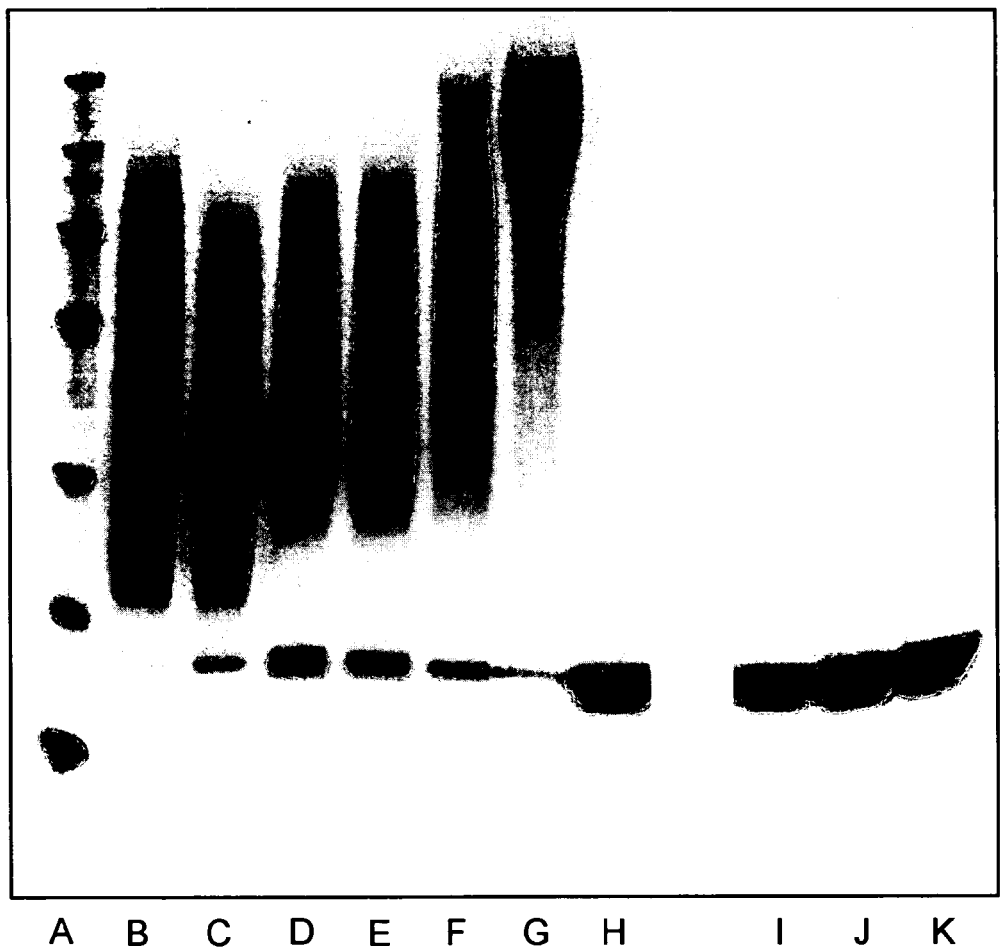

FIG. 24 shows the analysis of IFN-alpha-HES conjugates of example 8.3.1 by gel electrophoresis.

For gel electrophoresis a XCell Sure Lock Mini Cell (Invitrogen GmbH, Karlsruhe, D) and a Consort E143 power supply (CONSORTnv, Turnhout, B) were employed. A 10% Bis-Tris gel together with a MOPS SDS running buffer at reducing conditions (both Invitrogen GmbH, Karlsruhe, D) were used according to the manufacturer's instruction.

Lane X: Roti®-Mark STANDARD (Carl Roth GmbH+Co. KG, Karlsruhe, D) Molecular weight marker from top to bottom: 200 KD, 119 KD, 88 KD, 43 KD, 29 KD, 20 KD, 14.3 KD;
Lane A: Conjugation to aldehydoHES10/0.4 as described in ex. 8.3.1, entry A;
Lane B: Conjugation to aldehydoHES10/0.7 as described in ex. 8.3.1, entry B;
Lane C: Conjugation to aldehydoHES30/0.4 as described in ex. 8.3.1, entry C;
Lane D: Conjugation to aldehydoHES30/0.7 as described in ex. 8.3.1, entry D;
Lane E: Conjugation to aldehydoHES50/0.4 as described in ex. 8.3.1, entry E;
Lane F: Conjugation to aldehydoHES50/0.7 as described in ex. 8.3.1, entry F;
Lane G: Reaction control, without aldehydoHES as described in ex. 8.3.1, entry G;
Lane I: Reaction control, without aldehydoHES and without NaCNBH3 as described in ex. 8.3.1, entry I;
Lane J: Reaction control, with HES10/0.4 as described in ex. 8.3.1, entry J;
Lane K: Reaction control, with HES10/0.4 but without NaCNBH3 as described in ex. 8.3.1, entry K.

Figure 25:
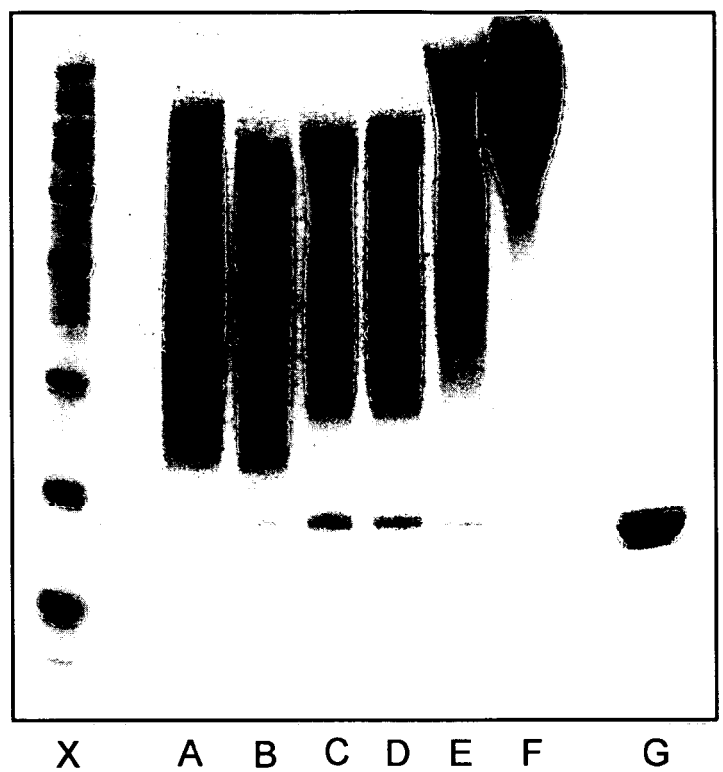

FIG. 25 shows the analysis of IFN-alpha-HES conjugates of example 8.3.2 by gel electrophoresis.

For gel electrophoresis a XCell Sure Lock Mini Cell (Invitrogen GmbH, Karlsruhe, D) and a Consort E143 power supply (CONSORTnv, Turnhout, B) were employed. A 10% Bis-Tris gel together with a MOPS SDS running buffer at reducing conditions (both Invitrogen GmbH, Karlsruhe, D) were used according to the manufacturer's instructions.

Lane X: Roti®-Mark STANDARD (Carl Roth GmbH+Co. KG, Karlsruhe, D) Molecular weight marker from top to bottom: 200 KD, 119 KD, 88 KD, 43 KD, 29 KD, 20 KD, 14.3 KD;
Lane A: Conjugation to aldehydo-HES as described in example 8.3.2 entry A;
Lane B: Conjugation to aldehydo-HES as described in example 8.3.2 entry B;
Lane C: Conjugation to aldehydo-HES as described in example 8.3.2 entry C;
Lane D: Conjugation to aldehydo-HES as described in example 8.3.2 entry D;
Lane E: Conjugation to aldehydo-HES as described in example 8.3.2 entry E;
Lane F: Conjugation to aldehydo-HES as described in example 8.3.2 entry F;
Lane G: Reaction control, with HES as described in example 8.3.2 entry G No reaction was observed for the reaction control G.

Figure 26:

FIG. 26 shows the analysis of IFN-alpha-HES conjugates of example 8.3.3 by gel electrophoresis.

For gel electrophoresis a XCell Sure Lock Mini Cell (Invitrogen GmbH, Karlsruhe, D) and a Consort E143 power supply (CONSORTnv, Turnhout, B) were employed. A 10%

Bis-Tris gel together with a MOPS SDS running buffer at reducing conditions (both Invitrogen GmbH, Karlsruhe, D) were used according to the manufacturer's instruction.

Analysis of the crude IFNα-HES conjugates by gel electrophoresis.

Lane A: Roti®-Mark STANDARD (Carl Roth GmbH+Co. KG, Karlsruhe, D) Molecular weight marker from top to bottom: 200 KD, 119 KD, 66 KD, 43 KD, 29 KD, 20 KD, 14.3 KD;

Lane B: Conjugation of IFNα to AldehydoHES as described in 8.3.3.1;

Lane C: Conjugation of IFNα to AldehydoHES as described in 8.3.3.2;

Lane D: Conjugation of IFNα to HES10/0.4 sodium (Reaction Control) as described in 8.3.3.3

Figure 27:
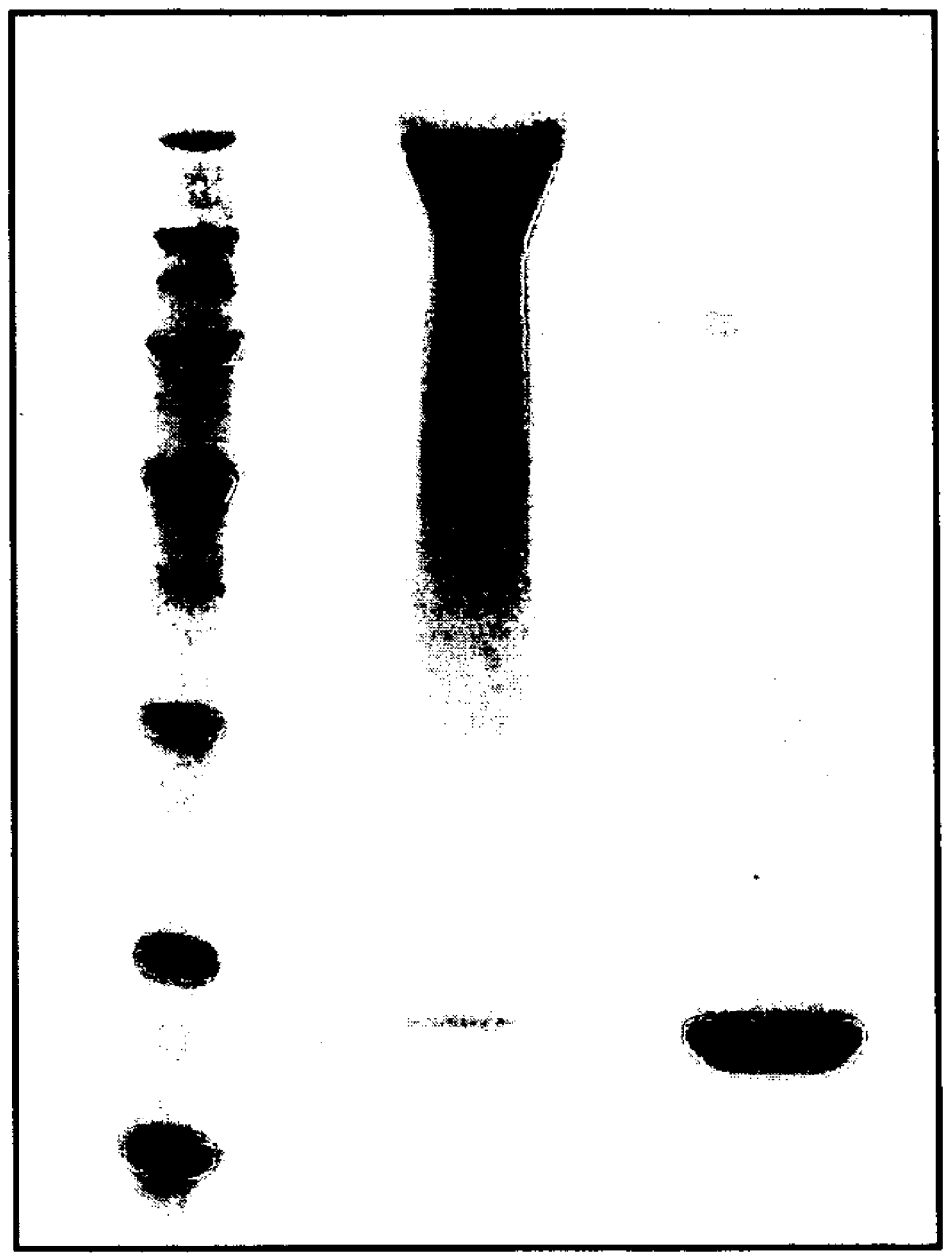

FIG. 27 shows the analysis of IFN-alpha-HES conjugates of example 8.3.4 by gel electrophoresis.

For gel electrophoresis a XCell Sure Lock Mini Cell (Invitrogen GmbH, Karlsruhe, D) and a Consort E143 power supply (CONSORTnv, Turnhout, B) were employed. A 10% Bis-Tris gel together with a MOPS SDS running buffer at reducing conditions (both Invitrogen GmbH, Karlsruhe, D) were used according to the manufacturer's instructions.

Lane X: Roti®-Mark STANDARD (Carl Roth GmbH+Co. KG, Karlsruhe, D) Molecular weight marker from top to bottom: 200 KD, 119 KD, 88 KD, 43 KD, 29 KD, 20 KD, 14.3 KD Lane A: Conjugation to aldehydo-HES as described in example 8.3.4;

Lane B: Reaction control; conjugation to HES (MW=7.6 kD, DS=0.41) as described in example 8.3.4.

No reaction was observed for the reaction control B.

Figure 28:
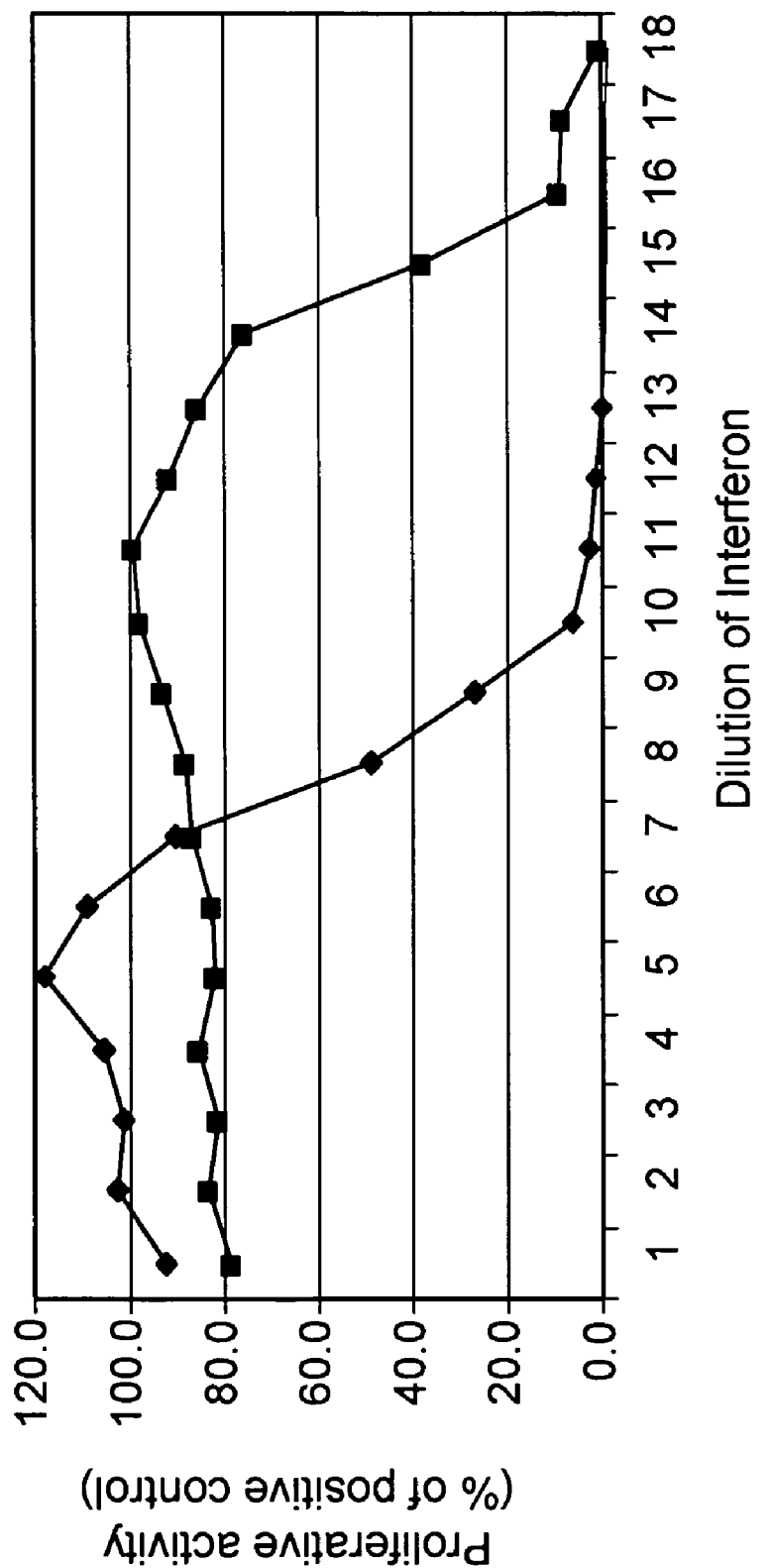

FIG. 28 shows the proliferative activity of Intron A compared to NIH standard rhIFN-alpha 2a according to example 9.1.

Figure 29:
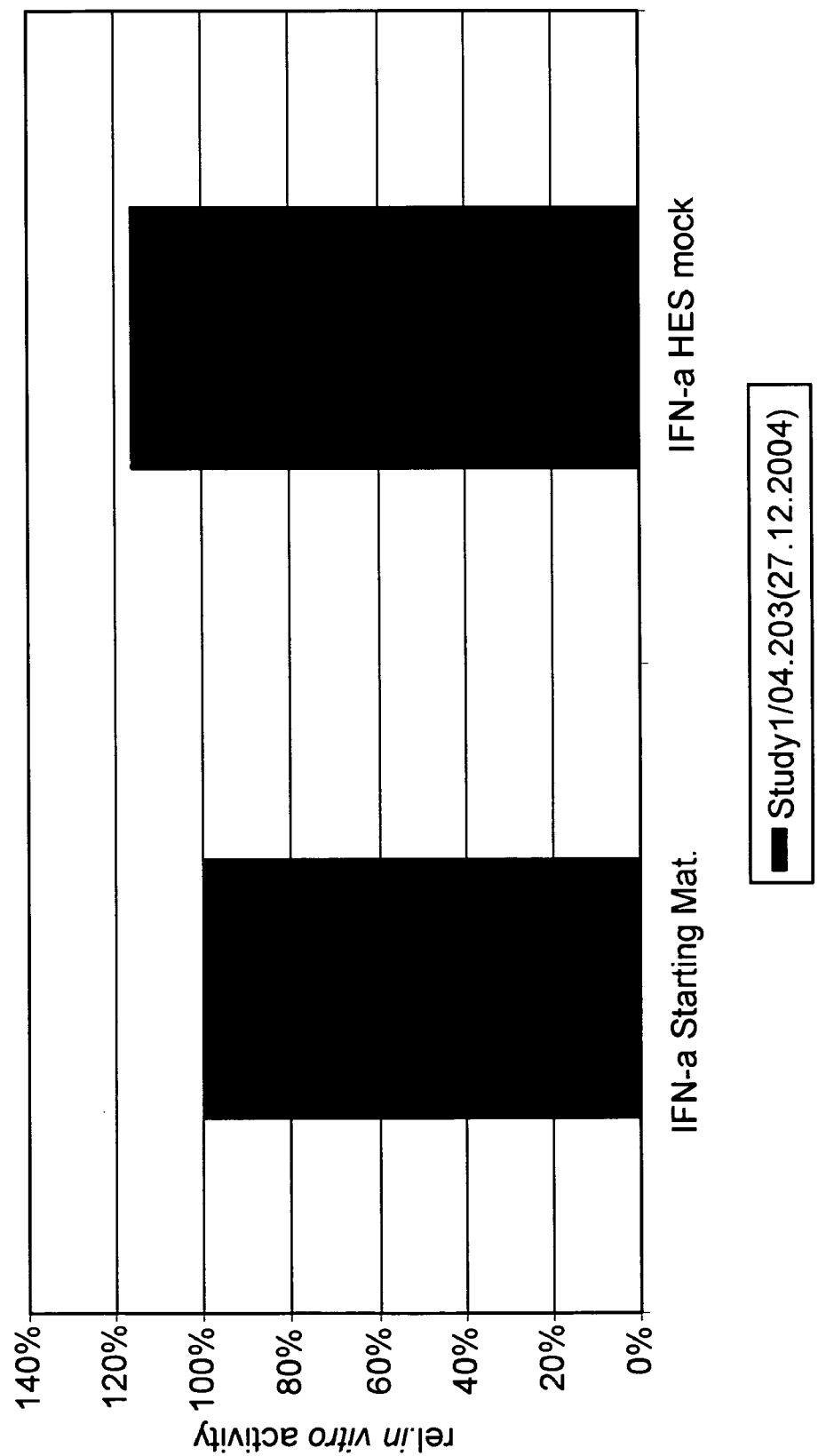

FIG. 29 shows the relative in vitro activity of mock incubated IFN-alpha-HES compared to unmodified IFN-alpha starting material according to example 9.2.

Figure 30:
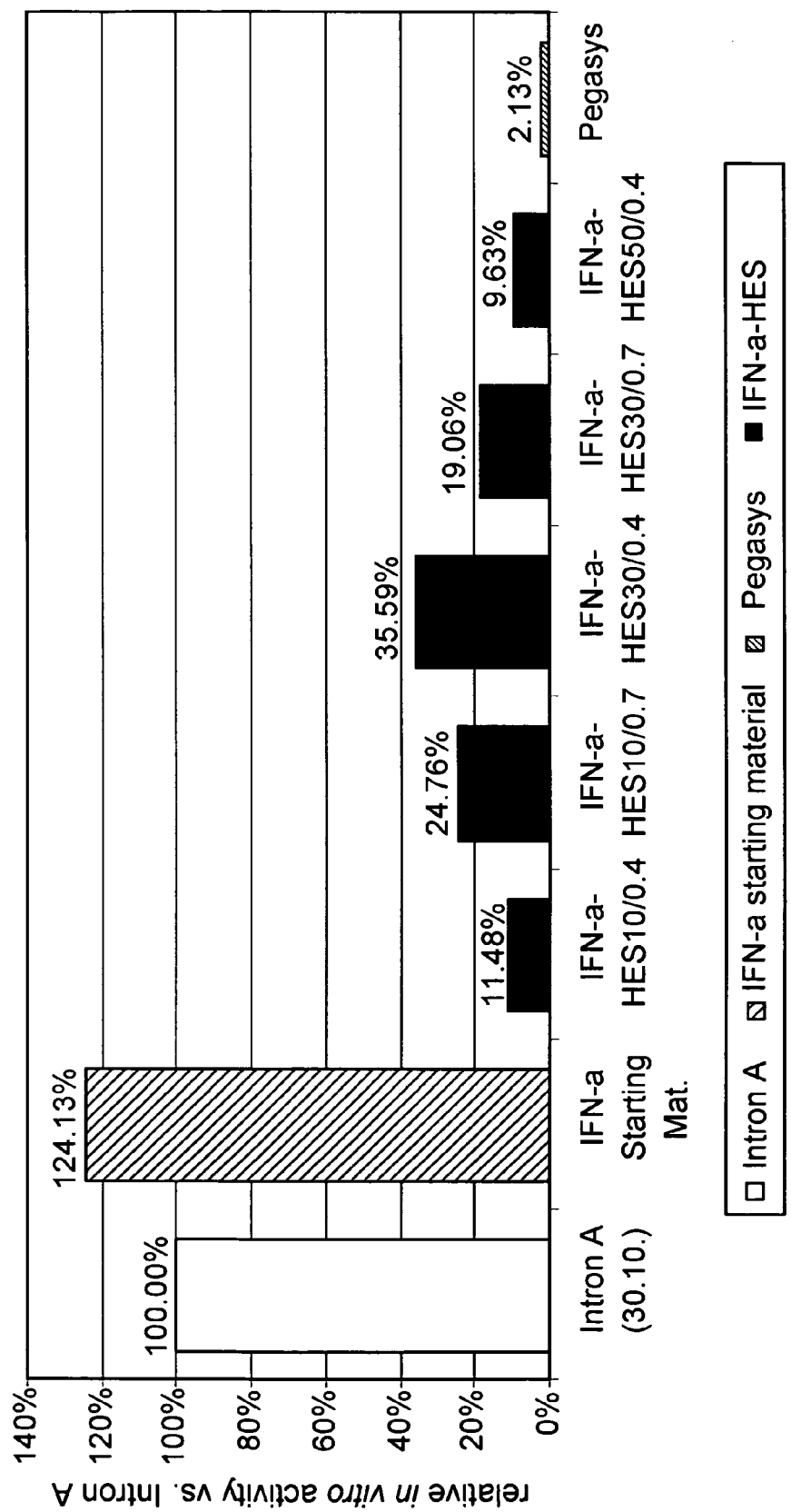

FIG. 30 shows relative in vitro activity of IFN-alpha-HES conjugates compared to unmodified IFN-alpha starting material, Intron A and Pegasys, respectively, according to example 9.3.

Figure 31:
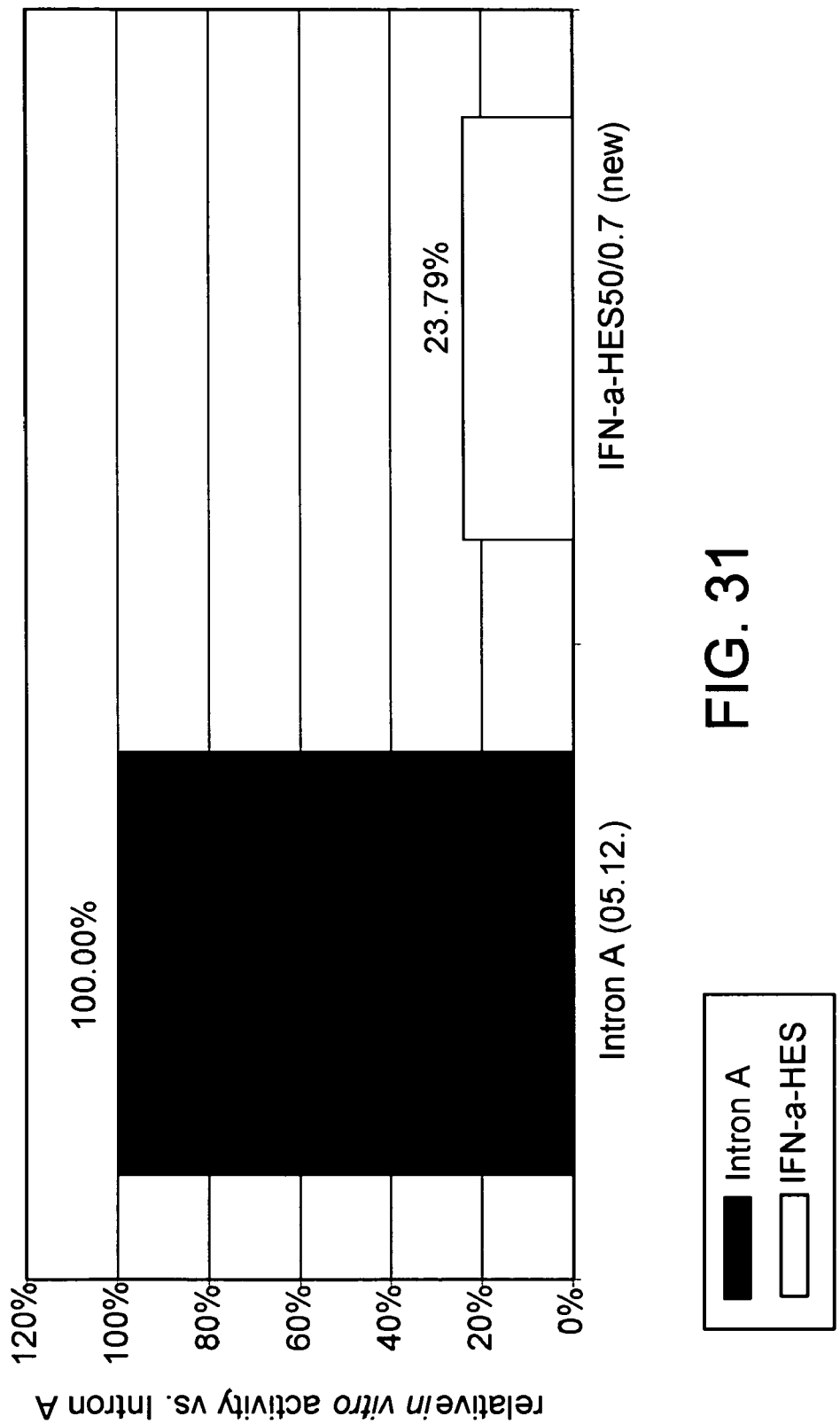

FIG. 31 shows the relative in vitro activity of IFN-alpha-HES conjugate compared to Intron A according to example 9.4.

Figure 32:
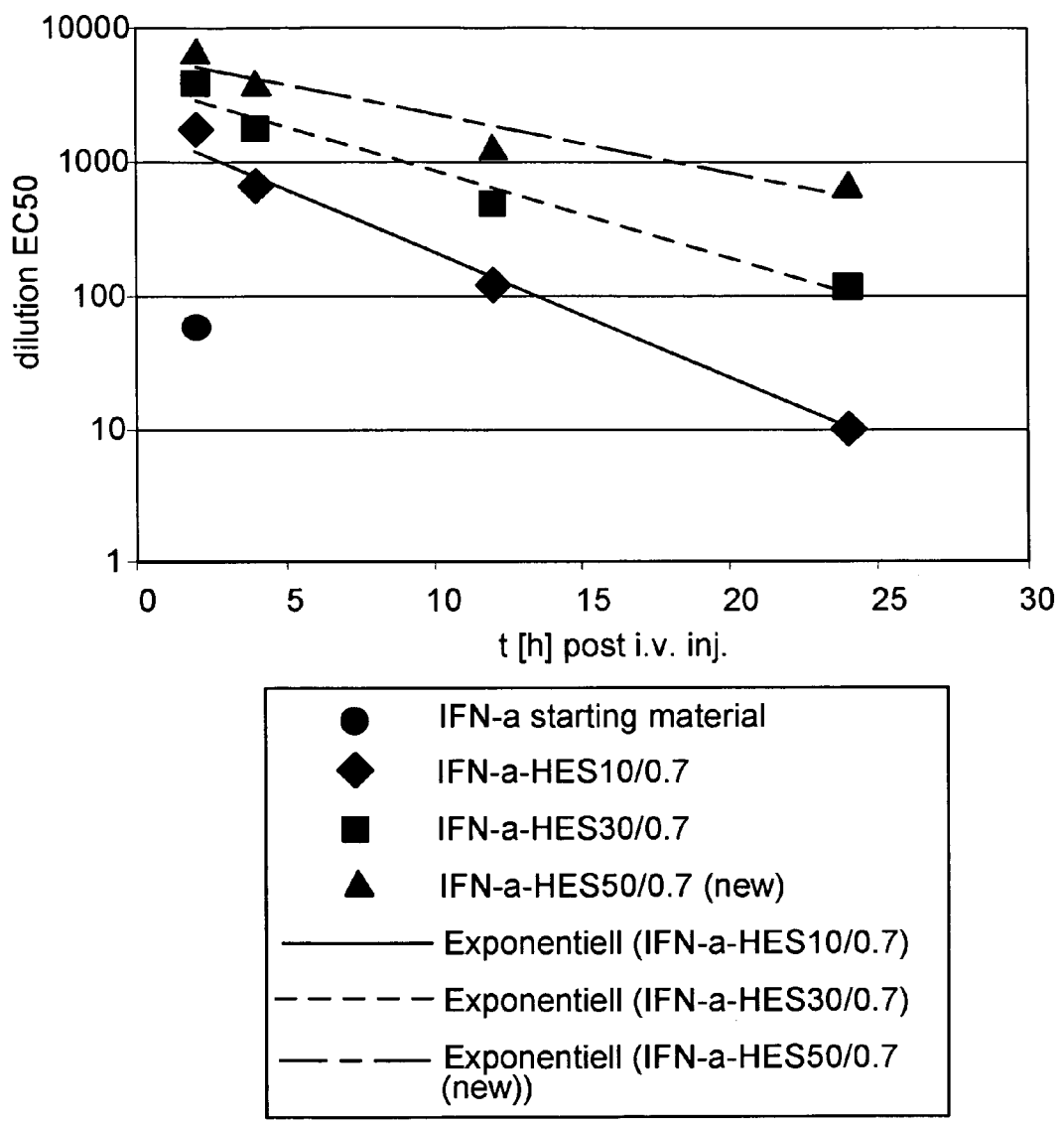

FIG. 32 shows the dilution of serum samples required to achieve a 50% protection of MDBK cells against viral infection vs. time post i.v. injection of 30 μg/gk in mice. Serum from mice treated with unmodified starting material has a very low antiviral effect. Modification of IFN-alpha with HES prolongs the antiviral effect of serum substantially. The half life increases with molecular weight of HES used for modification of IFN-alpha (see example 10).

Figure 33:
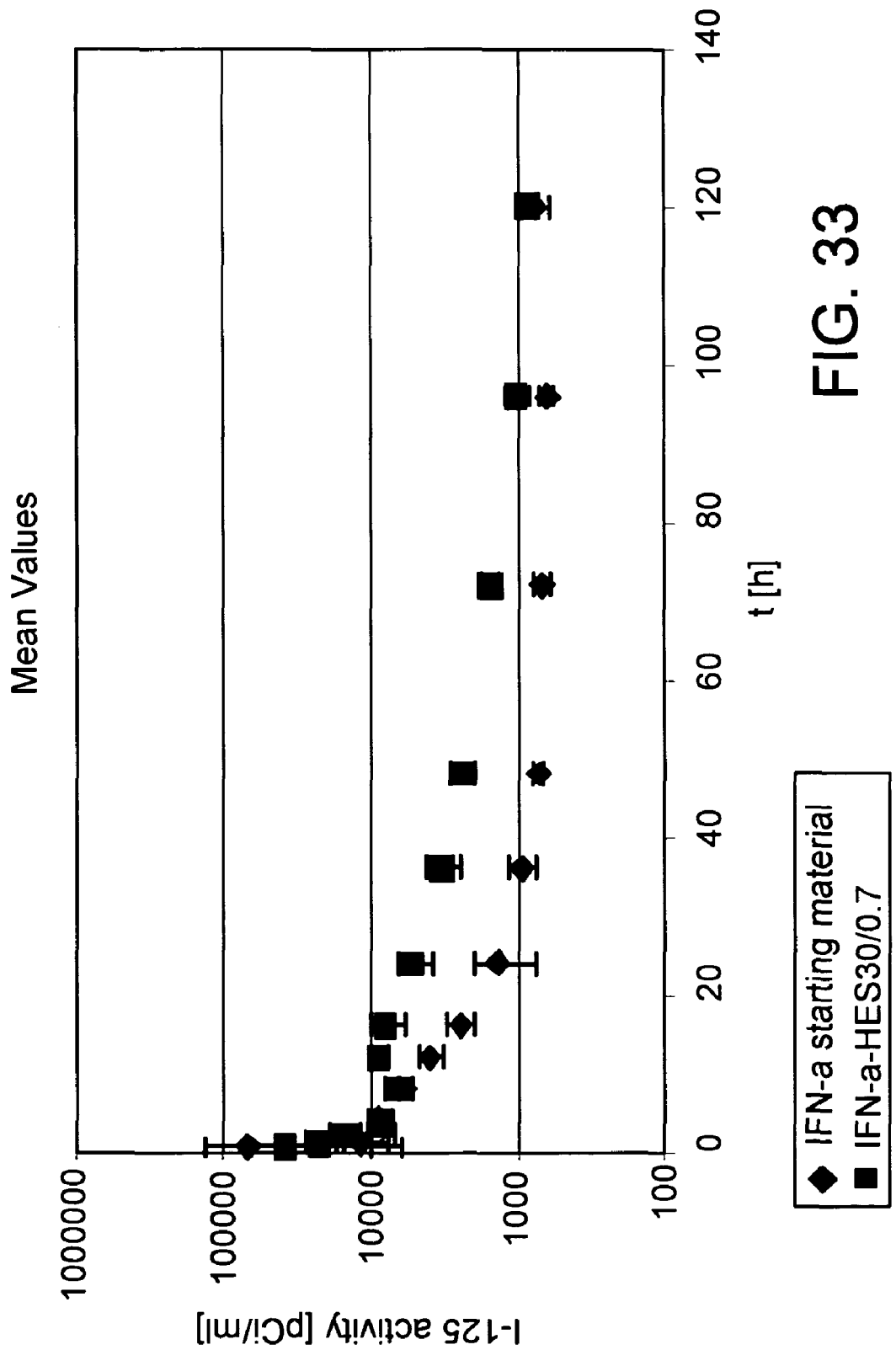
Figure 34:
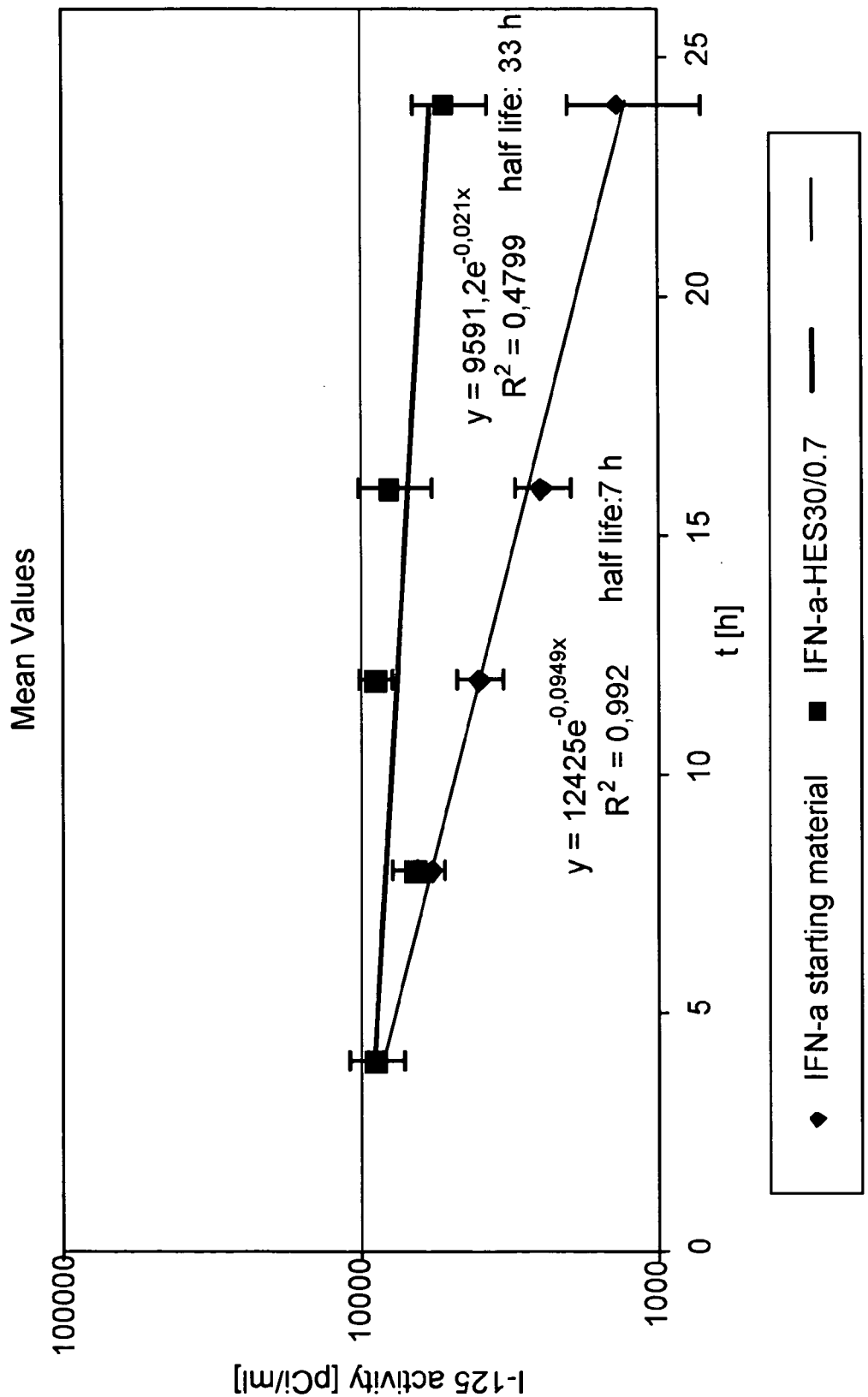

FIG. 33 shows data from the PK-Study in rabbits according to example 11. IFN-alpha-HES shows a distinct prolongation of half-life compared to the IFN-alpha starting material. For >24 h (approx. <1000 pCi/ml) the curve of the unmodified material levels off and almost no further decrease of activity can be observed FIG. 34 shows PK-Study in rabbits according to example 11. Data were evaluated in the period between 4 and 24 h. IFN-alpha-HES shows a distinct prolongation of half-life compared to the unmodified IFN-alpha starting material.

Figure 35A:
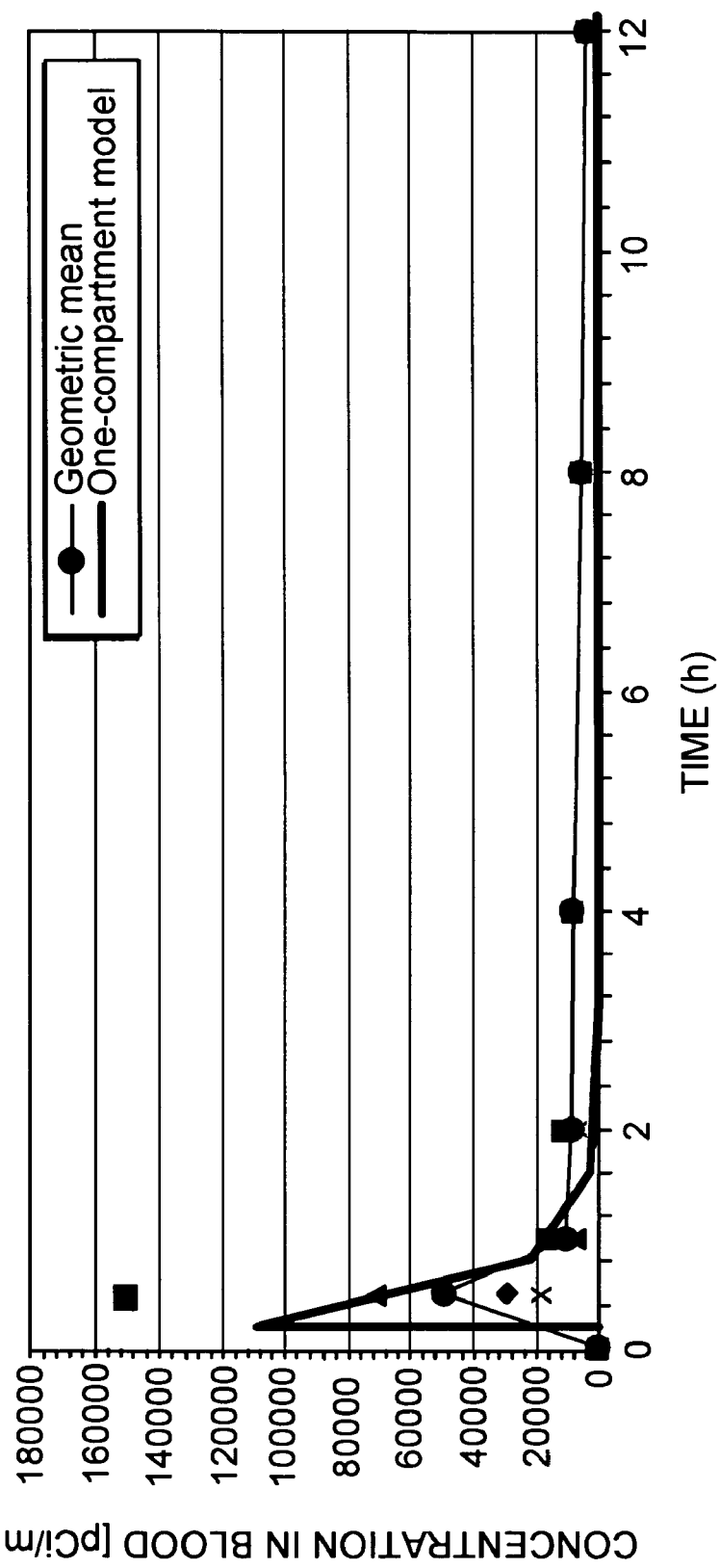
Figure 35B:
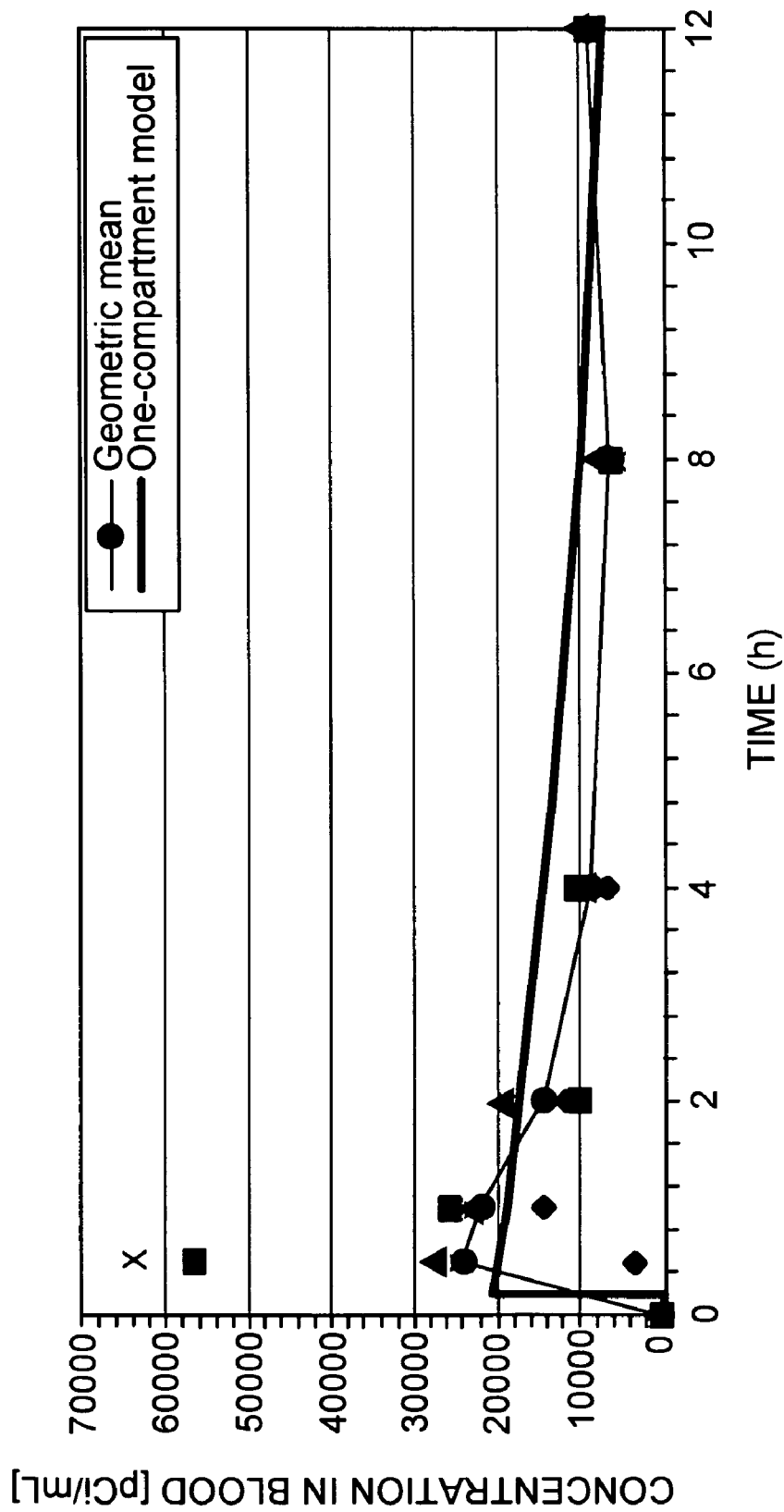

FIG. 35 shows the statistical evaluation of the PK-Study (shown: period up to 12 h) according to example 11. In the case of the unmodified starting material (see FIG. 35 (*a*)), the concentration dropped to almost zero during the first two hours, whereas IFNalpha-HES shows a distinctly prolonged half-life (FIG. 35 (*b*)).

Figure 36:
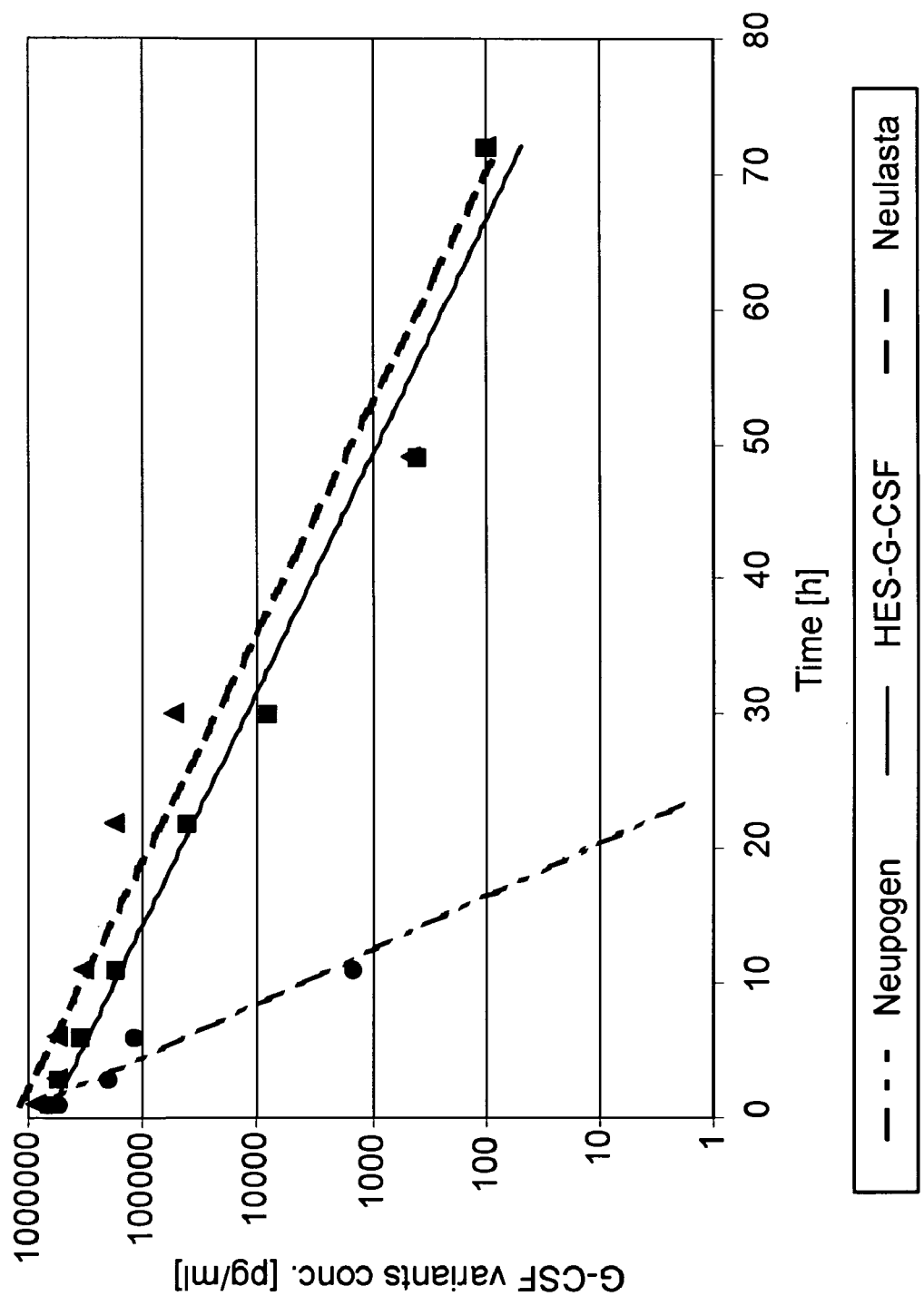

FIG. 36 shows the results of example 6.5 (comparison of half-live determination of a HES-G-CSF conjugate according to the invention, Neulasta® and Neupogen®).

Figure 37:
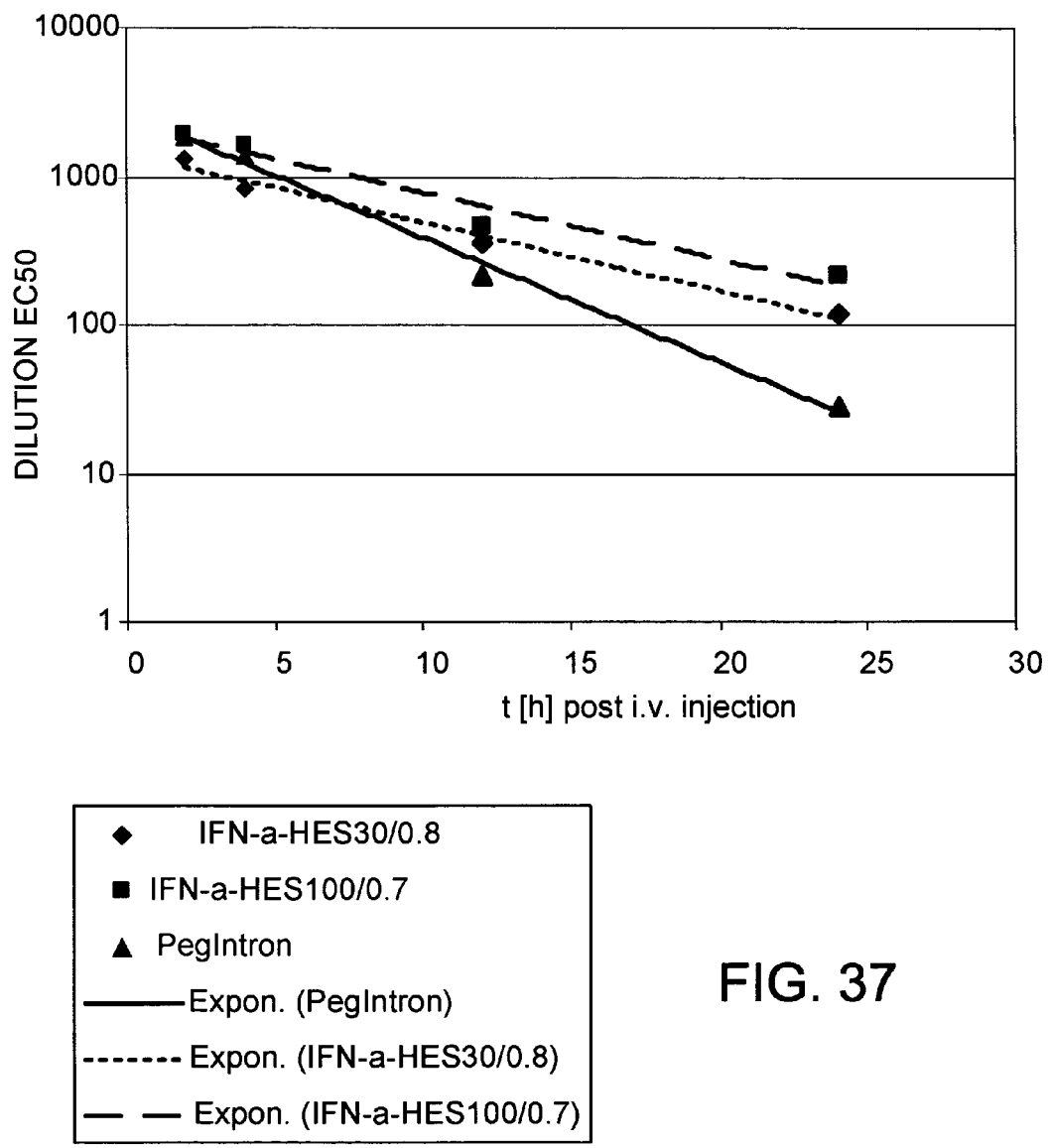

FIG. 37 shows the results of example 10.3 in a graph (antiviral activity of IFN-alpha-HES conjugates)

Figure 38:
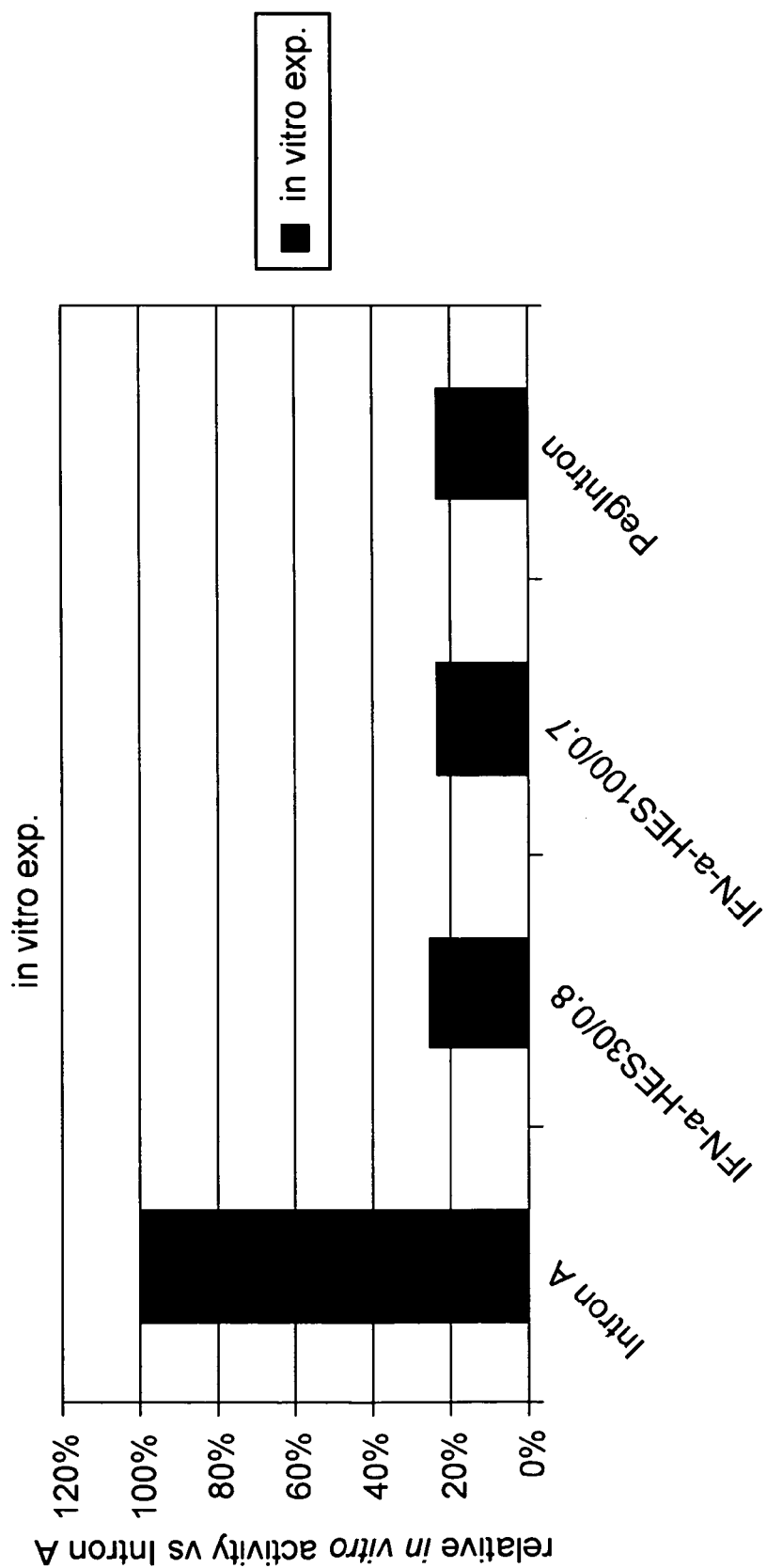

FIG. 38 shows the results of example 9.5 in a graph (antiviral activity of IFN-alpha-HES conjugates)

DETAILED DESCRIPTION

The term "protein" as used in the context of the present invention, relates to any amino acid sequence having at least 2, preferably at least 5, more preferably at least 10 more preferably at least 15, more preferably at least 20, more preferably at least 25, more preferably at least 30, more preferably at least 35, more preferably at least 40, more preferably at least 45, more preferably at least 50 and still more preferably at least 100 amino acids.

The protein can be produced by chemical synthetic procedures or can be of any human or another mammalian source and can be obtained by purification from naturally occurring sources.

According to the present invention, the protein can be a growth factor, a cytokine, an activator, an inhibitor, an enzyme, an antibody, an antigen, a transport protein, a bioadhesion protein, a hormone, a receptor, a suppressor, or a functional derivative or fragment thereof. The term "functional derivative or fragment" as used in the context of the present invention relates to a derivative or fragment that maintains the desired biological property or activity of the original molecule totally or partially, e.g. at least 10%, more preferably at least 20%, more preferably at least 30%, more preferably at least 40%, more preferably at least 50%, more preferably at least 60%, more preferably at least 70%, more preferably at least 80% and especially preferably at least 90% of the desired biological property or activity of the original molecule. Particularly preferred examples of such fragments are, e.g., antibody fragments.

Examples of proteins are erythropoietin (EPO) such as recombinant human EPO (rhEPO), colony-stimulating factors (CSF), such as G-CSF like recombinant human G-CSF (rhG-CSF), alpha-Interferon (IFN alpha), beta-Interferon (IFN beta) or gamma-Interferon (IFN gamma), such as IFN alpha and IFN beta like recombinant human IFN alpha or IFN beta (rhIFN alpha or rhIFN beta), interleukines, e.g. IL-1 to IL-18 such as IL-2 or IL-3 like recombinant human IL-2 or IL-3 (rhIL-2 or rhIL-3), serum proteins such as coagulation factors II-XIII like factors VII, VIII, IX, alpha1-antitrypsin (A1AT), activated protein C (APC), plasminogen activators such as tissue-type plasminogen activator (tPA), such as human tissue plasminogen activator (hTPA), AT III such as recombinant human AT III (rhAT III), myoglobin, albumin such as bovine serum albumin (BSA), growth factors, such as epidermal growth factor (EGF), thrombocyte growth factor (PDGF), fibroblast growth factor (FGF), brain-derived growth factor (BDGF), nerve growth factor (NGF), B-cell growth factor (BCGF), brain-derived neurotrophic growth factor (BDNF), ciliary neurotrophic factor (CNTF), transforming growth factors such as TGF alpha or TGF beta, BMP (bone morphogenic proteins), growth hormones such as human growth hormone, tumor necrosis factors such as TNF alpha or TNF beta, somatostatine, somatotropine, somatomedines, hemoglobin, hormones or prohormones such as insulin, gonadotropin, melanocyte-stimulating hormone (alpha-MSH), triptorelin, hypthalamic hormones such as antidiuretic hormones (ADH and oxytocin as well as releasing hormones and release-inhibiting hormones, parathyroid hormone, thyroid hormones such as thyroxine, thyrotropin, thyroliberin, prolactin, calcitonin, glucagon, glucagon-like peptides (GLP-1, GLP-2 etc.), exendines such as exendin-4, leptin, vasopressin, gastrin, secretin, integrins, glycoprotein hormones (e.g. LH, FSH etc.), melanoside-stimulating hormones, lipoproteins and apo-lipoproteins such as apo-B, apo-E, apo-$L_a$, immunoglobulins such as IgG, IgE, IgM, IgA, IgD and fragments thereof, hirudin, tissue-pathway inhibitor, plant proteins such as lectin or ricin, bee-venom, snake-venom, immunotoxins, antigen E, alpha-proteinase inhibitor, ragweed allergen, melanin, oligolysine proteins, RGD proteins or optionally corresponding receptors for one of these proteins; or a functional derivative or fragment of any of these proteins or receptors.

Preferred enzymes are, e.g., carbohydrate-specific enzymes, proteolytic enzymes, oxidases, oxidoreductases, transferases, hydrolases, lyases, isomerases, kinases and ligases. Specific non-limiting examples are asparaginase, arginase, arginin deaminase, adenosin deaminase, glutaminase, glutaminase-asparaginase, phenylalanin, tryptophanase, tyrosinase, superoxide dismutase (SOD), endotoxinase, catalase, peroxidase, kallikrein, trypsin, chymotrypsin, elastase, thermolysin, lipase, uricase, adenosine diphosphatase, purine nucleoside phosphorylase, bilirubin oxidase, glucose oxidase, glucodase, gluconate oxidase, galactosidase, glucocerebrosidase, glucuronidase, hyaluronidase, tissue factor, streptokinase, urokinase, MAP-kinases, DNAses, RNAses, lactoferrin and functional derivatives or fragments thereof.

According to preferred embodiments of the present invention, the protein is selected from the group consisting of EPO, G-CSF, IFN alpha, IFN beta, AT III, IL-2, IL-3, myoglobin, SOD, A1AT, and BSA.

According to especially preferred embodiments of the present invention, the protein is selected from the group consisting of rhEPO, rhG-CSF, rhIFN alpha, rhIFN beta, rhAT III, rhIL-2, rhIL-3, myoglobin, SOD, A1AT, and BSA.

Erythropoietin (EPO) is a glycoprotein hormone necessary for the maturation of erythroid progenitor cells into erythrocytes. In human adults, it is produced in the kidney. EPO is essential in regulating the level of red blood cells in the circulation. Conditions marked by low levels of tissue oxygen provoke an increased biosynthesis of EPO, which in turn stimulates erythropoiesis. A loss of kidney function as it is seen in chronic renal failure, for example, typically results in decreased biosynthesis of EPO and a concomitant reduction in red blood cells. Erythropoietin is an acid glycoprotein hormone of approximately 34,000 Da. Human erythropoietin is a 166 amino acid polypeptide that exists naturally as a monomer (Lin et al., 1985, PNAS 82, 7580-7584, EP 148 605 B2, EP 411 678 B2). The identification, cloning and expression of genes encoding erythropoietin are described, e.g., in U.S. Pat. No. 4,703,008. The purification of recombinant erythropoietin from cell culture medium that supported the growth of mammalian cells containing recombinant erythropoietin plasmids, for example, is described in U.S. Pat. No. 4,667,016. It is generally believed in this technical field that the biological activity of EPO in vivo mainly depends on the degree of sialic acids bound to EPO (see e.g. EP 428 267 B1). Theoretically, 14 molecules of sialic acid can be bound to one molecule EPO at the terminal ends of the carbohydrate side chains linked to N- and O-glycosylation sites. Highly sophisticated purification steps are necessary to obtain highly sialylated EPO preparations. For further detailed information on erythropoietin see Krantz, Erythropoietin, 1991, Blood, 77(3):419-34 (Review) and Cerami, Beyond erythropoiesis: novel applications for recombinant human erythropoietin, 2001, Semin Hematol., (3 Suppl 7):33-9 (Review).

G-CSF is a 21 kDa glycoprotein stabilized by two intrachain disulfide bonds and containing a single O-linked carbohydrate moiety. Mature G-CSF has 174 amino acids. In the animal body, G-CSF is synthesized by bone marrow stromal cells, macrophages and fibroblasts. It main function is to be a growth and differentiation factor for neutrophils and their precursor cells. However, it is also known in the art that G-CSF activates mature neutrophils. In addition, it stimulates growth/differentiation of various other haemopoietic progenitor cells (in synergy with additional haemopoietic growth factors) and promotes proliferation and migration of endothelial cells. Clinically, G-CSF is administered for the treatment of deficiencies in neutrophil levels (caused, e.g. by aplastic anaemia, myelodysplasia, AIDS, or chemotherapy).

The G-CSF can be produced by chemical synthetic procedures or can be of any human (see e.g. Burgess, A. W. et al. 1977, Stimulation by human placental conditioned medium of hemopoietic colony formation by human marrow cells, Blood 49 (1977), 573-583; Shah, R. G. et al. 1977, Characterization of colony-stimulating activity produced by human monocytes and phytohemagglutinin-stimulated lymphocytes, Blood 50 (1977), 811) or another mammalian source and can be obtained by purification from naturally occurring sources like human placenta, human blood or human urine. In addition, a lot of Epithelial carcinomas, acute myeloid leukemia cells and various tumor cell lines (bladder carcinomas, medulloblastomas), are capable to express this factor.

Furthermore, the expression G-CSF encompasses also a G-CSF variant wherein one or more amino acids (e.g. 1 to 25, preferably 1 to 10, more preferably 1 to 5, most preferred 1 or 2) have been exchanged by another amino acid and which exhibits G-CSF activity (see e.g. Riedhaar-Olson, J. F. et al. 1996, Identification of residues critical to the activity of human granulocyte colony-stimulating factor, Biochemistry 35:9034-9041 1996; U.S. Pat. Nos. 5,581,476; 5,214,132; 5,362,853; 4,904,584). The measurement of G-CSF activity is described in the art (for measurement of G-CSF activity in vitro see e.g. Shirafuji, N. et al. 1989, A new bioassay for human granulocyte colony-stimulating factor (hG-CSF) using murine myeloblastic NFS-60 cells as targets and estimation of its levels in sera from normal healthy persons and patients with infectious and hematological disorders, Exp. Hematol. 1989, 17, 116-119; for measurement of G-CSF activity in vivo see e.g. Tanaka, H. et al. 1991, Pharmacokinetics of recombinant human granulocyte colony-stimulating factor conjugated to polyethylene glycol in rats, Cancer Research 51, 3710-3714, 1991). Further publications where tests for the measurement of the activity of G-CSF are disclosed are U.S. Pat. No. 6,555,660; Nohynek, G. J. et al. 1997, Comparison of the potency of glycosylated and nonglycosylated recombinant human granulocyte colony-stimulating factors in neutropenic and nonneutropenic CD rats, Cancer Chemother Pharmacol (1997) 39; 259-266.

Preferably, the G-CSF is recombinantly produced. This includes prokaryotic or eukaryotic host expression of exogenous DNA sequences obtained by genomic or cDNA cloning or by DNA synthesis. Suitable prokaryotic hosts include various bacteria such as *E. coli*. Suitable eukaryotic hosts include yeast such as *S. cerevisiae* and mammalian cells such as Chinese hamster ovary cells and monkey cells.

The recombinant production of a protein is known in the art. In general, this includes the transfection of host cells with an appropriate expression vector, the cultivation of the host cells under conditions which enable the production of the protein and the purification of the protein from the host cells. For detailed information see e.g. Souza, L. M. et al. 1986, Recombinant human granulocyte colony-stimulating factor: effects on normal and leukemic myeloid cells, Science 1986 232:61-65, 1986; Nagata, S. et. al. 1986, Molecular cloning and expression of cDNA for human granulocyte colony-stimulating factor, Nature 319:415-418, 1986; Komatsu, Y. et al. 1987, Cloning of granulocyte colony-stimulating factor cDNA from human macrophages and its expression in *Escherichia coli*, Jpn J Cancer Res. 1987 78(11):1179-1181.

In a preferred embodiment, the G-CSF has the amino acid sequence of human mature G-CSF (see e.g.; Nagata, S. et. al. 1986, Molecular cloning and expression of cDNA for human granulocyte colony-stimulating factor, Nature 319:415-418, 1986), and may further contain a methionin at its amino terminus, which then results in a protein of 175 amino acids. Furthermore, instead of the methionine, G-CSF may contain a serine or a threonine residue.

The G-CSF used in the methods of the present invention and the conjugates according to the present invention may comprise one carbohydrate side chain attached to the G-CSF via O-linked glycosylation at the position Thr 133, i.e. the G-CSF is glycosylated (V. Gervais et al., Eur. J. Biochem. 1997, 247, 386-395). The structure of the carbohydrate side chain may be NeuNAc(alpha2-3)Gal(beta1-3)[NeuNAc(alpha2-6)]GalNAc und (alpha2-3)Gal(beta1-3)GalNAc (NeuNAc=N-acetylneuramic acid, GalNAc=N-acetylgalactosamine).

Modification of G-CSF and other polypeptides so as to introduce at least one additional carbohydrate chain as compared to the native polypeptide has been suggested (U.S. Pat. No. 5,218,092). Depending on the host employed, the G-CSF expression product may be glycosylated with mammalian or other eukaryotic carbohydrates. Usually, when G-CSF is produced in eukaryotic cells, the protein is posttranslationally glycosylated. Consequently, the carbohydrate side chain may have been attached to the G-CSF during biosynthesis in mammalian, especially human, insect or yeast cells.

Recombinant human G-CSF (rhG-CSF) is generally used for treating various forms of leukopenia. Thus, commercial preparations of rhG-CSF are available under the names filgrastim (Gran® and Neupogen®), lenograstim (Neutrogin® and Granocyte®) and nartograstim (Neu-up®). Gran® and Neupogen® are non-glycosylated and produced in recombinant *E. coli* cells. Neutrogin® and Granocyte® are glycosylated and produced in recombinant CHO cells and Neu-up® is non-glycosylated with five amino acids substituted at the N-terminal region of intact rhG-CSF produced in recombinant *E. coli* cells.

Interferons are cytokines that mediate antiviral, anti-proliferative and immuno-modulatory activities in response to viral infection and other biological inducers. In contrast to IFN alpha, IFN beta is highly species-specific. There are two subtypes of IFN beta, IFN beta 1a and IFN beta 1b. When it comes to industrial production then the main difference between IFN beta 1a and IFN beta 1b is the respective cell systems utilized for their production. IFN beta 1a is produced by mammalian cells and receives the designation 1a because its amino acid sequence is identical to that of the naturally occurring interferon beta. IFN beta 1b is produced by bacteria. Interferons, like most other mammalian proteins are modified post-translationally by glycosylation. Bacteria, however, lack the ability to glycosylate proteins and thus IFN beta 1b does not include the carbohydrate side chains found in the natural material. IFN beta 1a has 166 amino acids and a molecular weight of about 22,500 D, IFN beta 1b has 165 amino acids and a molecular weight of about 18,500 Da, because the N-terminal methionin is missing in IFN beta 1b as well as the glycosylation due to the bacterial production method. The amino acid sequence of human interferon beta is given, e.g. in EP 0 218 825 A1. The crystal structure of interferon beta was reported in: *Proc. Natl. Acad. Sci. USA* 94 (1997) pp 11813-11818, Biochemistry, Karpusas M, Nolte M, Benton C B, Meier W, Lipscomb W N, Goelz S. Commercial preparations of interferon beta are Betaseron® (IFN beta 1b), Avonex® and Rebif® (IFN beta 1a). Interferon beta 1b is manufactured by bacterial fermentation of a strain of *E. coli* that bears a genetically engineered plasmid containing the gene for human interferon beta$_{ser17}$. The native gene was obtained from human fibroblasts and altered in a way that substitutes serine for the cysteine residue found at position 17. Interferon beta 1a is produced by recombinant DNA technology using genetically engineered Chinese Hamster Ovary (CHO) cells into which the human interferon beta gene has been introduced. The amino acid sequence of IFN beta 1a is identical to that of natural fibroblast derived human interferon beta. Natural interferon beta and interferon beta 1a are glycosylated with each containing a single N-linked complex carbohydrate moiety at the Asn80. The interferon beta drugs are indicated for the treatment of relapsing remitting multiple sclerosis. However, there are many serious side effects related to the administration of the interferon beta drug products. Furthermore they are administered by injection (intramuscular or subcutaneously), leading to additional risks. Reducing the side effects and easier (e.g. less frequent) administration are the reason, why lot of development work is performed to improve the properties of IFN beta. Polymer modification of proteins is a technique which is applied to improve the properties of the proteins. The mainly used technique is the modification of interferon with polyethylen glycol, known as PEGylation.

IFN alpha forms are naturally produced by monocytes/macrophages, lymphoblastoid cells, fibroblasts and a number of different cell types following induction by viruses, nucleic acids, glucocorticoid hormones and other inductors. At least 23 different variants of IFN alpha are known. The individual proteins have molecular masses between 19-26 kD and consist of proteins with lengths of 156-166 and 172 amino acids. All IFN alpha subtypes possess a common conserved sequence region between amino acid positions 115-151 while the amino-terminal ends are variable. Many IFN alpha subtypes differ in their sequences at only one or two positions. Disulfide bonds are formed between cysteines at positions 1/98 and 29/138. The disulfide bond 29/138 is essential for biological activity while the 1/98 bond can be reduced without affecting biological activity. All IFN alpha forms contain a potential glycosylation site but most subtypes are not glycosylated. In contrast to IFN gamma, IFN alpha proteins are stable at a pH of 2. Industrial production of IFN alpha is performed using genetically modified *E. coli*. Because bacteria lack the ability to glycosylate proteins, the two variants of IFN alpha (IFN alpha 2a, and IFN alpha 2b), which are used in approved drug products, are both non-glycosylated. A major drawback of conventional IFN alpha are the side effects. Lot of work has been done on improvement of interferon alpha drugs, which are indicated for treatment of Hepatitis C. Polymer modification of proteins is a technique which is applied to improve the properties of the proteins. The mainly used technique is the modification of interferon with polyethylen glycol, known as PEGylation. Two commercially available PEGylated variants of IFN-alpha are PEGIntron® (SP) and Pegasys® (Roche).

Antithrombin III (AT III) is a serine protease inhibitor that inhibits thrombin and factor Xa (Travis, Annu. Rev. Biochem. 52: 655, 1983). To a lesser extent, factor IXa, XIa, XIIa, tPA, urokinase, trypsin, plasmin and kallikrein are also inhibited (Menache, Semin. Hematol. 28:1, 1991; Menache, Transfusion 32:580, 1992; Lahiri, Arch. Biochem. Biophys. 175:737, 1976). Human AT III is synthesized in the liver as a single chain glycoprotein of 432 amino acids with a molecular weight (MW) of approximately 58.000 D. Its plasma concentration is within the range of 14-20 mg/dL (Rosenberg, Rev. Hematol. 2:351, 1986; Murano, Thromb. Res. 18:259, 1980). The protein bears three disulfide bridges (Cys 8-128, Cys 21-95, Cys 247-430) and four N-linked carbohydrate chains (Asn 96, -135, -155, -192) which account of 15% of the total mass (Franzen, J. Biol. Chem. 255:5090, 1980; Peterson, The Physiological Inhibitions of Blood Coagulation and Fibrinolysis, Elsevier/North-Holland Biomedical Press 1979, p 43). Antithrombin is a serine proteinase inhibitor of the serpin type that is of major importance in the control of blood coagulation. AT III is the most abundant endogenous anticoagulant circulating in human plasma. This serine protease inhibitor participates in the regulation of clotting in both physiologic and pathologic states (Opal, Crit. Care Med. 2002, 30:325). It circulates in two forms with low thrombin inhibitory capacity (Pike, J. Biol. Chem. 272:19562, 1997; Ersdal-Badju, Fed. Proc. 44:404, 1985) (85-95% alpha isoform with 4 biantennary, mono- and di-sialylated oligosaccharide chains, 5-15% is the high heparin affinity beta isoform lacking glycosylation at Asn 135, 2-6 terminal sialic acid linkage). A small fraction of the circulating AT III is normally bound to proteoglycans on the surface of vascular endothelial cells. These proteoglycans are predominantly heparan sulfate, a molecule structurally similar to heparin, which is able to catalyze the inhibition of thrombin in the same way as heparin. The AT III binding to well defined pentasaccharide units of heparin causes a conformational change of the protein (Choay, Ann. NY Acad. Sci. 370:644, 1981; Choay, Biochem. Biophys. Res. Commun. 116:492, 1983; Olson, J. Biol. Chem. 266:6353, 1991; Bauer, Semin. Hematol. 28:10, 1991; Carell, Thromb. Haemost. 78:516, 1997). This binding catalyzes a 1000 fold increase of AT III inhibitory activity toward thrombin and Factor Xa (Rosenberg, Fed. Proc. 44:404, 1985; Bjork, Antithrombin and related inhibitors of coagulation proteinases in Barett, Salvesen (eds.): Proteinase Inhibitors, vol 17, Amsterdam, The Netherlands Elsevier Science Publishers (Biomedical Devision) 1986 p 489; Olson, J. Biol. Chem. 267:12528, 1992). This localization of a fraction of the AT III on the endothelial surface, where enzymes of the intrinsic coagulation cascade are commonly generated, enables AT III to rapidly neutralize these hemostatic enzymes and protect natural surfaces against thrombus formation. Thus, the key properties of AT III for prevention of thrombotic events are its ability to bind the catalyst heparin, undergo the conformational change that alters its inhibitory properties, and irreversibly bind thrombin or Factor Xa thereby inhibiting their activities. AT III also has remarkable anti-inflammatory properties, several of which result from its actions in the coagulation cascade (Roemisch, Blood Coagul Fibrinolysis. 2002, 13:657). Activated coagulation proteases like activated factor X and thrombin contribute to inflammation; for instance, by the release of pro-inflammatory mediators. Inhibition of these proteases by AT III prevents their specific interaction with cells and subsequent reactions (Roemisch, Blood Coagul Fibrinolysis 2002, 13:657). Anti-inflammatory properties of AT III independent of coagulation involve direct interactions with cells leading to the release of, for instance, prostacyclin. Binding of AT III to a recently identified cellular receptor, syndecan-4, leads to the interference with the intracellular signal induced by mediators like lipopolysaccharides and, thereby, to a down-modulation of the inflammatory response (Roemisch, Blood Coagul Fibrinolysis 2002, 13:657). Beside the analysis of the free AT III structure many studies have been conducted evaluating the complexation sites for oligosaccharide units of heparin due to the importance of the heparin AT III complex for the physiological function of AT III (Choay, Ann. NY Acad. Sci. 370:644, 1981; Choay, Biochem. Biophys. Res. Commun. 116:492, 1983; Olson, J. Biol. Chem. 266:6353, 1991; Bauer, Semin. Hematol. 28:10, 1991; Carell, Thromb. Haemost. 78:516, 1997). AT III can be produced following classical human plasma fractionating techniques. Affinity chromatography (heparin-sepharose) using the high affinity of heparin as a ligand for AT III followed by heat treatment for virus inactivation is used for the separation from plasma. Beside the fractionation from plasma more recent alternatives are available for the AT III production following recombinant production techniques that provide a safer access to this important therapeutic Protein (Levi, Semin Thromb Hemost 27: 405, 2001). ATryn™ is a recombinant human AT III (rh AT III) produced by GTC Biotherapeutics in transgenic goats. Detailed investigations have been conducted comparing the structural and functional properties of both plasma derived AT III (ph AT III) and rh AT III (Edmunds, Blood, 91:4561, 1998). Based on this experiments rh AT III is structurally identical to ph AT III with the exception of the glycosylation. Oligomannose structures were found on Asn 155 of the transgenically produced material whereas complex structures are detected in the case of the plasma derived protein. Some of the galactose units of the pd AT III are substituted by GalNac units in the rh AT III. A higher degree of fucosylation in rh AT III is another difference. Finally, the sialylation pattern of both proteins differs in two ways: the rh AT III is less sialylated and contains N-acetyl- as well as N-glycolylneuramin acids. This structural difference between the two carbohydrate parts of both molecules also results in different biochemical properties. The following AT III drugs are available on the European hospital market. (Source: IMS-ATC group 2001): Kybernin® (Aventis Behring), AT III (Baxter, Grifols), Atenativ® (Pharmacia), Aclotine® (LFB), Anbin® (Grifols).

Factor VIII participates in the intrinsic blood coagulation cascade of proteinases and serves as a cofactor in the reaction of factor IXa converting factor X to the active form, factor Xa, which ultimately leads to the formation of a fibrin clot. A lack or instability of factor VIII leads to haemophilia A, a common recessive x-linked coagulation disorder. The frequency of haemophilia A is 1-2 in 10,000 male births in all ethnic groups. Patients either do express levels of factor VIII well below normal or belong to the so-called group of crm (cross-reacting material) positive patients (approximately 5% of patients) that have considerable amount of factor VIII in their plasma (at least 30% of normal), but the protein is non-functional. About 50% of all patients have severe haemophilia a with a factor VIII activity of less than 1% of normal; they have frequent spontaneous bleeding into joints, muscles and internal organs. Mild haemophilia A, which occurs in 30-40% of patients, is associated with an activity of 5-30% of normal. Bleeding occurs only after significant trauma or surgery. Moderately severe haemophilia a occurs in about 10% of patients; Here, factor VIII activity is 2-5% of normal, and bleeding occurs already after minor trauma. The human in-vivo half-life of factor VIII is usually 10-15 hours but it has to be noted that the release, stability, and degradation kinetics are also influenced by another factor, the van Willebrand factor. Factor VIII is either produced by conventional extraction from donated human plasma or, more recently, using recombinant systems. For example, Baby hamster kidney (BHK) cells are used for production of Kogenate® (Bayer), whereas Chinese Hamster Ovary (CHO) cells are used for another product, Rekombinate® (Baxter). As the full single-chain protein of 2351 amino acids with a nominal molecular weight of 267 kD (Toole et al., 1984, Nature 312: 342) or in different versions, where the full B-domain or parts of it are deleted in order to have a product that is more stable and gives a higher yield in production (Bhattacharyya et al. 2003, CRIPS 4/3: 2-8). The precursor product is processed into two polypeptide chains of 200 and 80 kD in the Golgi and the two chains which are held together by metal ion(s) are expressed in the blood (Kaufman et al., 1988, J. Biol. Chem., 263: 6352). Procoagulant activity requires further thrombin cleavage to yield 54 kD and 44 kD fragments of the heavy chain plus a 72 kD light-chain fragment (Aly et al., 1992, Proc. Natl. Acad. Sci. USA: 4933). In factor VIII concentrates derived from human plasma several fragmented fully active factor VIII forms have thus been described (Anderson et al., 1986, Proc. Natl. Acad, Sci. 83: 2979). A common side effect of the administration of plasmatic or recombinant factor VIII are immunological reactions in quite a high number of patients (up to 30%), that forfeit the therapeutic value. In the past, various attempts to tolerate the patients by oral induction of tolerance were started but results were not all too encouraging. New genetic means of inducing tolerance have been proposed but not yet found widespread application. It is contemplated by the present inventors that a hesylated protein has a lower degree of immunogenicity and could thus reduce this complication. Factor VIII is very rich in lysine residues (over 220 of the overall 2350 amino acids), that could be used for the Reductive Amination approach.

Alpha1-Antitrypsin (A1AT, also referred to as alpha1-proteinase inhibitor) is a proteinase inhibitor that has been shown to inhibit virtually all mammalian serine proteinases (Travis *Ann. Rev. Biochem.* 52 (1983) p. 655) including neutrophil elastase, thrombin, factors Xa and XIa. A1AT is a single chain glycoprotein synthesized in the liver with 394 amino acids and a molecular weight of 53 kD. The plasma concentration is within a range of 1-1.3 g/l. The presence of only one cysteine in the whole protein does not allow the formation of intramolecular disuldide bridges. The molecule bears three carbohydrate side chains (Asn 46, 83, 247) (Mega *J. Biol. Chem.* 255 (1980) p. 4057; Mega *J. Biol. Chem.* 255 (1980) p. 4053; Carell *FEBS Letters* 135 (1981) p. 301; Hodges *Biochemistry* 21 (1982) p. 2805) that represent 12% of the molecular weight. Two types of carbohydrate chains were discovered having a bi- or triantennary structure, respectively (Hodges *J. Biol. Chem.* 254 (1979) p. 8208). Human A1AT occurs in at least twenty different forms in the general population. This micro-heterogenicity is a result of variable amounts of the two types of carbohydrate chains. The key function is the activity control of neutrophil elastase (Travis *Ann. Rev. Biochem.* 52 (1983) p. 655). An uncontrolled activity of elastase leads to an attack on epithelial tissues with the result of irreparable damage. During the inactivation process A1AT acts as a substrate for elastase binding to the active center of the protease which is subsequently inactivated by this complex formation. A deficiency of A1AT causes e.g. pulmonary emphysema which is in connected with a damage of the pulmonary epithelium. The distribution of the two types of carbohydrate side chains of A1AT to the three N-glycosylation sites of A1AT is different for each isotype of A1AT. The classical production of A1AT is conducted following plasma fractionation techniques using different affinity-chromatography steps from human plasma. However a more recent way of producing A1AT is the use of recombinant techniques. PPL Therapeutics have developed a process that allows to recover recombinant human A1AT (rHA1AT) from the milk of transgenic sheep (Olman *Biochem. Soc. Symp.* 63 (1998) p. 141; Tebbutt *Curr. Opin. Mol. Ther.* 2 (2000) p. 199; Carver *Cytotechnology* 9 (1992) p. 77; Wright *Biotechnology (NY)* 9 (1991) p. 830). With respect to the protein part of the molecule the rhA1AT shows an identical structure compared to pdA1AT. But—as is the case for other recombinant produced human proteins—differences occur in the carbohydrate side chains, especially with regard to the amount of sialic acid residues.

The tissue type plasminogen activator (tPA) is a trypsine like serine protease important in clot lysis. In the presence of a fibrin clot, tPA converts plasminogen to plasmin, which degrades fibrin. TPA exhibits enhanced activity in the presence of fibrin and as a result, causes fibrin-specific plasminogen activation (M. W. Spellman, L. J. Basa, C. K. Leonard, J. A. Chakel, J. V. O'Connor, *The Journal of Biological Chemistry* 264 (1989) p. 14100). Plasmin solubilizes fibrin, yielding fibrin degradation products. Through a positive feedback mechanism, fibrin enhances its own degradation by stimulating tPA mediated plasminogen activation (R. J. Stewart et. al. *The Journal of Biological Chemistry* 275 (2000) pp. 10112-10120). htPA is a physiological activator of fibrinolysis, which is present in different types of tissues. It is a glycoprotein with a molecular weight of approx. 68 kD. In native form tPA exists in a one-chain-form (single-chain tissue-type plasminogen activator, sctPA), which can be converted by cleavage of plasmin at the peptide bond Arg 275-Ile 276 to a two chain structure (two-chain tissue-type plasminogen activator, tctPA). For therapy of fibrinolysis it is produced recombinant as rtPA (recombinant tissue-type plasminogen activator). Different types of tPA exist showing structural differences in the carbohydrate structure. Type I tPA has N-linked oligosaccharides at amino acids Asn117, Asn184 and Asn448. Type II tPA is glycosylated at Asn117 and Asn448. Both types contain an O-linked fucose residue at Thr61 (K. Mori et. al. *The Journal of Biological Chemistry* 270 (1995) pp. 3261-3267). The carbohydrate structure of tPA expressed in CHO-cells was investigated, showing a large variety of di-, tri- and tetraantennary structures of the sugar chains (M. W. Spellman, L. J. Basa, C. K. Leonard, J. A. Chakel, J. V. O'Connor, *The Journal of Biological Chemistry* 264 (1989) p. 14100). The primary structure of tPA contains several cysteines, that are believed to be cross-linked and in addition a free cysteine residue at site 83, which may interact with another tPA, forming a dimer. Several results indicate that the in-vivo clearance of tPA is influenced by the carbohydrate structure, particularly by the high mannose oligosaccharide attached at site Asn117. Another proposed clearance mechanism involves the recognition of the O-linked fucose residue at Thr61 by a high affinity receptor on hepatocytes. This residue is close to Cys83. A bioengineered tPA (TNK-tPA) was developed to prolong the half-life. The glycosylation site at position 117 was shifted to position 103. Asparagine at site 117 was substituted by Glutamine and Threonine at site 103 substituted by Asparagine. TNK-tPA is resistant to inactivation by plasminogen activator inhibitor 1 because of a tetra-alanine substitution in the protease domain (R. J. Stewart et. al. *The Journal of Biological Chemistry* 275 (2000) pp. 10112-10120). TNK-tpA is on the market as Tenecteplase® (Boehringer Ingelheim). TNK-tPA can be administered as a single intravenous bolus, while tPA has to be administered as a bolus followed by an infusion.

Activated Protein C (APC) is a modulator of the coagulation and inflammation associated with severe sepsis. Activated Protein C is converted from its inactive precursor (protein C) by thrombin coupled to thrombomodulin. This complex cleaves off a short N-terminal activation peptide form the heavy chain of protein C, resulting in the activated protein C. Drotrecogin alpha (activated) is a recombinant human activated protein C (rhAPC). Its amino acid sequence is identical to plasma derived activated protein C and it has similar properties. Activated protein C is marketed by Eli Lilly as Xigris®. It is produced in a human cell line (HEK293), into which the protein C expression vectors are introduced. The cell line was used due to its ability to perform the correct series of complex post-translational modifications that are required for functional activity. Recombinant human activated protein C is a 2-chain glycoprotein containing 4 N-glycosylation sites and 12 disulfide bonds. The heavy chain contains 250 amino acids. In this chain, seven residues are cysteine and three N-linked glycosylation sites (Asn-248, Asn-313 and Asn-329). The seven cysteine residues form three disulfide bonds within the heavy chain and one disulfide bond between the chains. The light chain contains one N-linked glycosylation site (Asn-97) and 17 cysteine residues, which form eight disulfide bonds within the light chain and one disulfide bond between the chains. The first nine glutamic acids on the light chain are gamma carboxylated (Gla) and aspartic acid 71 is beta hydroxylated. rhAPC has an identical amino acid sequence as human plasma-derived activated protein C, but differs from the latter in its glycosylation pattern. Activated protein C is a protease belonging to the serine protease family. It plays a major role in the regulation of coagulation. Basis for the antithrombotic function of activated protein C is its ability to inhibit thrombin function. In addition, activated protein C is an important modulator of inflammation associated with severe sepsis. Endogenous serine protease inhibitors are natural inhibitors for activated protein C, resulting in activated protein C having a very short circulatory activity half-life (less than 30 min) in vivo. Clearance of activated protein C from the circulation is mediated by combination of at least three processes including the inhibition of the enzymatic activity of activated protein C by endogenous protease inhibitors, the clearance of activated protein C and/or activated protein C-serine protease inhibitor complexes by organs such as liver and kidney, and the degradation of activated protein C and/or activated protein C-serine protease inhibitor complexes by circulating or tissue proteases. Phase I clinical studies with 24 h-infusion at 24 µg/kg/h resulted in a steady state plasma concentration of 70 ng/ml. The half-life of rhAPC measured at the end of an infusion was 0.5-1.9 h. Plasma rhAPC concentrations fell below the detection limit of 10 ng/ml within 2 h after termination of the infusion. Due to its short physiological and pharmacokinetic half-life, in clinical use in sepsis therapy, activated protein C is continuously infused at a certain rate to maintain the desired plasma concentration. Some effort is made to improve the pharmacokinetic profile of activated protein C. For example D. T. Berg et. al. Proc. Natl. Acad. Sci. USA 100 (2003) pp. 4423-4428, describe an engineered variant of activated protein C with prolonged plasma half-life.

Factor VII participates in the intrinsic blood coagulation cascade of proteinases and promoting hemostatsis by activating the extrinsic pathway of the coagulation cascade. F VII is converted to factor VIIa by factor Xa, factor XIIa, factor IXa, or thrombin by minor proteolysis. In the presence of tissue factor and calcium ions, factor VIIa then converts factor X to factor Xa by limited proteolysis. Factor VIIa will also convert factor IX to factor IXa in the presence of tissue factor and calcium. Factor VII is a vitamin K-dependent glycoprotein consisting of 406 amino acid residues (MW 50 K Dalton). Factor VII is either produced by conventional extraction from donated human plasma or, more recently, using recombinant systems. Novo Nordisk uses Baby hamster kidney (BHK) cells for production of NovoSeven®. Expressed as the single-chain protein of 406 amino acids with a nominal molecular weight of 55 kDa (Thim, L. et al., Biochemistry 27:7785-7793(1988). The molecule bears four carbohydrate side chains. Two O-linked carbohydrate side chains at Ser 52, 60 and two N-linked carbohydrate side chains at Asn 145, 322 (Thim, L. et al., Biochemistry 27:7785-7793(1988).

Factor VII is indicated for the treatment of bleeding episodes in hemophilia A or B patients with inhibitors to Factor VIII or Factor IX. Therefore, the present invention also relates to the use of a HAS-Factor VII conjugate for the preparation of a medicament for the treatment of episodes in hemophilia A or B patients with inhibitors to Factor VIII or Factor IX.

Factor IX is a vitamin K-dependent plasma protein that participates in the intrinsic pathway of blood coagulation by converting factor X to its active form in the presence of Ca(2+) ions, phospholipids, and factor VIIIa. Factor IX is a glycoprotein with an approximate molecular mass of 55,000 Da consisting of 415 amino acids in a single chain (Yoshitake S. et al., Biochemistry 24:3736-3750(1985)). Factor IX is either produced by conventional extraction from donated human plasma or, more recently, using recombinant systems. Wyeth uses Chinese hamster ovary (CHO) cells for production of BeneFIX®. It has a primary amino acid sequence that is identical to the Ala[148] allelic form of plasma-derived factor IX, and has structural and functional characteristics similar to those of endogenous factor IX. The protein bears eight carbohydrate side chains. Six O-linked carbohydrate side chains at Ser 53, 61 and at Threonine 159, 169, 172, 179 and two N-linked carbohydrate side chains at Asn 157, 167 (Yoshitake S. et al., Biochemistry 24:3736-3750(1985); Balland A. et al., Eur J. Biochem. 1988; 172(3):565-72).

Factor IX is indicated for the control and prevention of hemorrhagic episodes in patients with hemophillia B (congenital factor IX deficiency or Christmas disease), including control and prevention of bleeding in surgical settings. Therefore, the present invention also relates to the use of a HAS-Factor IX conjugate for the preparation of a medicament for the control and prevention of hemorrhagic episodes in patients with hemophillia B (e.g. congenital factor IX deficiency or Christmas disease), including control and prevention of bleeding in surgical settings.

In the context of the present invention, the term "hydroxyalkyl starch" (HAS) refers to a starch derivative which has been substituted by at least one hydroxyalkyl group. A preferred hydroxyalkyl starch of the present invention has a constitution according to formula (I)

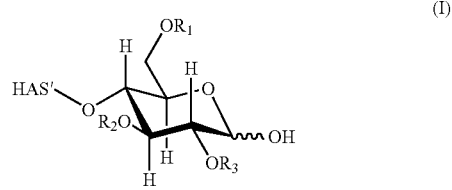

wherein the reducing end of the starch molecule is shown in the non-oxidized form and the terminal saccharide unit is shown in the hemiacetal form which, depending on e.g. the solvent, may be in equilibrium with the aldehyde form.

The term hydroxyalkyl starch as used in the present invention is not limited to compounds where the terminal carbohydrate moiety comprises hydroxyalkyl groups $R_1$, $R_2$, and/or $R_3$ as depicted, for the sake of brevity, in formula (I), but also refers to compounds in which at least one hydroxyalkyl group is present anywhere, either in the terminal carbohydrate moiety and/or in the remaining part of the starch molecule, HAS', is substituted by a hydroxyalkyl group $R_1$, $R_2$, or $R_3$.

Hydroxyalkyl starch comprising two or more different hydroxyalkyl groups are also possible.

The at least one hydroxyalkyl group comprised in HAS may contain two or more hydroxy groups. According to a preferred embodiment, the at least one hydroxyalkyl group comprised HAS contains one hydroxy group.

The expression "hydroxyalkyl starch" also includes derivatives wherein the alkyl group is mono- or polysubstituted. In this context, it is preferred that the alkyl group is substituted with a halogen, especially fluorine, or with an aryl group. Furthermore, the hydroxy group of a hydroxyalkyl group may be esterified or etherified.

Furthermore, instead of alkyl, also linear or branched substituted or unsubstituted alkene groups may be used.

Hydroxyalkyl starch is an ether derivative of starch. Besides of said ether derivatives, also other starch derivatives can be used in the context of the present invention. For example, derivatives are useful which comprise esterified hydroxy groups. These derivatives may be e.g. derivatives of unsubstituted mono- or dicarboxylic acids with 2-12 carbon atoms or of substituted derivatives thereof. Especially useful are derivatives of unsubstituted monocarboxylic acids with 2-6 carbon atoms, especially derivatives of acetic acid. In this context, acetyl starch, butyryl starch and propionyl starch are preferred.

Furthermore, derivatives of unsubstituted dicarboxylic acids with 2-6 carbon atoms are preferred.

In the case of derivatives of dicarboxylic acids, it is useful that the second carboxy group of the dicarboxylic acid is also esterified. Furthermore, derivatives of monoalkyl esters of dicarboxylic acids are also suitable in the context of the present invention.

For the substituted mono- or dicarboxylic acids, the substitute groups may be preferably the same as mentioned above for substituted alkyl residues.

Techniques for the esterification of starch are known in the art (see e.g. Klemm D. et al, Comprehensive Cellulose Chemistry Vol. 2, 1998, Whiley-VCH, Weinheim, N.Y., especially chapter 4.4, Esterification of Cellulose (ISBN 3-527-29489-9).

According to a preferred embodiment of the present invention, hydroxyalkyl starch according to above-mentioned formula (I) is employed. In formula (I), the saccharide ring described explicitly and the residue denoted as HAS' together represent the preferred hydroxyalkyl starch molecule. The other saccharide ring structures comprised in HAS' may be the same as or different from the explicitly described saccharide ring.

As far as the residues $R_1$, $R_2$ and $R_3$ according to formula (I) are concerned there are no specific limitations. According to a preferred embodiment, $R_1$, $R_2$ and $R_3$ are independently hydrogen or a hydroxyalkyl group, a hydroxyaryl group, a hydroxyaralkyl group or a hydroxyalkaryl group having of from 2 to 10 carbon atoms in the respective alkyl residue or a group $(CH_2CH_2O)_n$—H wherein n is an integer, preferably 1, 2, 3, 4, 5 or 6. Hydrogen and hydroxyalkyl groups having of from 2 to 10 are preferred. More preferably, the hydroxyalkyl group has from 2 to 6 carbon atoms, more preferably from 2 to 4 carbon atoms, and even more preferably from 2 to 3 carbon atoms. "Hydroxyalkyl starch" therefore preferably comprises hydroxyethyl starch, hydroxypropyl starch and hydroxybutyl starch, wherein hydroxyethyl starch and hydroxypropyl starch are particularly preferred and hydroxyethyl starch is most preferred.

The alkyl, aryl, aralkyl and/or alkaryl group may be linear or branched and suitably substituted.

Therefore, the present invention also relates to a method an a conjugate as described above wherein $R_1$, $R_2$ and $R_3$ are independently hydrogen or a linear or branched hydroxyalkyl group with from 2 to 6 carbon atoms.

Thus, $R_1$, $R_2$ and $R_3$ preferably may be hydroxyhexyl, hydroxypentyl, hydroxybutyl, hydroxypropyl such as 2-hydroxypropyl, 3-hydroxypropyl, 2-hydroxyisopropyl, hydroxyethyl such as 2-hydroxyethyl, hydrogen and the 2-hydroxyethyl group being especially preferred.

Therefore, the present invention also relates to a method and a conjugate as described above wherein $R_1$, $R_2$ and $R_3$ are independently hydrogen or a 2-hydroxyethyl group, an embodiment wherein at least one residue $R_1$, $R_2$ and $R_3$ being 2-hydroxyethyl being especially preferred.

Hydroxyethyl starch (HES) is most preferred for all embodiments of the present invention.

Therefore, the present invention relates to the method and the conjugate as described above, wherein the polymer is hydroxyethyl starch and the polymer derivative is a hydroxyethyl starch derivative.

Hydroxyethyl starch (HES) is a derivative of naturally occurring amylopectin and is degraded by alpha-amylase in the body. HES is a substituted derivative of the carbohydrate polymer amylopectin, which is present in corn starch at a concentration of up to 95% by weight. HES exhibits advantageous biological properties and is used as a blood volume replacement agent and in hemodilution therapy in the clinics (Sommermeyer et al., 1987, Krankenhauspharmazie, 8(8), 271-278; and Weidler et al., 1991, Arzneim.-Forschung/Drug Res., 41, 494-498).

Amylopectin consists of glucose moieties, wherein in the main chain alpha-1,4-glycosidic bonds are present and at the branching sites alpha-1,6-glycosidic bonds are found. The physical-chemical properties of this molecule are mainly determined by the type of glycosidic bonds. Due to the nicked alpha-1,4-glycosidic bond, helical structures with about six glucose-monomers per turn are produced. The physicochemical as well as the biochemical properties of the polymer can be modified via substitution. The introduction of a hydroxyethyl group can be achieved via alkaline hydroxyethylation. By adapting the reaction conditions it is possible to exploit the different reactivity of the respective hydroxy group in the unsubstituted glucose monomer with respect to a hydroxyethylation. Owing to this fact, the skilled person is able to influence the substitution pattern to a limited extent.

HES is mainly characterized by the molecular weight distribution and the degree of substitution. There are two possibilities of describing the substitution degree:

1. The degree of substitution can be described relatively to the portion of substituted glucose monomers with respect to all glucose moieties.
2. The degree of substitution can be described as the molar substitution, wherein the number of hydroxyethyl groups per glucose moiety are described.

In the context of the present invention, the degree of substitution, denoted as DS, relates to the molar substitution, as described above (see also Sommermeyer et al., 1987, Krankenhauspharmazie, 8(8), 271-278, as cited above, in particular p. 273).

HES solutions are present as polydisperse compositions, wherein each molecule differs from the other with respect to the polymerisation degree, the number and pattern of branching sites, and the substitution pattern. HES is therefore a mixture of compounds with different molecular weight. Consequently, a particular HES solution is determined by average molecular weight with the help of statistical means. In this context, $M_n$ is calculated as the arithmetic mean depending on the number of molecules. Alternatively, $M_w$ (or MW), the weight mean, represents a unit which depends on the mass of the HES.

In the context of the present invention, hydroxyethyl starch may preferably have a mean molecular weight (weight mean) of from 1 to 300 kD. Hydroxyethyl starch can further exhibit a preferred molar degree of substitution of from 0.1 to 3, preferably 0.1 to 2, more preferred, 0.1 to 0.9, preferably 0.1 to 0.8, and a preferred ratio between $C_2:C_6$ substitution in the range of from 2 to 20 with respect to the hydroxyethyl groups.

The term "mean molecular weight" as used in the context of the present invention relates to the weight as determined according to the LALLS—(low angle laser light scattering)-GPC method as described in Sommermeyer et al., 1987, Krankenhauspharmazie, 8(8), 271-278; and Weidler et al., 1991, Arzneim.-Forschung/Drug Res., 41, 494-498. For mean molecular weights of 10 kD and smaller, additionally, the calibration was carried out with a standard which had previously been qualified by LALLS-GPC.

According to a preferred embodiment of the present invention, the mean molecular weight of hydroxyethyl starch employed is from 1 to 300 kD, more preferably from 2 to 200 kD, more preferably of from 4 to 130 kD, more preferably of from 4 to 70 kD.

An example of HES having a mean molecular weight of about 130 kD is a HES with a degree of substitution of 0.1 to 0.9, preferably 0.2 to 0.8 such as 0.2, 0.3, 0.4, 0.5, 0.6, 0.7, or 0.8, preferably of 0.4 to 0.7 such as 0.4, 0.5, 0.6, or 0.7.

An example for HES with a mean molecular weight of about 130 kD is Voluven® from Fresenius. Voluven® is an artificial colloid, employed, e.g., for volume replacement used in the therapeutic indication for therapy and prophylaxis of hypovolaemia. The characteristics of Voluven® are a mean molecular weight of 130,000+/−20,000 D, a molar substitution of 0.4 and a C2:C6 ratio of about 9:1.

Therefore, the present invention also relates to a method and to conjugates as described above wherein the hydroxyalkyl starch is hydroxyethyl starch having a mean molecular weight of from 4 to 100 kD, preferably of from 4 to 70 kD.

Preferred ranges of the mean molecular weight are, e.g., 4 to 70 kD or 10 to 70 kD or 12 to 70 kD or 18 to 70 kD or 50 to 70 kD or 4 to 50 kD or 10 to 50 kD or 12 to 50 kD or 18 to 50 kD or 4 to 18 kD or 10 to 18 kD or 12 to 18 kD or 4 to 12 kD or 10 to 12 kD or 4 to 10 kD.

According to particularly preferred embodiments of the present invention, the mean molecular weight of hydroxyethyl starch employed is in the range of from more than 4 kD and below 70 kD, such as about 10 kD, or in the range of from 9 to 10 kD or from 10 to 11 kD or from 9 to 11 kD, or about 12 kD, or in the range of from 11 to 12 kD or from 12 to 13 kD or from 11 to 13 kD, or about 18 kD, or in the range of from 17 to 18 kD or from 18 to 19 kD or from 17 to 19 kD, or about 50 kD, or in the range of from 49 to 50 kD or from 50 to 51 kD or from 49 to 51 kD.

As to the upper limit of the molar degree of substitution (DS), values of up to 3.0 such as 0.9, 1.0, 1.1, 1.2, 1.3, 1.4, 1.5, 1.6, 1.7, 1.8, 1.9 or 2.0 are also possible, values of below 2.0 being preferred, values of below 1.5 being more preferred, values of below 1.0 such as 0.7, 0.8 or 0.9 being still more preferred.

Therefore, preferred ranges of the molar degree of substitution are from 0.1 to 2 or from 0.1 to 1.5 or from 0.1 to 1.0 or from 0.1 to 0.9 or from 0.1 to 0.8. More preferred ranges of the molar degree of substitution are from 0.2 to 2 or from 0.2 to 1.5 or from 0.2 to 1.0 or from 0.2 to 0.9 or from 0.2 to 0.8. Still more preferred ranges of the molar degree of substitution are from 0.3 to 2 or from 0.3 to 1.5 or from 0.3 to 1.0 or from 0.3 to 0.9 or from 0.3 to 0.8. Even more preferred ranges of the molar degree of substitution are from 0.4 to 2 or from 0.4 to 1.5 or from 0.4 to 1.0 or from 0.4 to 0.9 or from 0.4 to 0.8.

As far as the degree of substitution (DS) is concerned, DS is preferably at least 0.1, more preferably at least 0.2, more preferably at least 0.4 and more preferably at least 0.4. Preferred ranges of DS are from 0.1 to 3, preferably 0.1 to 2, more preferred, 0.1 to 0.9, more preferably from 0.1 to 0.8, more preferably from 0.2 to 0.8, more preferably from 0.3 to 0.8 and even more preferably from 0.4 to 0.8, still more preferably from 0.1 to 0.7, more preferably from 0.2 to 0.7, more preferably from 0.3 to 0.7 and more preferably from 0.4 to 0.7. Particularly preferred values of DS are, e.g., 0.1, 0.2, 0.3, 0.4, 0.5, 0.6, 0.7, 0.8 or 0.9, with 0.2, 0.3, 0.4, 0.5, 0.6, 0.7 or 0.8 being more preferred, 0.3, 0.4, 0.5, 0.6, 0.7 or 0.8 being even more preferred, 0.4, 0.5, 0.6, 0.7 or 0.8 being still more preferred and, e.g. 0.4 and 0.7 being particularly preferred.

In the context of the present invention, a given value of the molar degree of substitution such as 0.9 may be the exact value or may be understood as being in a range of from 0.85 to 0.94 or 0.8 may be the exact value or may be understood as being in a range of from 0.75 to 0.84. Therefore, for example, a given value of 0.1 may be the exact value of 0.1 or be in the range of from 0.05 to 0.14, a given value of 0.4 may be the exact value of 0.4 or in the range of from 0.35 to 0.44, or a given value of 0.7 may be the exact value of 0.7 or be in the range of from 0.65 to 0.74.

Particularly preferred combinations of molecular weight of the hydroxyalkyl starch, preferably hydroxyethyl starch, and its degree of substitution DS are, e.g., 10 kD and 0.4 or 10 kD and 0.7 or 12 kD and 0.4 or 12 kD and 0.7 or 18 kD and 0.4 or 18 kD and 0.7 or 50 kD and 0.4 or 50 kD and 0.7 or 100 kD and 0.7.

As far as the ratio of $C_2:C_6$ substitution is concerned, said substitution is preferably in the range of from 2 to 20, more preferably in the range of from 2 to 15 and even more preferably in the range of from 3 to 12.

According to a further embodiment of the present invention, also mixtures of hydroxyethyl starches may be employed having different mean molecular weights and/or different degrees of substitution and/or different ratios of $C_2:C_6$ substitution. Therefore, mixtures of hydroxyethyl starches may be employed having different mean molecular weights and different degrees of substitution and different ratios of $C_2:C_6$ substitution, or having different mean molecular weights and different degrees of substitution and the same or about the same ratio of $C_2:C_6$ substitution, or having different mean molecular weights and the same or about the same degree of substitution and different ratios of $C_2:C_6$ substitution, or having the same or about the same mean molecular weight and different degrees of substitution and different ratios of $C_2:C_6$ substitution, or having different mean molecular weights and the same or about the same degree of substitution and the same or about the same ratio of $C_2:C_6$ substitution, or having the same or about the same mean molecular weights and different degrees of substitution and the same or about the same ratio of $C_2:C_6$ substitution, or having the same or about the same mean molecular weight and the same or about the same degree of substitution and different ratios of $C_2:C_6$ substitution, or having about the same mean molecular weight and about the same degree of substitution and about the same ratio of $C_2:C_6$ substitution.

In different conjugates and/or different methods according to the present invention, different hydroxyalkyl starches, preferably different hydroxyethyl starches and/or different hydroxyalkyl starch mixtures, preferably different hydroxyethyl starch mixtures, may be employed.

The reductive amination reaction according to the invention, wherein the polymer or polymer derivative is covalently linked via at least one aldehyde group to at least one amino group of the protein by reductive amination, is preferably carried out at a temperature of from 0 to 40° C., more preferably 0 to 37° C., more preferably of from 0 to 25° C., in particular from 4 to 21° C., but especially preferably of from 0 to 21° C. The reaction time preferably ranges of from 0.5 to 72 h, more preferably of from 2 to 48 h and especially preferably of from 4 to 7 h. As solvent for the reaction, an aqueous medium is preferred.

Thus, the present invention also relates to a method and a conjugate as described above, wherein the reductive amination is carried out at a temperature of from 4 to 21° C., but especially preferably 0 to 21° C.

Therefore, the present invention also relates to a method and a conjugate as described above, wherein reductive amination is carried out in an aqueous medium.

Thus, the present invention also relates to a method and conjugate as described above, wherein the reductive amination is carried out at a temperature of from 4 to 21° C., but especially preferably 0 to 21° C., in an aqueous medium.

The term "aqueous medium" as used in the context of the present invention relates to a solvent or a mixture of solvents comprising water in the range of from at least 10% per weight, more preferably at least 20% per weight, more preferably at least 30% per weight, more preferably at least 40% per weight, more preferably at least 50% per weight, more preferably at least 60% per weight, more preferably at least 70% per weight, more preferably at least 80% per weight, even more preferably at least 90% per weight or up to 100% per weight, based on the weight of the solvents involved. The preferred reaction medium is water.

The pH value of the reaction medium is generally in the range of from 4 to 9 or from 4 to 8 or from 4 to 7.5 or from 4 to 7.3.

According to a preferred embodiment of the present invention, the pH at which the reductive amination reaction is carried out is below 10, preferably below 7.5, preferably 7.3, more preferably smaller or equal 7 and most preferably below 7, i.e. in the acidic range. Preferred ranges are therefore of from 3 to below 7, more preferably of from 3.5 to 6.5, still more preferably of from 4 to 6, still more preferably of from 4.5 to 5.5 and especially preferably about 5.0, i.e. 4.6 or 4.7 or 4.8 or 4.9 or 5.0 or 5.1 or 5.2 or 5.3 or 5.4. Preferred ranges, are among others, 3 to 6.9 or 3 to 6.5 or 3 to 6 or 3 to 5.5 or 3 to 5 or 3 to 4.5 or 3 to 4 or 3 to 3.5 or 3.5 to 6.9 or 3.5 to 6.5 or 3.5 to 6 or 3.5 to 5.5 or 3.5 to 5 or 3.5 to 4.5 or 3.5 to 4 or 4 to 6.9 or 4 to 6.5 or 4 to 6. or 4 to 5.5 or 4 to 5 or 4 to 4.5 or 4.5 to 6.9 or 4.5 to 6.5 or 4.5 to 6 or 4.5 to 5.5 or 4.5 to 5 or 5 to 6.9 or 5 to 6.5 or 5 to 6 or 5 to 5.5 or 5.5 to 6.9 or 5.5 to 6.5 or 5.5 to 6 or 6 to 6.9 or 6 to 6.5 or 6.5 to 6.9.

Therefore, the present invention also relates to a method and a conjugate as described above, wherein the reductive amination is carried out at a pH of 7 or less, more preferably at a pH of 6 or less.

Thus, the present invention also relates to a method and conjugate as described above, wherein the reductive amination is carried out at a temperature of from 0 to 21° C., preferably 4 to 21° C. at a pH of 7.5 or less, preferably 7 or less, preferably of 6 or less.

Hence, the present invention also relates to a method and conjugate as described above, wherein the reductive amination is carried out in an aqueous medium at a pH of 7 or less, preferably of 6 or less.

Accordingly, the present invention also relates to a method and conjugate as described above, wherein the reductive amination is carried out at a temperature of from 4 to 21° C. in an aqueous medium at a pH of 7 or less, preferably of 6 or less.

The molar ratio of polymer derivative:protein used for the reaction is preferably in the range of from 200:1 to 5:1, more preferably of from 100:1 to 10:1 and especially preferably of from 75:1 to 20:1.

It was surprisingly found that it was possible, especially at the preferred pH ranges given above, particularly at a pH below 7 and greater or equal 4, to react the polymer derivative predominantly with the amino group located at the N terminus of the protein. The term "predominantly" as used in the context of the present invention relates to an embodiment where at least 80%, preferably at least 85% of the N-terminal amino groups available are reacted via reductive amination. It is also possible to react at least 90% or at least 95% or at least 96% or at least 97% or at least 98% or at least 99% of the N-terminal amino groups available. Although coupling to amino groups other than the N-terminal amino group could not be ruled out completely, it is believed that coupling via reductive amination according to the present invention at a pH of below 7, preferably below 6, took place essentially selectively at the N-terminal amino group. In particular, these reaction conditions are preferred for proteins which are stable at these conditions. Should a protein e.g. be acid labile, such as alpha1-antitrypsin, then it is preferred to chose appropriate reaction conditions, in particular a pH from lower than 7.5 to greater than 5.

Therefore, the present invention also relates to a method and a conjugate as described above, wherein the protein comprises the N-terminal amino group and at least one further amino group, said conjugate comprises the polymer being predominantly coupled to the N-terminal amino group.

According to an especially preferred embodiment, the present invention relates to a method of linking aldehyde or keto or hemiacetal functionalized hydroxyalkyl starch or an aldehyde or keto or hemiacetal functionalized hydroxyalkyl starch derivative predominantly to the N-terminal amino group of a protein, said method comprising subjecting said hydroxyalkyl starch or derivative thereof to a reductive amination reaction, at a pH of 7 or less, preferably at a pH of 6 or less, said reductive amination reaction being carried out preferably in an aqueous medium.

According to the present invention, aldehyde functionalized hydroxyalkyl starch or an aldehyde functionalized hydroxyalkyl starch derivative is preferred.

According to a still further preferred embodiment, the present invention relates to a method of linking aldehyde or keto or hemiacetal functionalized hydroxyethyl starch or an aldehyde or keto or hemiacetal functionalized hydroxyethyl starch derivative selectively to the N-terminal amino group of a protein, said method comprising subjecting said hydroxyalkyl starch or derivative thereof to a reductive amination reaction, at a pH of 7 or less, preferably at a pH of 6 or less, said reductive amination reaction being carried out preferably in an aqueous medium, the hydroxyethyl starch employed preferably being hydroxyethyl starch having a mean molecular weight of about 10 kD and a DS of about 0.4 or hydroxyethyl starch having a mean molecular weight of about 10 kD and a DS of about 0.7 or hydroxethyl starch having a mean molecular weight of about 12 kD and a DS of about 0.4 or hydroxethyl starch having a mean molecular weight of about 12 kD and a DS of about 0.7 or hydroxethyl starch having a mean molecular weight of about 18 kD and a DS of about 0.4 or hydroxethyl starch having a mean molecular weight of about 18 kD and a DS of about 0.7 or hydroxethyl starch having a mean molecular weight of about 50 kD and a DS of about 0.4 or hydroxethyl starch having a mean molecular weight of about 50 kD and a DS of about 0.7 or hydroxethyl starch having a mean molecular weight of about 100 kD and a DS of about 0.7.

The reaction of the polymer derivative and the protein between the aldehyde group or keto group or hemiacetal group and the amino group is a reductive amination wherein a Schiff's base is produced. Subsequently after the reaction, this base may be reduced by at least one reductive agent to give a stable linkage between the polymer derivative and the protein. It is also possible to carry out the reaction in the presence of at least one reductive agent. According to a preferred embodiment, the reductive amination reaction is carried out in the presence of at least one reductive agent.

Preferred reductive agents are sodium borohydride, sodium cyanoborohydride, organic borane complex compounds such as a 4-(dimethylamin)pyridine borane complex, N-ethyldiisopropylamine borane complex, N-ethylmorpholine borane complex, N-methylmorpholine borane complex, N-phenylmorpholine borane complex, lutidine borane complex, triethylamine borane complex, or trimethylamine borane complex. Particularly preferred is sodium cyanoborohydride.

Therefore, the present invention also relates to a method and a conjugate as described above, wherein the reductive amination is carried out in the presence of $NaCNBH_3$.

Hence, the present invention also relates to a method and conjugate as described above, wherein the reductive amination is carried out in an aqueous medium at a pH of 7 or less, preferably of 6 or less in the presence of reductive agent, preferably $NaCNBH_3$.

Accordingly, the present invention also relates to a method and conjugate as described above, wherein the reductive amination is carried out at a temperature of from 4 to 21° C. in an aqueous medium at a pH of 7 or less, preferably of 6 or less in the presence of reductive agent, preferably $NaCNBH_3$.

The molar ratio of polymer derivative:protein used for the reaction is preferably in the range of from 200:1 to 10:1 more preferably of from 100:1 to 10:1 and especially preferably of from 75:1 to 20:1.

Therefore, the present invention also relates to a method of producing a conjugate, said method comprising reacting a polymer or a polymer derivative comprising an aldehyde group in an aqueous medium with an amino group of the protein in the presence of a reductive agent, said reductive agent preferably being $NaCNBH_3$.

According to the first preferred embodiment of the present invention, according to which the polymer comprises at least two aldehyde groups which are introducing in the polymer by a ring-opening oxidation reaction, the polymer preferably comprises at least one structure according to formula

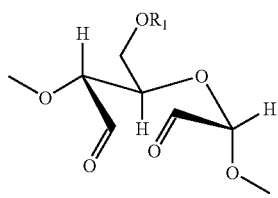

According to this embodiment of the present invention, each oxidation agent or combination of oxidation agents may be employed which is capable of oxidizing at least one saccharide ring of the polymer to give an opened saccharide ring having at least one, preferably at least two aldehyde groups. This reaction is illustrated by the following reaction scheme which shows a saccharide ring of the polymer which is oxidized to give an opened ring having two aldehyde groups:

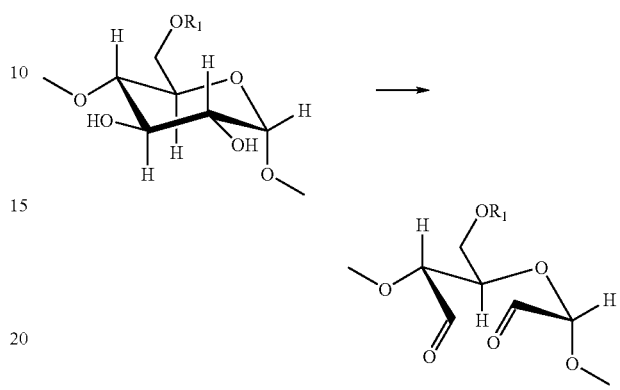

Suitable oxidating agents are, among others, periodates such as alkaline metal periodates or mixtures of two or more thereof, with sodium periodate and potassium periodate being preferred.

Therefore, the present invention also relates to a method and a conjugate as described above, wherein the polymer is subjected to a ring-opening oxidation reaction using a periodate to give a polymer derivative having at least one, preferably at least two aldehyde groups.

For this oxidation reaction, the polymer may be employed with its reducing end either in the oxidized or in the non-oxidized form, the non-oxidized form being preferred.

Therefore, the present invention also relates to a method and a conjugate as described above, wherein the polymer is employed with its reducing end in the non-oxidized form.

The reaction temperature is in a preferred range of from 0 to 40° C., more preferably of from 0 to 25° C. and especially preferably of from 0 to 5° C. The reaction time is in a preferred range of from 1 min to 5 h and especially preferably of from 10 min to 4 h. Depending on the desired degree of oxidation, i.e. the number of aldehyde groups resulting from the oxidation reaction, the molar ratio of periodate:polymer may be appropriately chosen.

Therefore, the present invention also relates to a method and a conjugate as described above, wherein the ring-opening oxidation reaction is carried out at a temperature of from 0 to 5° C.

The oxidation reaction of the polymer with periodate is preferably carried out in an aqueous medium, most preferably in water.

Therefore, the present invention also relates to a method and a conjugate as described above, wherein the ring-opening oxidation reaction is carried out in an aqueous medium. The suitable pH value of the reaction mixture may be adjusted by adding at least one suitable buffer. Among the preferred buffers, sodium acetate buffer, phosphate or borate buffers may be mentioned.

The hydroxyethyl starch subjected to said ring-opening oxidation reaction is preferably hydroxyethyl starch having a mean molecular weight of about 10 kD and a DS of about 0.4 or hydroxethyl starch having a mean molecular weight of about 10 kD and a DS of about 0.7 or hydroxethyl starch having a mean molecular weight of about 12 kD and a DS of about 0.4 or hydroxethyl starch having a mean molecular weight of about 12 kD and a DS of about 0.7 or hydroxyethyl starch having a mean molecular weight of about 18 kD and a DS of about 0.4 or hydroxethyl starch having a mean molecular weight of about 18 kD and a DS of about 0.7 or hydroxethyl starch having a mean molecular weight of about 50 kD and a DS of about 0.4 or hydroxethyl starch having a mean molecular weight of about 50 kD and a DS of about 0.7 or hydroxethyl starch having a mean molecular weight of about 100 kD and a DS of about 0.7.

The resulting polymer derivative may be purified from the reaction mixture by at least one suitable method. If necessary, the polymer derivative may be precipitated prior to the isolation by at least one suitable method.

If the polymer derivative is precipitated first, it is possible, e.g., to contact the reaction mixture with at least one solvent or solvent mixture other than the solvent or solvent mixture present in the reaction mixture at suitable temperatures. According to a particularly preferred embodiment of the present invention where an aqueous medium, preferably water is used as solvent, the reaction mixture is contacted with 2-propanol or with am mixture of acetone and ethanol, preferably a 1:1 mixture (v/v), indicating equal volumes of said compounds, at a temperature, preferably in the range of from −20 to +50° C. and especially preferably in the range of from −20 to 25° C.

Isolation of the polymer derivative may be carried out by a suitable process which may comprise one or more steps. According to a preferred embodiment of the present invention, the polymer derivative is first separated off the reaction mixture or the mixture of the reaction mixture with, e.g., aqueous 2-propanol mixture, by a suitable method such as centrifugation or filtration. In a second step, the separated polymer derivative may be subjected to a further treatment such as an after-treatment like dialysis, centrifugal filtration or pressure filtration, ion exchange chromatography, reversed phase chromatography, HPLC, MPLC, gel filtration and/or lyophilisation. According to an even more preferred embodiment, the separated polymer derivative is first dialysed, preferably against water, and then lyophilized until the solvent content of the reaction product is sufficiently low according to the desired specifications of the product. Lyophilisation may be carried out at temperature of from 20 to 35° C., preferably of from 20 to 30° C.

According to a preferred embodiment, the oxidized polymer resulting from the oxidation reaction is purified using at least one suitable method such as ultrafiltration and/or dialysis in order to, e.g., remove undesirable low molecular weight salts and polymer components, thereby also offering a means of controlling the molecular weight range of oxidized polymer.

The oxidized polymer can be used directly for the reaction with the protein or is suitably recovered in a first step, e.g. by lyophilization, and redissolved in water for conjugation to the protein in a second step. As to the coupling of at least one amino group of the protein with at least one aldehyde group of the polymer by reductive amination, reference is made to the detailed disclosure above concerning the specific reaction parameters of the reductive amination reaction such as pH or temperature. According to especially preferred embodiments of the present invention, according to which rhIL 2, rhIL 3, rhIFN alpha, rhIFN beta, rhEPO, rhAT III, rhG-CSF, BSA, Myoglobin and SOD are used as proteins, the reductive amination is preferably carried out at a temperature of from 0 to 5° C. such as about 4° C. at a pH of about 4.5 to 5.5 such as about 5.0 and for a reaction time of about 20 to 30 h such as about 24 h.

According to the second preferred embodiment, the polymer is reacted with an at least bifunctional compound comprising at least one functional group M capable of being reacted with the polymer and at least one functional group Q which is an aldehyde group or a keto group or a hemiacetal group and which is reacted with an amino group of the protein by reductive amination.

It is preferred to employ a compound having, apart from the aldehyde group or keto group or hemiacetal group, at least one carboxy group or at least one reactive carboxy group, preferably one carboxy group or one reactive carboxy group. The aldehyde group or keto group or hemiacetal group and the carboxy group or the reactive carboxy group may be separated by any suitable spacer. Among others, the spacer may be an optionally substituted, linear, branched and/or cyclic hydrocarbon residue. Generally, the hydrocarbon residue has from 1 to 60, preferably from 1 to 40, more preferably from 1 to 20, more preferably from 2 to 10, more preferably from 2 to 6 and especially preferably from 2 to 4 carbon atoms. If heteroatoms are present, the separating group comprises generally from 1 to 20, preferably from 1 to 8 and especially preferably from 1 to 4 heteroatoms. The hydrocarbon residue may comprise an optionally branched alkyl chain or an aryl group or a cycloalkyl group having, e.g., from 5 to 7 carbon atoms, or be an aralkyl group, an alkaryl group where the alkyl part may be a linear and/or cyclic alkyl group. According to an even more preferred embodiment, the hydrocarbon residue is an aryl residue having 5 to 7 and preferably 6 carbon atoms. Most preferably, the hydrocarbon residue is the benzene residue. According to this preferred embodiment, the carboxy group and the aldehyde group may be located at the benzene ring in 1,4-position, 1,3-position or 1,2-position, the 1,4-position being preferred.

As reactive carboxy group, a reactive ester, isothiocyanates or isocyanate may be mentioned. Preferred reactive esters are derived from N-hydroxy succinimides such as N-hydroxy succinimide or Sulfo-N-hydroxy succinimide, suitably substituted phenols such as p-nitrophenol, o,p-dinitrophenol, o,o'-dinitrophenol, trichlorophenol such as 2,4,6-trichlorophenol or 2,4,5-trichlorophenol, trifluorophenol such as 2,4,6-trifluorophenol or 2,4,5-trifluorophenol, pentachlorophenol, pentafluorophenol, or hydroxyazoles such as hydroxy benzotriazole. Especially preferred are N-hydroxy succinimides, with N-hydroxy succinimide and Sulfo-N-hydroxy succinimide being especially preferred. All alcohols may be employed alone or as suitable combination of two or more thereof. As reactive ester, pentafluorophenyl ester and N-hydroxy succinimide ester are especially preferred.

Thus, according to a preferred embodiment, the present invention relates to a method and a conjugate as described above, wherein the polymer is reacted with formylbenzoic acid.

According to another preferred embodiment, the present invention relates to a method and a conjugate as described above, wherein the polymer is reacted with formylbenzoic acid pentafluorophenyl ester.

According to yet another preferred embodiment, the present invention relates to a method and a conjugate as described above, wherein the polymer is reacted with formylbenzoic acid N-hydroxysuccinimide ester.

According to yet another embodiment, the present invention relates to a method and a conjugate as described above, wherein the polymer is reacted with 4-(4-formyl-3,5-dimethoxyphenoxy)butyric acid.

According to another preferred embodiment, the present invention relates to a method and a conjugate as described above, wherein the polymer is reacted with a bifunctional compound which is a biocompatible compound selected from the group consisting of alpha-keto carboxylic acids, sialic acids or derivatives thereof and pyridoxal phosphate.

As regards alpha-keto carboxylic acids, those are preferably alpha-keto carboxylic acids derived from amino acids and can in most instances also be found in the human body. Preferred alpha-keto carboxylic acids derived from amino acids are selected from the group consisting of keto-valine, keto-leucine, keto-isoleucine and keto-alanine. The carboxy group of the alpha-keto carboxylic acids is reacted with group Q of the polymer being an amino group. Therewith an amido group is formed. The remaining free keto group of the alpha-keto carboxylic acid may then be reacted with a functional group of the protein, in particular an amino group. Therewith an imino group is formed which may be hydrogenated.

Accordingly, the present invention relates to a method and a conjugate as described above, wherein the polymer is reacted with an alpha-keto carboxylic acid.

As regards sialic acids or derivatives thereof those are preferably biocompatible, in particular they are sugars found in the human body, which are N- and/or O-acetylated. In a preferred embodiment, sialic acids are N-acetyl neuramic acids. These compounds show a desired rigidity because of the pyranose structure in order to fulfill the function as a spacer. On the other hand, it may be possible to introduce an aldehyde group into these compounds through selective oxidation. Sialic acids are found in the human body e.g. as terminal monosaccarides in glycan chains of gylcosylated proteins.

In a preferred embodiment, the sialic acid may be selectively oxidized to an aldehyde group.

Methods to selectively oxidize sialic acids are known in the art, e.g. from L. W. Jaques, B. F. Riesco, W. Weltner, Carbohydrate Research, 83 (1980), 21-32 and T. Masuda, S. Shibuya, M. Arai, S. Yoshida, T. Tomozawa, A. Ohno, M. Yamashita, T. Honda, Bioorganic & Medicinal Chemistry Letters, 13 (2003), 669-673. Preferably the oxidation of the sialic acid may be conducted prior to the reaction with the amino group of the polymer The optionally oxidized sialic acid, may then be reacted via its carboxylic acid group with the amino group of the polymer.

The resulting compounds contain an aldehyde group which can then further be reacted by reductive amination with an amino group of a protein.

Accordingly, the present invention relates to a method and a conjugate as described above, wherein the polymer is reacted with an optionally oxidized sialic acid.

As regards pyridoxal phosphate (PyP), this is a highly biocompatible bifunctional compound and is also called vitamine B6. PyP is a co-enzyme which participates in transaminations, decarboxylations, racemizations, and numerous modifications of amino acid side chains. All PyP requiring enzymes act via the formation of a Schiff's base between the amino acid and the co-enzyme.

The phosphate group of the PyP may be reacted with the amino group of the polymer, preferably hydroxyalkyl starch, in particular hydroxyethyl starch, forming a phosphoramide. The aldehyde group of PyP may then be reacted with the amino group of a protein, forming a Schiff's base, which may then be reduced. In a preferred embodiment, the structure of the conjugate is HES-NH—P(O)2—O-(pyridoxal)-CH—NH— protein.

In case of PyP, the functional group of the polymer is preferably introduced into the polymer by use of a di-amino compound as described above.

Accordingly, the present invention relates to a method and a conjugate as described above, wherein the polymer is reacted with pyridoxal phosphate.

The hydroxyethyl starch subjected to the reaction with the compound comprising M, M preferably being a carboxy group or a reactive carboxy group and Q being an aldehyde group or a keto group or a hemiacetal group, is most preferably hydroxethyl starch having a mean molecular weight of about 10 kD and a DS of about 0.7. Also possible are hydroxethyl starches having a mean molecular weight of about 10 kD and a DS of about 0.4 or hydroxethyl starch having a mean molecular weight of about 12 kD and a DS of about 0.4 or hydroxethyl starch having a mean molecular weight of about 12 kD and a DS of about 0.7 or hydroxethyl starch having a mean molecular weight of about 18 kD and a DS of about 0.4 or hydroxethyl starch having a mean molecular weight of about 18 kD and a DS of about 0.7 or hydroxethyl starch having a mean molecular weight of about 50 kD and a DS of about 0.4 or hydroxethyl starch having a mean molecular weight of about 50 kD and a DS of about 0.7 or hydroxethyl starch having a mean molecular weight of about 100 kD and a DS of about 0.7. Particularly preferably, the hydroxyalkyl starch and even more preferably the hydroxyethyl starch is employed with its reducing end in the oxidized form.

The resulting polymer derivative with the aldehyde group or the keto group or the hemiacetal group is subsequently reacted with an amino group of the protein via reductive amination. As to the coupling of at least one amino group of the protein with at least one aldehyde group or keto group or hemiacetal group of the polymer by reductive amination, reference is made to the detailed disclosure above concerning the specific reaction parameters of the reductive amination reaction such as pH or temperature. According to an especially preferred embodiment of the present invention, according to which G-CSF is used as protein, the reaction with the amino group of the protein is preferably carried out at a temperature of from 0 to 40° C., more preferably of from 0 to 25° C. and especially preferably of from 4 to 21° C. The reaction time preferably ranges of from 30 min to 72 h, more preferably of from 2 to 48 h and especially preferably of from 4 h to 17 h. As solvent for the reaction, an aqueous medium is preferred. The pH value of the reaction medium is preferably in the range of from 4 to 9, more preferably of from 4 to 8 and especially preferably of from 4.5 to 5.5.

According to the third preferred embodiment, the polymer is reacted at its optionally oxidized reducing end with an at least bifunctional compound comprising an amino group M and a functional group Q, wherein said amino group M is reacted with the optionally oxidized reducing end of the polymer and wherein the functional group Q is chemically modified to give an aldehyde functionalized polymer derivative which is reacted with an amino group of the protein by reductive amination.

The term "the polymer is reacted via the reducing end" or "the polymer is reacted via the oxidized reducing end" as used in the context of the present invention may relate to a process according to which the hydroxyalkyl starch is reacted predominantly via its (selectively oxidized) reducing end. The polymer is hydroxyalkyl starch, in particular hydroxyethyl starch.

This term "predominantly via its (selectively oxidized) reducing end" relates to processes according to which statistically more than 50%, preferably at least 55%, more preferably at least 60%, more preferably at least 65%, more preferably at least 70%, more preferably at least 75%, more preferably at least 80%, more preferably at least 85%, more preferably at least 90%, and still more preferably at least 95% such as 95%, 96%, 97%, 98%, or 99% of the polymer molecules employed for a given reaction are reacted via at least one (selectively oxidized) reducing end per polymer molecule, wherein a given polymer molecule which is reacted via at least one reducing end can be reacted in the same given reaction via at least one further suitable functional group which is comprised in said polymer molecule and which is not a reducing end. If one or more polymer molecule(s) is (are) reacted via at least one reducing and simultaneously via at least one further suitable functional group which is comprised in this (these) polymer molecule(s) and which is not a reducing end, statistically preferably more than 50%, preferably at least 55%, more preferably at least 60%, more preferably at least 65%, more preferably at least 70%, more preferably at least 75%, more preferably at least 80%, more preferably at least 85%, more preferably at least 90%, and still more preferably at least 95% such as 95%, 96%, 97%, 98%, or 99% of all reacted functional groups of these polymer molecules, said functional groups including the reducing ends, are reducing ends.

The term "reducing end" as used in the context of the present invention relates to the terminal aldehyde group of a polymer molecule which may be present as aldehyde group and/or as corresponding acetal form. In case the reducing end is oxidized, the aldehyde or acetal group is in the form of a carboxy group and/or of the corresponding lactone.

As to functional group Q, the following functional groups are to be mentioned, among others:
C—C-double bonds or C—C-triple bonds or aromatic C—C-bonds;
the thio group or the hydroxy groups;
alkyl sulfonic acid hydrazide, aryl sulfonic acid hydrazide;
1,2-dioles;
1,2 amino-thioalcohols;
azides;
1,2-aminoalcohols;
the amino group —NH$_2$ or derivatives of the amino groups comprising the structure unit —NH— such as aminoalkyl groups, aminoaryl group, aminoaralkyl groups, or alkarlyamino groups;
the hydroxylamino group —O—NH$_2$, or derivatives of the hydroxylamino group comprising the structure unit —O—NH—, such as hydroxylalkylamino groups, hydroxylarylamino groups, hydroxylaralkylamino groups, or hydroxalalkarylamino groups;
alkoxyamino groups, aryloxyamino groups, aralkyloxyamino groups, or alkaryloxyamino groups, each comprising the structure unit —NH—O—;
residues having a carbonyl group, -Q-C(=G)-M, wherein G is O or S, and M is, for example,
—OH or —SH;
an alkoxy group, an aryloxy group, an aralkyloxy group, or an alkaryloxy group;
an alkylthio group, an arylthio group, an aralkylthio group, or an alkarylthio group;
an alkylcarbonyloxy group, an arylcarbonyloxy group, an aralkylcarbonyloxy group, an alkarylcarbonyloxy group;
activated esters such as esters of hydroxylamines having imid structure such as N-hydroxysuccinimide or having a structure unit O—N where N is part of a heteroaryl compound or, with G=O and Q absent, such as aryloxy compounds with a substituted aryl residue such as pentafluorophenyl, paranitrophenyl or trichlorophenyl;
wherein Q is absent or NH or a heteroatom such as S or O;
—NH—NH$_2$, or —NH—NH—;
—NO$_2$;
the nitril group;
carbonyl groups such as the aldehyde group or the keto group;
the carboxy group;
the —N=C=O group or the —N=C=S group;
vinyl halide groups such as the vinyl iodide or the vinyl bromide group or triflate;
—C≡C—H;
—(C=NH$_2$Cl)—OAlkyl
groups —(C=O)—CH$_2$-Hal wherein Hal is Cl, Br, or I;
—CH=CH—SO$_2$—;
a disulfide group comprising the structure —S—S—;
the group

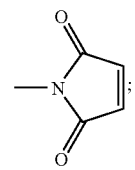

the group

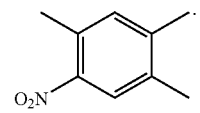

According to a preferred embodiment of the present invention, the term "functional group Q" relates to a functional group Q which comprises the chemical structure —NH—, e.g. —NH$_2$ or a derivative of the amino group comprising the structure unit —NH— such as aminoalkyl groups, aminoaryl group, aminoaralkyl groups, or alkarlyamino groups.

According to one preferred embodiment of the present invention, the functional group M is a group having the structure R'—NH— where R' is hydrogen or a alkyl, cycloalkyl, aryl, aralkyl, arylcycloalkyl, alkaryl or cycloalkylaryl residue where the cycloalkyl, aryl, aralkyl, arylcycloalkyl, alkaryl or cycloalkylaryl residue may be linked directly to the NH group or, according to another embodiment, may be linked by an oxygen bridge to the NH group. The alkyl, cycloalkyl, aryl, aralkyl, arylcycloalkyl, alkaryl, or cycloalkylaryl residues may be suitably substituted. As preferred substituents, halogenes such as F, Cl or Br may be mentioned. Especially preferred residues R' are hydrogen, alkyl and alkoxy groups, and even more preferred are hydrogen and unsubstituted alkyl and alkoxy groups.

Among the alkyl and alkoxy groups, groups with 1, 2, 3, 4, 5, or 6 C atoms are preferred. More preferred are methyl, ethyl, propyl, isopropyl, methoxy, ethoxy, propoxy, and isopropoxy groups. Especially preferred are methyl, ethyl, methoxy, ethoxy, and particular preference is given to methyl or methoxy.

According to another embodiment of the present invention, the functional group M has the structure R'—NH—R"— where R" preferably comprises the structure unit —NH— and/or the structure unit —(C=G)- where G is O or S, and/or the structure unit —SO$_2$—. Specific examples for the functional group R" are

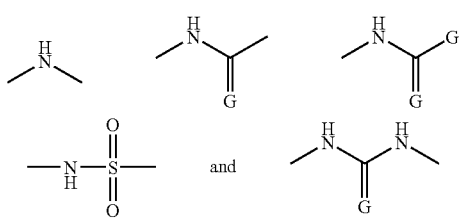

where, if G is present twice, it is independently O or S.

Therefore, the present invention also relates to a method and a conjugate as mentioned above wherein the functional group M is selected from the group consisting of

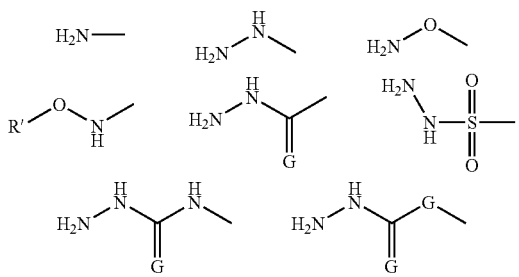

wherein G is O or S and, if present twice, independently O or S, and R' is methyl.

According to a particularly preferred embodiment of the present invention, the functional group M is an amino group —NH$_2$.

According to a first alternative, the functional group M being an amino group NH$_2$ is reacted with the oxidized reducing end of the polymer resulting in an amido group linking the polymer and the compound comprising M and Q.

According to a second alternative, the functional group M being an amino group NH$_2$ is reacted with the non-oxidized reducing end of the polymer via reductive amination resulting in an imino group which is subsequently preferably hydrogenated to give a amino group, the imino group and the amino group, respectively, linking the polymer and the compound comprising M and Q. In this case, it is possible that the functional group Q is an amino group. In case that the resulting polymer derivative shall be subjected to a subsequent reaction with an at least bifunctional compound via a carboxy group or a reactive carboxy group, as described hereinunder, or another group of an at least bifunctional compound which is to be reacted with an amino group, it is preferred that the compound comprising M and Q is a primary amine which contains—as functional group—only one amino group. In this specific case, although the compound contains only one functional group, it is regarded as bifunctional compound comprising M and Q wherein M is the amino group contained in the compound subjected to the reductive amination with the reducing end of the polymer, and wherein Q is the secondary amino group resulting from the reductive amination and subsequent hydrogenation.

According to a third alternative, the non-oxidized reducing end of the polymer is reacted with ammonia via reductive amination resulting in a terminal imino group of the polymer which is subsequently preferably hydrogenated to give a terminal amino group of the polymer and thus a terminal primary amino group. In this specific case, ammonia is regarded as bifunctional compound comprising M and Q wherein M is NH$_2$ comprised in the ammonia employed, and wherein Q is the primary amino group resulting from reductive amination and subsequent hydrogenation.

The term "amino group Q" relates to a functional group Q which comprises the chemical structure —NH—, e.g. —NH$_2$ or a derivative of the amino group comprising the structure unit —NH— such as aminoalkyl groups, aminoaryl group, aminoaralkyl groups, or alkarylamino groups.

According to a preferred embodiment of the present invention, the functional group Q is a group having the structure R'—NH— where R' is hydrogen or a alkyl, cycloalkyl, aryl, aralkyl, arylcycloalkyl, alkaryl or cycloalkylaryl residue where the cycloalkyl, aryl, aralkyl, arylcycloalkyl, alkaryl or cycloalkylaryl residue may be linked directly to the NH group or, according to another embodiment, may be linked by an oxygen bridge to the NH group. The alkyl, cycloalkyl, aryl, aralkyl, arylcycloalkyl, alkaryl, or cycloalkylaryl residues may be suitably substituted. As preferred substituents, halogenes such as F, Cl or Br may be mentioned. Especially preferred residues R' are hydrogen, alkyl and alkoxy groups, and even more preferred are hydrogen and unsubstituted alkyl and alkoxy groups.

Among the alkyl and alkoxy groups, groups with 1, 2, 3, 4, 5, or 6 C atoms are preferred. More preferred are methyl, ethyl, propyl, isopropyl, methoxy, ethoxy, propoxy, and isopropoxy groups. Especially preferred are methyl, ethyl, methoxy, ethoxy, and particular preference is given to methyl or methoxy.

According to another embodiment of the present invention, the functional group Q has the structure R'—NH—R''— where R'' preferably comprises the structure unit —NH— and/or the structure unit —(C=G)- where G is O or S, and/or the structure unit —SO$_2$—. According to more preferred embodiments, the functional group R'' is selected from the group consisting of

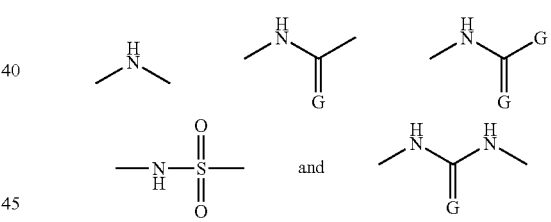

where, if G is present twice, it is independently O or S.

Therefore, the present invention also relates to a method and a conjugate as mentioned above wherein the functional group Q is selected from the group consisting of

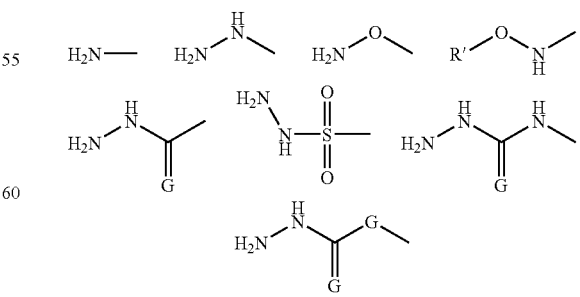

wherein G is O or S and, if present twice, independently O or S, and R' is methyl.

According to a particularly preferred embodiment of the present invention, the functional group Q is an amino group —NH$_2$.

According to a still further preferred embodiment of the present invention, both M and Q comprise an amino group —NH—. According to a particularly preferred embodiment, both M and Q are an amino group —NH$_2$.

According to a preferred embodiment of the present invention, the compound comprising M and Q is a homobifunctional compound, more preferably a homobifunctional compound comprising, as functional groups M and Q, most preferably the amino group —NH$_2$, or according to other embodiments, the hydroxylamino group —O—NH$_2$ or the group

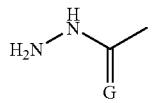

with G preferably being O. Specific examples for these compounds comprising M and Q are

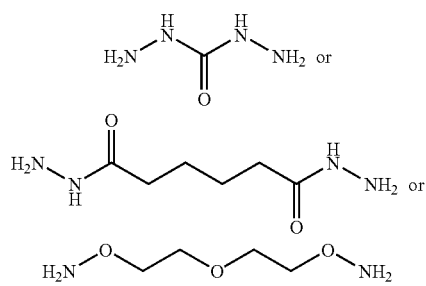

The hydroxyethyl starch subjected to the reaction with the compound comprising M, M preferably being an amino group —NH— and more preferably being an amino group —NH$_2$, still more preferably both M and Q comprising an amino group —NH— and particularly preferably both M and Q comprising an amino group —NH$_2$, is preferably hydroxyethyl starch having a mean molecular weight of about 10 kD and a DS of about 0.4 or hydroxyethyl starch having a mean molecular weight of about 10 kD and a DS of about 0.7. Also possible are or hydroxethyl starches having mean molecular weight of about 12 kD and a DS of about 0.4 or hydroxyethyl starch having a mean molecular weight of about 12 kD and a DS of about 0.7 or hydroxyethyl starch having a mean molecular weight of about 18 kD and a DS of about 0.4 or hydroxyethyl starch having a mean molecular weight of about 18 kD and a DS of about 0.7 or hydroxethyl starch having a mean molecular weight of about 50 kD and a DS of about 0.4 or hydroxyethyl starch having a mean molecular weight of about 50 kD and a DS of about 0.7 or hydroxyethyl starch having a mean molecular weight of about 100 kD and a DS of about 0.7.

In case both M and Q are an amino group —NH$_2$, M and Q may be separated by any suitable spacer. Among others, the spacer may be an optionally substituted, linear, branched and/or cyclic hydrocarbon residue. Generally, the hydrocarbon residue has from 1 to 60, preferably from 1 to 40, more preferably from 1 to 20, more preferably from 2 to 10, more preferably from 2 to 6 and especially preferably from 2 to 4 carbon atoms. If heteroatoms are present, the separating group comprises generally from 1 to 20, preferably from 1 to 8 and especially preferably from 1 to 4 heteroatoms. The hydrocarbon residue may comprise an optionally branched alkyl chain or an aryl group or a cycloalkyl group having, e.g., from 5 to 7 carbon atoms, or be an aralkyl group, an alkaryl group where the alkyl part may be a linear and/or cyclic alkyl group. According to an even more preferred embodiment, the hydrocarbon residue is an alkyl chain of from 1 to 20, preferably from 2 to 10, more preferably from 2 to 6, and especially preferably from 2 to 4 carbon atoms.

Therefore, the present invention also relates to a method and a conjugate as described above, wherein the polymer is reacted with 1,4-diaminobutane, 1,3-diaminopropane or 1,2-diaminoethane to give a polymer derivative.

The reaction of the at least bifunctional compound comprising M and Q with the polymer is preferably carried out at a temperature of from 0 to 100° C., more preferably of from 4 to 80° C. and especially preferably of from 20 to 80° C.; the reaction time preferably ranges of from 4 h to 7 d, more preferably of from 10 h to 5 d and especially preferably of from 17 to 4 h. The molar ratio of at least bifunctional compound:polymer is preferably in the range of from 10 to 200, especially from 50 to 100.

As solvent for the reaction of the at least bifunctional compound with the polymer, at least one aprotic solvent, particularly preferably an anhydrous aprotic solvent having a water content of not more than 0.5 percent by weight, preferably of not more than 0.1 percent by weight is preferred. Suitable solvents are, among others, dimethyl sulfoxide (DMSO), N-methylpyrrolidone, dimethyl acetamide (DMA), dimethyl formamide (DMF) and mixtures of two or more thereof.

As solvent for the reaction of the at least bifunctional compound with the polymer, also an aqueous medium may be used.

According to a preferred embodiment, the polymer derivative comprising the polymer and the at least bifunctional compound is chemically modified at the free functional group Q to give a polymer derivative comprising an aldehyde group or keto group or hemiacetal group. According to this embodiment, it is preferred to react the polymer derivative with at least one at least bifunctional compound which comprises a functional group capable of being reacted with the functional group Q and an aldehyde group or keto group or hemiacetal group.

As at least bifunctional compound, each compound is suitable which has an aldehyde group or keto group or hemiacetal group and at least one functional group which is capable of forming a linkage with the functional group Q of the polymer derivative. The at least one functional group is selected from the same pool of functional groups as Q and is chosen to be able to be reacted with Q. In the preferred case that Q is an amino group —NH$_2$, or a derivative of the amino group comprising the structure unit —NH— such as aminoalkyl groups, aminoaryl group, aminoaralkyl groups, or alkarylamino groups it is preferred to employ a compound having, apart from the aldehyde group or keto group or hemiacetal group, at least one carboxy group or at least one reactive carboxy group, preferably one carboxy group or one reactive carboxy group. The aldehyde group or keto group or hemiacetal group and the carboxy group or the reactive carboxy group may be separated by any suitable spacer. Among others, the spacer may be an optionally substituted, linear, branched and/or cyclic hydrocarbon residue. Generally, the hydrocarbon residue has from 1 to 60, preferably from 1 to 40, more preferably from 1 to 20, more preferably from 2 to 10, more preferably from 2 to 6 and especially preferably from 2 to 4 carbon atoms. If heteroatoms are present, the separating group comprises generally from 1 to 20, preferably from 1 to 8 and especially preferably from 1 to 4 heteroatoms. The hydrocarbon residue may comprise an optionally branched alkyl chain or an aryl group or a cycloalkyl group having, e.g., from 5 to 7 carbon atoms, or be an aralkyl group, an alkaryl group where the alkyl part may be a linear and/or cyclic alkyl group.

According to a preferred embodiment, the hydrocarbon residue is an alkyl group having 2 to 6 and preferably 2 to 4 carbon atoms. It is also possible that no carbon atom is present between the aldehyde or keto group and the carboxy group. Alternatively, the hydrocarbon residue can be a substituted or unsubstituted cyclic hydrocarbon group having 3 to 11 carbon atoms, preferably, 3 to 6 or 3 to 5 carbon atoms. When the cyclic hydrocarbon group is substituted, the substituent can be selected from the group consisting of substituted or unsubstituted amino or alkoxy groups. If present, the number of substituents is preferably 1 to 3. Further, the alkyl and/or cyclic hydrocarbon group can contain one or more heteroatoms, such as O or S, in particular O. In this case, preferably 1 to 3, in particular 1 or 2 heteroatoms are present. Preferred compounds in this context are selected from the following group of compounds.

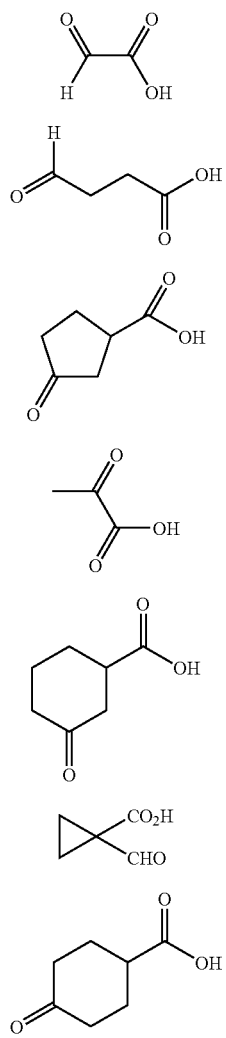

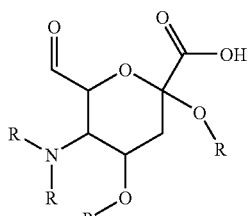

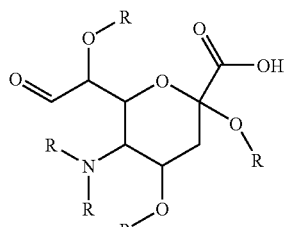

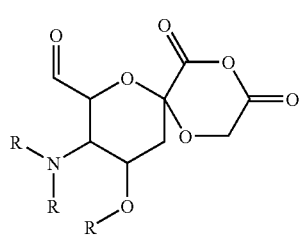

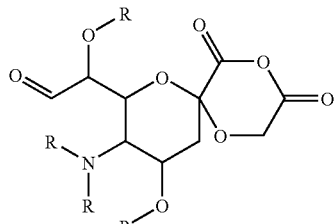

R = H, Alkyl, Aryl, Acyl, SiR'$_3$
R' = Alkyl, Aryl

According to an even more preferred embodiment, the hydrocarbon residue is an aryl residue having 5 to 7 and preferably 6 carbon atoms. Most preferably, the hydrocarbon residue is the benzene residue. According to this preferred embodiment, the carboxy group and the aldehyde group may be located at the benzene ring in 1,4-position, 1,3-position or 1,2-position, the 1,4-position being preferred.

As reactive carboxy group, a reactive ester, isothiocyanates or isocyanate may be mentioned. Preferred reactive esters are derived from N-hydroxy succinimides such as N-hydroxy succinimide or Sulfo-N-hydroxy succinimide, suitably substituted phenols such as p-nitrophenol, o,p-dinitrophenol, o,o'-dinitrophenol, trichlorophenol such as 2,4,6-trichlorophenol or 2,4,5-trichlorophenol, trifluorophenol such as 2,4,6-trifluorophenol or 2,4,5-trifluorophenol, pentachlorophenol, pentafluorophenol, or hydroxyazoles such as hydroxy benzotriazole. Especially preferred are N-hydroxy succinimides, with N-hydroxy succinimide and Sulfo-N-hydroxy succinimide being especially preferred. All alcohols may be employed alone or as suitable combination of two or more thereof. As reactive esters, pentafluorophenyl ester and N-hydroxy succinimide ester are especially preferred.

According to a specific embodiment, the functional group which is capable of forming a chemical linkage with the functional group Q, Q preferably being NH$_2$ or a derivative of the amino group comprising the structure unit —NH— such as aminoalkyl groups, aminoaryl group, aminoaralkyl groups, or alkarylamino groups, in particular being $NH_2$, is a reactive carboxy group.

In this case, the functional group which is capable of forming a chemical linkage with the functional group Q and which is a carboxy group, is suitably reacted to obtain a reactive carboxy group as described hereinabove. Therefore, it is preferred to subject the at least one at least bifunctional compound which comprises a carboxy group and an aldehyde group or keto group or hemiacetal group, to a reaction wherein the carboxy group is transformed into a reactive carboxy group, and the resulting at least bifunctional compound is purified and reacted with functional group Q of the polymer derivative.

Specific examples of the at least bifunctional compound comprising a carboxy group which may be reacted to obtain a reactive carboxy group are the compounds 1 to 11 of the list hereinabove. In this context, the term "carboxy group" also relates to a lacton and an internal anhydride of a dicarboxylic acid compound.

Thus, according to a preferred embodiment, the present invention relates to a method and a conjugate as described above, wherein the polymer derivative comprising Q, Q being an amino group —$NH_2$, or a derivative of the amino group comprising the structure unit —NH— such as aminoalkyl groups, aminoaryl group, aminoaralkyl groups, or alkarylamino groups, is further reacted with formylbenzoic acid.

According to another embodiment, the present invention relates to a method and a conjugate as described above, wherein the polymer derivative comprising Q, Q being an amino group, is further reacted with formylbenzoic acid pentafluorophenyl ester.

According to yet another embodiment, the present invention relates to a method and a conjugate as described above, wherein the polymer derivative comprising Q, Q being an amino group, is further reacted with formylbenzoic acid N-hydroxysuccinimide ester.

According to yet another embodiment, the present invention relates to a method and a conjugate as described above, wherein the polymer derivative comprising Q, Q being an amino group, is further reacted with 4-(4-formyl-3,5-dimethoxyphenoxy)butyric acid.

According to another preferred embodiment, the present invention relates to a method and a conjugate as described above, wherein the polymer is reacted with a bifunctional compound which is a biocompatible compound selected from the group consisting of alpha-keto carboxylic acids, sialic acids or derivatives thereof and pyridoxal phosphate.

As regards alpha-keto carboxylic acids, those are preferably alpha-keto carboxylic acids derived from amino acids and can in most instances also be found in the human body. Preferred alpha-keto carboxylic acids derived from amino acids are selected from the group consisting of keto-valine, keto-leucine, keto-isoleucine and keto-alanine. The carboxy group of the alpha-keto carboxylic acids is reacted with group Q of the polymer being an amino group. Therewith an amido group is formed. The remaining free keto group of the alpha-keto carboxylic acid may then be reacted with a functional group of the protein, in particular an amino group. Therewith an imino group is formed which may be hydrogenated.

Accordingly, the present invention relates to a method and a conjugate as described above, wherein the polymer is reacted with an alpha-keto carboxylic acid.

As regards sialic acids or derivatives thereof those are preferably biocompatible, in particular they are sugars found in the human body, which are N- and/or O-acetylated. In a preferred embodiment, the sialic acids are N-acetyl neuramic acids. These compounds show a desired rigidity because of the pyranose structure in order to fulfill the function as a spacer. On the other hand, it may be possible to introduce an aldehyde group into these compounds through selective oxidation. Sialic acids are found in the human body e.g. as terminal monosaccarides in glycan chains of gylcosylated proteins.

In a preferred embodiment, the sialic acid may be selectively oxidized to an aldehyde group.

Methods to selectively oxidize sialic acids are known in the art, e.g. from L. W. Jaques, B. F. Riesco, W. Weltner, Carbohydrate Research, 83 (1980), 21-32 and T. Masuda, S. Shibuya, M. Arai, S. Yoshida, T. Tomozawa, A. Ohno, M. Yamashita, T. Honda, Bioorganic & Medicinal Chemistry Letters, 13 (2003), 669-673. Preferably the oxidation of the sialic acid may be conducted prior to the reaction with amino group of the polymer.

The optionally oxidized sialic acid, may then be reacted via its carboxylic acid group with the amino group of the polymer.

The resulting compounds contain an aldehyde group which can then further be reacted by reductive amination with an amino group of a protein.

Accordingly, the present invention relates to a method and a conjugate as described above, wherein the polymer is reacted with an optionally oxidized sialic acid.

As regards pyridoxal phosphate (PyP), this is a highly biocompatible bifunctional compound and is also called vitamine B6. PyP is a co-enzyme which participates in transaminations, decarboxylations, racemizations, and numerous modifications of amino acid side chains. All PyP requiring enzymes act via the formation of a Schiff's base between the amino acid and the co-enzyme.

The phosphate group of the PyP may be reacted with the amino group of the polymer, preferably hydroxyalkyl starch, in particular hydroxyethyl starch, forming a phosphoramide. The aldehyde group of PyP may then be reacted with the amino group of a protein, forming a Schiff's base, which may then be reduced. In a preferred embodiment, the structure of the conjugate is HES-NH—P(O)2-O-(pyridoxal)-CH—NH— protein.

In case of PyP, the functional group of the polymer is preferably introduced into the polymer by use of a di-amino compound as described above.

Accordingly, the present invention relates to a method and a conjugate as described above, wherein the polymer is reacted with pyridoxal phosphate.

As solvent for the reaction of the polymer derivative comprising an amino group and, e.g., formylbenzoic acid, at least one aprotic solvent or at least one polar solvent is preferred. Suitable solvents are, among others, water, dimethyl sulfoxide (DMSO), N-methylpyrrolidone, dimethyl acetamide (DMA), dimethyl formamide (DMF) and mixtures of two or more thereof.

As solvent for the reaction of the polymer derivative comprising an amino group and the at least bifunctional compound comprising a carboxy group, it is also possible to use an aqueous medium. The term "aqueous medium" as used in this context of the present invention relates to a solvent or a mixture of solvents comprising water in the range of from at least 10% per weight or at least 20% per weight or at least 30% per weight or at least 40% per weight or at least 50% per weight or at least 60% per weight or at least 70% per weight or at least 80% per weight or at least 90% per weight or up to 100% per weight, based on the weight of the solvents involved.

The reaction is preferably carried out at a temperature of from 0 to 40° C., more preferably of from 0 to 25° C. and especially preferably of from 15 to 25° C. for a reaction time preferably of from 0.5 to 24 h and especially preferably of from 1 to 17 h.

According to a preferred embodiment, the reaction is carried out in the presence of an activating agent. Suitable activating agents are, among others, carbodiimides such as diisopropyl carbodiimde (DIC), dicyclohexyl carbodiimides (DCC), 1-ethyl-3-(3-dimethylaminopropyl)carbodiimide (EDC), with diisopropyl carbodiimde (DIC) being especially preferred.

The resulting polymer derivative may be purified from the reaction mixture by at least one suitable method. If necessary, the polymer derivative may be precipitated prior to the isolation by at least one suitable method.

If the polymer derivative is precipitated first, it is possible, e.g., to contact the reaction mixture with at least one solvent or solvent mixture other than the solvent or solvent mixture present in the reaction mixture at suitable temperatures. According to a particularly preferred embodiment of the present invention where an aqueous medium, preferably water is used as solvent, the reaction mixture is contacted with 2-propanol or with am mixture of acetone and ethanol, preferably a 1:1 mixture (v/v), indicating equal volumes of said compounds, at a temperature, preferably in the range of from −20 to +50° C. and especially preferably in the range of from −20 to 25° C.

Isolation of the polymer derivative may be carried out by a suitable process which may comprise one or more steps. According to a preferred embodiment of the present invention, the polymer derivative is first separated off the reaction mixture or the mixture of the reaction mixture with, e.g., aqueous 2-propanol mixture, by a suitable method such as centrifugation or filtration. In a second step, the separated polymer derivative may be subjected to a further treatment such as an after-treatment like dialysis, centrifugal filtration or pressure filtration, ion exchange chromatography, reversed phase chromatography, HPLC, MPLC, gel filtration and/or lyophilisation. According to an even more preferred embodiment, the separated polymer derivative is first dialysed, preferably against water, and then lyophilized until the solvent content of the reaction product is sufficiently low according to the desired specifications of the product. Lyophilisation may be carried out at temperature of from 20 to 35° C., preferably of from 20 to 30° C.

The resulting polymer derivative with the aldehyde group or keto group or hemiacetal group is subsequently reacted with an amino group of the protein via reductive amination. As to the coupling of at least one amino group of the protein with at least one aldehyde group or keto group or hemiacetal group of the polymer by reductive amination, reference is made to the detailed disclosure above concerning the specific reaction parameters of the reductive amination reaction such as pH or temperature. According to an especially preferred embodiment of the present invention, according to which G-CSF is used as protein, the reductive amination is carried out at a temperature of from 0 to 10° C. such as from 1 to 8° C. or from 2 to 6° C. such as about 4° C. at a pH of about 4.5 to 5.5 such as about 5.0. The reaction time is about 10 to 20 h such as from 12 to 19 h or from 14 to 18 h such as about 17 h or about 20 to 30 h such as about 24 h. According to especially preferred embodiments of the present invention, according to which rhIL 2, rhIL 3, rhIFN alpha, rhIFN beta, rhEPO, rhAT III, BSA, Myoglobin and SOD are used as proteins, the reductive amination is preferably carried out at a temperature of from 0 to 5° C. such as about 4° C. at a pH of about 4.5 to 5.5 such as about 5.0 and for a reaction time of about 20 to 30 h such as about 24 h.

Thus, according to the above-mentioned preferred embodiments, the present invention also relates, in case the polymer was reacted via its oxidized reducing end, to a conjugate according to the formula

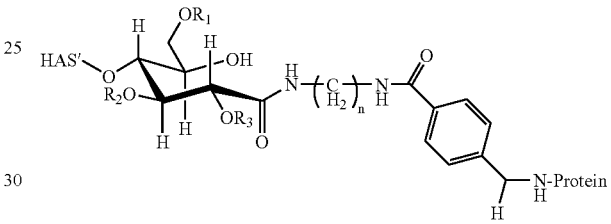

According to an especially preferred embodiment, the polymer is hydroxyethyl starch, i.e. HAS' is HES', and n=2, 3, or 4, most preferably 4, as described above. Therefore, in case the polymer was reacted via its oxidized reducing end, the present invention also relates to a conjugate according to the formula

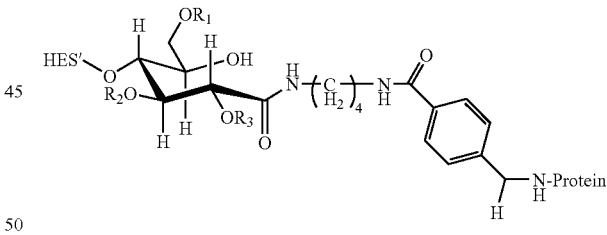

According to another preferred embodiment, the present invention also relates, in case the polymer was reacted via its oxidized reducing end, to a conjugate according to the formula

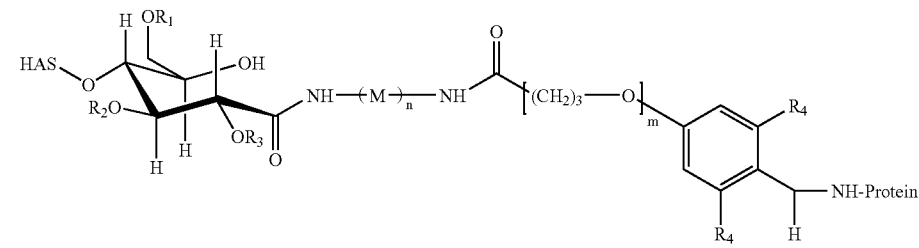

wherein n=2, 3, or 4, $R_4$ being independently hydrogen or a methoxy group, and m=0 in case $R_4$ is hydrogen and m=1 in case $R_4$ is methoxy, HAS preferably being HES'.

In each of the formulae above, the nitrogen attached to the protein derives from the amino group of the protein the polymer derivative is linked to via the aldehyde group.

With respect to the above-mentioned embodiments according to which the functional groups M and Q comprise an amino group —$NH_2$, it is also possible that M is an amino group —$NH_2$ and Q comprises a beta hydroxy amino group —CH(OH)—$CH_2$—$NH_2$ and preferably is a beta hydroxy amino group.

Therefore, the present invention also relates to a method and a conjugate as described above, wherein the amino group Q of the compound comprising two amino groups M and Q, is a beta hydroxy amino group —CH(OH)—$CH_2$—$NH_2$.

In this case, M and Q may be separated by any suitable spacer. Among others, the spacer may be an optionally substituted, linear, branched and/or cyclic hydrocarbon residue. Generally, the hydrocarbon residue has from 1 to 60, preferably from 1 to 40, more preferably from 1 to 20, more preferably from 2 to 10, more preferably from 1 to 6 and especially preferably from 1 to 2 carbon atoms. If heteroatoms are present, the separating group comprises generally from 1 to 20, preferably from 1 to 8 and especially preferably from 1 to 4 heteroatoms. The hydrocarbon residue may comprise an optionally branched alkyl chain or an aryl group or a cycloalkyl group having, e.g., from 5 to 7 carbon atoms, or be an aralkyl group, an alkaryl group where the alkyl part may be a linear and/or cyclic alkyl group. According to an even more preferred embodiment, the hydrocarbon residue is an alkyl chain of from 1 to 20, preferably from 1 to 10, more preferably from 1 to 6, more preferably from 1 to 4 carbon atoms and especially preferably from 1 to 2 carbon atoms. Still more preferably, M and Q are separated by a methylene group.

Therefore, the present invention also relates to a method and a conjugate as described above, wherein the polymer is reacted with 1,3-diamino-2-hydroxypropane.

In case the polymer is reacted via its oxidized reducing end, a polymer derivative according to the formula results

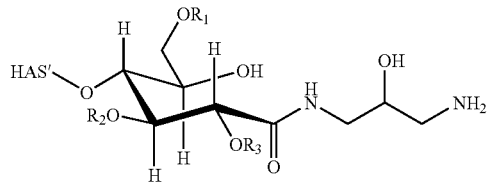

especially preferably with HAS'=HES'

The reaction of the at least bifunctional compound comprising M and Q, particularly preferably 1,3-diamino-2-hydroxypropane, with the polymer is preferably carried out at a temperature of from 40 to 120° C., more preferably of from 40 to 90° C. and especially preferably of from 60 to 80° C. The reaction time preferably ranges from 17 to 168 h, more preferably from 17 to 96 h and especially preferably from 48 to 96 h. The molar ratio of at least bifunctional compound:polymer is preferably in the range of from 200:1 to 10:1, specially from 50:1 to 100:1.

As solvent for the reaction of the at least bifunctional compound with the polymer, at least one aprotic solvent, preferably an anhydrous aprotic solvent having a water content of not more than 0.5 percent by weight, preferably of not more than 0.1 percent by weight is preferred. Suitable solvents are, among others, dimethyl sulfoxide (DMSO), N-methylpyrrolidone, dimethyl acetamide (DMA), dimethyl formamide (DMF) and mixtures of two or more thereof.

The beta hydroxy amino group Q of the polymer derivative generally may be reacted with an at least bifunctional compound comprising at least one functional group capable of being reacted with Q and further comprising at least one functional group being an aldehyde group or keto group or hemiacetal group or a functional group capable of being modified to give an aldehyde group or keto group or hemiacetal group. According to another embodiment of the present invention, the beta hydroxy amino group is directly chemically modified to give an aldehyde group by chemical oxidation.

This oxidation may be carried with all suitable oxidation agents which are capable of converting the beta hydroxy amino group to an aldehyde group. Preferred oxidation reagents are periodates such as alkaline metal periodates. Especially preferred is sodium periodate which is preferably employed as aqueous solution. This solution has a preferred iodate concentration of from 1 to 50 mM, more preferably from 1 to 25 mM and especially preferably of from 1 to 10 mM. Oxidation is carried out at a temperature of from 0 to 40° C., preferably from 0 to 25° C. and especially preferably from 4 to 20° C.

The resulting polymer derivative may be purified from the reaction mixture by at least one suitable method. If necessary, the polymer derivative may be precipitated prior to the isolation by at least one suitable method.

If the polymer derivative is precipitated first, it is possible, e.g., to contact the reaction mixture with at least one solvent or solvent mixture other than the solvent or solvent mixture present in the reaction mixture at suitable temperatures. According to a particularly preferred embodiment of the present invention where an aqueous medium, preferably water is used as solvent, the reaction mixture is contacted with 2-propanol or with am mixture of acetone and ethanol, preferably a 1:1 mixture (v/v), indicating equal volumes of said compounds, at a temperature, preferably in the range of from −20 to +50° C. and especially preferably in the range of from −20 to 25° C.

Isolation of the polymer derivative may be carried out by a suitable process which may comprise one or more steps. According to a preferred embodiment of the present invention, the polymer derivative is first separated off the reaction mixture or the mixture of the reaction mixture with, e.g., aqueous 2-propanol mixture, by a suitable method such as centrifugation or filtration. In a second step, the separated polymer derivative may be subjected to a further treatment such as an after-treatment like dialysis, centrifugal filtration or pressure filtration, ion exchange chromatography, reversed phase chromatography, HPLC, MPLC, gel filtration and/or lyophilisation. According to an even more preferred embodiment, the separated polymer derivative is first dialysed, preferably against water, and then lyophilized until the solvent content of the reaction product is sufficiently low according to the desired specifications of the product. Lyophilisation may be carried out at temperature of from 20 to 35° C., preferably of from 20 to 30° C.

Therefore, the present invention also relates to a method and a conjugate as described above, wherein the oxidation of the beta hydroxy amino group Q is carried out using a periodate.

Therefore, the present invention also relates to a method of producing a conjugate, wherein, in case the polymer was employed with oxidized reducing end, a polymer derivative having a beta hydroxy amino group, especially preferably

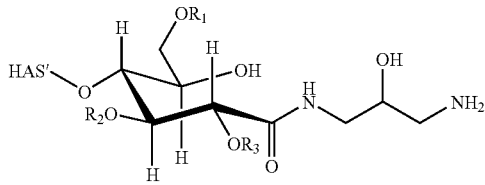

and particularly with HAS'=HES', is oxidized, preferably with a periodate, to a polymer derivative having an aldehyde group, especially preferably

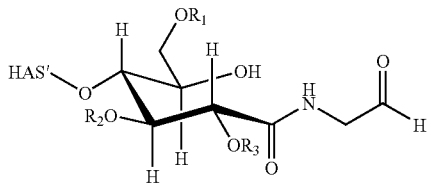

and particularly with HAS'=HES'.

According to the present invention, it is also possible to react the compound comprising an 1-amino 2-hydroxy structure depicted above with an at least bifunctional compound comprising a carboxy group or a reactive carboxy group and an aldehyde, keto or acetal group described hereinabove to obtain a polymer derivative which can be subjected to reductive amination with an amino group of the protein.

The resulting polymer derivative with the aldehyde group A is subsequently reacted with the protein. Therefore, the present invention also relates to a method of producing a conjugate, said method comprising reacting a polymer derivative having a beta hydroxy amino group, in case the polymer was employed with oxidized reducing end especially preferably according to the formula

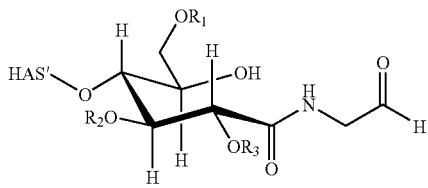

and particularly with HAS'=HES', with an amino group of the protein.

The resulting polymer derivative with the aldehyde group is subsequently reacted with an amino group of the protein via reductive amination. As to the coupling of at least one amino group of the protein with at least one aldehyde group of the polymer by reductive amination, reference is made to the detailed disclosure above.

Thus, according to the above-mentioned preferred embodiment, the present invention also relates to a conjugate according to the formula

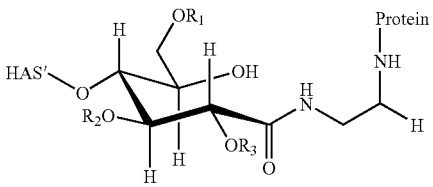

particularly with HAS'=HES', in case the polymer was employed with oxidized reducing end. In the formula above, the nitrogen attached to the protein derives from the amino group of the protein the polymer derivative is linked to via the aldehyde group.

According to a further embodiment of the present invention, the polymer is first reacted with a suitable compound to give a first polymer derivative comprising at least one reactive carboxy group. This first polymer derivative is then reacted with a further, at least bifunctional compound wherein at least one functional group of this further compound is reacted with at least one reactive carboxy group of the polymer derivative and at least one other functional group of the further compound is an aldehyde group or keto group or hemiacetal group or is a functional group which is chemically modified to give an aldehyde group or keto group or hemiacetal group, and wherein the resulting polymer derivative comprising said aldehyde group or keto group or hemiacetal group is reacted via reductive amination, as described above, with at least one amino group of the protein. It is also possible to alter the sequence of reacting the respective compounds with each other.

According to a first alternative of said further embodiment, the polymer comprising at least one reactive carboxy group is prepared by selectively oxidizing the polymer at its reducing end and subsequently reacting the oxidized polymer being a lactone

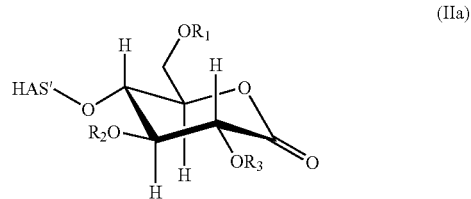

and/or a carboxylic acid

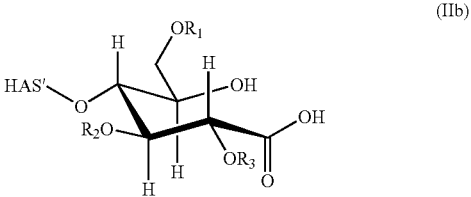

or a suitable salt of the carboxylic acid such as alkali metal salt, preferably as sodium and/or potassium salt, and HAS' preferably being HES', with a suitable compound to give the polymer comprising at least one reactive carboxy group.

Oxidation of the polymer, preferably hydroxyethyl starch, may be carried out according to each method or combination of methods which result in compounds having the above-mentioned structures (IIa) and/or (IIb).

Although the oxidation may be carried out according to all suitable method or methods resulting in the oxidized reducing end of hydroxyalkyl starch, it is preferably carried out using an alkaline iodine solution as described, e.g., in DE 196 28 705 A1 the respective contents of which (example A, column 9, lines 6 to 24) is incorporated herein by reference.

Introducing the reactive carboxy group into the polymer which is selectively oxidized at its reducing end may carried out by all conceivable methods and all suitable compounds.

According to a specific method of the present invention, the polymer which is selectively oxidized at its reducing end is reacted at the oxidized reducing end with at least one alcohol, preferably with at least one acidic alcohol such as acidic alcohols having a p$K_A$ value in the range of from 6 to 12 or of from 7 to 11 at 25° C. The molecular weight of the acidic alcohol may be in the range of from 80 to 500 g/mole, such as of from 90 to 300 g/mole or of from 100 to 200 g/mole.

Suitable acidic alcohols are all alcohols H—O—$R_A$ having an acidic proton and are capable of being with reacted with the oxidized polymer to give the respective reactive polymer ester, preferably according to the formula

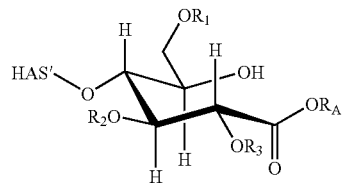

still more preferably according to formula

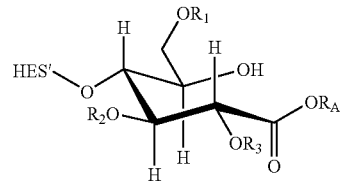

Preferred alcohols are N-hydroxy succinimides such as N-hydroxy succinimide or Sulfo-N-hydroxy succinimide, suitably substituted phenols such as p-nitrophenol, o,p-dinitrophenol, o,o'-dinitrophenol, trichlorophenol such as 2,4,6-trichlorophenol or 2,4,5-trichlorophenol, trifluorophenol such as 2,4,6-trifluorophenol or 2,4,5-trifluorophenol, pentachlorophenol, pentafluorophenol, or hydroxyazoles such as hydroxy benzotriazole. Especially preferred are N-hydroxy succinimides, with N-hydroxysuccinimide and Sulfo-N-hydroxysuccinimide being especially preferred. All alcohols may be employed alone or as suitable combination of two or more thereof. In the context of the present invention, it is also possible to employ a compound which releases the respective alcohol, e.g. by adding diesters of carbonic acid.

Therefore, the present invention also relates to a method as described above, wherein the polymer which is selectively oxidised at its reducing end is activated by reacting the oxidised polymer with an acidic alcohol, preferably with N-hydroxy succinimide and/or Sulfo-N-hydroxy succinimide.

According to a preferred embodiment of the present invention, the polymer which is selectively oxidized at its reducing end is reacted at the oxidized reducing end with at least one carbonic diester $R_B$—O—(C=O)—O—$R_C$, wherein $R_B$ and $R_C$ may be the same or different. Preferably, this method gives reactive polymers according to the formula

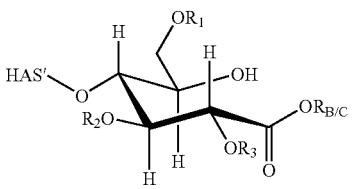

wherein HAS' is preferably HES'.

As suitable carbonic diester compounds, compounds may be employed whose alcohol components are independently N-hydroxy succinimides such as N-hydroxy succinimide or Sulfo-N-hydroxy succinimide, suitably substituted phenols such as p-nitrophenol, o,p-dinitrophenol, o,o'-dinitrophenol, trichlorophenol such as 2,4,6-trichlorophenol or 2,4,5-trichlorophenol, trifluorophenol such as 2,4,6-trifluorophenol or 2,4,5-trifluorophenol, pentachlorophenol, pentafluorophenol, or hydroxyazoles such as hydroxy benzotriazole. Especially preferred are N,N'-disuccinimidyl carbonate and Sulfo-N,N'-disuccinimidyl carbonate, with N,N'-disuccinimidyl carbonate being especially preferred.

Therefore, the present invention also relates a method as described above, wherein the polymer which is selectively oxidised at its reducing end is activated by reacting the oxidised polymer with N,N'-disuccinimidyl carbonate.

The acidic alcohol is reacted with the oxidized polymer or the salt of the oxidized polymer at a molar ratio of acidic alcohol:polymer preferably of from 5:1 to 50:1, more preferably of from 8:1 to 20:1, at a preferred reaction temperature of from 2 to 40° C., more preferably of from 10 to 30° C. and especially preferably of from 15 to 25° C. The reaction time is preferably in the range of from 1 to 10 h, more preferably of from 2 to 5 h, more preferably of from 2 to 4 h and particularly of from 2 to 3 h.

The carbonic diester compound is reacted with the oxidized polymer or the salt of the oxidized polymer at a molar ratio of diester compound:polymer generally of from 1:1 to 3:1, such as of from 1:1 to 1.5:1. The reaction time is generally in the range of from 0.1 to 12 h, like of from 0.2 to 6 h, or of from 0.5 to 2 h or of from 0.75 to 1.25 h.

According to a preferred embodiment of the present invention, reacting the oxidized polymer with acidic alcohol and/or carbonic diester is carried out in at least one aprotic solvent, such as in an anhydrous aprotic solvent having a water content of not more than 0.5 percent by weight, preferably of not more than 0.1 percent by weight. Suitable solvents are, among others, dimethyl sulfoxide (DMSO), N-methylpyrrolidone, dimethyl acetamide (DMA), dimethyl formamide (DMF) and mixtures of two or more thereof. The reaction temperatures are preferably in the range of from 2 to 40° C., more preferably of from 10 to 30° C.

For reacting the oxidized polymer with the at least one acidic alcohol, at least one additional activating agent is employed.

Suitable activating agents are, among others, carbonyldiimidazole, carbodiimides such as diisopropyl carbodiimde (DIC), dicyclohexyl carbodiimides (DCC), 1-ethyl-3-(3-dimethylaminopropyl)carbodiimide (EDC), with dicyclohexyl carbodiimides (DCC) and 1-ethyl-3-(3-dimethylaminopropyl)carbodiimide (EDC) being especially preferred.

Therefore, the present invention also relates to the method as described above, where the polymer which is oxidized at its reducing end, is reacted with an acidic alcohol in the presence of an additional activating agent to give the reactive polymer ester.

According to one embodiment of the present invention, the reaction of the oxidized polymer with carbonic diester and/or acidic alcohol is carried out at a low base activity which may be determined by adding the reaction mixture to water with a volume ratio of water to reaction mixture of 10:1. Prior to the addition, the water which comprises essentially no buffer, has a pH value of 7 at 25° C. After the addition of the reaction mixture and by measuring the pH value, the base activity of the reaction mixture is obtained, having a value of preferably not more than 9.0, more preferably of nor more than 8.0 and especially preferably of not more than 7.5.

According to another embodiment of the present invention, the oxidized polymer is reacted with N-hydroxy succinimide in dry DMA in the absence of water with EDC to selectively give the polymer N-hydroxy succinimide ester according to the formula

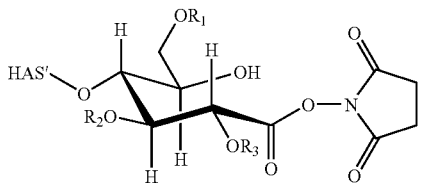

more preferably with HAS' being HES'.

Surprisingly, this reaction does not give by-products resulting from reactions of EDC with OH groups of HES, and the rearrangement reaction of the O-acyl isourea formed by EDC and the oxidized polymer to the respective N-acyl urea is surprisingly suppressed.

According to another preferred embodiment of the present invention, the oxidized polymer is reacted with N,N'-disuccinimidyl carbonate in dry DMF in the absence of water and in the absence of an activating agent to selectively give the polymer N-hydroxy succinimide ester according to the formula

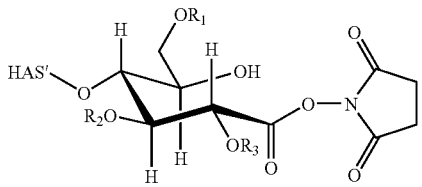

more preferably with HAS' being HES'.

According to another embodiment of the present invention, the polymer which is selectively oxidized at its reducing end is reacted at the oxidized reducing end with an azolide such as carbonyldiimidazole or carbonyl dibenzimidazole to give a polymer having a reactive carboxy group. In the case of carbonyldiimidazole, a reactive imidazolide polymer derivative according to formula

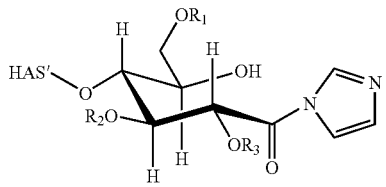

results, wherein HAS' is preferably HES'.

According to a second alternative of said further embodiment of the present invention regarding the introduction of at least one reactive carboxy group into the polymer, the reactive carboxy group is introduced into the polymer whose reducing end is not oxidized, by reacting at least one hydroxy group of the polymer with a carbonic diester.

Therefore, the present invention also relates to a method and conjugates wherein the reactive carboxy group is introduced in the polymer whose reducing end is not oxidized, by reacting at least one hydroxy group of the polymer with at least one carbonic diester carbonic diester $R_B$—O—(C=O)—O—$R_C$, wherein $R_B$ and $R_C$ may be the same or different.

According to another embodiment of the present invention, the polymer whose reducing end is not oxidized, is reacted at least one hydroxy group with an azolide such as carbonyldiimidazole, carbonyl-di-(1,2,4-triazole) or carbonyl dibenzimidazol to give a polymer having a reactive carboxy group.

As suitable carbonic diester compounds, compounds may be employed whose alcohol components are independently N-hydroxy succinimides such as N-hydroxy succinimide or Sulfo-N-hydroxy succinimide, suitably substituted phenols such as p-nitrophenol, o,p-dinitrophenol, o,o'-dinitrophenol, trichlorophenol such as 2,4,6-trichlorophenol or 2,4,5-trichlorophenol, trifluorophenol such as 2,4,6-trifluorophenol or 2,4,5-trifluorophenol, pentachlorophenol, pentafluorophenol, or hydroxyazoles such as hydroxy benzotriazole.

Especially preferred are symmetrical carbonic diester compounds, $R_B$ and $R_C$ thus being the same. The alcohol component of the carbonic diester is preferably selected from the group consisting of N-hydroxy succinimide, sulfonated N-hydroxy succinimide, N-hydroxy benzotriazole, and nitro- and halogen-substituted phenols. Among others, nitrophenol, dinitrophenol, trichlorophenol, trifluorophenol, pentachlorophenol, and pentafluorophenol are preferred. Especially preferred are N,N'-disuccinimidyl carbonate and Sulfo-N,N'-disuccinimidyl carbonate, with N,N'-disuccinimidyl carbonate being especially preferred.

Therefore, the present invention also relates to a hydroxyalkyl starch derivative, preferably a hydroxyethyl starch derivative, wherein at least one hydroxy group, preferably at least two hydroxy groups of said starch have been reacted with a carbonic diester compound to give the respective reactive ester.

According to one embodiment of the present invention, the reaction of the polymer whose reducing end is not oxidized, with the at least one carbonic diester compound is carried out at a temperature of from 2 to 40° C., more preferably of from 10 to 30° C. and especially of from 15 to 25° C. A preferred reaction time ranges from 0.5 to 5 h, more preferably from 1 to 3 h, and especially preferably from 2 to 3 h.

The molar ratio of carbonic diester compound:polymer depends on the degree of substitution of the polymer regarding the number of hydroxy groups reacted with carbonic diester compound relative to the number of hydroxy groups present in the non-reacted polymer.

According to one embodiment of the present invention, the molar ratio of carbonic diester compound:anhydroglucose units of the polymer is in the range of from 1:2 to 1:1000, more preferably of from 1:3 to 1:100 and especially preferably of from 1:10 to 1:50, to give a degree of substitution in the range of from 0.5 to 0.001, preferably of from 0.33 to 0.01 and especially preferably of from 0.1 to 0.02.

According to one embodiment of the present invention, reacting the polymer whose reducing end is not oxidized, with carbonic diester is carried out in at least one aprotic solvent, particularly preferably in an anhydrous aprotic solvent having a water content of not more than 0.5 percent by weight, preferably of not more than 0.1 percent by weight. Suitable solvents are, among others, dimethyl sulfoxide (DMSO), N-methyl pyrrolidone, dimethyl acetamide (DMA), dimethyl formamide (DMF) and mixtures of two or more thereof.

Therefore, the present invention also relates to a method as described above wherein the reaction of the at least one hydroxy group of the polymer whose reducing end is not oxidised, with the carbonic diester to give a reactive carboxy group is carried out in an anhydrous aprotic polar solvent, the solvent preferably being dimethyl acetamide, dimethyl formamide or a mixture thereof.

The reactive polymer derivative comprising at least one reactive carboxy group, preferably resulting from the reaction of the polymer with the acidic alcohol, the carbonate and/or the azolide, as described above, is further reacted with a further, at least bifunctional compound wherein at least one functional group $F_1$ of this further compound is reacted with at least one reactive carboxy group of the polymer derivative. As at least one functional group $F_1$ of the further compound no specific limitations exist given that a reaction with the at least one reactive carboxy group of the polymer is possible. Preferred functional groups $F_1$ are, e.g., an amino group or a hydroxy group or a thio group or a carboxy group.

The further, at least bifunctional compound comprises at least one other functional group $F_2$ being an aldehyde group or a functional group $F_2$ being capable of being chemically modified to give an aldehyde group. The chemical modification may be, e.g., a reaction of the functional group $F_2$ with a functional group $F_3$ a further linker compound or an oxidation or a reduction of a suitable functional group $F_2$.

In case $F_2$ is reacted with a functional group $F_3$ of a further compound, the functional group $F_2$ may be selected from, among others, C—C-double bonds or C—C-triple bonds or aromatic C—C-bonds;
the thio group or the hydroxy group;
alkyl sulfonic acid hydrazide, aryl sulfonic acid hydrazide;
1,2-dioles;
1,2-aminoalcohols;
1,2 amino-thioalcohols;
azides;
the amino group —NH$_2$ or derivatives of the amino groups comprising the structure unit —NH— such as aminoalkyl groups, aminoaryl group, aminoaralkyl groups, or alkarlyamino groups;
the hydroxylamino group —O—NH$_2$, or derivatives of the hydroxylamino group comprising the structure unit —O—NH—, such as hydroxylalkylamino groups, hydroxylarylamino groups, hydroxylaralkylamino groups, or hydroxalalkarylamino groups;
alkoxyamino groups, aryloxyamino groups, aralkyloxyamino groups, or alkaryloxyamino groups, each comprising the structure unit —NH—O—;
residues having a carbonyl group, -Q-C(=G)-M, wherein G is O or S, and M is, for example,
—OH or —SH;
an alkoxy group, an aryloxy group, an aralkyloxy group, or an alkaryloxy group;
an alkylthio group, an arylthio group, an aralkylthio group, or an alkarylthio group;
an alkylcarbonyloxy group, an arylcarbonyloxy group, an aralkylcarbonyloxy group, an alkarylcarbonyloxy group;
activated esters such as esters of hydroxylamines having imid structure such as N-hydroxysuccinimide or having a structure unit O—N where N is part of a heteroaryl compound or, with G=O and Q absent, such as aryloxy compounds with a substituted aryl residue such as pentafluorophenyl, paranitrophenyl or trichlorophenyl;
wherein Q is absent or NH or a heteroatom such as S or O;
—NH—NH$_2$, or —NH—NH—;
—NO$_2$;
the nitril group;
carbonyl groups such as the aldehyde group or the keto group;
the carboxy group;
the —N=C=O group or the —N=C=S group;

vinyl halide groups such as the vinyl iodide or the vinyl bromide group or triflate;
—C≡C—H;
—(C=NH$_2$Cl)—OAlkyl
groups —(C=O)—CH$_2$-Hal wherein Hal is Cl, Br, or I;
—CH=CH—SO$_2$—;
a disulfide group comprising the structure —S—S—;
the group

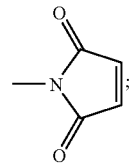

the group

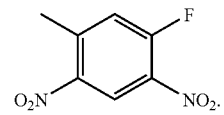

wherein $F_3$ is a group capable of forming a chemical linkage with one of the above-mentioned groups and is preferably selected from the above-mentioned groups. Moreover, the second linker compound preferably has at least one aldehyde group or keto group or hemiacetal group which is capable of being reacted with an amino group of the protein via reductive amination.

The functional group $F_1$ and the aldehyde group or keto group or hemiacetal group of the at least bifunctional linking compound which is reacted with the polymer, and/or the functional groups $F_1$ and $F_2$ of the at least bifunctional linking compound which is reacted with the polymer, and/or the functional group $F_3$ and the aldehyde group or keto group or hemiacetal group of the further, at least bifunctional linking compound, may be independently separated by any suitable spacer. Among others, the spacer may be an optionally substituted, linear, branched and/or cyclic, aliphatic and/or aromatic hydrocarbon residue. Generally, the hydrocarbon residue has up to 60, preferably up to 40, more preferably up to 20, more preferably up to 10 carbon atoms. If heteroatoms are present, the separating group comprises generally from 1 to 20, preferably from 1 to 8, more preferably 1 to 6, more preferably 1 to 4 and especially preferably from 1 to 2 heteroatoms. As heteroatom, O is preferred. The hydrocarbon residue may comprise an optionally branched alkyl chain or an aryl group or a cycloalkyl group having, e.g., from 5 to 7 carbon atoms, or be an aralkyl group, an alkaryl group where the alkyl part may be a linear and/or cyclic alkyl group.

Examples of a compound with functional groups $F_1$ and $F_2$ are, e.g., optionally substituted diaminoalkane having from 2 to 20 carbon atoms, especially preferably 1,2-diaminoethane, 1,3-diaminopropane, and 1,4-diaminobutane. Preferred examples of a compound with functional groups $F_3$ and an aldehyde group or a keto group or a hemiacetal group are, e.g., formylbenzoic acid, 4-formylbenzoic acid pentafluorophenyl ester, 4-formylbenzoic acid-N-hydroxysuccinimide ester and 4-(4-formyl-3,5-dimethoxyphenoxy)butyric, or a biocompatible compound selected from the group consisting of alpha-keto carboxylic acids, neuraminic acids or derivatices thereof and pyridoxal phosphate According to another preferred embodiment, the present invention relates to a method and a conjugate as described above, wherein the polymer is reacted with a bifunctional compound which is a biocompatible compound selected from the group consisting of alpha-keto carboxylic acids, neuraminic or sialic acids or derivatives thereof and pyridoxal phosphate.

As regards alpha-keto carboxylic acids, those are preferably alpha-keto carboxylic acids derived from amino acids and can in most instances also be found in the human body. Preferred alpha-keto carboxylic acids derived from amino acids are selected from the group consisting of keto-valine, keto-leucine, keto-isoleucine and keto-alanine. The carboxy group of the alpha-keto carboxylic acids is reacted with group Q of the polymer being an amino group. Therewith an amido group is formed. The remaining free keto group of the alpha-keto carboxylic acid may then be reacted with a functional group of the protein, in particular an amino group. Therewith an imino group is formed which may be hydrogenated.

Accordingly, the present invention relates to a method and a conjugate as described above, wherein the polymer is reacted with an alpha-keto carboxylic acid.

As regards sialic acids or derivatives thereof those are preferably biocompatible, in particular they are sugars found in the human body, which are N- and/or O-acetylated. In a preferred embodiment, the sialic acids are N-acetyl neuramic acids. These compounds show a desired rigidity because of the pyranose structure in order to fulfill the function as a spacer. On the other hand, it may be possible to introduce an aldehyde group into these compounds through selective oxidation. Sialic acids are found in the human body e.g. as terminal monosaccarides in glycan chains of gylcosylated proteins.

In a preferred embodiment, the sialic acid may be selectively oxidized to an aldehyde group.

Methods to selectively oxidize sialic acids are known in the art, e.g. from L. W. Jaques, B. F. Riesco, W. Weltner, Carbohydrate Research, 83 (1980), 21-32 and T. Masuda, S. Shibuya, M. Arai, S. Yoshida, T. Tomozawa, A. Ohno, M. Yamashita, T. Honda, Bioorganic & Medicinal Chemistry Letters, 13 (2003), 669-673. Preferably the oxidation of the sialic acid may be conducted prior to the reaction with the amino group of the polymer.

The optionally oxidized sialic acid, may then be reacted via its carboxylic acid group with the amino group of the polymer.

The resulting compounds contain an aldehyde group which can then further be reacted by reductive amination with an amino group of a protein.

Accordingly, the present invention relates to a method and a conjugate as described above, wherein the polymer is reacted with an optionally oxidized sialic acid.

As regards pyridoxal phosphate (PyP), this is a highly biocompatible bifunctional compound and is also called vitamine B6. PyP is a co-enzyme which participates in transaminations, decarboxylations, racemizations, and numerous modifications of amino acid side chains. All PyP requiring enzymes act via the formation of a Schiff's base between the amino acid and the co-enzyme.

The phosphate group of the PyP may be reacted with the amino group of the polymer, preferably hydroxyalkyl starch, in particular hydroxyethyl starch, forming a phosphoramide. The aldehyde group of PyP may then be reacted with the amino group of a protein, forming a Schiff's base, which may then be reduced. In a preferred embodiment, the structure of the conjugate is HES-NH—P(O)2-O-(pyridoxal)-CH—NH— protein.

In case of PyP, the functional group of the polymer is preferably introduced into the polymer by use of a di-amino compound as described above.

Accordingly, the present invention relates to a method and a conjugate as described above, wherein the polymer is reacted with pyridoxal phosphate.

Therefore, the present invention also relates to a method of producing a conjugate, said method comprising reacting the polymer, preferably hydroxyethyl starch, at its optionally oxidized reducing end with a compound, selected from the group consisting of acidic alcohols, carbonic diesters and azolides, to give a polymer derivative comprising at least one reactive carboxy group, reacting said polymer derivative with at least one at least bifunctional compound to give a polymer derivative comprising an aldehyde group or a keto group or a hemiacetal group or a functional group capable of being chemically modified to give an aldehyde group or a keto group or a hemiacetal group, optionally chemically modifying said functional group to give a polymer derivative comprising an aldehyde group or a keto group or a hemiacetal group, and reacting the polymer derivative comprising an aldehyde group or a keto group or a hemiacetal group with an amino group of a protein via reductive amination.

Accordingly, the present invention also relates to a conjugate comprising a polymer, preferably hydroxyethyl starch, and a protein covalently linked to each other, obtainable by a method of producing a conjugate, said method comprising reacting the polymer, at its optionally oxidized reducing end with a compound, selected from the group consisting of acidic alcohols, carbonic diesters and azolides, to give a polymer derivative comprising at least one reactive carboxy group, reacting said polymer derivative with at least one at least bifunctional compound to give a polymer derivative comprising an aldehyde group or a keto group or a hemiacetal group or a functional group capable of being chemically modified to give an aldehyde group or a keto group or a hemiacetal group, optionally chemically modifying said functional group to give a polymer derivative comprising an aldehyde group or a keto group or a hemiacetal group, and reacting the polymer derivative comprising an aldehyde group or a keto group or a hemiacetal group with an amino group of a protein via reductive amination.

A specific example of a compound having a functional group $F_1$ and a functional group $F_2$ which is oxidized to give an aldehyde group is, e.g., a compound having an amino group as $F_1$ and a beta hydroxy amino group as $F_2$. An especially preferred example is 1,3-diamino-2-hydroxypropane. This oxidation may be carried with all suitable oxidation agents which are capable of converting the beta hydroxy amino group to an aldehyde group. Preferred oxidation reagents are periodates such as alkaline metal periodates. Especially preferred is sodium periodate which is preferably employed as aqueous solution. This solution has a preferred iodate concentration of from 1 to 50 mM, more preferably from 1 to 25 mM and especially preferably of from 1 to 10 mM. Oxidation is carried out at a temperature of from 0 to 40° C., preferably from 0 to 25° C. and especially preferably from 4 to 20° C.

The resulting polymer derivative may be purified from the reaction mixture by at least one suitable method. If necessary, the polymer derivative may be precipitated prior to the isolation by at least one suitable method.

If the polymer derivative is precipitated first, it is possible, e.g., to contact the reaction mixture with at least one solvent or solvent mixture other than the solvent or solvent mixture present in the reaction mixture at suitable temperatures. According to a particularly preferred embodiment of the present invention where an aqueous medium, preferably water is used as solvent, the reaction mixture is contacted with 2-propanol or with a mixture of acetone and ethanol, preferably a 1:1 mixture (v/v), indicating equal volumes of said compounds, at a temperature, preferably in the range of from −20 to +50° C. and especially preferably in the range of from −20 to 25° C.

Isolation of the polymer derivative may be carried out by a suitable process which may comprise one or more steps. According to a preferred embodiment of the present invention, the polymer derivative is first separated off the reaction mixture or the mixture of the reaction mixture with, e.g., aqueous 2-propanol mixture, by a suitable method such as centrifugation or filtration. In a second step, the separated polymer derivative may be subjected to a further treatment such as an after-treatment like dialysis, centrifugal filtration or pressure filtration, ion exchange chromatography, reversed phase chromatography, HPLC, MPLC, gel filtration and/or lyophilisation. According to an even more preferred embodiment, the separated polymer derivative is first dialysed, preferably against water, and then lyophilized until the solvent content of the reaction product is sufficiently low according to the desired specifications of the product. Lyophilisation may be carried out at temperature of from 20 to 35° C., preferably of from 20 to 30° C.

The present invention also relates to conjugate comprising hydroxyalkyl starch and a protein, wherein hydroxyalkyl starch is coupled with its oxidized reducing end via an amide linkage to a first crosslinking compound, said crosslinking compound being additionally linked via an amide linkage to a second crosslinking compound, said second crosslinking compound being linked via an azomethine and/or amino linkage to a protein, wherein the first crosslinking compound was preferably employed as an diamino functionalized compound and the second crosslinking compound was preferably employed as a carboxy and aldehyde or keto or hemiacetal, more preferably as a carboxy and aldehyde functionalized compound.

The present invention also relates to conjugate, comprising a protein and a polymer or a derivative thereof, wherein the polymer is a hydroxyalkyl starch (HAS), having a structure according to the formula

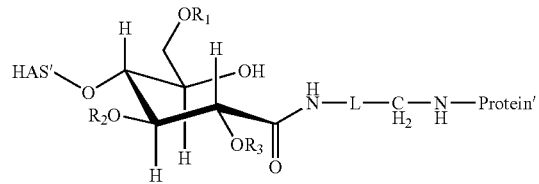

wherein $R_1$, $R_2$ and $R_3$ are independently hydrogen or a hydroxyalkyl group, a hydroxyaryl group, a hydroxyaralkyl group or a hydroxyalkaryl group having of from 1 to 10 carbon atoms, preferably hydrogen or a hydroxyalkyl group, more preferably hydrogen or a hydroxyethyl group, and wherein L is an optionally substituted, linear, branched and/or cyclic hydrocarbon residue, optionally comprising at least one heteroatom, having from 1 to 60 preferably from 1 to 40, more preferably from 1 to 20, more preferably from 1 to 10, more preferably from 1 to 6 more preferably from 1 to 2 carbon atoms and especially preferably 1 carbon atom, L being in particular $CH_2$.

The present invention also relates to conjugate, comprising a protein and a polymer or a derivative thereof, wherein the polymer is a hydroxyalkyl starch (HAS), having a structure according to the formula

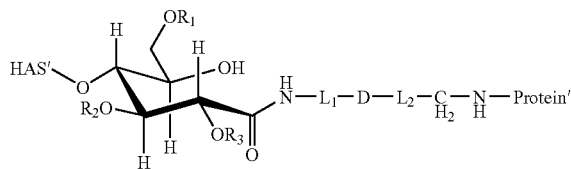

wherein $R_1$, $R_2$ and $R_3$ are independently hydrogen or a hydroxyalkyl group, a hydroxyaryl group, a hydroxyaralkyl group or a hydroxyalkaryl group having of from 1 to 10 carbon atoms, preferably hydrogen or a hydroxyalkyl group, more preferably hydrogen or a hydroxyethyl group, and
wherein $L_1$ and $L_2$ are independently an optionally substituted, linear, branched and/or cyclic hydrocarbon residue, optionally comprising at least one heteroatom, comprising an alkyl, aryl, aralkyl heteroalkyl, and/or heteroaralkyl moiety, said residue having from 1 to 60 preferably from 1 to 40, more preferably from 1 to 20, more preferably from 1 to 10 carbon atoms, and
wherein D is a linkage, preferably a covalent linkage which was formed by a suitable functional group $F^2$ linked to $L_1$ and a suitable functional group $F_3$ linked to $L_2$.

The present invention also relates to conjugate as described above, wherein $L_1$ is —$(CH_2)n$- with n=2, 3, 4, 5, 6, 7, 8, 9, 10, preferably 2, 3, 4, 5, 6, more preferably 2, 3, 4, and especially preferably 4.

The present invention also relates to conjugate as described above, wherein $L_2$ comprises an optionally suitably substituted aryl moiety, preferably an aryl moiety containing 6 carbon atoms, $L_2$ being especially preferably $C_6H_4$.

The present invention also relates to conjugate as described above, wherein $F_2$ and $F_3$ are selected from the group consisting of
C—C-double bonds or C—C-triple bonds or aromatic C—C-bonds;
the thio group or the hydroxy groups;
alkyl sulfonic acid hydrazide, aryl sulfonic acid hydrazide;
1,2-dioles;
1,2 amino-thioalcohols;
azides;
1,2-aminoalcohols;
the 1,2-amino group —$NH_2$ or derivatives of the amino groups comprising the structure unit —NH— such as aminoalkyl groups, aminoaryl group, aminoaralkyl groups, or alkarlyamino groups;
the hydroxylamino group —O—$NH_2$, or derivatives of the hydroxylamino group comprising the structure unit —O—NH—, such as hydroxylalkylamino groups, hydroxylarylamino groups, hydroxylaralkylamino groups, or hydroxalalkarylamino groups;
alkoxyamino groups, aryloxyamino groups, aralkyloxyamino groups, or alkaryloxyamino groups, each comprising the structure unit —NH—O—;
residues having a carbonyl group, -Q-C(=G)-M, wherein G is O or S, and M is, for example,
—OH or —SH;
an alkoxy group, an aryloxy group, an aralkyloxy group, or an alkaryloxy group;
an alkylthio group, an arylthio group, an aralkylthio group, or an alkarylthio group;
an alkylcarbonyloxy group, an arylcarbonyloxy group, an aralkylcarbonyloxy group, an alkarylcarbonyloxy group;
activated esters such as esters of hydroxylamines having imid structure such as N-hydroxysuccinimide or having a structure unit O—N where N is part of a heteroaryl compound or, with G=O and Q absent, such as aryloxy compounds with a substituted aryl residue such as pentafluorophenyl, paranitrophenyl or trichlorophenyl;

wherein Q is absent or NH or a heteroatom such as S or O;

—NH—NH$_2$, or —NH—NH—;

—NO$_2$;

the nitril group;

carbonyl groups such as the aldehyde group or the keto group;

the carboxy group;

the —N=C=O group or the —N=C=S group;

vinyl halide groups such as the vinyl iodide or the vinyl bromide group or triflate;

—C≡C—H;

—(C=NH$_2$Cl)—OAlkyl groups —(C=O)—CH$_2$-Hal wherein Hal is Cl, Br, or I;

—CH=CH—SO$_2$—;

a disulfide group comprising the structure —S—S—;

the group

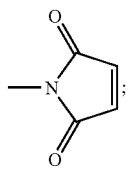

the group

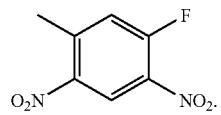

and wherein $F_3$ is a functional group capable of forming a chemical linkage with $F_2$ and is preferably selected from the above-mentioned group, $F_2$ preferably comprising the moiety —NH—, more preferably comprising an amino group, $F_3$ preferably comprising the moiety —(C=G)-, more preferably —(C=O)—, more preferably the moiety —(C=G)-G-, still more preferably —(C=O)-G-, and especially preferably —(C=O)—O, D being particularly preferably an amide linkage.

The present invention also relates to conjugate as described above, having a structure according to the formula n=2, 3, or 4, $R_4$ being independently hydrogen or a methoxy group, and m=0 in case $R_4$ is hydrogen and m=1 in case $R_4$ is methoxy.

The present invention also relates to conjugate, comprising a protein and a polymer or a derivative thereof, wherein the polymer is a hydroxyalkyl starch (HAS) and the protein is a granulocyte colony stimulating factor (G-CSF), having a structure according to the formula

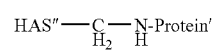

wherein the carbon atom of the moiety —CH$_2$—N2- is derived from an aldehyde group which was introduced in the polymer by a ring-opening oxidation reaction, and wherein the nitrogen atom is derived from an amino group of the protein.

The present invention also relates to conjugate as described above, wherein the hydroxyalkyl starch is hydroxyethyl starch.

The present invention also relates to any of the conjugates as described wherein the hydroxyethyl starch has a molecular weight of from 2 to 200 kD, preferably of from 4 to 130 kD, more preferably of from 4 to 70 kD.

The present invention also relates to conjugate as described above, wherein the protein is selected from the group consisting of EPO, G-CSF, IFN alpha, IFN beta, AT III, IL-2, IL-3, myoglobin, SOD, and BSA, preferably from the group consisting of rhEPO, rhG-CSF, rhIFN alpha, rhIFN beta, rhAT III, rhIL-2, rhIL-3, myoglobin, SOD, and BSA, and/or from the group consisting of A1AT, factor VII, factor VIII, factor IX, tPA, and APC.

In the methods for preparing a conjugate of the invention the conversion rate in the above described methods may be at least 50%, more preferred at least 70%, even more preferred at least 80% and in particular 95% or even more, such as at least 98% or 99%.

The conjugates according to the invention may be at least 50% pure, even more preferred at least 70% pure, even more preferred at least 90%, in particular at least 95% or at least 99% pure. In a most preferred embodiment, the conjugates may be 100% pure, i.e. there are no other by-products present.

Therefore, according to another aspect, the present invention also relates to a composition which may comprise the conjugate(s) of the invention, wherein the amount of the conjugate(s) may be at least 50 wt-%, even more preferred at least 70 wt-%, even more preferred at least 90 wt-%, in particular at least 95 wt.-% or at least 99 wt.-%. In a most preferred embodiment, the composition may consist of the conjugate(s), i.e. the amount of the conjugate(s) is 100 wt.-%.

According to another aspect, the present invention also relates to a conjugate as described above or a conjugate,

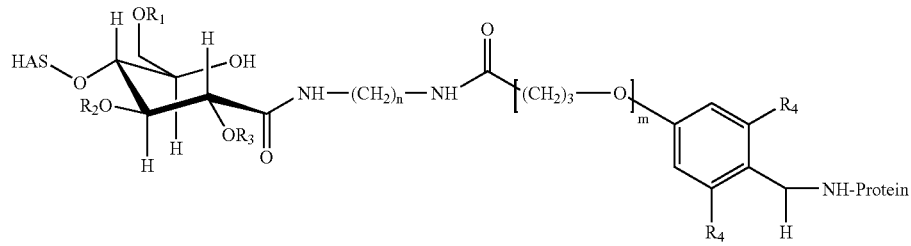

obtainable by a method as described, for use in a method for the treatment of the human or animal body.

Accordingly, the present invention relates to a pharmaceutical composition comprising in a therapeutically effective amount a conjugate as described above or a conjugate, obtainable by a method as described above.

The term "therapeutically effective amount" as used in the context of the present invention relates to that amount which provides therapeutic effect for a given condition and administration regimen.

Thus, in a preferred embodiment, the pharmaceutical composition further comprises at least one pharmaceutically acceptable diluent, adjuvant and/or carrier. Preferably, this pharmaceutically acceptable diluent, adjuvant and/or carrier is especially useful in IFN alpha, IFN beta, EPO, AT III, G-CSF, APC, A1AT, tPA, Factor VII, Factor VIII or Factor IX therapy.

All protein-HAS conjugates of the present invention are preferably administered by i.v., s.c. or i.m. routes. The specific route chosen will depend upon the condition being treated. Preferably, the conjugates are administered together with a suitable carrier, such as known in the art (e.g. as used in the first generation/unmodified biopharmaceutical, albumin-free or with albumin as an excipient), a suitable diluent, such as sterile solutions for i.v., i.m., or s.c. application. The required dosage will depend on the severity of the condition being treated, the patients individual response, the method of administration used, and the like. The skilled person is able to establish a correct dosage based on his general knowledge.

According to another aspect, the present invention also relates to the use a HAS-, preferably a HES-protein conjugate as described above or a HAS-, preferably a HES-protein conjugate, obtainable by a method as described above, wherein the protein is EPO, for the preparation of a medicament for the treatment of anemic disorders or hematopoietic dysfunction disorders or diseases related thereto.

The administration of erythropoietin isoforms is preferably by parenteral routes. The specific route chosen will depend upon the condition being treated. The administration of erythropoietin isoforms is preferably done as part of a formulation containing a suitable carrier, such as human serum albumin, a suitable diluent, such as a buffered saline solution, and/or a suitable adjuvant. The required dosage will be in amounts sufficient to raise the hematocrit of patients and will vary depending upon the severity of the condition being treated, the method of administration used and the like. The object of the treatment with the pharmaceutical composition of the invention is preferably an increase of the hemoglobin value of more than 6.8 mmol/l in the blood. For this, the pharmaceutical composition may be administered in a way that the hemoglobin value increases between 0.6 mmol/l and 1.6 mmol/l per week. If the hemoglobin value exceeds 8.7 mmol/l, the therapy should be preferably interrupted until the hemoglobin value is below 8.1 mmol/l. The composition of the invention is preferably used in a formulation suitable for subcutaneous or intravenous or parenteral injection. For this, suitable excipients and carriers are e.g. sodium dihydrogen phosphate, disodium hydrogen phosphate, sodium chlorate, polysorbate 80, HSA and water for injection. The composition may be administered three times a week, preferably two times a week, more preferably once a week, and most preferably every two weeks. Preferably, the pharmaceutical composition is administered in an amount of 0.01-10 µg/kg body weight of the patient, more preferably 0, 1 to 5 µg/kg, 0.1 to 1 µg/kg, or 0.2-0.9 µg/kg, most preferably 0.3-0.7 µg/kg, and most preferred 0.4-0.6 µg/kg body weight. In general, preferably between 10 µg and 200 µg, preferably between 15 µg and 100 µg are administered per dose.

According to another aspect, the present invention also relates to the use a HAS-, preferably a HES-protein conjugate as described above or a HAS-, preferably a HES-protein conjugate, obtainable by a method as described above, wherein the protein is G-CSF, for the preparation of a medicament for the treatment of a disorder characterized by a reduced hematopoietic or immune function, said disorder preferably being a result of chemotherapy, radiation therapy, infectious disease, severe chronic neutropenia, or leukemia.

According to another aspect, the present invention also relates to the use a HAS-, preferably a HES-protein conjugate as described above or a HAS-, preferably a HES-protein conjugate, obtainable by a method as described above, wherein the protein is Factor VIII, for the preparation of a medicament for the treatment of haemophilia A.

According to another aspect, the present invention also relates to the use of a HAS-AT III conjugate as described above or a HAS-protein conjugate, obtainable by a method as described, for the preparation of a medicament for the treatment of AT III hereditary deficiency, veno-Occlusive disease, burns and heparin resistance in coronary arterial bypass Graft (CABG) surgery, bowel perforation resulting from trauma or gastrointestinal surgery; disseminated intravascular coagulation (DIC) and/or sepsis as well as for the prevention of micro-clot formation associated with ventilation therapy. The pharmaceutical composition comprising the HAS-AT III conjugate of the invention may therefore be used for these purposes.

According to another aspect, the present invention also relates to the use a HAS-, preferably a HES-protein conjugate as described above or a HAS-, preferably a HES-protein conjugate, obtainable by a method as described above, wherein the protein is A1AT, for the preparation of a medicament for the treatment of emphysema, cystic fibrosis, atopic dermatitis, chronic obstructive pulmonary disease (COPD), and/or bronchitis. The pharmaceutical composition of the invention comprising the HAS-A1AT-conjugate of the invention may also be used for these purposes.

According to another aspect, the present invention also relates to the use a HAS-, preferably a HES-protein conjugate as described above or a HAS-, preferably a HES-protein conjugate, obtainable by a method as described above, wherein the protein is tPA, for the preparation of a medicament for the treatment of myocardial infarcts (heart attacks), thrombosis, thromboembolim or occulsive diseases, especially occlusive arterial diseases.

According to another aspect, the present invention also relates to the use a HAS-, preferably a HES-protein conjugate as described above or a HAS-, preferably a HES-protein conjugate, obtainable by a method as described above, wherein the protein is APC, for the preparation of a medicament for the treatment of severe sepsis, thrombosis, thromboembolim or occulsive diseases, especially occlusive arterial diseases.

According to another aspect, the present invention also relates to the use a HAS-, preferably a HES-protein conjugate as described above or a HAS-, preferably a HES-protein conjugate, obtainable by a method as described above, wherein the protein is IFN alpha, for the preparation of a medicament for the treatment of leukaemia e.g. hairy cell leukaemia, chronic myelogeneous leukaemia, multiple myeloma, follicular lymphoma, cancer, e.g. carcinoid tumour, malignant melanoma and hepatitis, eg. chronic hepatitis B and chronic hepatitis C.

According to another aspect, the present invention also relates to the use a HAS-, preferably a HES-protein conjugate as described above or a HAS-, preferably a HES-protein conjugate, obtainable by a method as described above, wherein the protein is IFN beta, for the preparation of a medicament for the treatment of multiple sclerosis, preferably relapsing forms of multiple sclerosis.

The present invention also relates to the use of a HAS-Factor VII conjugate for the preparation of a medicament for the treatment of episodes in hemophilia A or B patients with inhibitors to Factor VIII or Factor IX.

The present invention also relates to the use of a HAS-Factor IX conjugate for the preparation of a medicament for the control and prevention of hemorrhagic episodes in patients with hemophillia B (e.g. congenital factor IX deficiency or Christmas disease), including control and prevention of bleeding in surgical settings.

The invention will be further described in the following examples, which do not limit the scope of the invention described in the claims.

EXAMPLES

Example 1

Synthesis of Aldehyde Functionalized Hydroxyethyl Starch

Example 1.1(a)

Synthesis by Periodate Oxidation of Hydroxyethyl Starch Selectively Oxidized at its Reducing End and Incubation at 0° C.

100 mg of Oxo-HES10/0.4 (MW=10 kD, DS=0.4, prepared by Supramol Parenteral Colloids GmbH, Rosbach-Rodheim, D; according to DE 196 28 705 A1) were dissolved in 5 ml 20 mM sodium phosphate buffer, pH 7.2 and cooled to 0° C. 21.4 mg sodium periodate (Fluka, Sigma-Aldrich Chemie GmbH, Taufkirchen, D) were dissolved in 5 ml of the same buffer and cooled to 0° C. Both solutions were mixed and after incubation for 10 min at 0° C., 0.73 ml glycerol were added and the reaction mixture was incubated at 21° C. for 10 min. The reaction mixture was dialysed for 24 h against water (SnakeSkin dialysis tubing, 3.5 kD cut off, Perbio Sciences Deutschland GmbH, Bonn, D) and lyophilized.

The molecular weight of the HES10/0.4 when measured with LALLS-GPC was 10.5 kD and the DS was 0.41.

Example 1.1(b)

Synthesis by Periodate Oxidation of Hydroxyethyl Starch Selectively Oxidized at its Reducing End and Incubation at 21° C.

100 mg of Oxo-HES10/0.4 (MW=10 kD, DS=0.4, prepared by Supramol Parenteral Colloids GmbH, Rosbach-Rodheim, D; according to DE 196 28 705 A1) were dissolved in 5 ml 20 mM sodium phosphate buffer, pH 7.2. 21.4 mg sodium periodate (Fluka, Sigma-Aldrich Chemie GmbH, Taufkirchen, D) were dissolved in 5 ml of the same buffer. Both solutions were mixed and after incubation for 10 min at 21° C. 0.73 ml glycerol were added and the reaction mixture was incubated at 21° C. for 10 min. The reaction mixture was dialysed for 24 h against water (SnakeSkin dialysis tubing, 3.5 kD cut off, Perbio Sciences Deutschland GmbH, Bonn, D) and lyophilized.

The molecular weight of the HES10/0.4 when measured with LALLS-GPC was 10.5 kD and the DS was 0.41.

Example 1.2(a)

Synthesis of aldehyde Functionalized Hydroxyethyl Starch by Periodate Oxidation of Hydroxyethyl Starch with Non-Oxidized Reducing End and Incubation at 0° C.

100 mg of HES10/0.4 (MW=10 kD, DS=0.4, Supramol Parenteral Colloids GmbH, Rosbach-Rodheim, D) were dissolved in 5 ml 20 mM sodium phosphate buffer, pH 7.2 and cooled to 0° C. 21.4 mg sodium periodate (Fluka, Sigma-Aldrich Chemie GmbH, Taufkirchen, D) were dissolved in 5 ml of the same buffer and cooled to 0° C. Both solutions were mixed and after incubation for 10 min at 0° C. 0.73 ml glycerol were added and the reaction mixture was incubated at 21° C. for 10 min. The reaction mixture was dialysed for 24 h against water (SnakeSkin dialysis tubing, 3.5 kD cut off, Perbio Sciences Deutschland GmbH, Bonn, D) and lyophilized.

The molecular weight of the HES10/0.4 when measured with LALLS-GPC was 8.5 kD and the DS was 0.41.

Example 1.2(b)

Synthesis of Aldehyde Functionalized Hydroxyethyl Starch by Periodate Oxidation of Hydroxyethyl Starch with Non-Oxidized Reducing End and Incubation at 21° C.

100 mg of HES10/0.4 (MW=10 kD, DS=0.4, prepared by Supramol Parenteral Colloids GmbH, Rosbach-Rodheim, D) were dissolved in 5 ml 20 mM sodium phosphate buffer, pH 7.2. 21.4 mg sodium periodate (Fluka, Sigma-Aldrich Chemie GmbH, Taufkirchen, D) were dissolved in 5 ml of the same buffer. Both solutions were mixed and after incubation for 10 min at 21° C. 0.73 ml glycerol were added and the reaction mixture was incubated at 21° C. for 10 min. The reaction mixture was dialysed for 24 h against water (SnakeSkin dialysis tubing, 3.5 kD cut off, Perbio Sciences Deutschland GmbH, Bonn, D) and lyophilized.

The molecular weight of the HES10/0.4 when measured with LALLS-GPC was 8.5 kD and the DS was 0.41.

Example 1.3

Synthesis of Aldehyde Functionalized Hydroxyethyl Starch from Amino Functionalized Hydroxyethyl Starch and Formylbenzoic Acid Oxo-HES10/0.4 (MW=10 kD, DS=0.4) was prepared by Supramol Parenteral Colloids GmbH, Rosbach-Rodheim, D; according to DE 196 28 705 A1.

The molecular weight of the HES10/0.4 when measured with LALLS-GPC was 14.5 kD and the DS was 0.41.

5.1 g (0.51 mmol) of oxo-HES10/0.4 were dissolved in 15 ml anhydrous dimethyl sulfoxide (DMSO, Fluka, Sigma-Aldrich Chemie GmbH, Taufkirchen, D)) and added dropwise under nitrogen to a solution of 5.1 ml (51 mmol) 1,4-diaminobutane in 10 ml anhydrous dimethyl sulfoxide and stirred at 40° C. for 19 h. The reaction mixture was added to a mixture of 80 ml ethanol and 80 ml acetone. The resulting precipitate was separated by centrifugation, washed with a mixture of 20 ml ethanol and 20 ml acetone and re-dissolved in 80 ml water. The solution was dialyzed for 4 days against water (SnakeSkin dialysis tubing, 3.5 kD cut off, Perbio Science Deutschland GmbH, Bonn, D) and subsequently lyophilized. The yield was 67% (3.4 g) amino-HES10/0.4.

150 mg 4-formylbenzoic acid and 230 mg 1-hydroxy-1H-benzotriazole (both Aldrich, Sigma-Aldrich Chemie GmbH, Taufkirchen, D) were dissolved in 10 ml N,N-dimethylformamide (Peptide synthesis grade, Biosolve, Valkenswaard, NL) and 204 μl N,N'-diisopropylcarbodiimide were added. After incubation at 21° C. for 30 min, 1 g of the amino-HES10/0.4 were added. After shaking for 19 h at 22° C., the reaction mixture was added to 84 mL of an ice-cold 1:1 mixture of acetone and ethanol (v/v). The precipitated product was collected by centrifugation at 4° C., re-dissolved in 50 m water, dialysed for 2 d against water (SnakeSkin dialysis tubing, 3.5 kD cut off, Perbio Sciences Deutschland GmbH, Bonn, D) and lyophilized.

Example 1.4

Synthesis of Aldehyde Functionalized Hydroxyethyl Starch from Hydroxyethyl Starch and Formylbenzoic Acid Oxo-HES10/0.7 (MW=10 kD, DS=0.7) was prepared by Supramol Parenteral Colloids GmbH, Rosbach-Rodheim, D; according to DE 196 28 705 A1.

The molecular weight of the HES10/0.7 when measured with LALLS-GPC was 14.5 kD and the DS was 0.76.

83 mg of 4-formylbenzoic acid and 180 mg 1-hydroxy-1H-benzotriazole (both Aldrich, Sigma-Aldrich Chemie GmbH, Taufkirchen, D) were dissolved in 5 mL N,N-dimethylformamide (DMF, Peptide synthesis grade, Biosolve, Valkenswaard, NL) and 78 μl N,N'-diisopropylcarbodiimide were added. After incubation at 21° C. for 30 min, 0.5 g of oxo-HES10/0.7 were added. After shaking for 19 h at 22° C., the reaction mixture was added to 37.5 ml of an ice-cold 1:1 mixture of acetone and ethanol (v/v). The precipitated product was collected by centrifugation at 4° C., re-dissolved in a mixture of 2.5 ml water and 2.5 ml DMF and precipitated again as described above. The reaction product was collected by centrifugation as described, re-dissolved in 10 ml water, dialysed for 2 d against water (SnakeSkin dialysis tubing, 3.5 kD cut off, Perbio Sciences Deutschland GmbH, Bonn, D) and lyophilized.

Example 1.5

Synthesis of Aldehyde Functionalized Hydroxyethyl Starch from Hydroxyethyl Starch and Formylbenzoic Acid HES10/0.7 (MW=10 kD, DS=0.7) was prepared by Supramol Parenteral Colloids GmbH, Rosbach-Rodheim, D.

The molecular weight of the HES10/0.7 when measured with LALLS-GPC was 10.5 kD and the DS was 0.76.

50 mg 4-formylbenzoic acid and 108 mg 1-hydroxy-1H-benzotriazole (both Aldrich, Sigma-Aldrich Chemie GmbH, Taufkirchen, D) were dissolved in 3 ml N,N-dimethylformamide (Peptide synthesis grade, Biosolve, Valkenswaard, NL) and 47 μl N,N'-diisopropylcarbodiimide were added. After incubation at 21° C. for 30 min, 0.3 g of HES10/0.7 were added. After shaking for 19 h at 22° C., the reaction mixture was added to 23 ml of an ice-cold 1:1 mixture of acetone and ethanol (v/v). The precipitated product was collected by centrifugation at 4° C., re-dissolved in a mixture of 1.5 ml water and 1.5 ml DMF and precipitated again as described above. The reaction product was collected by centrifugation as described, re-dissolved in 10 ml water, dialysed for 2 d against water (SnakeSkin dialysis tubing, 3.5 kD cut off, Perbio Sciences Deutschland GmbH, Bonn, D) and lyophilized.

Example 1.6

Synthesis of Aldehyde Functionalized Hydroxyethyl Starch from Amino Functionalized Hydroxyethyl Starch and Formylbenzoic Acid Pentafluorophenyl Ester Oxo-HES10/0.7 (MW=10 kD, DS=0.7) was prepared by Supramol Parenteral Colloids GmbH, Rosbach-Rodheim, D; according to DE 196 28 705 A1.

The molecular weight of the HES10/0.7 when measured with LALLS-GPC was 14.5 kD and the DS was 0.76.

6.0 g (0.6 mmol) of oxo-HES10/0.7 were dissolved in 20 ml anhydrous dimethyl sulfoxide (DMSO, Fluka, Sigma-Aldrich Chemie GmbH, Taufkirchen, D)) and added dropwise under nitrogen to a solution of 6 ml (60 mmol) 1,4-diaminobutane in 11 ml anhydrous dimethyl sulfoxide and stirred at 40° C. for 19 h. The reaction mixture was added to a mixture of 80 ml ethanol and 80 ml acetone. The resulting precipitate was separated by centrifugation, washed with a mixture of 20 ml ethanol and 20 ml acetone and re-dissolved in 80 ml water. The solution was dialyzed for 4 days against water (SnakeSkin dialysis tubing, 3.5 kD cut off, Perbio Science Deutschland GmbH, Bonn, D) and subsequently lyophilized. The yield was 52% (3.15 g) amino-HES10/0.7.

4-formylbenzoic acid pentafluorophenyl ester was synthesized as described in J. S. Lindsey at al., Tetrahedron 50 (1994) pp. 8941-68, especially p. 8956. 50 mg of amino-HES10/0.7 were dissolved in 0.5 ml N,N-dimethylformamide (Peptide synthesis grade, Biosolve, Valkenswaard, NL) and 15.3 mg 4-formylbenzoic acid pentafluorophenylester were added. After shaking for 22 h at 22° C., the reaction mixture was added to 3.5 ml of ice-cold 2-propanol. The precipitated product was collected by centrifugation at 4° C., washed with 4 ml ice-cold 2-propanol, re-dissolved in 50 ml water, dialysed for 2 d against water (SnakeSkin dialysis tubing, 3.5 kD cut off, Perbio Sciences Deutschland GmbH, Bonn, D) and lyophilized.

Example 1.7

Synthesis of Aldehyde Functionalized Hydroxyethyl Starch from Hydroxyethyl Starch and Formylbenzoic Acid Pentafluorophenyl Ester Oxo-HES10/0.7 (MW=10 kD, DS=0.7) was prepared by Supramol Parenteral Colloids GmbH, Rosbach-Rodheim, D; according to DE 196 28 705 A1.

The molecular weight of the HES10/0.7 when measured with LALLS-GPC was 14.5 kD and the DS was 0.76.

4-formylbenzoic acid pentafluorophenyl ester was synthesized as described in J. S. Lindsey at al., Tetrahedron 50 (1994) pp. 8941-68, especially p. 8956. 200 mg oxo-HES10/0.7 were dissolved in 2 ml N,N-dimethylformamide (Peptide synthesis grade, Biosolve, Valkenswaard, NL) and 61.2 mg 4-formylbenzoic acid pentafluorophenyl ester were added. After shaking for 22 h at 22° C., the reaction mixture was added to 15 mL of ice-cold 1:1 mixture of acetone and ethanol (v/v). The precipitated product was collected by centrifugation at 4° C., re-dissolved in a mixture of 1.4 ml water and 0.7 ml DMF and precipitated again as described above. The reaction product was collected by centrifugation as described, re-dissolved in 10 ml water, dialysed for 2 d against water (SnakeSkin dialysis tubing, 3.5 kD cut off, Perbio Sciences Deutschland GmbH, Bonn, D) and lyophilized.

Example 1.8

Synthesis of Aldehyde Functionalized Hydroxyethyl Starch from Amino Functionalized Hydroxyethyl Starch and 4-(4-formyl-3,5-dimethoxyphenoxy)butyric Acid Oxo-HES10/0.4 (MW=10 kD, DS=0.4) was prepared by Supramol Parenteral Colloids GmbH, Rosbach-Rodheim, D; according to DE 196 28 705 A1.

The molecular weight of the HES10/0.4 when measured with LALLS-GPC was 14.5 kD and the DS was 0.41.

5.1 g (0.51 mmol) of oxo-HES10/0.4 were dissolved in 15 ml anhydrous dimethyl sulfoxide (DMSO, Fluka, Sigma-Aldrich Chemie GmbH, Taufkirchen, D)) and added dropwise under nitrogen to a solution of 5.1 ml (51 mmol) 1,4-diaminobutane in 10 ml anhydrous dimethyl sulfoxide and stirred at 40° C. for 19 h. The reaction mixture was added to a mixture of 80 ml ethanol and 80 ml acetone. The resulting precipitate was separated by centrifugation, washed with a mixture of 20 ml ethanol and 20 ml acetone and re-dissolved in 80 ml water. The solution was dialyzed for 4 days against water (SnakeSkin dialysis tubing, 3.5 kD cut off, Perbio Science Deutschland GmbH, Bonn, D) and subsequently lyophilized. The yield was 67% (3.4 g) amino-HES10/0.4.

80.5 mg 4-(4-formyl-3,5-dimethoxyphenoxy)butyric acid (Calbiochem-Novabiochem, Läufelfingen, CH) and 61 mg 1-hydroxy-1H-benzotriazole (Aldrich, Sigma-Aldrich Chemie GmbH, Taufkirchen, D) were dissolved in 3 ml N,N-dimethylformamide (Peptide synthesis grade, Biosolve, Valkenswaard, NL) and 45.4 µl N,N'-diisopropylcarbodiimide were added. After incubation at 21° C. for 30 min, 0.3 g of amino-HES10/0.4 were added. After shaking for 22 h at 22° C., the reaction mixture was added to 23 ml of ice-cold 1:1 mixture of acetone and ethanol (v/v). The precipitated product was collected by centrifugation at 4° C., re-dissolved in a mixture of 2 ml water and 1 ml DMF and precipitated again as described above. The reaction product was collected by centrifugation as described, re-dissolved in 10 ml water, dialysed for 1 d against water (SnakeSkin dialysis tubing, 3.5 kD cut off, Perbio Sciences Deutschland GmbH, Bonn, D) and lyophilized.

Example 1.9

Synthesis of Aldehyde Functionalized Hydroxyethyl Starch from Amino Functionalized Hydroxyethyl Starch and 4-formylbenzoic Acid Oxo-HES10/0.4 (MW=10 kD, DS=0.4) was prepared by Supramol Parenteral Colloids GmbH, Rosbach-Rodheim, D; according to DE 196 28 705 A1.

The molecular weight of the HES10/0.4 when measured with LALLS-GPC was 14.5 kD and the DS was 0.41.

5.1 g (0.51 mmol) of oxo-HES10/0.4 were dissolved in 15 ml anhydrous dimethyl sulfoxide (DMSO, Fluka, Sigma-Aldrich Chemie GmbH, Taufkirchen, D)) and added dropwise under nitrogen to a solution of 5.1 ml (51 mmol) 1,4-diaminobutane in 10 ml anhydrous dimethyl sulfoxide and stirred at 40° C. for 19 h. The reaction mixture was added to a mixture of 80 ml ethanol and 80 ml acetone. The resulting precipitate was separated by centrifugation, washed with a mixture of 20 ml ethanol and 20 ml acetone and re-dissolved in 80 ml water. The solution was dialyzed for 4 days against water (SnakeSkin dialysis tubing, 3.5 kD cut off, Perbio Science Deutschland GmbH, Bonn, D) and subsequently lyophilized. The yield was 67% (3.4 g) amino-HES10/0.4.

150 mg 4-formylbenzoic acid and 230 mg 1-hydroxy-1H-benzotriazole (both Aldrich, Sigma-Aldrich Chemie GmbH, Taufkirchen, D) were dissolved in 10 ml N,N-dimethylformamide (peptide synthesis grade, Biosolve, Valkenswaard, NL) and 204 µl N,N'-diisopropylcarbodiimide were added. After incubation at 21° C. for 30 min, 1 g of the amino-HES10/0.4 were added. After shaking for 19 h at 22° C., the reaction mixture was added to 84 ml of an ice-cold 1:1 mixture of acetone and ethanol (v/v). The precipitated product was collected by centrifugation at 4° C., re-dissolved in 50 ml water, dialysed for 2 d against water (SnakeSkin dialysis tubing, 3.5 kD cut off, Perbio Sciences Deutschland GmbH, Bonn, D) and lyophilized.

Example 1.10

Synthesis of Aldehyde Functionalized Hydroxyethyl Starch by Periodate Oxidation of Hydroxyethyl Starch Selectively Oxidized at its Reducing End Oxo-HES10/0.4 (MW=10 kD, DS=0.4) was prepared by Supramol Parenteral Colloids GmbH, Rosbach-Rodheim, D; according to DE 196 28 705 A1.

The molecular weight of the HES10/0.4 when measured with LALLS-GPC was 10.5 kD and the DS was 0.41.

300 mg of oxo-HES10/0.4 were dissolved in 15 ml 20 mM sodium phosphate buffer, pH 7.2. 64.2 mg sodium periodate (Fluka, Sigma-Aldrich Chemie GmbH, Taufkirchen, D) were dissolved in 15 ml of the same buffer. Both solutions were mixed and after incubation for 30 min at 21° C., 2 ml glycerol were added and the reaction mixture was incubated at 21° C. for 10 min. The reaction mixture was dialysed for 24 h against water (SnakeSkin dialysis tubing, 3.5 kD cut off, Perbio Sciences Deutschland GmbH, Bonn, D) and lyophilized.

Example 2

Synthesis of G-CSF Conjugates by Reductive Amination

G-CSF is a purified G-CSF having essentially the same characteristics as the commercially available product Neupogen® (Amgen, München, D).

Example 2.1(a)

Synthesis of G-CSF-Conjugates by Reductive Amination with Hydroxyethyl Starch with Non-Oxidized Reducing End at pH=7.4

Comparative Example

In Example 2.1, it was tried to use the synthesis method of WO 03/074087 (example 12, page 22-23) for the production of a HES-G-CSF conjugate.

To 3.33 µl of an aqueous solution of G-CSF (Neupogen® from Amgen, München, D, or Granocyte® from Aventis Pharma AG, Zürich, CH, respectively, 3 mg/ml) in 0.1 M sodium phosphate buffer with pH 7.4, 3.33 µl of a solution of HES10/0.4 (MW=10 kD, DS=0.4, Supramol Parenteral Colloids GmbH, Rosbach-Rodheim, D, 79 mg/ml) in the same buffer were added. To this mixture, 3.33 µl of a 60 mM solution of sodium cyanoborohydride in the same buffer was added, and the resulting mixture was incubated for 4 h at 22° C. Subsequently, another 3.33 μl of the freshly prepared 60 mM sodium cyanoborohydride solution were added. During the incubation time of 30 h, altogether 5 portions of 3.33 μl of the freshly prepared 60 mM sodium cyanoborohydride solution were added. The reaction mixture was analysed by gel electrophoresis. No reaction was observed.

Example 2.1(b)

Synthesis of G-CSF-Conjugates by Reductive Amination with Hydroxyethyl Starch with Non-Oxidized Reducing End at pH=5.0 to 9.2 (Comparative Example)

To 3.33 μL of an aqueous solution of G-CSF (3 mg/mL) in a given buffer, 3.33 μl of a HES solution (300 mg/ml) in the same buffer were added. The mixture was cooled to 4° C., and 3.33 μl of a 60 mM solution of sodium cyanoborohydride in the same buffer at 4° C. were added, and the resulting mixture was incubated for 20 h at 4° C.

The following HES preparations and buffer were employed:
a) Buffer: 0.1 M Sodium Acetate Buffer pH 5.0
  HES10/0.4 (MW=10 kD, DS=0.4, Supramol Parenteral Colloids GmbH, Rosbach-Rodheim, D). The molecular weight of the HES10/0.4 when measured with LALLS-GPC was 8.5 kD and the DS was 0.41.
  HES10/0.7 (MW=10 kD, DS=0.7, Supramol Parenteral Colloids GmbH, Rosbach-Rodheim, D). The molecular weight of the HES10/0.7 when measured with LALLS-GPC was 10.5 kD and the DS was 076.
  HES50/0.4 (MW=50 kD, DS=0.4, Supramol Parenteral Colloids GmbH, Rosbach-Rodheim, D). The molecular weight of the HES50/0.4 when measured with LALLS-GPC was 57 kD and the DS was 0.41.
  HES50/0.7 (MW=50 kD, DS=0.7, Supramol Parenteral Colloids GmbH, Rosbach-Rodheim, D). The molecular weight of the HES50/0.7 when measured with LALLS-GPC was 47 kD and the DS was 0.76.
b) Buffer: 0.1 M Sodium Phosphate Buffer pH 7.2
  HES10/0.7 (MW=10 kD, DS=0.7, Supramol Parenteral Colloids GmbH, Rosbach-Rodheim, D). The molecular weight of the HES10/0.7 when measured with LALLS-GPC was 10.5 kD and the DS was 0.76.
c) Buffer: 0.1 M Sodium Borate Buffer pH 8.3
  HES10/0.7 (MW=10 kD, DS=0.7, Supramol Parenteral Colloids GmbH, Rosbach-Rodheim, D). The molecular weight of the HES10/0.7 when measured with LALLS-GPC was 10.5 kD and the DS was 0.76.
d) Buffer: 0.2 M Potassium Borate Buffer pH 9.2
  HES10/0.7 (MW=10 kD, DS=0.7, Supramol Parenteral Colloids GmbH, Rosbach-Rodheim, D). The molecular weight of the HES10/0.7 when measured with LALLS-GPC was 10.5 kD and the DS was 0.76.

Each reaction mixture was analysed by gel electrophoresis. No or negligible conjugation was observed (gel scans for reactions b) to d) not shown).

Example 2.2

Synthesis of G-CSF-Conjugates by Reductive Amination with Hydroxyethyl Starch with Oxidized Reducing End at pH=5.0 to 9.2 (Comparative Example)

To 3.33 μL of an aqueous solution of G-CSF (3 mg/ml) in a given buffer, 3.33 μl of a solution of oxo-HES (300 mg/ml) in the same buffer were added. The mixture was cooled to 4° C., and 3.33 μl of a 60 mM solution of sodium cyanoborohydride in the same buffer at 4° C. were added, and the mixture was incubated for 17 h at 4° C.

The following HES preparations and buffer were employed:
a) Buffer: 0.1 M Sodium Acetate Buffer pH 5.0
  oxo-HES10/0.7 (MW=10 kD, DS=0.7, Supramol Parenteral Colloids GmbH, Rosbach-Rodheim, D). The molecular weight of the HES10/0.7 when measured with LALLS-GPC was 14.5 kD and the DS was 0.76.
  oxo-HES50/0.4 (MW=50 kD, DS=0.4, Supramol Parenteral Colloids GmbH, Rosbach-Rodheim, D). The molecular weight of the HES50/0.4 when measured with LALLS-GPC was 42 kD and the DS was 0.41.
  oxo-HES50/0.7 (MW=50 kD, DS=0.7, Supramol Parenteral Colloids GmbH, Rosbach-Rodheim, D). The molecular weight of the HES50/0.7 when measured with LALLS-GPC was 57 kD and the DS was 0.76.
b) Buffer: 0.1 M Sodium Phosphate Buffer pH 7.2
  HES10/0.7 (MW=10 kD, DS=0.7, Supramol Parenteral Colloids GmbH, Rosbach-Rodheim, D). The molecular weight of the HES10/0.7 when measured with LALLS-GPC was 10.5 kD and the DS was 0.76.
c) Buffer: 0.1 M Sodium Borate Buffer pH 8.3
  HES10/0.7 (MW=10 kD, DS=0.7, Supramol Parenteral Colloids GmbH, Rosbach-Rodheim, D). The molecular weight of the HES10/0.7 when measured with LALLS-GPC was 10.5 kD and the DS was 0.76.
d) Buffer: 0.2 M Potassium Borate Buffer pH 9.2
  HES10/0.7 (MW=10 kD, DS=0.7, Supramol Parenteral Colloids GmbH, Rosbach-Rodheim, D). The molecular weight of the HES10/0.7 when measured with LALLS-GPC was 10.5 kD and the DS was 0.76.

Each reaction mixture was analysed by gel electrophoresis. No or negligible conjugation was observed (gel scans for reactions b) to d) not shown).

Oxidation of HES10/0.4 (MW=8.4 kD, DS=0.41 was carried out by Supramol Parenteral Colloids GmbH, Rosbach-Rodheim, D; according to DE 196 28 705 A1.

Example 2.3

Synthesis of G-CSF-Conjugates by Reductive Amination with Aldehyde Functionalized Hydroxyethyl Starch Synthesized by Periodate Oxidation To 3.33 μl of an aqueous solution of G-CSF (Granocyte® from Aventis Pharma AG, Zürich, CH, and Neupogen® from Amgen, München, D, respectively, 3 mg/mL) in 0.1 M sodium acetate buffer pH 5.0, 3.33 μl of a solution of an aldehydo-HES (79 mg/mL) in the same buffer were added. To the mixture 3.33 μL of a 60 mM solution of sodium cyanoborohydride in the same buffer were added and the mixture was incubated for 25 h at 21° C. The reaction mixture was analysed by gel electrophoresis.

The following aldehyde functionalized HES conjugates were employed:
(i-N) prepared with Neupogen® according to Example 1.1(a) hereinabove;
(ii-N) prepared with Neupogen® according to Example 1.1 (b) hereinabove;
(iii-N) prepared with Neupogen® according to Example 1.2 (a) hereinabove;
(iv-N) prepared with Neupogen® according to Example 1.2 (b) hereinabove;

(i-G) prepared with Granocyte®D according to Example 1.1 (a) hereinabove;
(ii-G) prepared with Granocyte® according to Example 1.1 (b) hereinabove;
(iii-G) prepared with Granocyte® according to Example 1.2 (a) hereinabove;
(iv-G) prepared with Granocyte® according to Example 1.2 (b) hereinabove.

Example 2.4

Synthesis of G-CSF-Conjugates by Reductive Amination with Aldehyde Functionalized Hydroxyethyl Starch Synthesized by Conjugation of Hydroxyethyl Starch to a Formyl-Carboxylic Acid To 3.33 µl of an aqueous solution of G-CSF (3 mg/ml) in 0.1 M sodium acetate buffer pH 5.0, 3.33 µl of a solution of an aldehydo-HES (118.5 mg/mL) in the same buffer were added and cooled to 4° C. To the mixture 3.33 µl of a 60 mM solution of sodium cyanoborohydride in the same buffer at 4° C. were added and the mixture was incubated for 17 h at 4° C. The reaction mixture was analysed by gel electrophoresis.

The following aldehyde functionalized HES conjugates were employed:
(v) prepared according to Example 1.4 hereinabove;
(vi) prepared according to Example 1.5 hereinabove;
(vii) prepared according to Example 1.6 hereinabove;
(viii) prepared according to Example 1.7 hereinabove;
(ix) prepared according to Example 1.8 hereinabove.

Example 2.5

Synthesis of G-CSF-Conjugates by Reductive Amination with Aldehyde Functionalized Hydroxyethyl Starch Synthesized by Conjugation of Hydroxyethyl Starch to Formyl-Carboxylic Acid To 2.5 ml of an aqueous solution of G-CSF (2.27 mg/ml) in 0.1 M sodium acetate buffer pH 5.0, 136 mg aldehydo-HES10/0.4, prepared as described in Example 1.3 hereinabove, were added, and the solution was cooled to 0° C. To the mixture 2.5 ml of an ice-cold 40 mM solution of sodium cyanoborohydride in the same buffer were added and the mixture was incubated for 17 h at 4° C. The reaction mixture was analysed by gel electrophoresis.

Example 2.6

Synthesis of Various Protein Conjugates by Reductive Amination with Aldehyde Functionalized Hydroxyethyl Starch Synthesized According to Examples 1.9 and 1.10, Respectively To w µl (see Table I hereinunder) of a solution of the Protein P (see Table I hereinunder) in 0.1 M sodium acetate buffer pH 5.0 (x mg/ml; see Table I hereinunder) y µl (see Table I hereinunder) of a solution of the HES-derivative (synthesized as described in Examples 1.9 or 1.10) in the same buffer (200 mg/mL) were added. The mixture was cooled to 4° C. and z µl of a 120 mM solution of sodium cyanoborohydride in the same buffer at 4° C. were added and the mixture was incubated for 24 h at 4° C. The crude reaction mixture was analysed by gel electrophoresis. A successful conjugation was observed for all proteins, as indicated by the migration of the protein bands to higher molecular weights (see FIGS. 7 to 11). The increased band-with is due to the molecular weight distribution of the HES derivatives used and the number of HES derivatives linked to the protein.

TABLE I

Experiments carried out according to Example 2.6

| Entry | Protein P | w | x | y | z |
|---|---|---|---|---|---|
| 1 | rhIL-2 (Strathmann Biotec, Hamburg, D) | 15 | 1 | 4.41 | 3.88 |
| 2 | rhIFN-alpha (Strathmann Biotec, Hamburg, D) | 15 | 1 | 3.91 | 3.78 |
| 3 | rhIL-3 (Strathmann Biotec, Hamburg, D) | 10 | 1 | 3.34 | 2.67 |
| 4 | Superoxide Dismutase SOD (from bovine erythrocytes, Sigma, Sigma-Aldrich Chemie GmbH, Taufkirchen, D) | 6.67 | 3 | 3.21 | 1.97 |
| 5 | Myoglobin (from equine skeletal muscle, Sigma, Sigma-Aldrich Chemie GmbH, Taufkirchen, D) | 6.67 | 3 | 5 | 2.33 |
| 6 | rhEPO | 6.67 | 3 | 3.34 | 2 |
| 7 | rhAT III (ATryn ®, GTC Biotherapeutics, Framingham, MA, U.S.A.) | 6.67 | 3 | 1.73 | 1.68 |
| 8 | rhIFN-beta | 40 | 0.5 | 5 | 9 |
| 9 | BSA (Frakt. V, Carl Roth GmbH, Karlsruhe, D) | 6.67 | 3 | 1.49 | 1.63 |

The IFN beta used was a rhIFN beta 1a produced in CHO cells containing di- and triantennary carbohydrate side chains and N-acetyllactosamine repeats.

The EPO used was recombinantly produced EPO having the amino acid sequence of human EPO and essentially the same characteristics as the commercially available Erypo® (ORTHO BIOTECH, Jansen-Cilag) or NeoRecormon® (Roche), cf. EP 0 148 605, EP 0 205 564, EP 0 411 678.

Example 3

Analysis of the G-CSF-Conjugate Obtained in Example 2.5

A. Purification
G-CSF being purified hG-CSF having essentially the same characteristics as the commercial product Neupogen® was obtained and one aliquot was kept unmodified as a control.
1. Buffer Exchange of G-CSF and the G-CSF-Conjugate Samples Before Purification by Anion-Exchange Chromatography The HES-modified G-CSF sample or unmodified G-CSF (as a control) (0.5-5 mg protein) were subjected to buffer exchange using Vivaspin 6 Concentrator units (10.000 MWCO PES, Vivascience, Cat. Nr. VS0602). Samples were concentrated to 0.5-0.7 ml and were diluted to 5 ml with 10 mM Na-phosphate buffer pH 7.2. Each sample was subjected 3 times to this concentration/buffer exchange cycle.
2. Anion Exchange Chromatography of G-CSF and HES-Modified Forms Thereof on a DEAE-Sepharose Column The G-CSF samples after HES-modification and, for comparison, samples of unmodified G-CSF were purified and analyzed by anion exchange chromatography at room temperature by using an ÄKTA explorer 10 system as described. Aliquots of G-CSF either before or after HESylation were dialyzed by ultrafiltration against said buffer A (10 mM Na-phosphate, pH 7.2) or were diluted with about 13 volumes of buffer A. The column containing 2 ml DEAE-Sepharose (DEAE-Sepharose CL-6B, Pharmacia Kat. Nr. 17-0710-01) was regenerated by applying 5.0 column volumes (CV) of 6.5

M guanidine/HCl, 5.0 CV buffer A, 5.0 CV of buffer C (1.5 M NaCl in 10 mM Na-phosphate, pH 7.2) and then 10 CV of buffer A. The samples (0.8-4.5 ml in 10 mM Na-phosphate buffer pH 7.2) were then injected by using a flow rate of 0.6 ml/min. Following washing of the sample loop with 10 ml (2 ml sample loop) or 20 ml (5 ml sample loop) buffer A, depending on the sample applied, the column was further washed with 0-22 CV of buffer A (flow rate=0.8 ml/min). Elution was performed by applying a linear gradient from 0-100% buffer B over 5 CV and an isocratic run with 2.5 CV of 100% buffer B using a flow rate of 0.6 ml/min. The column was re-equilibrated with 5 CV of buffer A and was regenerated as detailed above by using a flow rate of 1 ml/min.

If required, samples were concentrated using a Vivaspin concentrator and buffer exchange was performed as described above. Samples were stored at 0-8° C. in 10 mM Na-Acetat buffer pH 4.0 before or after sterile filtration using a 0.2 µm filtrations unit, Corning, Cat. No. 431215). The following samples were prepared for in-vitro bioassays and for further analytical analysis. Protein concentration was determined as described in section B1 below:

I. 0401-15/A33, 0.44 mg/ml, volume=500 µl G-CSF (*E. coli*)
II. 0401-13/A32, 0.28 mg/ml, volume=900 µl G-CSF (*E. coli*) HES-modified
III. 0401-28/A58, 0.60 mg/ml, volume=350 µl Neupogen
IV. 0401-28/A57, 0.50 mg/ml, volume=400 µl Neulasta B. Analysis Aliquots of the sample were analyzed for their protein content and for modifications.

1. G-CSF Protein Quantitation by RP-HPLC.

G-CSF protein content of the sample was quantitated using the unmodified protein preparation (concentration: 0.453 mg/ml) as a standard.

A Dionex HPLC system consisting of a pump P 680 A HPG, degassing unit Degasys DG 1210, an autosampler and injector ASI-100, a sample loop 250 µl, a thermostated column department TCC 100 along with a UV/Vis-Detektor UVD170U equipped with a Software Chromeleon Chromatography Management System was used.

A precolumn CC 8/4 Nucleosil 120-5 C4, Macherey-Nagel, Cat. No. 721889, and a separation column 40 C-4 Nucleosil MPN, 5 µm, 125×4 mm RP-column (Macherey-Nagel, ordering No. 7200 45.40) were used. Solvent A was H₂O plus 0.06% (v/v) trifluoroacetic acid and solvent B was 90% acetonitrile in H₂O, containing 0.06% (v/v) trifluoroacetic acid; flow rate was: 1 ml/min.

UV detection was at 214, 221, 260 and at 280 nm wavelength.

Samples of approximately 10-20 µg were injected into a RP-HPLC column. The following gradient was used:
0-5 min: 0-10% B
17 min: 10-45% B
35 min: 45-80% B
36 min: 80-100% B
38 min: 100% B
39 min: 10% B
45 min: 10% B The resulting peak area at the elution position of the standard G-CSF preparation was used and compared to the reference standard by comparing the peak appearing at around 29 min at 280 nm wavelength.

2. Reduction+Carboxamidomethylation of G-CSF Protein

Aliquots from the G-CSF protein samples were reduced and carboxamidomethylated as described elsewhere (Guillermina Forno, Mariela Bollati Fogolin, Marcos Oggero, Ricardo Kratje, Marina Etcheverrigaray, Harald S. Conradt, Manfred Nimtz (2004) N- and O-linked carbohydrates and glycosylation site occupancy in recombinant human granulocyte-macrophage colony-stimulating factor secreted by a Chinese hamster ovary cell line; European J. Biochem, 273 (5), 907-919). Carboxamidomethylation leads to modified cystein residues. Endoproteinase Glu-C digestion of the carboxamidomethylated protein was performed in 25 mM NH₄HCO₃ containing 1 M urea at pH 7.8 and using an enzyme/substrate ratio of 0.2:10 for 18-24 hours.

3. Separation of Endo-Glu-C Peptides by RP-HPLC

The peptides generated by the Endo-Glu-C digestion were separated on a Dionex HPLC system consisting of a pump P 680 A HPG, degassing unit Degasys DG 1210, an autosampler and injector ASI-100, a sample loop 250 µl, a thermostatted column department TCC 100 along with a UV/Vis-Detektor UVD170U equipped with a Software Chromeleon Chromatography Management System was used.

A precolumn CC 8/4 Nucleosil 120-5 C4, Macherey-Nagel, Cat. No. 721889, and a separation column 40 C-4 Nucleosil MPN, 5 µm, 125×4 mm RP-column (Macherey-Nagel, ordering No. 7200 45.40) were used. Solvent A was H₂O plus 0.06% (v/v) trifluoroacetic acid and solvent B was 90% acetonitrile in H₂O, containing 0.06% (v/v) trifluoroacetic acid; flow rate was: 1 ml/min. The following gradient was applied:
0-5 min: 10% B
17 min: 45% B
65 min: 100% B
67 min: 100% B
69 min: 10% B
75 min: 10% B UV detection was at 214, 221, 260 and at 280 nm wavelength. Peptides generated by the Endo-Glu-C digestion were separable (data not shown).

4. Analysis of Proteolytic Peptides by Matrix-Assisted Laser Desorption/Ionization Time-of-Flight Mass Spectrometry (MALDI/TOF/TOF-MS)

Mass spectrometry was used to detect the intact N-terminus of G-CSF's in the different samples prepared. Samples (3-5 µg) resulting from Endoproteinase Glu-C digestions of reduced and carboxamidomethylated protein samples were used directly for MS-analysis (without the RP-HPLC of step 3) and purified using ZipTip pipette tips containing C18 reversed-phase material according to the manufacturer's instructions. After washing with 0.1% (v/v) formic acid, elution of peptides was performed with 10 µl 0.1% (v/v) formic acid in 60% (v/v) acetonitrile.

Proteolytic (Endo-Glu-C) peptide fragments were analyzed with a Bruker ULTRAFLEX time-of-flight (TOF/TOF) instrument in the linear positive ion mode using a matrix of 22.4 mg 3,5-dimethoxy-4-hydroxy-cinnamic acid in 400 µl acetonitrile and 600 µl 0.1% (v/v) trifluoroacetic acid in H₂O; (glyco)-peptides were measured using a matrix of 19 mg α-cyano-4-hydroxycinnamic acid in the same solvent mixture using the reflectron for enhanced resolution. Sample solutions of 1 µl and an approximate concentration of 1-10 pmol·µl⁻¹ were mixed with equal amounts of the respective matrix. This mixture was spotted onto a stainless steel target and dried at room temperature before analysis. Spectra were recorded in the mass range 900-5000 dalton. Table II correlates the expected masses with the respective G-CSF peptides.

TABLE II

Theoretical (monoisotopic) masses of Endo-Glu-C peptides resulting from G-CSF

| Mass (Dalton) | Observed in this study | aa position | artif.modification(s) | peptide sequence |
|---|---|---|---|---|
| 2132.11 | + | 1-20 | Cys_CAM: pos 18 m/z 2189.13 | MTPLGPASSLPQSFLLKCLE (SEQ ID NO: 1) |
| 1512.81 | + | 21-34 | — | QVRKIQGDGAALQE (SEQ ID NO: 2) |
| 1534.74 | + | 35-47 | Cys_CAM: pos 37, 43 m/z 1648.78 | KLCATYKLCHPEE (SEQ ID NO: 3) |
| 4942.63 | − | 48-94 | Cys_CAM: Pos 65, 75 m/z 5056.68 | LVLLGHSLGIPWAPLSSCPS QALQLAGCLSQLHSGLFLYQ GLLQALE (SEQ ID NO: 4) |
| 502.25 | − | 95-99 | — | GISPE (SEQ ID NO: 5) |
| 2835.37 | − | 100-124 | — | LGPTLDTLQLDVADFATTIW QQMEE (SEQ ID NO: 6) |
| 4026.08 | + | 125-163 | — | LGMAPALQPTQGAMPAFASA FQRRAGGVLVASHLQSFLE (SEQ ID NO: 7) |
| 1438.83 | + | 164-175 | — | VSYRVLRHLAQP (SEQ ID NO: 8) |

Cystein residues were carboxamidomethylated; peptides marked as fat were detected in MALDI/TOF spectrum of the non modified G-CSF.

The N-terminal Endo-Glu-C peptide (MTPLGPASS-LPQSFLLKCLE (SEQ ID NO:1); m/z 2189.1) comprising position 1-20 of the protein was detected in MALDI/TOF-MS spectra of samples after proteolytic treatment of G-CSF with endoproteinase Glu-C as described above.

Results

I. Purification of G-CSF and HES Modified Variant

HES-modified G-CSF and non modified G-CSF were subjected to purification using a DEAE-Sepharose CL-6B column as described under A4.

In the case of the unmodified sample 0401-15/A33, no significant absorption at 280 nm was detected in the flow-through and the protein eluted at a concentration of 40-50% buffer B (0.16-0.20 M NaCl) in a volume of 6 ml, with a specific peak area of 660 mAU×ml×mg$^{-1}$ at 280 nm.

The sample (HES-modified G-CSF) eluted over a large range of the gradient at a concentration of buffer B from 20-80% (0.08-0.32 M NaCl) in a volume of 12 ml. About 90% of the total peak area detected at 280 nm was found in the flow-through, containing about 50% of the total protein with an apparently slightly higher molecular mass when compared to the eluted protein, as detected by SDS-PAGE analysis as shown in FIG. 13.

Recovery of proteins was calculated based on the peak area (A280 nm) of the eluting fractions compared to the non modified G-CSF protein.

TABLE III

Comparison of the peak areas at 280 nm detection

| DEAE-Sepharose Run no. | Description | Calculated protein amount for injection | Eluate Area [280 nm] (mAU × ml) | Yield in eluate compared to eluate from run DS01 A33 ** |
|---|---|---|---|---|
| DS01 A33 | G-CSF | 0.5 mg | 330 | (0.50 mg) |
| DS03 A32 | HES-modified G-CSF | 4.0 mg | 1560 | 2.36 mg |

** RP-HPLC quantitation of the protein confirmed these results

II. Analysis of Proteins by Peptide Mapping and MALDI/TOF MS after Treatment with Endoproteinase Glu-C The N-terminal peptide resulting from endoproteinase Glu-C digestion of both the carbo-xamidomethylated unmodified G-CSF (FIG. 14) and the market product Neupogen (data not shown), was clearly detected by MALDI/TOF-MS (MTPLGPASSLPQSFLLKC*LE (SEQ ID NO:1), m/z 2189.1; cysteine carboxamidomethylated). This signal was absent in samples subjected to HES-modification (FIG. 15) and in Neulasta (data not shown), indicating modification of this peptide.

N-terminal sequencing of HE S-modified G-CSF revealed a blocked N-terminus suggesting that in fact the N-terminal methionine residue of this protein derivative is modified by HAS derivative.

| Sample code | description | MALDI/TOF spectrum |
|---|---|---|
| G-CSF A32 | HES-modified G-CSF | I/4810 |
| G-CSF A33 | G-CSF | I/4811 |
| G-CSF A57 | Neulasta | I/4812 |
| G-CSF A58 | Neupogen | I/4813 |
| G-CSF A08 | G-CSF | I/4815 |

Example 4

In Vitro Results of the G-CSF-Conjugate Obtained in Example 2.5 and Purified According to Example 3: Mitogenicity of G-CSF Variants for Mouse NFS-60 Cells G-CSF is known for its specific effects on the proliferation, differentiation, an activation of hematopoietic cells of the neutrophilic granulocyte lineage. The mitogenic capacity of G-CSF variants was tested using mouse NFS-60 cells (N. Shirafuji et al., Exp. Hematol. 1989, 17, 116-119). Cells grown in RPMI medium with 10% fetal calf serum (Gibco INVITROGEN GmbH, Karlsruhe, D) containing 5-10% WEHI-3B (DSMZ, Braunschweig, D; cultivated as described by the DSMZ) conditioned medium as source of exogenous IL-3 were harvested by centrifugation, washed and aliquoted at 100,000 cells per well in a 24-well plate. Cells were allowed to adapt for 1 hour at 37° C. in RPMI medium without WEHI-3B conditioned media before G-CSF growth factors sample diluted in the same media were added. NFS-60 cells were exposed to purified G-CSF variants for 3 days at 37° C. and than the cells were electronically counted (Casy TT Cell Counter, Schärfe System, Reutlingen, D). The results are summarised in FIG. 12. As seen in FIG. 12, the different G-CSF variants (0.5-50 pg/ml) were able to stimulate an increase in the number of cells after 3 days compared to medium that did not contain added growth factors.

Unmodified control proteins G-CSF/A33 and G-CSF/A58 stimulated cells at a very similar extend ($ED_{50}$=5-10 pg/ml) while G-CSF conjugates G-CSF/A32 and G-CSF/A57 showed only a minor decrease in activity if compared to the unmodified version ($ED_{50}$=10-25 pg/ml).

Example 5

A1AT (α1AT, Alpha1aT) Conjugates Synthesized Via Reductive Amination

Example 5.1

Synthesis of Amino-HES (A) from Oxidized HES 6.09 g of oxo-HES (MW=57,000 D, DS=0.76, Supramol Parenteral Colloids GmbH, Rosbach-Rodheim, D, prepared according to DE 196 28 705 A1) were heated over night at 80° C. in vacuo, dissolved under nitrogen in 32 ml dry dimethyl sulphoxide (Fluka, Sigma-Aldrich Chemie GmbH, Taufkirchen, D,) and 1.22 ml of 1,4-diaminobutane (Fluka, Sigma-Aldrich Chemie GmbH, Taufkirchen, D) were added. After stirring at 40° C. for 17 h the reaction mixture was added to 150 ml of an ice-cold 1:1 mixture of acetone and ethanol (v/v). The precipitated product was collected by centrifugation at 4° C., washed with 40 ml of an ice-cold 1:1 mixture of acetone and ethanol (v/v) and collected by centrifugation. The crude product was dissolved in 80 ml water, dialysed for 4 d against water (SnakeSkin dialysis tubing, 3.5 kD cut off, Perbio Sciences Deutschland GmbH, Bonn, D) and lyophilized. The yield of isolated product was 82%.

Example 5.2

Synthesis of Aldehydo-HES (A) from Amino-HES (A) of Example 5.1

125 mg 4-formylbenzoic acid and 174 mg 1-hydroxy-1H-benzotriazole (both Aldrich, Sigma-Aldrich Chemie GmbH, Taufkirchen, D) were dissolved in 38 ml N,N-dimethylformamide (Peptide synthesis grade, Biosolve, Valkenswaard, NL), and 155 μL N,N'-diisopropylcarbodiimide (Fluka, Sigma-Aldrich Chemie GmbH, Taufkirchen, D) were added. After incubation at 21° C. for 30 min, 3.8 g of amino-HES (A) (prepared as described in example 5.1) were added. After shaking for 19 h at 22° C., the reaction mixture was added to 160 ml of an ice-cold 1:1 mixture of acetone and ethanol (v/v). The precipitated product was collected by centrifugation at 4° C., re-dissolved in 20 ml N,N-dimethylformamide and precipitated with 80 ml of an ice-cold 1:1 mixture of acetone and ethanol (v/v) as described above in example 5.1. After centrifugation, the precipitate was dissolved in 50 ml water, dialysed for 2 d against water (SnakeSkin dialysis tubing, 3.5 kD cut off, Perbio Sciences Deutschland GmbH, Bonn, D) and lyophilized. The yield of isolated product was 77%.

Example 5.3

Synthesis of Amino-HES (B) from Oxidized HES 10 g of oxo-HES (MW=57,000 D, DS=0.76, Supramol Parenteral Colloids GmbH, Rosbach-Rodheim, D, prepared according to DE 196 28 705 A1) were heated over night at 80° C. in vacuo, dissolved under nitrogen in 52 ml dry dimethyl sulphoxide (Fluka, Sigma-Aldrich Chemie GmbH, Taufkirchen, D) and 2 ml of 1,4-diaminobutane (Fluka, Sigma-Aldrich Chemie GmbH, Taufkirchen, D) were added. After stirring at 40° C. for 17 h the reaction mixture was added to 350 ml of ice-cold 2-propanol (Carl Roth GmbH+Co. KG, Karlsruhe, D). The precipitated product was collected by centrifugation at 4° C., washed with 80 ml of ice-cold 2-propanol and collected by centrifugation. The crude product was dissolved in 80 ml water, dialysed for 2 d against water (SnakeSkin dialysis tubing, 3.5 kD cut off, Perbio Sciences Deutschland GmbH, Bonn, D) and lyophilized. The yield of isolated product was 85%.

Example 5.4

Synthesis of Aldehydo-HES (B) from Amino-HES (B) of Example 5.3

153 mg 4-formylbenzoic acid and 241 mg 1-hydroxy-1H-benzotriazole (both Aldrich, Sigma-Aldrich Chemie GmbH, Taufkirchen, D) were dissolved in 51 ml N,N-dimethylformamide (Peptide synthesis grade, Biosolve, Valkenswaard, NL) and 170 μL N,N'-diisopropylcarbodiimide (Fluka, Sigma-Aldrich Chemie GmbH, Taufkirchen, D) were added. After incubation at 21° C. for 30 min, 5.1 g of amino-HES (B) (prepared as described in example 5.3) were added. After shaking for 16 h at 22° C., the reaction mixture was added to 360 ml of an ice-cold 1:1 mixture of acetone and ethanol (v/v). The precipitated product was collected by centrifugation at 4° C., re-dissolved in 50 ml water and precipitated with 360 ml of an ice-cold 1:1 mixture of acetone and ethanol (v/v) as described above in example 5.1. After centrifugation, the precipitate was dissolved in 50 ml water, dialysed for 2 d against water (SnakeSkin dialysis tubing, 3.5 kD cut off, Perbio Sciences Deutschland GmbH, Bonn, D) and lyophilized. The yield of isolated product was 87%.

Example 5.5

Conjugation of Aldehydo-HES (A) and (B) to A1AT by Reductive Amination

A mixture of 189 mg aldehydo-HES (B) (prepared as described in example 5.4) and 172 mg aldehydo-HES (A) (prepared as described in example 5.2) were dissolved in 2.88 ml reaction buffer (0.1 M sodium phosphate buffer, 150 mM sodium chloride, pH 7.2). At 20° C., 1.67 ml of a 60 mM sodium cyanoborohydride solution in the same buffer were added followed by 0.455 ml of an A1AT solution (c(A1AT) =11.0 mg/ml in 20 mM sodium phosphate buffer, 150 mM sodium chloride, pH 7.2, A1AT=rh A1AT provided by GTC Biotherapeutics Inc., Framingham, Mass., lot No. 080604A). The mixture was incubated at 20° C. After 17 h, additional 6.7 mg sodium cyanoborohydride dissolved in 200 μl of the reaction buffer were added and the mixture was incubated for additional 24 h at the same temperature. 10 μL of this solution were analysed after a total incubation time of 25 h by gel electrophoresis (see FIG. 16)

Example 5.6

Conjugation of HES to A1AT by Reductive Amination (Reaction Control)

362 mg HES (MW=56,000 D, DS=0.41, Supramol Parenteral Colloids GmbH, Rosbach-Rodheim, D) were dissolved in 2.88 ml reaction buffer (0.1 M sodium phosphate buffer, 150 mM sodium chloride, pH 7.2). At 20° C., 1.67 ml of a 60 mM sodium cyanoborohydride solution in the same buffer were added followed by 0.455 ml of a A1AT solution (c (A1AT)=11.0 mg/ml in 20 mM sodium phosphate buffer, 150 mM sodium chloride, pH 7.2, α1AT=rh α1AT provided by GTC Biotherapeutics Inc., Framingham, Mass., lot No. 080604A). The mixture was incubated at 20° C. After 17 h, additional 6.7 mg sodium cyanoborohydride dissolved in 200 μl of the reaction buffer were added and the mixture was incubated for additional 24 h at the same temperature. 10 μL of this solution were analysed after a total incubation time of 25 h by gel electrophoresis (see FIG. 17).

Example 5.7

Purification of HES-A1A T Conjugate by Ion Exchange Chromatography (IEC)

Conjugates of A1AT were purified by Ion Exchange Chromatography on a HiTrap Q HP column using an ÄKTA-Explorer chromatography system (both from Amersham Biosciences). The purification was performed in accordance with the isolation of A1AT from human plasma as described in "Chen, Hammond, Lang and Lebing, Purification of α₁Proteinase Inhibitor from Human Plasma Fraction IV-1 by Ion Exchange Chromatography, VoxSanguinis 1998, 74, 232-241".

Sample preparation: buffer exchange on a HiPrep 26/10 Desalting column (Amersham Biosciences) in combination with the ÄKTA-Explorer chromatography system using 20 mM sodium phosphate, 20 mM sodium chloride, pH 8 as eluent.

Buffer exchange was performed after dilution of the crude reaction mixture (preparation as described in example 5.5, approximately 5 ml) with desalted water to a final volume of 10 ml using the following parameters:

| | |
|---|---|
| Column: | HiPrep 26/10 Desalting |
| Flow rate: | 10 ml/min |
| Eluent: | 20 mM sodium phosphate, 20 mM sodium chloride, pH 8 |
| Sample volume: | 10 ml |
| Eluate fractionation: | 2.5 ml |
| Equilibration: | 5 column volumes |
| Length of elution: | 2 column volumes |

The first 14 ml of eluent were pooled, and binding buffer was added to yield a final volume of 20 ml. This solution, containing approximately 5 mg protein, was purified by IEC using the following parameters:

| | |
|---|---|
| Column: | HiTrap Q HP 1 ml |
| Flow rate: | 1 ml/min |
| Binding Buffer (BB): | 20 mM sodium phosphate, 20 mM sodium chloride, pH 8 |
| Elution Buffer (EB): | 20 mM sodium phosphate, 1 M sodium chloride, pH 8 |
| Sample volume: | 20 ml |
| Flow trough fractionation: | 2 ml |
| Eluate fractionation: | 1 ml |
| Start concentration EB: | 0% |
| Equilibration: | 5 column volumes |
| Wash out unbound sample: | 15 ml |
| Target concentration EB: | 15% |
| Length of gradient: | 20 ml |

The fractions collected after chromatography were analysed by SDS-Page. Fractions containing HES-A1AT conjugate were pooled (elution volume from 40 to 47 ml corresponding to fractions B1-C6, see FIG. 17). In some of the pooled fractions a small amount of unreacted A1AT was detectable. The initial concentration of the pooled fraction after chromatography determined by BCA (Pierce Cat. No. 23225), using A1AT (provided by GTC Biotherapeutics Inc., Framingham, Mass., lot No. 080604A) as reference standard) was 170 μg/ml. After dilution and buffer exchange into 20 mM sodium phosphate, 150 mM sodium chloride, pH 7.2 the resulting protein concentration was 54.5 μg/ml (BCA (pierce with A1AT from GTC Biothearpeutics Inc., Framingham, Mass., lot No. 080604A (as reference standard)). This final solution was used to determinate the inhibitory efficiency of the conjugate.

Example 5.8

Determination of the In Vitro Inhibition Capacity of HES-A1AT Conjugate for Human Granulocyte Elastase Elastase Inhibitory activity tests of the conjugates were performed according to Castillo et al., *Anal. Biochem.* 1979, 99, 53-64 using a Tecan UV-VIS-Platereader Model Sunrise. This assay is based on the release of p-nitroaniline from N-Met-O-succinyl-Ala-Ala-Pro-Val-p-NO₂-anilin (SEQ ID NO:9) catalyzed by elastase. This hydrolysis can be followed by the increase of absorbance at 405 nm. The initial hydrolysis rate is in close correlation to the activity of the enzyme. The assay was carried out in absence and in the presence of different concentrations of the inhibitor to be tested. The decrease of enzyme activity according to the inhibitory activity of the substances tested is represented in a decrease of the slope in the $A_{405}$ versus time plot. The residual elastase activity in presence of a certain inhibitor concentration is given by the slope of the inhibited curve divided by the slope of the uninhibited curve. There is a linear correlation between the residual enzyme activity and the inhibitor concentration. By using linear regression, a linear smooth line can be achieved and the residual enzyme activity for a given inhibitor concentration can be calculated. By this way the inhibitory activity (=1-residual enzyme activitiy) of the same concentration of different inhibitors can be compared (see FIG. 18).

The following parameters were used:

| | |
|---|---|
| Substrate concentration: | 1.5 mM |
| Elastase activity: | 7.5 mU |
| Wavelength: | 405 nm |
| Temperature: | 20° C. |

-continued

| Time interval: | 15 s |
| Kinetic cycles: | 25 |
| Measure Mode: | Center |

The assay solution consisted of 300 µl buffer (0.1 M Hepes, 0.5 M NaCl, 0.05% (m/v) Triton X-100, pH 7.5) containing 10% DMSO, 1.5 mM N-Met-O-succinyl-Ala-Ala-Pro-Val-p-NO$_2$-anilin, 7.5 mU Elastase and varying amounts of inhibitors.

Elastase was purchased from Serva Electrophoresis GmbH, Heidelberg. All other 1.5 substances were purchased from Sigma Aldrich, Taufkirchen.

The inhibitory activity of the conjugate synthesized as described in example 5.5 was tested in comparison with Prolastin® HS (Bayer Vital GmbH, Leverkusen, Germany Lot No. PR4HA43) as reference and with A1AT (GTC Biotherapeutics Inc., Framingham, Mass., lot No. 080604A) as starting material for the conjugation. The residual enzyme activity vs. concentration plot is given in FIG. 18. Linearity for all curves was $R^2 > 0.98$. In the below, $IC_{50}$-values and elastase inhibition for c (inhibitor)=1 µg/ml are given, as well as the inhibitory activity of starting material and conjugate in relation to the reference. Data outlined in the table below clearly demonstrate that the major part of the A1AT activity remained after conjugation with HES.

TABLE IV

| inhibitor | linear smooth line Equitation | $IC_{50}$ [µg/ml] | elastase inhibition c (inhibitor) = 1 µg/ml [%] | inhibition activity in relation to Prolastin [%] |
|---|---|---|---|---|
| Prolastin | y = −0.6754x + 0.9627 | 0.685 | 71.3 | |
| A1AT | y = −0.5046x + 0.9558 | 0.903 | 54.9 | 77.0 |
| HES-A1AT-conjugate | y = −0.3757x + 0.9627 | 1.232 | 41.3 | 57.9 |

Example 5.9

Determination of the In-Vivo Half-Live of HES-Rh Alpha1AT Conjugate in Comparison to Rh Alpha1AT and Plasma Derived H Alpha1AT Female mice aged 8-10 weeks (BALB/cOlaHsd, Harlan GmbH, Borchen, Germany) were utilized as test organism (42 mice, 14 per sample). The "is bodyweight" of each animal was detected right before administration of the different sample solutions. 100 µl of a 50 µg/ml solution of the samples outlined below in a puffer pH=7.2 (20 mmol sodium phosphate, 150 mmol sodium chloride) were injected intravenously in the tail vein of the mice.

Sample 1: rh alpha1AT (GTC Biotherapeutics Inc., Framingham, Mass., lot No. 080604A)

Sample 2: rh alpha1AT-HES conjugate as prepared in example 5.5

Sample 3: plasma derived h alpha1 AT (SERVA Electrophoresis GmbH, Heidelberg, Germany)

At 1, 2, 4, 10, 24, 31, 5 and 48, hours after injection, two mice of each group were killed and whole blood samples (~500 µl) were withdrawn from the heart of the animals. Serum was prepared using Microvette® 500 Z-Gel (Sarstedt, Nümbrecht, Germany). The serum samples were stored at −80° C. until the beginning of the alpha1AT concentration measurements.

alpha1AT concentrations were detected using a commercially available alpha1AT-ELISA (Immundiagnostik, Bensheim, Germany) following the manufacturers instructions.

The results obtained demonstrate a significant plasma half-life increase for the rh alpha1AT-HES conjugate in comparison to the not modified rh alpha1AT starting material. The measured half-life of the conjugate is in the same range than the one of the plasma derived h alpha1AT according to Table V.

TABLE V

Plasma half-life of samples 1-3.

| Sample No | Plasma half-life in mice [h] |
|---|---|
| 1 | 1.2 |
| 2 | 3.6 |
| 3 | 3.2 |

Example 6

Synthesis of G-CSF-Conjugates

Example 6.1

Synthesis of the Aldehydo-HES Derivatives

Example 6.1(a)

Synthesis of AminoHES10/0.4

5.12 g of oxo HES10/0.4 (MW=14,500 D, DS=0.41, Supramol Parenteral Colloids GmbH, Rosbach-Rodheim, D, prepared according to DE 196 28 705 A1) were heated over night at 80° C. in vacuo and dissolved under nitrogen in 25 mL dry dimethyl sulphoxide (Fluka, Sigma-Aldrich Chemie GmbH, Taufkirchen, D) and 5.13 mL of 1,4-diaminobutane were added. After stirring at 40° C. for 17 h the reaction mixture was added to 150 mL of an ice-cold 1:1 mixture of acetone and ethanol (v/v). The precipitated product was collected by centrifugation at 4° C., washed with 40 mL of an ice-cold 1:1 mixture of acetone and ethanol (v/v) and collected by centrifugation. The crude product was dissolved in 80 mL water, dialysed for 4 d against water (SnakeSkin dialysis tubing, 3.5 kD cut off, Perbio Sciences Deutschland GmbH, Bonn, D) and lyophilized. The yield of isolated product was 67%.

Example 6.1(b)

Synthesis of AldehydoHES10/0.4

105 mg 4-formylbenzoic acid and 135 mg 1-hydroxy-1H-benzotriazole (both Aldrich, Sigma-Aldrich Chemie GmbH, Taufkirchen, D) were dissolved in 7 mL N,N-dimethylformamide (Peptide synthesis grade, Biosolve, Valkenswaard, NL) and 135 µL N,N'-diisopropylcarbodiimide (Fluka, Sigma-Aldrich Chemie GmbH, Taufkirchen, D) were added. After incubation at 21° C. for 30 min, 0.7 g of aminoHES10/0.4 (synthesised as described in example 6.1(a)) were added. After shaking for 18 h at 22° C., the reaction mixture was added to 42 mL of an ice-cold 1:1 mixture of acetone and ethanol (v/v). The precipitated product was collected by centrifugation at 4° C., re-dissolved in 5 mL DMF and precipitated with 42 mL ethanol/acetone as described above. After centrifugation, the collected precipitate was dissolved with water, dialysed for 1 d against water (SnakeSkin dialysis tubing, 3.5 kD cut off, Perbio Sciences Deutschland GmbH, Bonn, D) and lyophilized. The yield of isolated product was 95%.

Example 6.1(c)

Synthesis of AminoHES10/0.7

6.02 g of oxo-HES10/0.7 (MW=15,000 D, DS=0.76, Supramol Parenteral Colloids GmbH, Rosbach-Rodheim, D, according to DE 196 28 705) were dissolved under nitrogen in 32 mL dry dimethyl sulphoxide (Fluka, Sigma-Aldrich Chemie GmbH, Taufkirchen, D) and 6.03 mL of 1,4-diaminobutane were added. After stirring at 40° C. for 17 h the reaction mixture was added to 150 mL of an ice-cold 1:1 mixture of acetone and ethanol (v/v). The precipitated product was collected by centrifugation at 4° C., washed with 40 mL of an ice-cold 1:1 mixture of acetone and ethanol (v/v) and collected by centrifugation. The crude product was dissolved in 80 mL water, dialysed for 4 d against water (SnakeSkin dialysis tubing, 3.5 kD cut off, Perbio Sciences Deutschland GmbH, Bonn, D) and lyophilized. The yield of isolated product was 52%.

Example 6.1(d)

Synthesis of AldehydoHES10/0.7

150 mg 4-formylbenzoic acid and 230 mg 1-hydroxy-1H-benzotriazole (both Aldrich, Sigma-Aldrich Chemie GmbH, Taufkirchen, D) were dissolved in 10 mL N,N-dimethylformamide (Peptide synthesis grade, Biosolve, Valkenswaard, NL) and 204 µL N,N'-diisopropylcarbodiimide (Fluka, Sigma-Aldrich Chemie GmbH, Taufkirchen, D) were added. After incubation at 21° C. for 30 min, 1 g of aminoHES10/0.7 (synthesised as described in example 6.1(c)) were added. After shaking for 19 h at 22° C., the reaction mixture was added to 84 mL of ice-cold 2-propanol. The precipitated product was collected by centrifugation at 4° C., re-dissolved in 50 mL water, dialysed for 2 d against water (SnakeSkin dialysis tubing, 3.5 kD cut off, Perbio Sciences Deutschland GmbH, Bonn, D) and lyophilized. The yield of isolated product was 83%.

Example 6.1(e)

Synthesis of AminoHES30/0.4

5 g of oxo-HES 30/0.4 (MW=28,000 D, DS=0.41, Supramol Parenteral Colloids GmbH, Rosbach-Rodheim, D, using molar ratios of the ingredients according to DE 196 28 705 A1) were heated over night at 80° C. in vacuo and were then dissolved under nitrogen in 28 mL dry dimethyl sulphoxide (Fluka, Sigma-Aldrich Chemie GmbH, Taufkirchen, D) and 1.67 mL of 1,4-diaminobutane were added. After stirring at 40° C. for 17 h the reaction mixture was added to 175 mL of an ice-cold 1:1 mixture of acetone and ethanol (v/v). The precipitated product was collected by centrifugation at 4° C. The crude product was dissolved in 40 mL water, dialysed for 2 d against water (SnakeSkin dialysis tubing, 3.5 kD cut off, Perbio Sciences Deutschland GmbH, Bonn, D) and lyophilized. The yield of isolated product was not determined.

Example 6.1(f)

Synthesis of AldehydoHES30/0.4

130 mg 4-formylbenzoic acid and 153 mg 1-hydroxy-1H-benzotriazole (both Aldrich, Sigma-Aldrich Chemie GmbH, Taufkirchen, D) were dissolved in 36 mL N,N-dimethylformamide (Peptide synthesis grade, Biosolve, Valkenswaard, NL) and 110 µL N,N'-diisopropylcarbodiimide (Fluka, Sigma-Aldrich Chemie GmbH, Taufkirchen, D) were added. After incubation at 21° C. for 30 min, 2.61 g of aminoHES30/0.4 (synthesised as described in example 6.1(e)) were added. After shaking for 22.5 h at 22° C., the reaction mixture was added to 160 mL of an ice-cold 1:1 mixture of acetone and ethanol (v/v). The precipitated product was collected by centrifugation at 4° C. and washed with an ice-cold 1:1 mixture of acetone and ethanol (v/v). After centrifugation, the precipitate was dissolved in 30 mL water, dialysed for 1 d against water (SnakeSkin dialysis tubing, 3.5 kD cut off, Perbio Sciences Deutschland GmbH, Bonn, D) and lyophilized. The yield of isolated product was 81%.

Example 6.1(g)

Synthesis of AminoHES30/0.7

5 g of oxo-HES 30/0.7 (MW=31,000 D, DS=0.76, Supramol Parenteral Colloids GmbH, Rosbach-Rodheim, D, using molar ratios of the ingredient according to DE 196 28 705 A1) were heated over night at 80° C. in vacuo and were then dissolved under nitrogen in 28 mL dry dimethyl sulphoxide (Fluka, Sigma-Aldrich Chemie GmbH, Taufkirchen, D) and 1.67 mL of 1,4-diaminobutane were added. After stirring at 40° C. for 17 h the reaction mixture was added to 175 mL of an ice-cold 1:1 mixture of acetone and ethanol (v/v). The precipitated product was collected by centrifugation at 4° C. The crude product was dissolved in 40 mL water, dialysed for 2 d against water (SnakeSkin dialysis tubing, 3.5 kD cut off, Perbio Sciences Deutschland GmbH, Bonn, D) and lyophilized. The yield of isolated product was not determined.

Example 6.1(h)

Synthesis of AldehydoHES30/0.7

122 mg 4-formylbenzoic acid and 144 mg 1-hydroxy-1H-benzotriazole (both Aldrich, Sigma-Aldrich Chemie GmbH, Taufkirchen, D) were dissolved in 34 mL N,N-dimethylformamide (Peptide synthesis grade, Biosolve, Valkenswaard, NL) and 103 μL N,N'-diisopropylcarbodiimide (Fluka, Sigma-Aldrich Chemie GmbH, Taufkirchen, D) were added. After incubation at 21° C. for 30 min, 2.46 g of aminoHES30/0.7 (synthesised as described in example 6.1(g)) were added. After shaking for 22.5 h at 22° C., the reaction mixture was added to 160 mL of an ice-cold 1:1 mixture of acetone and ethanol (v/v). The precipitated product was collected by centrifugation at 4° C. and washed with an ice-cold 1:1 mixture of acetone and ethanol (v/v). After centrifugation, the precipitate was dissolved in 30 mL water, dialysed for 1 d against water (SnakeSkin dialysis tubing, 3.5 kD cut off, Perbio Sciences Deutschland GmbH, Bonn, D) and lyophilized. The yield of isolated product was 87%.

Example 6.1(i)

Synthesis of AminoHES50/0.7

6.09 g of oxo-HES 50/0.7 (MW=57,000 D, DS=0.76, Supramol Parenteral Colloids GmbH, Rosbach-Rodheim, D, using molar rations of the ingredients according to DE 196 28 705 A1) were heated over night at 80° C. in vacuo and were then dissolved under nitrogen in 32 mL dry dimethyl sulphoxide (Fluka, Sigma-Aldrich Chemie GmbH, Taufkirchen, D) and 1.22 mL of 1,4-diaminobutane were added. After stirring at 40° C. for 17 h the reaction mixture was added to 150 mL of an ice-cold 1:1 mixture of acetone and ethanol (v/v). The precipitated product was collected by centrifugation at 4° C., washed with 40 mL of an ice-cold 1:1 mixture of acetone and ethanol (v/v) and collected by centrifugation. The crude product was dissolved in 80 mL water, dialysed for 4 d against water (SnakeSkin dialysis tubing, 3.5 kD cut off, Perbio Sciences Deutschland GmbH, Bonn, D) and lyophilized. The yield of isolated product was 82%.

Example 6.1(j)

Synthesis of AldehydoHES50/0.7

125 mg 4-formylbenzoic acid and 174 mg 1-hydroxy-1H-benzotriazole (both Aldrich, Sigma-Aldrich Chemie GmbH, Taufkirchen, D) were dissolved in 38 mL N,N-dimethylformamide (Peptide synthesis grade, Biosolve, Valkenswaard, NL) and 155 μL N,N'-diisopropylcarbodiimide (Fluka, Sigma-Aldrich Chemie GmbH, Taufkirchen, D) were added. After incubation at 21° C. for 30 min, 3.8 g of aminoHES50/0.7 (synthesised as described in example 6.1(i)) were added. After shaking for 19 h at 22° C., the reaction mixture was added to 160 mL of an ice-cold 1:1 mixture of acetone and ethanol (v/v). The precipitated product was collected by centrifugation at 4° C., re-dissolved in 20 mL N,N-dimethylformamide and precipitated with 80 mL of an ice-cold 1:1 mixture of acetone and ethanol (v/v) as described above. After centrifugation, the precipitate was dissolved in 50 mL water, dialysed for 2 d against water (SnakeSkin dialysis tubing, 3.5 kD cut off, Perbio Sciences Deutschland GmbH, Bonn, D) and lyophilized. The yield of isolated product was 77%.

Example 6.2

Synthesis of the HES-G-CSF Conjugates by Reductive Amination

Example 6.2(a)

Buffer Exchange A 33 mL of a 0.454 mg/mL solution of hG-CSF (purified hG-CSF having essentially the same characteristics as the commercial product Neupogen in 10 mM sodium acetate, 50 mg/mL sorbitol and 0.004% Tween 80 at pH 4.0 were concentrated by diafiltration at 0° C. to 4 mL with a Vivaspin 15R concentrator (VS15RH11, 5 KD MWCO, Vivascience AG, Hannover, D) and re-diluted to 15 mL with a 0.1 M sodium acetate buffer at pH 5.0. This diafiltration was repeated twice. The final concentration in the last diafiltration step was 3 mg/mL.

Example 6.2(b)

Reaction of hG-CSF with aldehydoHES Derivatives of Examples 6.1(b), 6.1(d) and 6.1(j)

To 1.67 mL of a solution of hG-CSF after buffer exchange into 0.1 M sodium acetate buffer, pH 5.0 (as described in example 6.2(a) above) 1.67 mL of a solution of the HES-derivative and 1.67 mL of a 60 mM solution of sodium cyanoborohydride, both in the same buffer, were added and the solution was incubated for 15.5 h at 4° C. All solutions were cooled to 0° C. before mixing.

The following final HES concentrations were employed:

39.4 mg/mL for the HES derivatives prepared according to example 6.1(b) and 6.1(d).

197 mg/mL for the HES derivative prepared according to example 6.1(j).

197 mg/mL HES50/0.7 (MW=47,000 D, DS=0.76, Supramol Parenteral Colloids GmbH, Rosbach-Rodheim, D) as reaction control.

The reaction mixtures were analysed by gel electrophoresis (see FIG. 19).

Example 6.2(c)

Buffer Exchange B 20 mL of a 0.454 mg/mL solution of hG-CSF (Purified hG-CSF having essentially the same characteristics as the commercial product Neupogen®) in 10 mM sodium acetate, 50 mg/mL sorbitol and 0.004% Tween 80 at pH 4.0 was concentrated by diafiltration at 15° C. to 4 mL with a Vivaspin 15R concentrator (VS15RH11, 5 KD MWCO, Vivascience AG, Hannover, D) and re-diluted to 15 mL with a 0.1 M sodium acetate buffer at pH 5.0. This diafiltration was repeated twice. The final concentration in the last diafiltration step was 1.5 mg/mL.

Example 6.2(d)

Reaction of hG-CSF with AldehydoHES Derivatives of Examples 6.1(f) and 6.1(h)

To 3.3 mL of a solution of hG-CSF after buffer exchange into 0.1 M sodium acetate buffer, pH 5.0 (as described in example 6.2(c) above) 3.3 mL of a solution of 789 mg of the HES-derivative and 3.3 mL of a 60 mM solution of sodium cyanoborohydride, both in the same buffer, were added and the solution was incubated for 30 h at 4° C. All solutions were cooled to 0° C. before mixing.

After 17 h samples were removed for reaction control. The reaction mixtures were analysed by gel electrophoresis (see FIG. 20).

Example 6.3

In Vitro Assay

Mitogenicity of G-CSF Variants for Mouse NFS-60 Cells

G-CSF is known for its specific effects on the proliferation, differentiation and activation of hematopoietic cells of the neutrophilic granulocyte lineage. The mitogenic capacity of G-CSF variants was tested using mouse NFS-60 cells (N. Shirafuji et al., Exp. Hematol. 1989, 17, 116-119). Cells grown in RPMI medium with 10% fetal calf serum (Gibco INVITROGEN GmbH, Karlsruhe, D) containing 5-10% WEHI-3B (DSMZ, Braunschweig, D; cultivated as described by the DSMZ) conditioned medium as source of exogenous IL-3 were harvested by centrifugation, washed and aliquoted at 100,000 cells per well in a 24-well plate. Cells were allowed to adapt for 1 hour at 37° C. in RPMI medium without WEHI-3B conditioned media before G-CSF growth factor samples diluted in the same media were added. NFS-60 cells were exposed to purified G-CSF variants (purification according to examples 3A 1 und 2, protein quantification according to example 3B1):
Neupogen®, Neulasta® both from Amgen,
"HES-GCFS10/0.4 conjugate" prepared in example 6.2(b),
"HES-GCFS10/0.7 conjugate" prepared in example 6.2(b),
"HES-GCFS30/0.4 conjugate" prepared in example 6.2(d),
"HES-GCFS30/0.7 conjugate" prepared in example 6.2(d),
"HES-GCFS50/0.7 conjugate" prepared in example 6.2(b),
"Mock incubation" (=reaction control, 197 mg/ml HES50/ 0.7, MW 47,000 D, DS 0.76, Supramol Parenteral Colloids GmbH, Rosbach Rodheim, Germany), for 3 days at 37° C. and then the cells were electronically counted (Casy TT Cell Counter, Schärfe System, Reutlingen, D).

The results are summarised in Table VI below and in FIG. 21. In all cases, the amounts of protein given in the table below and FIG. 21 represent the G-CSF content of the conjugates only. As can be seen in FIG. 21, all of the different G-CSF variants (2.5-250 pg/ml) were able to stimulate an increase in the number of cells after 3 days compared to a medium that did not contain added growth factors. All variants reached the same maximum stimulation level at a concentration of 250 pg/ml.

Example 6.4

In Vivo Biological Effects of hG-CSF Conjugates in Rats

Upon arrival, the rats [male CRL:CD® rats (7 weeks old), Charles River Deutschland GmbH, Sanghofer Weg 7, D-97633 Sulzfeld)] were randomly sorted into groups of 5. After 7 days acclimatization, rats in poor condition were excluded and replaced by spare animals. The weight of the rats upon arrival was 181-203 g. Each group of five randomly selected rats was then intravenously administered 100 µg protein per kg body weight (injection speed 15 sec/dosis, vehicle: 5 ml PBS/kg bodyweight) of the following non-conjugated or conjugated G-CSF samples (purification according to examples 3A1 and 2, protein quantification according to example 3B1):
Neupogen® and Neulasta®, both from Amgen,
"HES-GCSF10/0.4 conjugate" (10/0.4) prepared in example 6.2(b),
"HES-GCSF10/0.7 conjugate" (10/0.7) prepared in example 6.2(b),
"HES-GCSF30/0.4 conjugate" (30/0.4) prepared in example 6.2(d),
"HES-GCSF30/0.7 conjugate" (30/0.7) prepared in example 6.2(d),
"HES-GCSF50/0.7 conjugate" (50/0.7) prepared in example 6.2(b),
"Mock incubation" (=reaction control, 197 mg/ml HES50/ 0.7, MW 47,000 D, DS 0.76, Supramol Parenteral Colloids GmbH, Rosbach Rodheim, Germany) and a vehicle control (PBS, application volume 5 ml/kg b.w.).

Blood samples from all animals of approx. 200 µl EDTA whole blood were taken from the retrobulbar venous plexus under light ether anaesthesia. On test day −5 blood was taken once in the morning from all animals after overnight fasting. On test days 1 to 8 blood was taken twice daily at an interval of 12 hours. The first blood sample on day 1 was taken prior to G-CSF/G-CSF-HES-conjugate administration.

White blood cell (WBC) counts were carried out using a Bayer ADVIA™ 120 (Femwald, Germany). The results are shown in FIG. 22.

TABLE VI

Proliferation of mouse NFS-60 cells, induced by G-CSF variants

| Conc. [pg/ml] | 0 | 2.5 | 2.8 | 5 | 5.7 | 10 | 11.3 | 25 | 28.4 | 50 | 56.7 | 250 | 283.5 |
|---|---|---|---|---|---|---|---|---|---|---|---|---|---|
| Neupogen | 0.44 | 0.86 | | 1.20 | | 1.69 | | 2.33 | | 2.49 | | 2.41 | |
| HES-GCSF 10/0.7 | 0.44 | 0.72 | | 0.93 | | 1.44 | | 2.14 | | 2.41 | | 2.41 | |
| HES-GCSF 10/0.4 | 0.44 | 0.72 | | 0.97 | | 1.40 | | 2.17 | | 2.67 | | 2.75 | |
| HES-GCSF 50/0.7 | 0.44 | 0.62 | | 0.70 | | 0.97 | | 1.68 | | 2.15 | | 2.32 | |
| Mock-incubation | 0.44 | 0.85 | | 1.31 | | 1.91 | | 2.38 | | 2.47 | | 2.41 | |
| HES-GCSF 30/0.4 | 0.44 | 0.82 | | 1.21 | | 1.62 | | 2.28 | | 2.50 | | 2.60 | |
| HES-GCSF 30/0.7 | 0.44 | 0.80 | | 1.09 | | 1.66 | | 2.20 | | 2.35 | | 2.44 | |
| Neulasta | 0.44 | 0.63 | | 0.80 | | 1.12 | | 1.83 | | 2.25 | | 2.33 | |

Example 6.5

Measurement of In Vivo Half-Life of the Conjugate Prepared from HES50/0.7 and G-CSF Via Reductive Amination (Example 6.2(b)) Compared to Neupogen® and Neulasta® (Amgen)

Female mice BALB/cOlaHsd (Harlan GmbH/Borchen) were used. On the day of administration, the is weights of the animals were measured (19-22 g). 100 μg per kg body weight of the chemically modified rh-G-CSF sample as prepared in Example 6.2(b) as well as Neupogen® and Neulasta® (Amgen) samples were each injected intravenously in the tail vein of nine mice. At 1, 3, 6, 11, 22, 30, 49, 72 hours after injection (see table below), samples of approx. 150 μl whole blood were taken from the tail vein or the retrobulbar venous plexus from 3 mice of the respective group using capillaries containing sodium-heparin (Hirschmann, Eberstadt) and stored on ice until preparation of plasma.

TABLE VII

Conduct of the sampling procedure

| Sample | Mouse no. | 1 h | 3 h | 6 h | 11 h | 22 h | 30 h | 49 h | 72 h |
|---|---|---|---|---|---|---|---|---|---|
| Neulasta | 1 | | | | | | | | |
| | 2 | x | | | | x | | x | |
| | 3 | | | | | | | | |
| | 4 | | | | | | | | |
| | 5 | | x | | | | x | | x |
| | 6 | | | | | | | | |
| | 7 | | | | | | | | |
| | 8 | | | x | x | | | | |
| | 9 | | | | | | | | |
| Neupogen | 10 | | | | | | | | |
| | 11 | x | | | | x | | x | |
| | 12 | | | | | | | | |
| | 13 | | | | | | | | |
| | 14 | | x | | | | x | | |
| | 15 | | | | | | | | |
| | 16 | | | | | | | | |
| | 17 | | | x | x | | | | |
| | 18 | | | | | | | | |
| HES-G-CSF | 19 | | | | | | | | |
| | 20 | x | | | | x | | x | |
| | 30 | | | | | | | | |
| | 22 | | | | | | | | |
| | 23 | | x | | | | x | | x |
| | 24 | | | | | | | | |
| | 25 | | | | | | | | |
| | 26 | | | x | x | | | | |
| | 27 | | | | | | | | |

Whole blood was centrifuged for 10 minutes at 2000 g. Plasma was transferred to another tube and recentrifuged for 5 min at 3500 g. Aliquots were stored at −80° C. until the day of analysis. The amount of G-CSF in the plasma samples were quantified by utilizing a ELISA (R&D GambH, Wiesbaden) method, following the instruction of the manufacturer.

The results are shown in FIG. 36 wherefrom it becomes evident that compared to Neupogen, the HES-G-CSF conjugate according to the invention has a highly increased half-life (5.1 compared to 1.2 h), and compared to Neulasta, it has a half-life which is almost the same (5.1 compared to 5.2 h).

Example 7

Conjugation of a HES to Recombinant hEPO by Reductive Amination

Recombinant human EPO was used, having the amino acid sequence of human EPO and essentially the same characteristics as the commercially available Erypo® (Orhto Biotech, Jansen-Cilag) or NeoRecormon® (Roche), cf. EP 0 148 605, EP 0 205 564, EP 0 411 678.

Example 7.1

Synthesis of Amino-HES 10 g of oxidized HES (MW=57,000 D, DS=0.76, Supramol Parenteral Colloids GmbH, Rosbach-Rodheim, D, prepared according to DE 196 28 705 A1) were heated over night at 80° C. in vacuo, dissolved under nitrogen in 53 ml dry dimethyl sulphoxide (Fluka, Sigma-Aldrich Chemie GmbH, Taufkirchen, D) and 2 ml of 1,4-diaminobutane (Fluka, Sigma-Aldrich Chemie GmbH, Taufkirchen, D) were added. After stirring at 40° C. for 17 h the reaction mixture was added to 350 ml of ice-cold 2-propanol (Carl Roth GmbH+Co. KG, Karlsruhe, D). The precipitated product was collected by centrifugation at 4° C., washed with 80 ml of ice-cold 2-propanol and collected by centrifugation. The crude product was dissolved in 80 ml water, dialysed for 2 d against water (SnakeSkin dialysis tubing, 3.5 kD cut off, Perbio Sciences Deutschland GmbH, Bonn, D) and lyophilized. The yield of isolated product was 85%.

Example 7.2

Synthesis of Aldehydo-HES 153 mg 4-formylbenzoic acid and 241 mg 1-hydroxy-1H-benzotriazole (both Aldrich, Sigma-Aldrich Chemie GmbH, Taufkirchen, D) were dissolved in 51 ml N,N-dimethylformamide (Peptide synthesis grade, Biosolve, Valkenswaard, NL) and 170 μL N,N'-diisopropylcarbodiimide (Fluka, Sigma-Aldrich Chemie GmbH, Taufkirchen, D) were added. After incubation at 21° C. for 30 min, 5.1 g of amino-HES, prepared according to example 7.1, were added. After shaking for 16 h at 22° C., the reaction mixture was added to 360 ml of an ice-cold 1:1 mixture of acetone and ethanol (v/v). The precipitated product was collected by centrifugation at 4° C., re-dissolved in 50 ml water and precipitated with 360 ml of an ice-cold 1:1 mixture of acetone and ethanol (v/v) as described above. After centrifugation, the precipitate was dissolved in 50 ml water, dialysed for 2 d against water (SnakeSkin dialysis tubing, 3.5 kD cut off, Perbio Sciences Deutschland GmbH, Bonn, D) and lyophilized. The yield of isolated product was 87%.

Example 7.3

Conjugation of Aldehydo-HES to EPO by Reductive Amination 625 mg aldehydo-HES, prepared according to example 7.2, were dissolved to 1.67 ml in reaction buffer (0.1 M sodium acetate buffer pH 5.0) and cooled to 0° C. 1.67 ml of the EPO solution (3 mg/ml) and 1.67 ml of a 60 mM sodium cyanoborohydride solution, both in the same buffer and cooled to 0° C., were added and the mixture was incubated at 0° C. After 17 h, the reaction mixture was purified after analysis by gel electrophoresis (see FIG. 23, Lane B).

Example 7.4

Reaction Control A: Reaction of Aldehydo-HES with EPO without Sodium Cyanoborohydride 313 mg aldehydo-HES, prepared according to example 7.2, were dissolved to 0.83 ml in reaction buffer (0.1 M sodium acetate buffer pH 5.0) and cooled to 0° C. 0.83 ml of the EPO solution (3 mg/ml) in the same buffer and 0.83 ml of reaction buffer, both cooled to 0° C., were added and the mixture was incubated at 0° C. After 17 h, the reaction mixture was purified after analysis by gel electrophoresis (see FIG. 23, Lane C).

Example 7.5

Reaction Control B: Reaction of EPO with Sodium Cyanoborohydride 0.83 ml of the EPO solution (3 mg/ml) in reaction buffer (0.1 M sodium acetate buffer pH 5.0) were cooled to 0° C., 0.83 ml of a 60 mM sodium cyanoborohydride solution in the same buffer and 0.83 ml of reaction buffer, both cooled to 0° C., were added and the mixture was incubated at 0° C. After 17 h, the reaction mixture was purified after analysis by gel electrophoresis (see FIG. 23, Lane D).

Example 7.6

Ion Exchange Chromatography for the Purification of EPO and EPO Derivatives

The purification of EPO samples was performed at room temperature using an ÄKTA explorer 10 system (Amersham Pharmacia Biotech) consisting of a pump P-903, a Mixer M-925, with 0.6 ml chamber, a Monitor UV-900, with 10 mm flow cell, a Monitor pH/C-900, a fraction Collector Frac-900, a sample loop 2 ml along with the Unicorn software Version 3.2.1. The column containing 5 ml Q-Sepharose Fast Flow was equilibrated with 10 CV of buffer A (20 mM N-morpholino-propane sulfonic acid/NaOH buffer, pH 8.0). The EPO samples were diluted 1:10 with buffer A (and finally adjusted to pH 7.8-8.2 and were applied by using the sample pump at a flow rate of 1 ml/min. Following washing of the sample pump with 10 ml of buffer A, the column was further washed with 6 CV of buffer A at a flow rate of 1.0 ml/min. Subsequently a 4 volumes of 20 mM Na-Phosphat, pH 6.5; buffer B at a flow rate of 0.8 ml/min and EPO was eluted using a steep gradient from 0-40% buffer C (0.5M NaCl in 20 mM Na-Phosphat, pH 6.5) within 37 min. Elution profiles were recorded at 206, 260 and 280 nm absorbance. After completion of elution, the column was regenerated by 25 ml of buffer C at a flow rate of 1 ml/min. Finally the column was run with 1 M NaOH for 60 min and reconditioned with buffer C and stored until further use.

Example 7.7

EPO Protein Determination

Quantitative determination of EPO protein was performed by measuring UV absorption at 280 nm according to the Eur. Phar. (European Pharmacopeia 4, Monography 01/2002: 1316: erythropoietin concentrated solution) in a cuvette with 1 cm path length. In addition, EPO was quantitated by applying a RP-HPLC method using a RP-C4 column (Vydac Protein C4, Cat.#214TP5410, Grace Vydac, Ca, US); the HPLC method was calibrated using the erythropoietin BRP 1 reference standard (European Pharmacopeia, Conseil de l'Europe B.P. 907-F67029, Strasbourg Cedex 1).

Example 7.8

In-Vivo Assay of the Biological Activity of HES-Modified EPO

The EPO-bioassay in the normocythaemic mouse system was performed according to the procedures described in the European Pharmacopeia 4, Monography 01/2002:1316: Erythropoietin concentrated solution and Ph. Eur. Chapter 5.3: "Statistical Analysis of Results of Biological Assays and Tests"; For the HES-modified EPO according to example 7.3 a value for the specific activity of 418 500 units per mg EPO of protein was measured indicating an approximately 4-5 fold higher specific activity when compared to the EPO starting material.

The results of the study are summarized in Table VIII.

TABLE VIII

| Sample description | Calculated specific activity of EPO sample (based on A280 and RP-HPLC determination) |
|---|---|
| EPO starting material (not modified) | 89000 U/mg |
| EPO starting material (Reaction control A) | 88500 U/mg |
| EPO HES according to example 7.3 | 418500 U/mg |

Example 8

Synthesis of HES-IFN-Alpha Conjugates Via Reductive Amination

The IFN-α used was a recombinant human Interferon alpha-2b manufactured by recombinant DNA technology using *Escherichia coli* (*E. coli*). It is composed of 165 amino acids and presents an amino acid sequence which is identical to the natural human interferon alpha 2b (hIFN-alpha 2b).

Example 8.1

Synthesis of Oxo-HES

HES oxidised at its reducing end as described hereinunder (oxo-HES) was prepared from HES using an alkaline iodine solution as described in DE 196 28 705 A1 the respective contents of which (example A, column 9, lines 6 to 24) is incorporated herein by reference.

Example 8.2

Synthesis of HES Derivatives

In a two step procedure, oxo-HES of example 8.1 was modified at its reducing end with an amine, and an aldehydo group was introduced in a second reaction. The resulting aldhydo-HES was used to produce the IFN-alpha-HES conjugates via reductive amination as described in example 8.3.

Example 8.2.1

Synthesis of Amino-HES from Oxo-HES of Example 8.1

5.12 g of oxo-HES of example 8.1 (MW=14.5 kD, DS=0.41, Supramol Parenteral Colloids GmbH, Rosbach- Rodheim, D) were heated over night at 80° C. in vacuo and dissolved under nitrogen in 25 mL dry dimethyl sulphoxide (Fluka, Sigma-Aldrich Chemie GmbH, Taufkirchen, D) and 5.13 mL of 1,4-diaminobutane were added. After stirring at 40° C. for 17 h the reaction mixture was added to 150 mL of an ice-cold 1:1 mixture of acetone and ethanol (v/v). The precipitated product was collected by centrifugation at 4° C., washed with 40 mL of an ice-cold 1:1 mixture of acetone and ethanol (v/v) and collected by centrifugation. The crude product was dissolved in 80 mL water, dialysed for 4 d against water (SnakeSkin dialysis tubing, 3.5 kD cut off, Perbio Sciences Deutschland GmbH, Bonn, D) and lyophilized. The yield of isolated product was 67%.

Example 8.2.2

Synthesis of Aldehydo-HES from Amino-HES of Example 8.2.1

105 mg 4-formylbenzoic acid and 135 mg 1-hydroxy-1H-benzotriazole (both Aldrich, Sigma-Aldrich Chemie GmbH, Taufkirchen, D) were dissolved in 7 mL N,N-dimethylformamide (Peptide synthesis grade, Biosolve, Valkenswaard, NL) and 135 µL N,N'-diisopropylcarbodiimide (Fluka, Sigma-Aldrich Chemie GmbH, Taufkirchen, D) were added. After incubation at 21° C. for 30 min, 0.7 g of amino-HES (synthesised as described in example 8.2.1) were added. After shaking for 18 h at 22° C., the reaction mixture was added to 42 mL of an ice-cold 1:1 mixture of acetone and ethanol (v/v). The precipitated product was collected by centrifugation at 4° C., re-dissolved in 5 mL DMF and precipitated with 42 mL ethanol/acetone as described above. After centrifugation, the collected precipitate was dissolved with water, dialysed for 4 d against water (SnakeSkin dialysis tubing, 3.5 kD cut off, Perbio Sciences Deutschland GmbH, Bonn, D) and lyophilized. The yield of isolated product was 95%.

Example 8.2.3

Synthesis of Amino-HES from Oxo-HES of Example 8.1

6.02 g of oxo-HES of example 8.1 (MW=14.7 kD, DS=0.76, Supramol Parenteral Colloids GmbH, Rosbach-Rodheim, D) were heated over night at 80° C. in vacuo and dissolved under nitrogen in 32 mL dry dimethyl sulphoxide (Fluka, Sigma-Aldrich Chemie GmbH, Taufkirchen, D) and 6.03 mL of 1,4-diaminobutane were added. After stirring at 40° C. for 17 h the reaction mixture was added to 150 mL of an ice-cold 1:1 mixture of acetone and ethanol (v/v). The precipitated product was collected by centrifugation at 4° C., washed with 40 mL of an ice-cold 1:1 mixture of acetone and ethanol (v/v) and collected by centrifugation. The crude product was dissolved in 80 mL water, dialysed for 4 d against water (SnakeSkin dialysis tubing, 3.5 kD cut off, Perbio Sciences Deutschland GmbH, Bonn, D) and lyophilized. The yield of isolated product was 52%.

Example 8.2.4

Synthesis of Aldehydo-HES from Amino-HES of Example 8.2.3

150 mg 4-formylbenzoic acid and 230 mg 1-hydroxy-1H-benzotriazole (both Aldrich, Sigma-Aldrich Chemie GmbH, Taufkirchen, D) were dissolved in 10 mL N,N-dimethylformamide (Peptide synthesis grade, Biosolve, Valkenswaard, NL) and 204 µL N,N'-diisopropylcarbodiimide (Fluka, Sigma-Aldrich Chemie GmbH, Taufkirchen, D) were added. After incubation at 21° C. for 30 min, 1 g of amino-HES (synthesised as described in example 8.2.3) were added. After shaking for 19 h at 22° C., the reaction mixture was added to 84 mL of ice-cold 2-propanol. The precipitated product was collected by centrifugation at 4° C., re-dissolved in 50 mL water, dialysed for 2 d against water (SnakeSkin dialysis tubing, 3.5 kD cut off, Perbio Sciences Deutschland GmbH, Bonn, D) and lyophilized. The yield of isolated product was 83%.

Example 8.2.5

Synthesis of Amino-HES from Oxo-HES of Example 8.1

5 g of oxo-HES of example 8.1 (MW=28 kD, DS=0.41, Supramol Parenteral Colloids GmbH, Rosbach-Rodheim, D) were heated over night at 80° C. in vacuo and were then dissolved under nitrogen in 28 mL dry dimethyl sulphoxide (Fluka, Sigma-Aldrich Chemie GmbH, Taufkirchen, D) and 1.67 mL of 1,4-diaminobutane were added. After stirring at 40° C. for 17 h the reaction mixture was added to 175 mL of an ice-cold 1:1 mixture of acetone and ethanol (v/v). The precipitated product was collected by centrifugation at 4° C. The crude product was dissolved in 40 mL water, dialysed for 2 d against water (SnakeSkin dialysis tubing, 3.5 kD cut off, Perbio Sciences Deutschland GmbH, Bonn, D) and lyophilized. The yield of isolated product was not determined.

Example 8.2.6

Synthesis of Aldehydo-HES from Amino-HES of Example 8.2.5

130 mg 4-formylbenzoic acid and 153 mg 1-hydroxy-1H-benzotriazole (both Aldrich, Sigma-Aldrich Chemie GmbH, Taufkirchen, D) were dissolved in 36 mL N,N-dimethylformamide (Peptide synthesis grade, Biosolve, Valkenswaard, NL) and 110 µL N,N'-diisopropylcarbodiimide (Fluka, Sigma-Aldrich Chemie GmbH, Taufkirchen, D) were added. After incubation at 21° C. for 30 min, 2.61 g of amino-HES (synthesised as described in example 8.2.5) were added. After shaking for 22.5 h at 22° C., the reaction mixture was added to 160 mL of an ice-cold 1:1 mixture of acetone and ethanol (v/v). The precipitated product was collected by centrifugation at 4° C. and washed with an ice-cold 1:1 mixture of acetone and ethanol (v/v). After centrifugation, the precipitate was dissolved in 30 mL water, dialysed for 1 d against water (SnakeSkin dialysis tubing, 3.5 kD cut off, Perbio Sciences Deutschland GmbH, Bonn, D) and lyophilized. The yield of isolated product was 81%.

Example 8.2.7

Synthesis of Amino-HES from Oxo-HES of Example 8.1

5 g of oxo-HES of example 8.1 (MW=30.8 kD, DS=0.76, Supramol Parenteral Colloids GmbH, Rosbach-Rodheim, D) were heated over night at 80° C. in vacuo and were then dissolved under nitrogen in 28 mL dry dimethyl sulphoxide (Fluka, Sigma-Aldrich Chemie GmbH, Taufkirchen, D) and 1.67 mL of 1,4-diaminobutane were added. After stirring at 40° C. for 17 h the reaction mixture was added to 175 mL of an ice-cold 1:1 mixture of acetone and ethanol (v/v). The precipitated product was collected by centrifugation at 4° C. The crude product was dissolved in 40 mL water, dialysed for 2 d against water (SnakeSkin dialysis tubing, 3.5 kD cut off, Perbio Sciences Deutschland GmbH, Bonn, D) and lyophilized. The yield of isolated product was not determined.

Example 8.2.8

Synthesis of Aldehydo-HES from Amino-HES of Example 8.2.7

122 mg 4-formylbenzoic acid and 144 mg 1-hydroxy-1H-benzotriazole (both Aldrich, Sigma-Aldrich Chemie GmbH, Taufkirchen, D) were dissolved in 34 mL N,N-dimethylformamide (Peptide synthesis grade, Biosolve, Valkenswaard, NL) and 103 µL N,N'-diisopropylcarbodiimide (Fluka, Sigma-Aldrich Chemie GmbH, Taufkirchen, D) were added. After incubation at 21° C. for 30 min, 2.46 g of amino-HES (synthesised as described in example 8.2.7) were added. After shaking for 22.5 h at 22° C., the reaction mixture was added to 160 mL of an ice-cold 1:1 mixture of acetone and ethanol (v/v). The precipitated product was collected by centrifugation at 4° C. and washed with an ice-cold 1:1 mixture of acetone and ethanol (v/v). After centrifugation, the precipitate was dissolved in 30 mL water, dialysed for 4 d against water (SnakeSkin dialysis tubing, 3.5 kD cut off, Perbio Sciences Deutschland GmbH, Bonn, D) and lyophilized. The yield of isolated product was 87%.

Example 8.2.9

Synthesis of Amino-HES from Oxo-HES of Example 8.1

10 g of oxo-HES (MW=42.1 kD, DS=0.41, Supramol Parenteral Colloids GmbH, Rosbach-Rodheim, D) were heated for two days at 80° C. in vacuo and were then dissolved under nitrogen in 53 mL dry dimethyl sulphoxide (Fluka, Sigma-Aldrich Chemie GmbH, Taufkirchen, D) and 2.01 mL of 1,4-diaminobutane were added. After stirring at 40° C. for 17 h the reaction mixture was added to 350 mL of ice-cold 2-propanol (Carl Roth GmbH+Co. KG, Karlsruhe, D). The precipitated product was collected by centrifugation at 4° C., washed with 80 mL of ice-cold 2-propanol and collected by centrifugation. The crude product was dissolved in 80 mL water, dialysed for 2 d against water (SnakeSkin dialysis tubing, 3.5 kD cut off, Perbio Sciences Deutschland GmbH, Bonn, D) and lyophilized. The yield of isolated product was 76%.

Example 8.2.10

Synthesis of Aldehydo-HES from Amino-HES of Example 8.2.9

900 mg 4-formylbenzoic acid and 1053 mg 1-hydroxy-1H-benzotriazole (both Aldrich, Sigma-Aldrich Chemie GmbH, Taufkirchen, D) were dissolved in 30 mL N,N-dimethylformamide (Peptide synthesis grade, Biosolve, Valkenswaard, NL) and 930 µL N,N'-diisopropylcarbodiimide (Fluka, Sigma-Aldrich Chemie GmbH, Taufkirchen, D) were added. After incubation at 21° C. for 30 min, 3 g of amino-HES (synthesised as described in example 88.2.9 and dissolved in 20 mL N,N-dimethylformamide) were added. After shaking for 22.5 h at 22° C., the reaction mixture was added to 210 mL of an ice-cold 1:1 mixture of acetone and ethanol (v/v). The precipitated product was collected by centrifugation at 4° C. and washed with an ice-cold 1:1 mixture of acetone and ethanol (v/v). After centrifugation, the precipitate was dissolved in 30 mL water, dialysed for 2 d against water (SnakeSkin dialysis tubing, 3.5 kD cut off, Perbio Sciences Deutschland GmbH, Bonn, D) and lyophilized. The yield of isolated product was 97%.

Example 8.2.11

Synthesis of Amino-HES from Oxo-HES of Example 8.1(A)

6.09 g of oxo-HES (MW=56.8 kD, DS=0.76, Supramol Parenteral Colloids GmbH, Rosbach-Rodheim, D) were heated over night at 80° C. in vacuo and were then dissolved under nitrogen in 32 mL dry dimethyl sulphoxide (Fluka, Sigma-Aldrich Chemie GmbH, Taufkirchen, D) and 1.22 mL of 1,4-diaminobutane were added. After stirring at 40° C. for 17 h the reaction mixture was added to 150 mL of an ice-cold 1:1 mixture of acetone and ethanol (v/v). The precipitated product was collected by centrifugation at 4° C., washed with 40 mL of an ice-cold 1:1 mixture of acetone and ethanol (v/v) and collected by centrifugation. The crude product was dissolved in 80 mL water, dialysed for 4 d against water (SnakeSkin dialysis tubing, 3.5 kD cut off, Perbio Sciences Deutschland GmbH, Bonn, D) and lyophilized. The yield of isolated product was 82%.

Example 8.2.12

Synthesis of Aldehydo-HES from Amino-HES of Example 8.2.11

125 mg 4-formylbenzoic acid and 174 mg 1-hydroxy-1H-benzotriazole (both Aldrich, Sigma-Aldrich Chemie GmbH, Taufkirchen, D) were dissolved in 38 mL N,N-dimethylformamide (Peptide synthesis grade, Biosolve, Valkenswaard, NL) and 155 µL N,N'-diisopropylcarbodiimide (Fluka, Sigma-Aldrich Chemie GmbH, Taufkirchen, D) were added. After incubation at 21° C. for 30 min, 3.8 g of amino-HES (synthesised as described in example 8.2.11) were added. After shaking for 19 h at 22° C., the reaction mixture was added to 160 mL of an ice-cold 1:1 mixture of acetone and ethanol (v/v). The precipitated product was collected by centrifugation at 4° C., re-dissolved in 20 mL N,N-dimethylformamide and precipitated with 80 mL of an ice-cold 1:1 mixture of acetone and ethanol (v/v) as described above. After centrifugation, the precipitate was dissolved in 50 mL water, dialysed for 2 d against water (SnakeSkin dialysis tubing, 3.5 kD cut off, Perbio Sciences Deutschland GmbH, Bonn, D) and lyophilized. The yield of isolated product was 77%.

Example 8.2.13

Synthesis of Amino-HES from Oxo-HES of Example 8.1(B)

10 g of oxo-HES (MW=56.8 kD, DS=0.76, Supramol Parenteral Colloids GmbH, Rosbach-Rodheim, D) were heated over night at 80° C. in vacuo and were then dissolved under nitrogen in 53 mL dry dimethyl sulphoxide (Fluka, Sigma-Aldrich Chemie GmbH, Taufkirchen, D) and 2 mL of 1,4-diaminobutane were added. After stirring at 40° C. for 17 h the reaction mixture was added to 350 mL of ice-cold 2-propanol (Carl Roth GmbH+Co. KG, Karlsruhe, D). The precipitated product was collected by centrifugation at 4° C., washed with 80 mL of ice-cold 2-propanol and collected by centrifugation. The crude product was dissolved in 80 mL water, dialysed for 2 d against water (SnakeSkin dialysis tubing, 3.5 kD cut off, Perbio Sciences Deutschland GmbH, Bonn, D) and lyophilized. The yield of isolated product was 85%.

Example 8.2.14

Synthesis of Aldehydo-HES from Amino-HES of Example 8.2.13

153 mg 4-formylbenzoic acid and 241 mg 1-hydroxy-1H-benzotriazole (both Aldrich, Sigma-Aldrich Chemie GmbH, Taufkirchen, D) were dissolved in 51 mL N,N-dimethylformamide (Peptide synthesis grade, Biosolve, Valkenswaard, NL) and 170 μL N,N'-diisopropylcarbodiimide (Fluka, Sigma-Aldrich Chemie GmbH, Taufkirchen, D) were added. After incubation at 21° C. for 30 min, 5.1 g of amino-HES (synthesised as described in example 8.2.13) were added. After shaking for 16 h at 22° C., the reaction mixture was added to 360 mL of an ice-cold 1:1 mixture of acetone and ethanol (v/v). The precipitated product was collected by centrifugation at 4° C., re-dissolved in 50 mL water and precipitated with 360 mL of an ice-cold 1:1 mixture of acetone and ethanol (v/v) as described above. After centrifugation, the precipitate was dissolved in 50 mL water, dialysed for 2 d against water (SnakeSkin dialysis tubing, 3.5 kD cut off, Perbio Sciences Deutschland GmbH, Bonn, D) and lyophilized. The yield of isolated product was 87%.

Example 8.2.15

Synthesis of Amino-HES from Oxo-HES of Example 8.1

5.0 g of oxo-HES (MW=29.3 kD, DS=0.86, Supramol Parenteral Colloids GmbH, Rosbach-Rodheim, D) were heated over night at 80° C. in vacuo, dissolved under nitrogen in 20 ml dry dimethyl sulphoxide (Fluka, Sigma-Aldrich Chemie GmbH, Taufkirchen, D) and 1.67 ml of 1,4-diaminobutane (Fluka, Sigma-Aldrich Chemie GmbH, Taufkirchen, D) were added. After stirring at 40° C. for 30.5 h the reaction mixture was added to 175 ml of ice-cold 1:1 (v/v) mixture of acetone (Carl Roth GmbH+Co. KG, Karlsruhe, D) and ethanol (Sonnenberg, DAB, Braunschweig, D). The precipitated product was collected by centrifugation for 120 min at 4° C., dissolved in 40 ml water, dialysed for 2 d against water (SnakeSkin dialysis tubing, 10 kD cut off, Perbio Sciences Deutschland GmbH, Bonn, D) and lyophilized. The yield of isolated product was 87%.

Example 8.2.16

Synthesis of Aldehydo-HES from Amino-HES of Example 8.2.15

150 mg 4-formylbenzoic acid and 230 mg 1-hydroxy-1H-benzotriazole (both Aldrich, Sigma-Aldrich Chemie GmbH, Taufkirchen, D) were dissolved in 10 ml N,N-dimethylformamide (Peptide synthesis grade, Biosolve, Valkenswaard, NL) and 166 μL N,N'-diisopropylcarbodiimide (Fluka, Sigma-Aldrich Chemie GmbH, Taufkirchen, D) were added. After incubation at 21° C. for 30 min, a solution of 3.02 g AminoHES (synthesized as described in example 8.2.15) in 20 ml DMF were added. After shaking for 16 h at 22° C., the reaction mixture was added to 215 ml of an ice-cold 1:1 mixture (v/v) of acetone (Carl Roth GmbH+Co. KG, Karlsruhe, D) and ethanol (Sonnenberg, DAB, Braunschweig, D). The precipitated product was collected by centrifugation at 4° C., re-dissolved in 20 ml water and precipitated with acetone/ethanol as described above. After centrifugation, the precipitate was dissolved in 30 ml water, dialysed for 2.5 d against water (SnakeSkin dialysis tubing, 10 kD cut off, Perbio Sciences Deutschland GmbH, Bonn, D) and lyophilized. The yield of isolated product was 87%.

Example 8.2.17

Synthesis of Amino-HES from Oxo-HES of Example 8.1

5.0 g of oxo-HES (MW=97.9 kD, DS=0.76, Supramol Parenteral Colloids GmbH, Rosbach-Rodheim, D) were heated over night at 80° C. in vacuo, dissolved under nitrogen in 20 ml dry dimethyl sulphoxide (Fluka, Sigma-Aldrich Chemie GmbH, Taufkirchen, D) and 0.50 ml of 1,4-diaminobutane (Fluka, Sigma-Aldrich Chemie GmbH, Taufkirchen, D) were added. After stirring at 40° C. for 30.5 h the reaction mixture was added to 175 ml of ice-cold 1:1 (v/v) mixture of acetone (Carl Roth GmbH+Co. KG, Karlsruhe, D) and ethanol (Sonnenberg, DAB, Braunschweig, D). The precipitated product was collected by centrifugation for 120 min at 4° C., dissolved in 40 ml water, dialysed for 2 d against water (SnakeSkin dialysis tubing, 10 kD cut off, Perbio Sciences Deutschland GmbH, Bonn, D) and lyophilized. The yield of isolated product was 90%.

Example 8.2.18

Synthesis of Aldehydo-HES from Amino-HES of Example 8.2.17

73 mg 4-formylbenzoic acid and 112 mg 1-hydroxy-1H-benzotriazole (both Aldrich, Sigma-Aldrich Chemie GmbH, Taufkirchen, D) were dissolved in 10 ml N,N-dimethylformamide (Peptide synthesis grade, Biosolve, Valkenswaard, NL) and 81.3 μL N,N'-diisopropylcarbodiimide (Fluka, Sigma-Aldrich Chemie GmbH, Taufkirchen, D) were added. After incubation at 21° C. for 30 min, a solution of 3.09 g AminoHES (prepared as described in example 8.2.17) in 20 ml DMF were added. After shaking for 16 h at 22° C., the reaction mixture was added to 215 ml of an ice-cold 1:1 mixture (v/v) of acetone (Carl Roth GmbH+Co. KG, Karlsruhe, D) and ethanol (Sonnenberg, DAB, Braunschweig, D). The precipitated product was collected by centrifugation at 4° C., re-dissolved in 20 ml water and precipitated with acetone/ethanol as described above. After centrifugation, the precipitate was dissolved in 30 ml water, dialysed for 2.5 d against water (SnakeSkin dialysis tubing, 10 kD cut off, Perbio Sciences Deutschland GmbH, Bonn, D) and lyophilized. The yield of isolated product was 96%.

Example 8.3

Synthesis IFN-Alpha Conjugates Via Reductive Amination

Example 8.3.1

Conjugation to IFN-Alpha at a 20 μg Scale

To 0.675 mg IFN-alpha, dissolved in 0.375 ml of 25 mM sodium phosphate buffer pH 7.5, containing 150 mM NaCl and 0.3 mM EDTA, were added 4 ml of the reaction buffer (0.1 M sodium acetate buffer pH 5.0) and the solution was centrifuged for 30 min at 3939×g in a Vivaspin 6 concentrator (Viva Science, 5 kD MWCO, Hannover, Germany). The washing procedure was repeated twice by dilution of the residual solution with the reaction buffer to 6 ml and centrifugation as described. The volume of the final IFN-alpha solution was 0.236 ml, corresponding to a calculated final concentration of 2.86 mg/ml IFN-alpha. The protein concentration was not checked experimentally. To 7 μl of the IFN-alpha solution prepared as described above and cooled to 0° C., 10 μl (50 equiv.) of the respective aldehydo-HES (see Table IX below) solution and 11.3 μl of a 60 mM sodium cyanoborohydride solution, both in the same buffer (sodium acetate, pH 5.0) and cooled to 0° C., were added and the mixture was incubated for 17 h at 0° C. The reaction mixture was analysed by gel electrophoresis. The following concentrations of the aldehydo-HES solutions were employed:

TABLE IX

| Entry | HES-Derivative | Concentration [mg/ml] |
|---|---|---|
| A | aldehydo-HES (example 8.2.2) | 52 |
| B | aldehydo-HES (example 8.2.4) | 52 |
| C | aldehydo-HES (example 8.2.6) | 156 |
| D | aldehydo-HES (example 8.2.8) | 156 |
| E | aldehydo-HES (example 8.2.10) | 260 |
| F | aldehydo-HES (A) (example 8.2.12) | 260 |
| G | Without HES derivative but with NaCNBH$_3$ | — |
| I | Without HES derivative and without NaCNBH$_3$ | — |
| J | non-oxidized HES10/0.4 (Mw 7.6 kD; DS = 0.41) with NaCNBH$_3$ | 52 |
| K | non-oxidized HES10/0.4 (Mw 7.6 kD; DS = 0.41), without NaCNBH$_3$ | 52 |

SDS-Page analysis of the conjugates is shown in FIG. 24.

Example 8.2.2

Conjugation to IFN-Alpha at a 3 mg Scale

To 20 mg IFN-alpha, dissolved in 25 mM sodium phosphate buffer pH 7.5, containing 150 mM NaCl and 0.3 mM EDTA, were added 8 ml of the reaction buffer (0.1 M sodium acetate buffer pH 5.0) and the solution was centrifuged for 99 min at 3939×g in a Vivaspin 15R concentrator (Viva Science, 5 kD MWCO, Hannover, Germany). The washing procedure was repeated twice by dilution of the residual solution with the reaction buffer to 18 ml and centrifugation as described. The final IFN-alpha solution was diluted with reaction buffer to 6.66 ml giving a final calculated concentration of 3 mg/ml IFN-alpha. The protein concentration was not checked experimentally.

To 1 ml of the IFN-alpha solution prepared as described above and cooled to 0° C., 1 ml of the aldehydoHES solution (75 equiv.) and 1 ml of a 60 mM sodium cyanoborohydride solution, both in the same buffer (sodium acetate, pH 5.0) and cooled to 0° C., were added and the mixture was incubated for 22 h at 0° C. The reaction mixture was purified after analysis by gel electrophoresis. For the reaction described in entry G, only 0.666 μl of the corresponding solutions were used. The following concentrations of the aldehydoHES solutions were employed:

TABLE X

| Entry | HES-Derivative | Concentration [mg/ml] |
|---|---|---|
| A | aldehydo-HES (example 8.2.2) | 117 |
| B | aldehydo-HES (example 8.2.4) | 117 |
| C | aldehydo-HES (example 8.2.6) | 350 |
| D | aldehydo-HES (example 8.2.8) | 350 |
| E | aldehydo-HES (example 8.2.10) | 584 |
| F | aldehydo-HES (A) (example 8.2.12) | 584 |
| G | non-oxidized HES10/0.4 (Mw 7.6 kD; DS 0.41) | 117 |

SDS-Page analysis of the conjugates is shown in FIG. 25.

Example 8.3.3

Conjugation to IFN-Alpha at a 3 mg Scale 8.3.3.1 Conjugation of AldehydoHES as Prepared in Example 8.2.16 to IFNα by Reductive Amination To 10 mg IFNα, dissolved in 25 mM sodium phosphate buffer pH 7.5, containing 150 mM NaCl and 0.3 mM EDTA, were added 8 ml of the reaction buffer (0.1 M sodium acetate buffer pH 5.0) and the solution was centrifuged for 30 min at 3939×g in a Vivaspin 15R concentrator (Viva Science, 5 kD MWCO, Hannover, Germany). The washing procedure was repeated twice by dilution of the residual solution with the reaction buffer to 18 ml and centrifugation as described. The final IFNα solution was diluted with reaction buffer to 3.33 ml giving a final calculated concentration of 3 mg/ml IFNα. The protein concentration was not checked experimentally.

To 1 ml of the IFNα solution prepared as described above and cooled to 0° C., 1 ml of the aldehydoHES solution as prepared in example 8.2.16 (75 equiv., 352 mg/ml) and 1 ml of a 60 mM sodium cyanoborohydride solution, both in the same buffer and cooled to 0° C., were added and the mixture was incubated for 22 h at 0° C. The reaction mixture was purified after analysis by gel electrophoresis. For gel electrophoresis an XCell Sure Lock Mini Cell (Invitrogen GmbH, Karlsruhe, D) and a Consort E143 power supply (CONSORTnv, Turnhout, B) were employed. A 12% Bis-Tris gel together with a MOPS SDS running buffer at reducing conditions (both Invitrogen GmbH, Karlsruhe, D) were used according to the manufactures instruction.

8.3.3.2 Conjugation of AldehydoHES as Prepared in Example 8.2.18 to IFNα by Reductive Amination To 1 ml of the IFNα solution prepared as described in 8.3.3.1 and cooled to 0° C., 2 ml of the aldehydoHES solution as prepared in example 8.2.18 (75 equiv., 369 mg/ml) and 1.5 ml of a 60 mM sodium cyanoborohydride solution, both in the same buffer and cooled to 0° C., were added and the mixture was incubated for 22 h at 0° C. The reaction mixture was purified after analysis by gel electrophoresis. For gel electrophoresis a XCell Sure Lock Mini Cell (Invitrogen GmbH, Karlsruhe, D) and a Consort E143 power supply (CONSORTnv, Turnhout, B) were employed. A 12% Bis-Tris gel together with a MOPS SDS running buffer at reducing conditions (both Invitrogen GmbH, Karlsruhe, D) were used according to the manufactures instruction.

8.3.3.3 Reaction Control: Conjugation of HES10/0.4 (Mw 7.6 kD DS=0.41) to IFNα by Reductive Amination To 1 ml of the IFNα solution prepared as described in 8.3.3.1 and cooled to 0° C., 1 ml of the HES10/0.4 solution (75 equiv., 117 mg/ml) and 1 ml of a 60 mM sodium cyanoborohydride solution, both in the same buffer and cooled to 0° C., were added and the mixture was incubated for 22 h at 0° C. The reaction mixture was purified after analysis by gel electrophoresis. For gel electrophoresis an XCell Sure Lock Mini Cell (Invitrogen GmbH, Karlsruhe, D) and a Consort E143 power supply (CONSORTnv, Turnhout, B) were employed. A 12% Bis-Tris gel together with a MOPS SDS running buffer at reducing conditions (both Invitrogen GmbH, Karlsruhe, D) were used according to the manufactures instruction.

SDS-Page analysis of the conjugates is shown in FIG. 26.

Example 8.3.4

Conjugation to IFN-Alpha at a 16 mg Scale

The buffer of 20 mg IFN-alpha solution was exchanged as described in example 8.3.2. The final IFN-alpha solution was diluted with reaction buffer to 6.37 ml giving a final calculated concentration of 3.14 mg/ml IFN-alpha. 100 μl of this solution were diluted with 900 μl reaction buffer and the protein concentration was determined spectrophotometrically at 279 nm to 3.01 mg/ml, based on the molar extinction coefficient of 18000. After combination with the material used for protein concentration determination the final volume was 7.0 ml with a protein concentration of 2.74 mg/ml. To 5.91 ml of this IFN-alpha solution (16.2 mg) prepared as described above and cooled to 0° C., a solution of 3.152 g of aldehydo-HES of example 8.2.14 (75 equiv.) in 5 ml reaction buffer and 6 ml of a 60 mM sodium cyanoborohydride solution, both in the same buffer (sodium acetate, pH 5.0) and cooled to 0° C., were added and the mixture was incubated for 22 h at 0° C. (see FIG. 27, Line A).

As a reaction control, 1.09 ml of the pre-cooled IFN-alpha solution (3 mg) were mixed with 1 ml of a solution of 122 mg non-oxidized HES10/0.4 (Mw 7.6 kD DS=0.41) in the reaction buffer and 1 ml of a 60 mM sodium cyanoborohydride solution, both in the same buffer and cooled to 0° C. (see FIG. 27, line B).

SDS-Page analysis of the conjugate is shown in FIG. 27.

Example 8.4

Purification of the IFN-Alpha-HES Conjugates 8.4.1 Purification of HES-IFN-α from Incubations of the Reductively Aminated Protein with Activated HES Derivatives (Separation of the Modified and Unmodified Protein from HES-Derivatives)

The purification of all samples was performed at room temperature using an ÄKTA explorer 10 equipment. The column containing 3 ml Q-Sepharose Fast Flow was equilibrated with 10 CV of buffer A (20 mM Tris/HCl, pH 8.0). The samples were diluted 1:10 with buffer A and were applied by using the sample pump at a flow rate of 1 ml/min. Following washing of the sample pump with 10 ml of buffer A, the column was further washed with 6 CV of buffer A at a flow rate of 1.0 ml/min. Elution was performed by using a linear gradient from 0-100% of buffer B (0.3 M NaCl in 20 mM Tris/HCl, pH 8.0) over 2 CV and an isocratic run with 0.5 CV of buffer B at a flow rate of 0.8 ml/min. The column was regenerated by using 2 CV of buffer C (1.5 M NaCl in 20 mM Tris/HCl, pH 8.0) followed by 0.5 CV of buffer B at a flow rate of 0.8 ml/min. Reequilibration for the next run was performed by using 6 CV of buffer A and a flow rate of 1.0 ml/min.

8.4.2 Materials and Methods

| Equipment: | ÄKTA explorer 10 (Amersham Pharmacia Biotech), with: Pump P-903 Mixer M-925, with 0.6 ml chamber Monitor UV-900, with 10 mm flow cell Monitor pH/C-900 Pump P-950 (sample pump) Software Unicorn Version 3.21 |
|---|---|
| Column: | Amersham Biosciences C 10/10 |
| Column material: | Q-Sepharose Fast Flow, Code no. 17-0510-01, Lot no. OD 06453 |
| Column volume: | 3 ml |
| Buffer A: | 20 mM Tris/HCl, pH 8.0, Lot-Nr. PL0746 |
| Buffer B: | 0.3 M NaCl in 20 mM Tris/HCl, pH 8.0, Lot-Nr. PL0747 |
| Buffer C: | 1.5 M NaCl in 20 mM Tris/HCl, pH 8.0, Lot-Nr. PL0748 |

| Method | | | |
|---|---|---|---|
| Volume | Step | Buffer | Flow rate |
| 1 CV | Equilibration | 100% buffer A | 1.0 ml/min |
| 5-28 ml | Load sample | sample 1:10 in buffer A | 1.0 ml/min |
| 10 ml | Wash sample pump | 100% buffer A | 1.0 ml/min |
| 5 CV | Wash out unbound sample | 100% buffer A | 1.0 ml/min |
|  | Start Fractionation | 100% buffer A | 1.0 ml/min |
| 6 CV | Elution, linear gradient | 0-100% buffer B | 0.8 ml/min |
| 2 CV | Elution, isocratic | 100% buffer B | 0.8 ml/min |
| 2 CV | Regeneration | 100% buffer C | 0.8 ml/min |
| 0.5 CV | Regeneration | 100% buffer B | 0.8 ml/min |
|  | Stop Fractionation | 100% buffer B | 0.8 ml/min |
| 5 CV | Reequilibration | 100% buffer A | 1.0 ml/min |

| Detection: | 280 nm, 260 nm, 220 nm pH Conductivity |
|---|---|
| Fractionation: | 1 ml fractions |

8.4.3 Results 8.4.3.1 Sample According to Example 8
sample composition: 1 mg EP2001 (rhIFN-a2b) in 25 mM Na-phosphate, 0.13 M NaCl and 0.3 mM EDTA, pH 7.5±0.2
starting volume: 0.5 ml, diluted 1:10 in buffer A=5 ml
flow-through/wash 9.3 ml
run date: 2004 Sep. 29
run no.: QS24 D39 (see Table for example 8.4.4.1)

8.4.3.2 Sample According to Example 8.3.2 (Entry A)
sample composition: 2.5 mg EP2001+97.5 mg AldehydoHES10/0.4 (NZA256) in 0.1 M Na-acetate, 20 mM Na-cyanoborohydride, pH 5.0
starting volume: 2.5 ml, diluted 1:10 in buffer A=25 ml
flow-through/wash: 44 ml
run date: 2004 Sep. 29
run no.: QS25 D56 (see Table for example 8.4.4.1)

8.4.3.3 Sample According to Example 8.3.2 (Entry B)
sample composition: 2.5 mg EP2001+97.5 mg AldehydoHES10/0.7 (NZA235A) in 0.1 M Na-acetate, 20 mM Na-cyanoborohydride, pH 5.0 starting volume: 2.5 ml, diluted 1:10 in buffer A=25 ml
flow-through/wash: 41 ml
run date: 2004 Sep. 30
run no.: QS26 D57 (see Table for example 8.4.4.1

8.4.3.4 Sample According to Example 8.3.2 (Entry C)
sample composition: 2.5 mg EP2001+292 mg AldehydoHES30/0.4 (NZA328) in 0.1 M Na-acetate, 20 mM Na-cyanoborohydride, pH 5.0
starting volume: 2.5 ml, diluted 1:10 in buffer A=25 ml
flow-through/wash: 42 ml
run date: 2004 Sep. 30
run no.: QS27 D58 (see Table for example 8.4.4.1)

8.4.3.5 Sample According to Example 8.3.2 (Entry D)
sample composition: 2.5 mg EP2001+292 mg AldehydoHES30/0.7 (NZA329) in 0.1 M Na-acetate, 20 mM Na-cyanoborohydride, pH 5.0
starting volume: 2.5 ml, diluted 1:10 in buffer A=25 ml
flow-through/wash: 40 ml
run date: 2004 Sep. 30
run no.: QS28 D59 (see Table for example 8.4.4.1)

8.4.3.6 Sample According to Example 8.3.2 (Entry E)
sample composition: 2.5 mg EP2001+487 mg AldehydoHES50/0.4 (NZA303) in 0.1 M Na-acetate, 20 mM Na-cyanoborohydride, pH 5.0
starting volume: 2.7 ml, diluted 1:10 in buffer A=27 ml
flow-through/wash: 50 ml
run date: 2004 Sep. 30
run no.: QS29 D60 (see Table 8.4.4.1)

8.4.3.7 Sample According to Example 8.3.2 (Entry F)
sample composition: 2.5 mg EP2001+487 mg AldehydoHES50/0.7 (NZA309) in 0.1 M Na-acetate, 20 mM Na-cyanoborohydride, pH 5.0
starting volume: 2.6 ml, diluted 1:10 in buffer A=26 ml
flow-through/wash: 50 ml
run date: 2004 Sep. 30
run no.: QS30 D61 (see Table for example 8.4.4.1)

8.4.3.8 Sample According to Example 8.3.2 (Entry G)
sample composition: 1.7 mg EP2001+98 mg HES10/0.4 (Supramol Lot. 407B) in 0.1 M Na-acetate, 20 mM Na-cyanoborohydride, pH 5.0
starting volume: 2.5 ml, diluted 1:10 in buffer A=25 ml
flow-through/wash: 42 ml
run date: 2004 Oct. 1
run no.: QS31 D62 (see Table for example 8.4.4.1)

8.4.4 Comparison of the Results
8.4.4.1 SDS-PAGE Analysis of IFN-Alpha Elution Peaks

TABLE XI

Comparison of the peak areas detected at 280 nm during Q-Sepharose chromatography of HESylated IFN-α (Table for example 8.4.4.1)

| Run no. | Calculated applied amount of unmodified IFN-α | Eluate Area (280 nm) [mAU × ml] | Eluate Area (280 nm)/mg unmodified Protein [mAU × ml × mg − 1] | Calculated yield total protein [mg] (HPLC-Quantification at 280 nm*) |
|---|---|---|---|---|
| QS-24 D39 | 1.0 mg | 961 | 961 | 0.42 |
| QS-25 D56 | 2.5 mg | 4370 | 1748 | 1.20 |
| QS-26 D57 | 2.5 mg | 5669 | 2268 | 1.64 |
| QS-27 D58 | 2.5 mg | 3350 | 1340 | 1.60 |
| QS-28 D59 | 2.5 mg | 2854 | 1142 | 1.54 |
| QS-29 D60 | 2.5 mg | 2255 | 902 | 1.52 |
| QS-30 D61 | 2.5 mg | 9278 | 3711 | 3.44 |
| QS-31 D62 | 1.7 mg | 1918 | 1128 | 1.40 |

*data of quantitative analysis derived from RP-HPLC-3

Example 9

Description of IFN Alpha Antiviral Activity Bioassay

Description of the Test Procedure: Antiviral Activity of Interferon-Alpha

After pre-diluting the Test Items in cell culture medium, serial two-fold dilutions were prepared. In 96 well microtiter plates, diluted Interferon was added—in four-fold replicate per dilution—to freshly trypsinized MDBK cells (40.000 cells per well). The assays were incubated for 24 hours at 37° C. (total volume per well: 150 μL (example 9.1) or 175 μl (example 9.2, 9.3, 9.4, 10)).

Subsequently, 50 μL diluted VSV stock solution were added to each well (except for the positive control wells) resulting in a multiplicity of infection of 0.1.

The following controls were included in each assay: 12 wells that received virus plus cell culture medium instead of Interferon (negative control) and 12 wells that received cell culture medium instead of Interferon and virus (positive control).

The assays were incubated for 42 hours at 37° C.

At the end of the incubation period the cell culture supernatant of each well was replaced with 50 μL of a solution of MTT (at least 2 mg/mL in cell culture medium). The cells were incubated for three hours. The purple formazan dye formed by the proliferating cells was solubilized by adding 100 μL solution of isopropanol/HCl (isopropanol with 40 mM HCl) to each well. Subsequently, the absorbance values of the solutions were measured at 570/630 nm in a microtiter plate reader.

The proliferative activity of MDBK cells grown in the presence of Interferon and VSV was calculated for each dilution of Interferon as follows:

$$\frac{\left(\text{(Mean absorbance of four Interferon treated wells)} - \text{(Mean absorbance of negative control)}\right)}{\text{(Mean absorbance of positive control)} - \text{(Mean absorbance of negative control)}} * 100$$

The antiviral activity of Interferon-alpha was determined in four separate assays for each of the Test Items.

Example 9.1

Antiviral Activity of Intron A Relative to NIH Standard

In all experiments, Intron A (IFN-alpha 2b, Schering-Plough), calibrated against NIH-standard rhIFN-alpha 2a (NIAID, NIH, Bethesda, USA, Gxa01-901-535) was used as an internal lab reference. The NIH-standard had a specific activity of 9,000 IU/ml. The internal lab reference Intron A had a specific activity of 8,487,000 IU/ml in the test as described in example 9.

Proliferative activity of Intron A compared to NIH standard rhIFN-alpha 2a is shown in FIG. 28.

Example 9.2

Antiviral Activity of Mock Incubated IFN-α-HES Relative to Unmodified Starting Material As described in example 8.3.4 mock incubated IFN-alpha-HES (described in example 8.3.2, entry G) was used as a reaction control. The antiviral activity of the material was compared to that of unmodified starting material to investigate the influence of the coupling and purification process on the bioactivity. Mock incubation did not affect the in vitro bioactivity of IFN-alpha.

Relative in vitro activity of mock incubated IFN-alpha-HES compared to unmodified IFN-alpha starting material is shown in FIG. 29.

Example 9.3

Antiviral Activity of IFN-Alpha-HES Conjugates Relative to Intron A

In the assay system described in example 9, the conjugates (entries A, B, C, D, E from example 8.3.2 purified according to example 8.4) were tested compared to unmodified IFN-alpha starting material, Intron A and Pegasys (Roche). The CPE50 concentration of the materials was calculated. All IFN-alpha-HES conjugates retained an antiviral activity which was substantially higher than that of Pegasys.

The relative in vitro activity of IFN-alpha-HES conjugates compared to unmodified IFN-alpha starting material, Intron A and Pegasys is shown in FIG. 30.

Example 9.4

Antiviral Activity of IFN-Alpha-HES Conjugate Compared to Intron A

In the assay system described in example 9, the IFN-alpha-HES conjugate of example 8.3.4 purified according to example 8.4 was tested compared to Intron A. The CPE50 concentration of the materials was calculated. The IFN-alpha-HES conjugate retained high antiviral activity of more than 25% compared to Intron A.

The relative in vitro activity of IFN-alpha-HES conjugates compared to Intron A is shown in FIG. 31.

Example 9.5

Antiviral Activity of IFN-Alpha-HES Conjugate Compared to Intron A

In the assay system described in example 9, the IFN-alpha-HES conjugates of example 8.3.3, purified according to example 8.4 was tested compared to Intron A and PegIntron. The CPE50 concentration of the materials was calculated. The IFN-alpha-HES conjugates retained an antiviral activity of approx. 25% compared to Intron A, which is on the same level as the in vitro activity of PegIntron.

The relative in vitro activity of IFN-alpha-HES conjugates compared to Intron A is shown in FIG. 38.

Example 10

In Vivo Bioactivity of IFN-Alpha-HES Conjugates (PK Study in Mice)

Example 10.1

Influence of Mouse Serum on Assay System as Described in Example

Dilutions of Interferon-alpha were prepared in cell culture medium (control) and in mouse serum (1:40 dilution and 1:80 dilution). The assay was performed as described in example 9.

The antiviral activity of Interferon-alpha was determined in two separate assays for the control, for mouse serum 1:40 diluted as well as for mouse serum 1:80 diluted. The results indicated that mouse serum at 1:40 dilution and 1:80 does not affect the bioassay for antiviral activity of Interferon-alpha.

Example 10.2

In Vivo Study in Mice (I)

Antiviral activity of pooled serum was tested in the antiviral assay. Serum was collected from two mice (female BALB/c mice, aged 8 weeks) at each time, which were sacrificed 2 h, 4 h, 12 h, and 24 h post i.v.-injection of 30 µg/kg (based on the protein content) of IFN-alpha or the IFN-alpha-HES conjugate.

The serum samples were thawed and thoroughly homogenized by vortexing (and diluted). Serial two-fold dilutions were prepared in cell culture medium. A vial of Intron A (diluted) was thawed and thoroughly homogenized by vortexing. Serial two-fold dilutions were prepared in cell culture medium.

The EC50-dilutions in the CPE-assay were determined from dose response curves of a 1:2 dilution series as described in example 9.

The half life of the materials was determined compared to unmodified starting material and Pegasys. The half life was calculated from a semi-logarithmic plot of the EC50-dilution vs. time post injection.

Antiviral activity was detected for (i) IFN-alpha-HES (example 8.3.2, entry B of the table), (ii) IFN-alpha-HES (example 8.3.2, entry D of the table), (iii) IFN-alpha-HES (example 8.3.4) up to 24 h. As can be seen from FIG. 32, half-life increased from (i) (approx. 3 h) over (ii) (approx 5 h) to (iii) (approx. 7 h).

For unmodified IFN-alpha, the antiviral activity of serum was too low to calculate a serum half-life. In K. R. Reddy et al. *Advanced Drug Delivery Reviews* 54 (2002) 571-586 a serum half-life of IFN-alpha in rats (i.v.) of 2 h was determined.

Example 10.3

In Vivo Study in Mice (II)

Antiviral activity of pooled serum was tested in the antiviral assay. Serum was collected from two mice (female BALB/c mice, aged 8 weeks) at each time, which were sacrificed 2 h, 4 h, 12 h, and 24 h post i.v.-injection of 30 μg/kg (based on the protein content) of IFN-alpha or the IFN-alpha-HES conjugate.

The serum samples were thawed and thoroughly homogenized by vortexing (and diluted). Serial two-fold dilutions were prepared in cell culture medium. A vial of Intron A (diluted) was thawed and thoroughly homogenized by vortexing. Serial two-fold dilutions were prepared in cell culture medium.

The EC50-dilutions in the CPE-assay were determined from dose response curves of a 1:2 dilution series as described in example 9.

The half life of the materials was determined compared to unmodified starting material and Pegasys. The half life was calculated from a semi-logarithmic plot of the EC50-dilution vs. time post injection.

Antiviral activity was detected for (i) PegIntron, (ii) IFN-alpha-HES 30/0.8 (example 8.3.3.1) and (iii) IFN-alpha-HES 100/0.7 (example 8.3.3.2) up to 24 h. As can be seen from FIG. 37, half life increased from (i) (approx. 3.6 h) to (ii) and (iii) (approx. 6.5 and 6.8 h).

Example 11

In Vivo Bioactivity of IFN-Alpha-HES Conjugates (PK Study in Rabbits)

Example 11.1

Radioactive Labeling of IFN-Alpha and IFN-Alpha-HES Conjugates

The samples used for the PK study were labeled with $^{125}$I with the Chloramine T method. Chloramine T is reacted with iodide and an interhalogen species (I-Cl) is formed. The interhalogen reacts on the aromatic ring of Tyrosine and substitutes it in o-position.

Example 11.2

Reference Experiment: Labeling of Oxo-HES 50/0.4 with $^{125}$I

In a first experimental series under the given reaction conditions it was investigated whether trace amounts of iodine could be detected e.g. by iodine, polyiodine or polyiodide forming complexes with HES. In comparison, oxo-HES (MW 42.1 kD DS=0.41) and IFN-alpha-HES (example 8.3.2, entry E of table) were labeled under the same conditions and after the purification process, radioactivity in the samples was measured. According to literature amylopectine can form complexes with iodine, polyiodine or polyiodide when the helical structures have at least 11 anhydroglucose units.

Only in the IFN-alpha-HES sample, radioactivity was detected. This result proved that radioactivity was exclusively caused by covalent modification of Tyrosine residues in of IFN-alpha but not by potentially physically bound iodine, which was not removed in the purification process. oxo-HES 50/0.4 (MW=42.1 kD, DS=0.41) can be considered as negative control. Due to the high molecular weight and the low degree of substitution in this oxo-HES species, the longest helical structures would be expected if any are present and thus, in this case there would have been the highest risk of complexation of iodine.

Example 11.3

Labelling of Interferon-Alpha with Non-Radioactive Iodine ("Cold Iodination")

Interferon alpha was labeled with non-radioactive iodine in the same labelling and purification process as the IFN-alpha-HES-conjugates 50/0.4. In the antiviral assay antiviral activity was retained. However, no quantification was performed, because in the labelling and purification process the concentration was changed and could not be determined due to the small amount of material available.

Example 11.4

Radioactive Labeling of IFN-Alpha-HES Conjugates

Samples were labeled according to example 11.1 with radioactive $^{125}$I. The samples were IFN-alpha starting material, IFN-alpha-HES (example 8.3.2, entry D of table). The samples had a specific activity of 38 μCi/μg (IFN-alpha starting material), 41 μCi/μg (IFN-alpha-HES 30/0.7).

Example 11.5

In Vivo PK Study in Rabbits

Example 11.5.1

Experimental Procedure

The test items were used as a dilution. A solution of 4 μCi/ml was prepared. Dilution buffer was PBS.

Four New Zealand White Rabbits HsdIf:NZW. Source Harlan Winkelmann GmbH, D-33178 Borchen,. Sex: female; body weight at the commencement of the study: >2.5 kg. All animals have been applicated intraveneously with the radiolabelled test substances, receiving a volume of 1 ml/kg body weight, which is equivalent to a dosage of 4 μCi/kg body weight. Blood samples have been taken at defined time points. At each sampling point approx. 600 μl blood from the auricular vein of the animals was taken for further investigations.

For the blood sampling an intravenous indwelling catheter was layed under general anaesthesia (Ketamin/Rompun) into the auricular vein. Anaesthesia rested for the blood sampling point before application, for the application itself and the first three blood samplings after application (0.5 hours, 1 hour, and 2 hours). Catheters were let into animals for the further sampling points until they were excised by the animals themselfes. Further blood samplings were determined with a cannula through different areas of the auricular veins.

Further processing of the blood samples was performed after blood sampling. To determine the radiolabelled test item in the blood, the collected blood samples were processed according to a specific solubilization protocol. For this 250 μl of the blood samples were transferred to a new vial and an equal volume of Solvable™ was added. The samples were incubated for one hour at 50° C. in a shaking water bath. After the incubation time the samples were cooled to room temperature and 100 μl of EDTA-solution [100 mM] was added. Subsequent 300 μl of $H_2O_2$ [30%] was added and after shaking again the samples were incubated for one hour at 50° C. in a shaking water bath. Before further processing the samples were collected.

At the end of blood collecting and solubilization the samples were transferred to a 20 ml scintillation vial and 10 ml of the scintillation cocktail Ultima Gold™ was added. Until measurement of the isotop $^{125}$I in a scintillation-counter (about 72 h after cocktail addition) the samples were stored in the dark at 2-8° C.

Prior to the processing and statistical analysis of the data the quench of the activity detection under the specific experimental conditions was determined. The regression coefficient ($r^2$=0.9970) is a measure of the fit to the line. The quench factor [pCi/cpm] was found to be 3.315938.

Results (see FIG. 33):

IFN-alpha-HES showed a distinct prolongation of half-life compared to the starting material. Beyond 24 h (approx. <1000 pCi/ml) the curve of the unmodified material leveled off and almost no decrease of activity was observed. The small standard deviation of the measured radioactivity for all samples proves the quality of the experiment.

The half-life was calculated from the concentration of IFN-alpha in the blood samples. For the evaluation shown in FIG. 34, only the data from blood samples taken between 4 and 24 h were considered. For the unmodified material a half-life of 7 h was calculated. With IFN-alpha-HES, a substantial increase of half-life was observed (approx. 33 h).

Data were evaluated statistically according to different compartment models as shown in the diagrams in FIG. 35 *a*, and *b* (cut-out 0-12 h). In the one-compartment model, it is obvious, that the concentration of IFN-alpha rapidly drops during the first 2 hours after injection. For IFN-alpha-HES the half-life is clearly prolonged. Statistically calculated half-life was 0.26 h for IFN-alpha, 7.7 h for IFN-alpha-HES. According to the non-compartment model the statistical evaluation results in a half-life of 147 h for unmodified IFN-alpha (based on data 24-120 h), 42.7 h for IFN-alpha-HES (based on data 36-120 h). As described above the half-life of the unmodified IFN-alpha is substantially prolonged since the curve levels off beyond 24 h.

The half life of the two samples is summarized in Table XI, based on the described models for the calculation.

TABLE XI

Half-life of IFN-alpha and IFN-alpha-HES calculated according to different models

|  | IFN-alpha starting material $t_{1/2}$ | IFN-alpha-HES $t_{1/2}$ |
|---|---|---|
| non compartment model | (147.0*) | 42.7** |
| one compartment model | 0.26 | 7.7 |
| semi logarithmic plot (see FIG. 33, 4-24 h) | 7 | 33 |

*evaluated data 24-120 h,
**evaluated data 36-120 h

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for preparing a conjugate comprising a protein and a polymer derivative, wherein the polymer is a hydroxyalkyl starch (HAS), said method comprising
   (a)(1) reacting the polymer at its optionally oxidized reducing end with an at least bifunctional compound, said compound comprising two functional groups M and Q, functional group M being reacted with the optionally oxidized reducing end of the polymer, and functional group Q being an aldehyde group or keto group or hemiacetal group, to give an aldehyde or keto or hemiacetal functionalized polymer derivative; or
   (a)(2) reacting the polymer at its optionally oxidized reducing end with an at least bifunctional compound, said compound comprising two functional groups M and Q, functional group M being reacted with the optionally oxidized reducing end of the polymer to give a polymer derivative comprising a free functional group Q, the method further comprising reacting said polymer derivative with a further at least bifunctional compound comprising a functional group capable of being reacted with the functional group Q, and an aldehyde group or keto group or hemiacetal group, to give an aldehyde or keto or hemiacetal functionalized polymer derivative; and
   (b) covalently linking the aldehyde group or keto group or hemiacetal group of the aldehyde or keto or hemiacetal functionalized polymer derivative to at least one amino group of the protein by reductive amination.

2. The method as claimed in claim 1 wherein the HAS is hydroxyethyl starch (HES).

3. The method as claimed in claim 2 wherein the HES has a molecular weight of from 2 to 200 kD.

4. The method as claimed in claim 1, wherein the reductive amination is carried out in an aqueous medium.

5. The method as claimed in claim 1, wherein the reductive amination is carried out in the presence of $NaCNBH_3$.

6. The method as claimed in claim 1, wherein the reductive amination is carried out at a pH of 7.5 or less.

7. The method as claimed in claim 6, wherein the pH is 6 or less.

8. The method as claimed in claim 1, wherein the reductive amination is carried out at a temperature of from 0 to 25° C.

9. The method as claimed in claim 1, wherein in (a)(1), the functional group M is a carboxy group or a reactive carboxy group and the functional group Q is an aldehyde group or keto group or hemiacetal group.

10. The method as claimed in claim 1, wherein in (a)(2), the bifunctional compound comprising M and Q is selected from the group consisting of formylbenzoic acid, 4-formylbenzoic acid pentafluorophenyl ester, 4-formylbenzoic acid N-hydroxysuccinimide ester, and 4-(4-formyl-3,5-dimethoxyphenoxy)butyric acid.

11. The method as claimed in claim 1, wherein in (a)(2), the functional group M is an amino group and the functional group Q is an amino group.

12. The method as claimed in claim 11, wherein the compound comprising two amino groups M and Q is an optionally substituted diaminoalkane having from 2 to 20 carbon atoms.

13. The method as claimed in claim 12, wherein the diaminoalkane is selected from the group consisting of 1,2-diaminoethane, 1,3-diaminopropane, and 1,4-diaminobutane.

14. The method as claimed in claim 11, wherein the further at least bifunctional compound comprises a carboxy group or a reactive carboxy group and the aldehyde group or keto group or hemiacetal group, to give the aldehyde or keto or hemiacetal functionalized polymer derivative.

15. The method as claimed in claim 14, wherein the further bifunctional compound is selected from the group consisting of formylbenzoic acid, 4-formylbenzoic acid pentafluorophenyl ester, 4-formylbenzoic acid N-hydroxysuccinimide ester, and 4-(4-formyl-3,5-dimethoxyphenoxy)butyric acid.

16. The method as claimed in claim 11, wherein the amino group Q of the compound comprising two amino groups M and Q, is a beta hydroxy amino group.

17. The method as claimed in claim 16, wherein the beta hydroxyamino group is oxidized to give an aldehyde group.

18. The method as claimed in claim 17, wherein the oxidation reaction is carried out using a periodate.

19. The method as claimed in claim 16, wherein the compound comprising two amino groups M and Q, Q being a beta hydroxy amino group, is 1,3-diamino-2-hydroxypropane.

20. The method as claimed in claim 1, wherein the protein is selected from the group consisting of erythropoietin (EPO), granulocyte-colony stimulating factor (G-CSF), interferon (IFN) alpha, IFN beta, antithrombin (AT) III, interleukin-(IL-)2, IL-3, myoglobin, superoxide dismutase (SOD), and bovine serum albumin (BSA), or from the group consisting of alpha1-antitrypsin (A1AT), factor VII, factor VIII, factor IX, tissue-type plasminogen activator (tPA), and activated protein C (APC).

21. A conjugate comprising a protein and a polymer derivative, obtained by a method as defined in claim 1.

22. The conjugate as claimed in claim 21, wherein the polymer derivative is predominantly coupled to the N-terminal amino group of the protein via an amino linkage, the protein used for the reaction comprising the N-terminal amino group and at least one further amino group.

23. The conjugate as claimed in claim 21, wherein the protein is covalently linked to the polymer derivative via an amino linkage, said derivative resulting from the reaction of the polymer with the compound comprising two amino groups M and Q via functional group M, the resulting compound having been further reacted via Q with a further bifunctional compound comprising a carboxy group or a reactive carboxy group and an aldehyde group or a keto group or a hemiacetal group, said carboxy group or reactive carboxy group forming an amide linkage with the amino group Q, and said aldehyde group or keto group or hemiacetal group having been reacted with an amino group of the protein by reductive amination.

24. The conjugate as claimed in claim 23, wherein the further bifunctional compound comprising a carboxy group or a reactive carboxy group and an aldehyde group or keto group or hemiacetal group is selected from the group consisting of formylbenzoic acid, 4-formylbenzoic acid pentafluorophenyl ester, 4-formylbenzoic acid N-hydroxysuccinimide ester, and 4-(4-formyl-3,5-dimethoxyphenoxy)butyric acid.

25. The conjugate as claimed in claim 24, having the structure

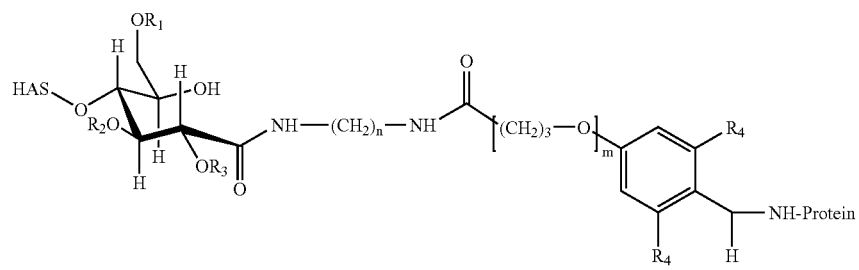

wherein the polymer was reacted via its oxidized reducing end, wherein $R_1$, $R_2$ and $R_3$ independently are hydrogen or a hydroxyalkyl group, n=2, 3, or 4, $R_4$ independently is hydrogen or a methoxy group, and m=0 when $R_4$ is hydrogen or m=1 when $R_4$ is methoxy.

26. The conjugate as claimed in claim 21, wherein the protein is covalently linked to the polymer derivative via an amino linkage, said derivative resulting from the reaction of the polymer with the compound comprising two amino groups M and Q, Q being a beta hydroxy amino group, and oxidation of the beta hydroxyamino group Q to give an aldehyde group.

27. The conjugate as claimed in claim 26, wherein the compound comprising two amino groups M and Q, Q being a beta hydroxy amino group, is 1,3-diamino-2-hydroxypropane.

28. The conjugate as claimed in claim 27, having the structure

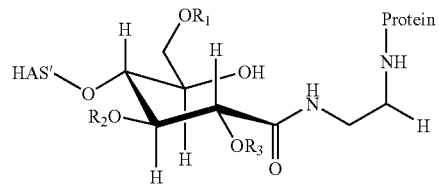

wherein the polymer was reacted at its oxidized reducing end, wherein $R_1$, $R_2$ and $R_3$ independently are hydrogen or a hydroxyalkyl group.

29. The conjugate as claimed in claim 21, wherein the protein is selected from the group consisting of EPO, G-CSF, IFN alpha, IFN beta, AT III, IL-2, IL-3, myoglobin, SOD, and BSA.

30. The conjugate as claimed in claim 21, wherein the protein is selected from the group consisting of rhEPO, rhG-CSF, rhIFN alpha, rhIFN beta, rhAT III, rhIL-2, rhIL-3, myoglobin, SOD, and BSA.

31. The conjugate as claimed in claim 21, wherein the protein is selected from the group consisting of A1AT, factor VII, factor VIII, factor IX, tPA, and APC.

32. A method for the treatment of a human or animal body, comprising administering a pharmaceutically effective amount of the conjugate of claim 21 to a human or animal in need of treatment,
   wherein the protein is EPO and the human or animal suffers from an anemic disorder or a hematopoietic dysfunction disorder, or
   wherein the protein is G-CSF and the human or animal suffers from a disorder characterized by a reduced hematopoietic or immune function, or
   wherein the protein is AT III and the human or animal suffers from hereditary deficiency, veno-occlusive disease, burns and/or heparin resistance in coronary arterial bypass graft (CABG), bowel perforation resulting from trauma or gastrointestinal surgery, disseminated intravascular coagulation (DIC) or sepsis, or wherein the protein is Factor VIII and the human or animal suffers from hemophilia A, or wherein the protein is A1AT and the human or animal suffers from emphysema, cystic fibrosis, atopic dermatitis, chronic obstructive pulmonary disease (COPD), or bronchitis, or wherein the protein is tPA and the human or animal suffers from myocardial infarction, thrombosis, thromboembolism or an occlusive disease, or wherein the protein is APC and the human or animal suffers from severe sepsis, thrombosis, thromboembolism or an occlusive disease, or wherein the protein is IFN alpha and the human or animal suffers from leukemia, multiple myeloma, follicular lymphoma, cancer, or hepatitis, or wherein the protein is IFN beta and the human or animal suffers from multiple sclerosis, or wherein the protein is Factor VII and the human or animal suffers from episodes in hemophilia A or B due to inhibitors of Factor VIII or Factor IX, or wherein the protein is Factor IX and the human or animal suffers from hemorrhagic episodes with hemophilia B or from bleeding in surgical settings.

33. The method of claim 32, wherein the protein is G-CSF and the disorder characterized by a reduced hematopoietic or immune function, is a result of chemotherapy, radiation therapy, infectious disease, severe chronic neutropenia, or leukemia.

34. The method of claim 32, wherein the protein is tPA and the occlusive disease is an occlusive arterial disease.

35. The method of claim 32, wherein the protein is APC and the occlusive disease is an occlusive arterial disease.

36. The method of claim 32, wherein the protein is IFN alpha and the human or animal suffers from hairy cell leukemia, chronic myelogeneous leukemia, a carcinoid tumor, malignant melanoma chronic hepatitis B, or chronic hepatitis C.

37. The method of claim 32, wherein the protein is IFN beta and the multiple sclerosis is a relapsing form of multiple sclerosis.

38. The method of claim 32, wherein the protein is Factor IX and the human or animal suffers from a congenital factor IX deficiency or Christmas disease.

39. A pharmaceutical composition comprising in a therapeutically effective amount a conjugate as claimed in claim 21.

40. The pharmaceutical composition as claimed in claim 29, further comprising at least one pharmaceutically acceptable diluent, adjuvant, or carrier.

41. A composition for the treatment of anemic disorders or hematopoietic dysfunction disorders, comprising a conjugate as claimed in claim 21, wherein the protein is EPO and the polymer is HAS.

42. A composition for the treatment of a disorder characterized by a reduced hematopoietic or immune function, comprising a conjugate as claimed in claim 21, wherein the protein is G-CSF and the polymer is HAS.

43. A composition for the treatment of hereditary deficiency, veno-occlusive disease, burns and heparin resistance in coronary arterial bypass graft (CABG) surgery, bowel perforation resulting from trauma or gastrointestinal surgery, disseminated intravascular coagulation (DIC) or sepsis, comprising a conjugate as claimed in claim 21, wherein the protein is AT III and the polymer is HAS.

44. A composition for the treatment of haemophilia A, comprising a conjugate as claimed in claim 21, wherein the protein is Factor VIII and the polymer is HAS.

45. A composition for the treatment of emphysema, cystic fibrosis, atopic dermatitis, chronic obstructive pulmonary disease (COPD) or bronchitis, comprising a conjugate as claimed in claim 21, wherein the protein is A1AT and the polymer is HAS.

46. A composition for the treatment of myocardial infarctions (heart attacks), thrombosis, thromboembolism or occlusive diseases, comprising a conjugate as claimed in claim 21, wherein the protein is tPA and the polymer is HAS.

47. A composition for the treatment of severe sepsis, thrombosis, thromboembolism or occlusive diseases, comprising a conjugate as claimed in claim 21, wherein the protein is APC and the polymer is HAS.

48. A composition for the treatment of cancer or hepatitis, comprising a conjugate as claimed in claim 21, wherein the protein is IFN alpha and the polymer is HAS.

49. A composition for the treatment of multiple sclerosis, comprising a conjugate as claimed in claim 21, wherein the protein is IFN beta and the polymer is HAS.

50. A composition for the treatment of episodes in hemophilia A or B patients with inhibitors to Factor VIII or Factor IX, comprising a conjugate as claimed in claim 21, wherein the protein is Factor VII and the polymer is HAS.

51. A composition for the control and prevention of hemorrhagic episodes in patients with hemophilia B, including control and prevention of bleeding in surgical settings, comprising a conjugate as claimed in claim 21, wherein the protein is Factor IX and the polymer is HAS.

52. A conjugate comprising HAS and a protein, wherein HAS is coupled at its oxidized reducing end via an amide linkage to a first crosslinking compound, said first crosslinking compound being additionally linked via an amide linkage to a second crosslinking compound, said second crosslinking compound being linked via an azomethine or amino linkage to said protein.

53. The conjugate as claimed in claim 52, wherein the protein is selected from the group consisting of EPO, G-CSF, IFN alpha, IFN beta, AT III, IL-2, IL-3, myoglobin, SOD, BSA, A1AT, factor VII, factor VIII, factor IX, tPA, and APC.

54. A conjugate comprising a protein and a polymer, wherein the polymer is a HAS, the conjugate having a structure according to the formula

127

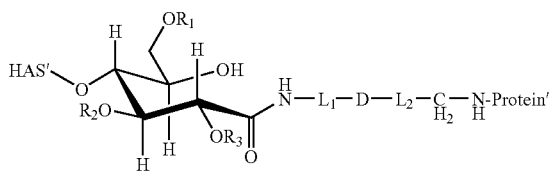

wherein $R_1$, $R_2$ and $R_3$ are independently hydrogen or a hydroxyalkyl group, a hydroxyaryl group, a hydroxyaralkyl group or a hydroxyalkaryl group having of from 1 to 10 carbon atoms, and wherein L is an optionally substituted, linear, branched or cyclic hydrocarbon residue, optionally comprising at least one heteroatom, having from 1 to 60 carbon atoms.

55. A conjugate comprising a protein and a polymer, wherein the polymer is a HAS, the conjugate having a structure according to the formula

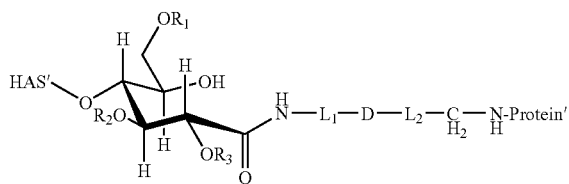

wherein $R_1$, $R_2$ and $R_3$ are independently hydrogen or a hydroxyalkyl group, a hydroxyaryl group, a hydroxyaralkyl group or a hydroxyalkaryl group having of from 1 to 10 carbon atoms, and wherein $L_1$ and $L_2$ are independently an optionally substituted, linear, branched or cyclic hydrocarbon residue, optionally comprising at least one heteroatom, comprising an alkyl, aryl, aralkyl, heteroalkyl, or heteroaralkyl moiety, said residue having from 1 to 60 carbon atoms, and wherein D is a linkage formed by a functional group $F_2$ linked to $L_1$ and a functional group $F_3$ linked to $L_2$, wherein $F_3$ is a functional group capable of forming a chemical linkage with $F_2$.

56. The conjugate as claimed in claim 55, wherein $L_1$ is —$(CH_2)_n$- with n=2, 3, 4, 5, 6, 7, 8, 9, 10.

57. The conjugate as claimed in claim 55, wherein $L_2$ comprises an optionally substituted aryl moiety.

58. The conjugate as claimed in claim 55, wherein $F_2$ and $F_3$ are independently selected from the group consisting of
- a C—C-double bond or a C—C-triple bond or an aromatic C—C-bond;
- a thio group or a hydroxy group;
- an alkyl sulfonic acid hydrazide or an aryl sulfonic acid hydrazide;
- a 1,2-diol;
- a 1,2 amino-thioalcohol;
- an azide;
- a 1,2-aminoalcohol;

128

- an amino group —$NH_2$ or an aminoalkyl group, aminoaryl group, aminoaralkyl group, or alkarylamino group;
- a hydroxylamino group —O—$NH_2$, or a hydroxylalkylamino group, hydroxylarylamino group, hydroxylaralkylamino group, or hydroxyalkarylamino group;
- an alkoxyamino group, an aryloxyamino group, an aralkyloxyamino group, or an alkaryloxyamino group, each comprising the structure unit —NH—O—;
- a residue having a carbonyl group, -Q-C(=G)-M, wherein G is O or S, and M is
  —OH or —SH;
- an alkoxy group, an aryloxy group, an aralkyloxy group, or an alkaryloxy group;
- an alkylthio group, an arylthio group, an aralkylthio group, or an alkarylthio group;
- an alkylcarbonyloxy group, an arylcarbonyloxy group, an aralkylcarbonyloxy group, or an alkarylcarbonyloxy group;
- an activated ester having imide structure or having a structure unit O—N where N is part of a heteroaryl compound or, with G=O and Q absent, an aryloxy compound with a substituted aryl residue;

wherein Q is absent or NH or a heteroatom S or O;
—NH—$NH_2$, or —NH—NH—;
—$NO_2$;
a nitrile group;
a carbonyl group;
a carboxy group;
a —N=C=O group or a —N=C=S group;
a vinyl halide group;
—C≡C—H;
—(C=$NH_2$Cl)—OAlkyl;
a group —(C=O)—$CH_2$-Hal wherein Hal is Cl, Br, or I;
—CH=CH—$SO_2$—;
a disulfide group comprising the structure —S—S—;
the group

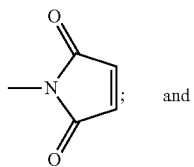 and the group

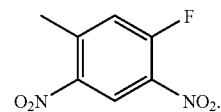

59. The conjugate as claimed in claim 58, having a structure according to the formula

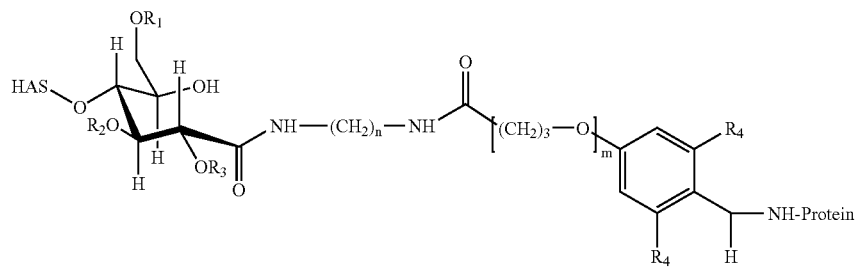
wherein n=2, 3, or 4, $R_4$ independently is hydrogen or a methoxy group, and m=0 when $R_4$ is hydrogen or m=1 when $R_4$ is methoxy.
* * * * *

UNITED STATES PATENT AND TRADEMARK OFFICE
CERTIFICATE OF CORRECTION

PATENT NO. : 8,287,850 B2
APPLICATION NO. : 11/518352
DATED : October 16, 2012
INVENTOR(S) : Wolfram Eichner et al.

Page 1 of 1

It is certified that error appears in the above-identified patent and that said Letters Patent is hereby corrected as shown below:

Column 125, lines 57-58 (Claim 40), please delete "claim 29" and insert --claim 39,--, therefor.

Column 127, lines 1-8, please delete

"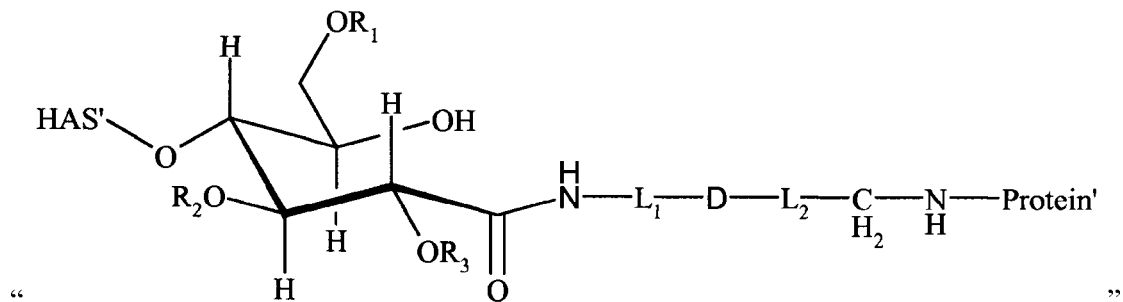"

and insert --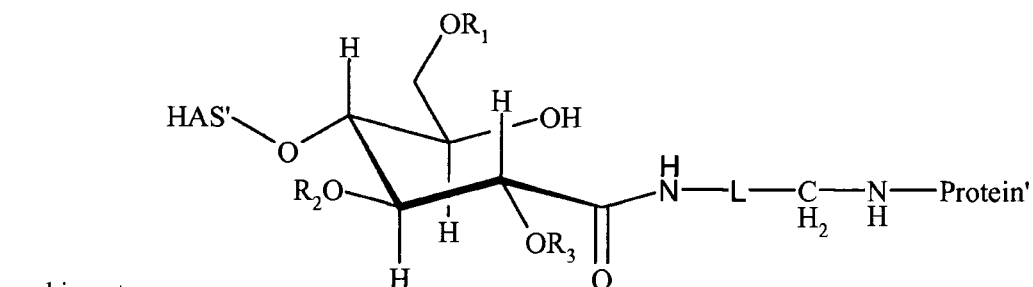--, therefor.

Signed and Sealed this
Nineteenth Day of February, 2013

Teresa Stanek Rea
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 8,287,850 B2 | |
| APPLICATION NO. | : 11/518352 | |
| DATED | : October 16, 2012 | |
| INVENTOR(S) | : Eichner et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 574 days.

Signed and Sealed this
Fifth Day of April, 2016

Michelle K. Lee
*Director of the United States Patent and Trademark Office*

SEQUENCE LISTING

<160> NUMBER OF SEQ ID NOS: 9

<210> SEQ ID NO 1
<211> LENGTH: 20
<212> TYPE: PRT
<213> ORGANISM: Homo sapien

<400> SEQUENCE: 1

Met Thr Pro Leu Gly Pro Ala Ser Ser Leu Pro Gln Ser Phe Leu Leu
1               5                   10                  15

Lys Cys Leu Glu
            20

<210> SEQ ID NO 2
<211> LENGTH: 14
<212> TYPE: PRT
<213> ORGANISM: Homo sapien

<400> SEQUENCE: 2

Gln Val Arg Lys Ile Gln Gly Asp Gly Ala Ala Leu Gln Glu
1               5                   10

<210> SEQ ID NO 3
<211> LENGTH: 13
<212> TYPE: PRT
<213> ORGANISM: Homo sapien

<400> SEQUENCE: 3

Lys Leu Cys Ala Thr Tyr Lys Leu Cys His Pro Glu Glu
1               5                   10

```
<210> SEQ ID NO 4
<211> LENGTH: 47
<212> TYPE: PRT
<213> ORGANISM: Homo sapien

<400> SEQUENCE: 4

Leu Val Leu Leu Gly His Ser Leu Gly Ile Pro Trp Ala Pro Leu Ser
 1               5                   10                  15

Ser Cys Pro Ser Gln Ala Leu Gln Leu Ala Gly Cys Leu Ser Gln Leu
            20                  25                  30

His Ser Gly Leu Phe Leu Tyr Gln Gly Leu Leu Gln Ala Leu Glu
        35                  40                  45

<210> SEQ ID NO 5
<211> LENGTH: 5
<212> TYPE: PRT
<213> ORGANISM: Homo sapien

<400> SEQUENCE: 5

Gly Ile Ser Pro Glu
 1               5

<210> SEQ ID NO 6
<211> LENGTH: 25
<212> TYPE: PRT
<213> ORGANISM: Homo sapien

<400> SEQUENCE: 6

Leu Gly Pro Thr Leu Asp Thr Leu Gln Leu Asp Val Ala Asp Phe Ala
 1               5                   10                  15

Thr Thr Ile Trp Gln Gln Met Glu Glu
            20                  25

<210> SEQ ID NO 7
<211> LENGTH: 39
<212> TYPE: PRT
<213> ORGANISM: Homo sapien

<400> SEQUENCE: 7

Leu Gly Met Ala Pro Ala Leu Gln Pro Thr Gln Gly Ala Met Pro Ala
 1               5                   10                  15

Phe Ala Ser Ala Phe Gln Arg Arg Ala Gly Gly Val Leu Val Ala Ser
            20                  25                  30

His Leu Gln Ser Phe Leu Glu
        35

<210> SEQ ID NO 8
<211> LENGTH: 12
<212> TYPE: PRT
<213> ORGANISM: Homo sapien

<400> SEQUENCE: 8

Val Ser Tyr Arg Val Leu Arg His Leu Ala Gln Pro
 1               5                   10

<210> SEQ ID NO 9
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: 1
<223> OTHER INFORMATION: Xaa= N-Met
```

```
<220> FEATURE:
<221> NAME/KEY: VARIANT
<222> LOCATION: 2
<223> OTHER INFORMATION: Xaa= O-succinyl-Ala

<400> SEQUENCE: 9

Xaa Xaa Ala Pro Val
 1               5
```